(12) United States Patent
Liik et al.

(10) Patent No.: US 7,973,135 B2
(45) Date of Patent: Jul. 5, 2011

(54) COMPOSITIONS AND METHODS FOR TARGETING CANCER-SPECIFIC TRANSCRIPTION COMPLEXES

(75) Inventors: Anzelika Liik, Tallinn (EE); Anna Kazantseva, Tallinn (EE)

(73) Assignee: Oncotx, Inc., Los Angeles, CA (US)

( * ) Notice: Subject to any disclaimer, the term of this patent is extended or adjusted under 35 U.S.C. 154(b) by 529 days.

(21) Appl. No.: 11/777,271

(22) Filed: Jul. 12, 2007

(65) Prior Publication Data

US 2008/0027002 A1    Jan. 31, 2008

Related U.S. Application Data

(60) Provisional application No. 60/807,190, filed on Jul. 12, 2006.

(51) Int. Cl.
| | |
|---|---|
| *C12P 21/08* | (2006.01) |
| *C07K 2/00* | (2006.01) |
| *A61K 38/00* | (2006.01) |
| *C07K 4/00* | (2006.01) |
| *A61K 39/395* | (2006.01) |
| *A01N 37/18* | (2006.01) |
| *G01N 33/53* | (2006.01) |

(52) U.S. Cl. .................. 530/387.1; 530/300; 424/130.1; 514/2; 435/7.1

(58) Field of Classification Search ........................ None
See application file for complete search history.

(56) References Cited

U.S. PATENT DOCUMENTS

| | | | |
|---|---|---|---|
| 6,248,520 | B1 | 6/2001 | Roeder et al. |
| 6,268,173 | B1 * | 7/2001 | Chambon et al. ............ 435/69.1 |
| 6,380,373 | B1 * | 4/2002 | O'Malley ..................... 536/23.5 |
| 6,586,185 | B2 * | 7/2003 | Wolf et al. ......................... 435/6 |
| 6,861,508 | B2 | 3/2005 | Chambon et al. |
| 6,965,850 | B2 | 11/2005 | Baxter et al. |
| 2003/0228607 | A1 | 12/2003 | Wagner et al. |
| 2004/0031072 | A1 | 2/2004 | La Rosa et al. |
| 2004/0214272 | A1 | 10/2004 | La Rosa et al. |
| 2004/0219575 | A1 | 11/2004 | Neuman et al. |
| 2005/0202440 | A1 | 9/2005 | Fletterick et al. |

FOREIGN PATENT DOCUMENTS

| | | |
|---|---|---|
| JP | 2003/000270 | 1/2003 |
| WO | WO 99/60014 | 11/1999 |
| WO | WO 2000/001820 | * 1/2000 |
| WO | WO 02/02488 | 1/2002 |
| WO | WO 02/40716 | 5/2002 |
| WO | WO 02/095652 | 11/2002 |
| WO | WO 03/033515 | 4/2003 |

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin-binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Onate, S.A., et al., "The Steroid Receptor Coactivator-1 Contains Multiple . . . Receptors", J of Biological Chemistry, vol. 273, No. 20, May 15, 1998, pp. 12101-12108.

Ding, X.F. et al., "Nuclear Receptor-Bonding Sites of Coactivators . . . Specificities", Mol. Endocrinol., vol. 12(2):302-313, Feb. 1998.

Flajollet, S. et al., "Distinct Roles of the Steroid Receptor Coactivator 1 . . . Differentiation", J. of Biological Chemistry, 281(29):20338-20348, Jul. 2006.

Giangrande, P. et al., "The Opposing Transcriptional Activities of the Two Isoforms . . . Binding", Molecular & Cellular Biology, 20(9):3102-3115, May 2000.

Wu, J. et al., Repression of p65 Transcriptional Activation . . . Receptor, Molecular Endocrinology, 18(1):53-62, Jan 2004. (Abstract & result of sequence search).

Scarabel, L, Molecular Basis and Genetic Characterisation of Evolved . . . Rhoeas, Plant Science, 166:703-709, 2004, (Abstract & result of sequence search).

European Patent Office Search Report dated Dec. 23, 2009 from corresponding EP Patent Application No. 07812873.3.

* cited by examiner

*Primary Examiner* — Anne M. Gussow
(74) *Attorney, Agent, or Firm* — Karen S. Canady; canady + lortz LLP

(57) ABSTRACT

The invention provides molecules that target cancer-specific transcription complexes (CSTC), compositions and kits comprising CSTC-targeting molecules, and methods of using CSTC-targeting molecules for the treatment) detection and monitoring of cancer.

22 Claims, No Drawings

SEQUENCE LISTING

```
<160> NUMBER OF SEQ ID NOS: 175

<210> SEQ ID NO 1
<211> LENGTH: 23
<212> TYPE: PRT
<213> ORGANISM: Homo sapiens
```

<400> SEQUENCE: 1

Pro Gln Met Gln Gln Asn Val Phe Gln Tyr Pro Gly Ala Gly Met Val
1               5                   10                  15

Pro Gln Gly Glu Ala Asn Phe
            20

<210> SEQ ID NO 2
<211> LENGTH: 22
<212> TYPE: PRT
<213> ORGANISM: Homo sapiens

<400> SEQUENCE: 2

Asn Asp Arg Leu Ser Asp Gly Asp Ser Lys Tyr Ser Gln Thr Ser His
1               5                   10                  15

Lys Leu Val Gln Leu Leu
            20

<210> SEQ ID NO 3
<211> LENGTH: 7
<212> TYPE: PRT
<213> ORGANISM: Homo sapiens

<400> SEQUENCE: 3

Arg Arg Arg Arg Arg Arg Arg
1               5

<210> SEQ ID NO 4
<211> LENGTH: 6
<212> TYPE: PRT
<213> ORGANISM: Homo sapiens

<400> SEQUENCE: 4

Pro Lys Lys Arg Lys Val
1               5

<210> SEQ ID NO 5
<211> LENGTH: 36
<212> TYPE: PRT
<213> ORGANISM: Homo sapiens

<400> SEQUENCE: 5

Pro Lys Lys Arg Lys Val Arg Arg Arg Arg Arg Arg Pro Gln Met
1               5                   10                  15

Gln Gln Asn Val Phe Gln Tyr Pro Gly Ala Gly Met Pro Gln Gly
            20                  25                  30

Glu Ala Asn Phe
        35

<210> SEQ ID NO 6
<211> LENGTH: 35
<212> TYPE: PRT
<213> ORGANISM: Homo sapiens

<400> SEQUENCE: 6

Pro Lys Lys Arg Lys Val Arg Arg Arg Arg Arg Arg Asn Asp Arg
1               5                   10                  15

Leu Ser Asp Gly Asp Ser Lys Tyr Ser Gln Thr Ser His Lys Leu Val
            20                  25                  30

Gln Leu Leu
        35

```
<210> SEQ ID NO 7
<211> LENGTH: 23
<212> TYPE: PRT
<213> ORGANISM: Homo sapiens
<220> FEATURE:
<221> NAME/KEY: Q(N)
<222> LOCATION: (2)..(9)
<223> OTHER INFORMATION: Xaa is Q or N
<220> FEATURE:
<221> NAME/KEY: G(A)
<222> LOCATION: (12)..(14)
<223> OTHER INFORMATION: Xaa is G or A
<220> FEATURE:
<221> NAME/KEY: V(L)
<222> LOCATION: (16)..(16)
<223> OTHER INFORMATION: Xaa is V or L
<220> FEATURE:
<221> NAME/KEY: Q(N)
<222> LOCATION: (18)..(18)
<223> OTHER INFORMATION: Xaa is Q or N
<220> FEATURE:
<221> NAME/KEY: E(D)
<222> LOCATION: (20)..(20)
<223> OTHER INFORMATION: Xaa is E or D
<220> FEATURE:
<221> NAME/KEY: A(G)
<222> LOCATION: (21)..(21)
<223> OTHER INFORMATION: Xaa is A or G
<220> FEATURE:
<221> NAME/KEY: Q(N)
<222> LOCATION: (22)..(22)
<223> OTHER INFORMATION: Xaa is Q or N

<400> SEQUENCE: 7

Pro Xaa Met Xaa Xaa Xaa Val Phe Xaa Tyr Pro Xaa Xaa Xaa Met Xaa
1               5                   10                  15

Pro Xaa Gly Xaa Xaa Xaa Phe
            20

<210> SEQ ID NO 8
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is D or E
<220> FEATURE:
<221> NAME/KEY: MISC_FEATURE
<222> LOCATION: (3)..(3)
<223> OTHER INFORMATION: X is R or K
<220> FEATURE:
<221> NAME/KEY: MISC_FEATURE
<222> LOCATION: (4)..(4)
<223> OTHER INFORMATION: X is L or V
<220> FEATURE:
<221> NAME/KEY: MISC_FEATURE
<222> LOCATION: (6)..(8)
<223> OTHER INFORMATION: X is D or E
<220> FEATURE:
<221> NAME/KEY: MISC_FEATURE
<222> LOCATION: (10)..(10)
<223> OTHER INFORMATION: X is K or R
<220> FEATURE:
<221> NAME/KEY: MISC_FEATURE
<222> LOCATION: (13)..(13)
<223> OTHER INFORMATION: X is Q or N
<220> FEATURE:
<221> NAME/KEY: MISC_FEATURE
<222> LOCATION: (17)..(17)
<223> OTHER INFORMATION: X is K or R
<220> FEATURE:
<221> NAME/KEY: MISC_FEATURE
<222> LOCATION: (18)..(22)
<223> OTHER INFORMATION: X is L or V

<400> SEQUENCE: 8
```

```
Asn Xaa Xaa Ser Xaa Gly Xaa Ser Xaa Tyr Ser Xaa Thr Ser His
1               5                   10                  15

Xaa Xaa Xaa Gln Xaa Xaa
            20
```

<210> SEQ ID NO 9
<211> LENGTH: 7
<212> TYPE: PRT
<213> ORGANISM: Homo sapiens

<400> SEQUENCE: 9

```
Pro Pro Lys Lys Arg Lys Val
1               5
```

<210> SEQ ID NO 10
<211> LENGTH: 411
<212> TYPE: PRT
<213> ORGANISM: Homo sapiens

<400> SEQUENCE: 10

```
Met Ser Lys Arg Pro Ser Tyr Ala Pro Pro Thr Pro Ala Pro Ala
1               5                   10                  15

Thr Gln Met Pro Ser Thr Pro Gly Phe Val Gly Tyr Asn Pro Tyr Ser
                20                  25                  30

His Leu Ala Tyr Asn Asn Tyr Arg Leu Gly Gly Asn Pro Gly Thr Asn
            35                  40                  45

Ser Arg Val Thr Ala Ser Ser Gly Ile Thr Ile Pro Lys Pro Pro Lys
        50                  55                  60

Pro Pro Asp Lys Pro Leu Met Pro Tyr Met Arg Tyr Ser Arg Lys Val
65                  70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Glu Lys
            100                 105                 110

Gln Glu Tyr Leu Asn Glu Tyr Glu Ala Glu Lys Ile Glu Tyr Asn Glu
        115                 120                 125

Ser Met Lys Ala Tyr His Asn Ser Pro Ala Tyr Leu Ala Tyr Ile Asn
130                 135                 140

Ala Lys Ser Arg Ala Glu Ala Ala Leu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp Asp Tyr Asp Asp Gly Phe Ser Met Lys His Thr Ala
            180                 185                 190

Thr Ala Arg Phe Gln Arg Asn His Arg Leu Ile Ser Glu Ile Leu Ser
        195                 200                 205

Glu Ser Val Val Pro Asp Val Arg Ser Val Val Thr Thr Ala Arg Met
210                 215                 220

Gln Val Leu Lys Arg Gln Val Gln Ser Leu Met Val His Gln Arg Lys
225                 230                 235                 240

Leu Glu Ala Glu Leu Leu Gln Ile Glu Glu Arg His Gln Glu Lys Lys
                245                 250                 255

Arg Lys Phe Leu Glu Ser Thr Asp Ser Phe Asn Asn Glu Leu Lys Arg
            260                 265                 270

Leu Cys Gly Leu Lys Val Glu Val Asp Met Glu Lys Ile Ala Ala Glu
        275                 280                 285
```

-continued

Ile Ala Gln Ala Glu Glu Ala Arg Lys Arg Gln Glu Glu Arg Glu
    290                 295                 300

Lys Glu Ala Ala Glu Ala Glu Arg Ser Gln Ser Ser Ile Val Pro
305                 310                 315                 320

Glu Glu Glu Gln Ala Ala Asn Lys Gly Glu Glu Lys Lys Asp Asp Glu
                325                 330                 335

Asn Ile Pro Met Glu Thr Glu Thr His Leu Glu Glu Thr Thr Glu
                340                 345                 350

Ser Gln Gln Asn Gly Glu Glu Gly Thr Ser Thr Pro Glu Asp Lys Glu
            355                 360                 365

Ser Gly Gln Glu Gly Val Asp Ser Met Ala Glu Gly Thr Ser Asp
370                 375                 380

Ser Asn Thr Gly Ser Glu Ser Asn Ser Ala Thr Val Glu Glu Pro Pro
385                 390                 395                 400

Thr Asp Pro Ile Pro Glu Asp Glu Lys Lys Glu
                405                 410

<210> SEQ ID NO 11
<211> LENGTH: 472
<212> TYPE: PRT
<213> ORGANISM: Homo sapiens

<400> SEQUENCE: 11

Met Ser Lys Arg Pro Ser Tyr Ala Pro Pro Thr Pro Ala Pro Ala
1               5                   10                  15

Thr Gln Met Pro Ser Thr Pro Gly Phe Val Gly Tyr Asn Pro Tyr Ser
                20                  25                  30

His Leu Ala Tyr Asn Asn Tyr Arg Leu Gly Gly Asn Pro Gly Thr Asn
            35                  40                  45

Ser Arg Val Thr Thr Leu Phe Ile Gly Asp Phe Leu Gly Pro Cys Ser
50                  55                  60

Ser Val Ser Thr Val Leu Pro Ala Ser Pro Leu Glu Ile Glu Ser Arg
65                  70                  75                  80

Lys Leu Glu Arg Glu Leu Leu Leu Glu Val Gly Phe Leu Ile Val Ala
                85                  90                  95

Arg Lys Glu Thr Val Gln Lys Trp Lys His Ile Leu Gln Lys His Ser
                100                 105                 110

Pro Ala Ser Ser Gly Ile Thr Ile Pro Lys Pro Pro Lys Pro Pro Asp
            115                 120                 125

Lys Pro Leu Met Pro Tyr Met Arg Tyr Ser Arg Lys Val Trp Asp Gln
130                 135                 140

Val Lys Ala Ser Asn Pro Asp Leu Lys Leu Trp Glu Ile Gly Lys Ile
145                 150                 155                 160

Ile Gly Gly Met Trp Arg Asp Leu Thr Asp Glu Glu Lys Gln Glu Tyr
                165                 170                 175

Leu Asn Glu Tyr Glu Ala Glu Lys Ile Glu Tyr Asn Glu Ser Met Lys
            180                 185                 190

Ala Tyr His Asn Ser Pro Ala Tyr Leu Ala Tyr Ile Asn Ala Lys Ser
        195                 200                 205

Arg Ala Glu Ala Ala Leu Glu Glu Glu Ser Arg Gln Arg Gln Ser Arg
    210                 215                 220

Met Glu Lys Gly Glu Pro Tyr Met Ser Ile Gln Pro Ala Glu Asp Pro
225                 230                 235                 240

Asp Asp Tyr Asp Asp Gly Phe Ser Met Lys His Thr Ala Thr Ala Arg
                245                 250                 255

```
Phe Gln Arg Asn His Arg Leu Ile Ser Glu Ile Leu Ser Glu Ser Val
                260                 265                 270

Val Pro Asp Val Arg Ser Val Thr Thr Ala Arg Met Gln Val Leu
            275                 280                 285

Lys Arg Gln Val Gln Ser Leu Met Val His Arg Lys Leu Glu Ala
290                 295                 300

Glu Leu Leu Gln Ile Glu Arg His Gln Glu Lys Lys Arg Lys Phe
305                 310                 315                 320

Leu Glu Ser Thr Asp Ser Phe Asn Asn Glu Leu Lys Arg Leu Cys Gly
                325                 330                 335

Leu Lys Val Glu Val Asp Met Glu Lys Ile Ala Ala Glu Ile Ala Gln
                340                 345                 350

Ala Glu Glu Gln Ala Arg Lys Arg Gln Glu Arg Glu Lys Glu Ala
                355                 360                 365

Ala Glu Gln Ala Glu Arg Ser Gln Ser Ser Ile Val Pro Glu Glu Glu
                370                 375                 380

Gln Ala Ala Asn Lys Gly Glu Lys Lys Asp Asp Glu Asn Ile Pro
385                 390                 395                 400

Met Glu Thr Glu Thr His Leu Glu Thr Thr Glu Ser Gln Gln
                405                 410                 415

Asn Gly Glu Glu Gly Thr Ser Thr Pro Glu Asp Lys Glu Ser Gly Gln
                420                 425                 430

Glu Gly Val Asp Ser Met Ala Glu Glu Gly Thr Ser Asp Ser Asn Thr
                435                 440                 445

Gly Ser Glu Ser Asn Ser Ala Thr Val Glu Glu Pro Pro Thr Asp Pro
450                 455                 460

Ile Pro Glu Asp Glu Lys Lys Glu
465                 470

<210> SEQ ID NO 12
<211> LENGTH: 989
<212> TYPE: PRT
<213> ORGANISM: Homo sapiens

<400> SEQUENCE: 12

Met Lys Val Val Asn Leu Lys Gln Ala Ile Leu Gln Ala Trp Lys Glu
1               5                   10                  15

Arg Trp Ser Tyr Tyr Gln Trp Ala Ile Asn Met Lys Lys Phe Phe Pro
                20                  25                  30

Lys Gly Ala Thr Trp Asp Ile Leu Asn Leu Ala Asp Ala Leu Leu Glu
            35                  40                  45

Gln Ala Met Ile Gly Pro Ser Pro Asn Pro Leu Ile Leu Ser Tyr Leu
50                  55                  60

Lys Tyr Ala Ile Ser Ser Gln Met Val Ser Tyr Ser Ser Val Leu Thr
65                  70                  75                  80

Ala Ile Ser Lys Phe Asp Asp Phe Ser Arg Asp Leu Cys Val Gln Ala
                85                  90                  95

Leu Leu Asp Ile Met Asp Met Phe Cys Asp Arg Leu Ser Cys His Gly
                100                 105                 110

Lys Ala Glu Glu Cys Ile Gly Leu Cys Arg Ala Leu Leu Ser Ala Leu
            115                 120                 125

His Trp Leu Leu Arg Cys Thr Ala Ala Ser Ala Glu Arg Leu Arg Glu
130                 135                 140

Gly Leu Glu Ala Gly Thr Pro Ala Ala Gly Glu Lys Gln Leu Ala Met
145                 150                 155                 160
```

-continued

```
Cys Leu Gln Arg Leu Glu Lys Thr Leu Ser Ser Thr Lys Asn Arg Ala
            165                 170                 175

Leu Leu His Ile Ala Lys Leu Glu Glu Ala Ser Ser Trp Thr Ala Ile
        180                 185                 190

Glu His Ser Leu Leu Lys Leu Gly Glu Ile Leu Thr Asn Leu Ser Asn
    195                 200                 205

Pro Gln Leu Arg Ser Gln Ala Glu Gln Cys Gly Thr Leu Ile Arg Ser
210                 215                 220

Ile Pro Thr Met Leu Ser Val His Ala Glu Gln Met His Lys Thr Gly
225                 230                 235                 240

Phe Pro Thr Val His Ala Val Ile Leu Leu Glu Gly Thr Met Asn Leu
                245                 250                 255

Thr Gly Glu Thr Gln Ser Leu Val Glu Gln Leu Thr Met Val Lys Arg
            260                 265                 270

Met Gln His Ile Pro Thr Pro Leu Phe Val Leu Glu Ile Trp Lys Ala
        275                 280                 285

Cys Phe Val Gly Leu Ile Glu Ser Pro Glu Gly Thr Glu Glu Leu Lys
    290                 295                 300

Trp Thr Ala Phe Thr Phe Leu Lys Ile Pro Gln Val Leu Val Lys Leu
305                 310                 315                 320

Lys Lys Tyr Ser His Gly Asp Lys Asp Phe Thr Glu Asp Val Asn Cys
                325                 330                 335

Ala Phe Glu Phe Leu Leu Lys Leu Thr Pro Leu Leu Asp Lys Ala Asp
            340                 345                 350

Gln Arg Cys Asn Cys Asp Cys Thr Asn Phe Leu Leu Gln Glu Cys Gly
        355                 360                 365

Lys Gln Gly Leu Leu Ser Glu Ala Ser Val Asn Asn Leu Met Ala Lys
    370                 375                 380

Arg Lys Ala Asp Arg Glu His Ala Pro Gln Gln Lys Ser Gly Glu Asn
385                 390                 395                 400

Ala Asn Ile Gln Pro Asn Ile Gln Leu Ile Leu Arg Ala Glu Pro Thr
                405                 410                 415

Val Thr Asn Ile Leu Lys Thr Met Asp Ala Asp His Ser Lys Ser Pro
            420                 425                 430

Glu Gly Leu Leu Gly Val Leu Gly His Met Leu Ser Gly Lys Ser Leu
        435                 440                 445

Asp Leu Leu Leu Ala Ala Ala Ala Thr Gly Lys Leu Lys Ser Phe
    450                 455                 460

Ala Arg Lys Phe Ile Asn Leu Asn Glu Phe Thr Thr Tyr Gly Ser Glu
465                 470                 475                 480

Glu Ser Thr Lys Pro Ala Ser Val Arg Ala Leu Leu Phe Asp Ile Ser
                485                 490                 495

Phe Leu Met Leu Cys His Val Ala Gln Thr Tyr Gly Ser Glu Val Ile
            500                 505                 510

Leu Ser Glu Ser Arg Thr Gly Ala Glu Val Pro Phe Phe Glu Thr Trp
        515                 520                 525

Met Gln Thr Cys Met Pro Glu Glu Gly Lys Ile Leu Asn Pro Asp His
    530                 535                 540

Pro Cys Phe Arg Pro Asp Ser Thr Lys Val Glu Ser Leu Val Ala Leu
545                 550                 555                 560

Leu Asn Asn Ser Ser Glu Met Lys Leu Val Gln Met Lys Trp His Glu
                565                 570                 575

Ala Cys Leu Ser Ile Ser Ala Ala Ile Leu Glu Ile Leu Asn Ala Trp
            580                 585                 590
```

```
Glu Asn Gly Val Leu Ala Phe Glu Ser Ile Gln Lys Ile Thr Asp Asn
            595                 600                 605

Ile Lys Gly Lys Val Cys Ser Leu Ala Val Cys Ala Val Ala Trp Leu
        610                 615                 620

Val Ala His Val Arg Met Leu Gly Leu Asp Arg Glu Lys Ser Leu
625                 630                 635                 640

Gln Met Ile Arg Gln Leu Ala Gly Pro Leu Phe Ser Glu Asn Thr Leu
                645                 650                 655

Gln Phe Tyr Asn Glu Arg Val Val Ile Met Asn Ser Ile Leu Glu Arg
            660                 665                 670

Met Cys Ala Asp Val Leu Gln Gln Thr Ala Thr Gln Ile Lys Phe Pro
        675                 680                 685

Ser Thr Gly Val Asp Thr Met Pro Tyr Trp Asn Leu Leu Pro Pro Lys
    690                 695                 700

Arg Pro Ile Lys Glu Val Leu Thr Asp Ile Phe Ala Lys Val Leu Glu
705                 710                 715                 720

Lys Gly Trp Val Asp Ser Arg Ser Ile His Ile Phe Asp Thr Leu Leu
                725                 730                 735

His Met Gly Gly Val Tyr Trp Phe Cys Asn Asn Leu Ile Lys Glu Leu
            740                 745                 750

Leu Lys Glu Thr Arg Lys Glu His Thr Leu Arg Ala Val Glu Leu Leu
        755                 760                 765

Tyr Ser Ile Phe Cys Leu Asp Met Gln Gln Val Thr Leu Val Leu Leu
    770                 775                 780

Gly His Ile Leu Pro Gly Leu Leu Thr Asp Ser Ser Lys Trp His Ser
785                 790                 795                 800

Leu Met Asp Pro Pro Gly Thr Ala Leu Ala Lys Leu Ala Val Trp Cys
                805                 810                 815

Ala Leu Ser Ser Tyr Ser Ser His Lys Gly Gln Ala Ser Thr Arg Gln
            820                 825                 830

Lys Lys Arg His Arg Glu Asp Ile Glu Asp Tyr Ile Ser Leu Phe Pro
        835                 840                 845

Leu Asp Asp Val Gln Pro Ser Lys Leu Met Arg Leu Leu Ser Ser Asn
    850                 855                 860

Glu Asp Asp Ala Asn Ile Leu Ser Ser Pro Thr Asp Arg Ser Met Ser
865                 870                 875                 880

Ser Ser Leu Ser Ala Ser Gln Leu His Thr Val Asn Met Arg Asp Pro
                885                 890                 895

Leu Asn Arg Val Leu Ala Asn Leu Phe Leu Leu Ile Ser Ser Ile Leu
            900                 905                 910

Gly Ser Arg Thr Ala Gly Pro His Thr Gln Phe Val Gln Trp Phe Met
        915                 920                 925

Glu Glu Cys Val Asp Cys Leu Glu Gln Gly Gly Arg Gly Ser Val Leu
    930                 935                 940

Gln Phe Met Pro Phe Thr Thr Val Ser Glu Leu Val Lys Val Ser Ala
945                 950                 955                 960

Met Ser Ser Pro Lys Val Val Leu Ala Ile Thr Asp Leu Ser Leu Pro
                965                 970                 975

Leu Gly Arg Gln Val Ala Ala Lys Ala Ile Ala Ala Leu
            980                 985

<210> SEQ ID NO 13
<211> LENGTH: 1043
<212> TYPE: PRT
```

<213> ORGANISM: Homo sapiens

<400> SEQUENCE: 13

```
Met Lys Val Val Asn Leu Lys Gln Ala Ile Leu Gln Ala Trp Lys Glu
1               5                   10                  15
Arg Trp Ser Tyr Tyr Gln Trp Ala Ile Asn Met Lys Lys Phe Phe Pro
            20                  25                  30
Lys Gly Ala Thr Trp Asp Ile Leu Asn Leu Ala Asp Ala Leu Leu Glu
        35                  40                  45
Gln Ala Met Ile Gly Pro Ser Pro Asn Pro Leu Ile Leu Ser Tyr Leu
    50                  55                  60
Lys Tyr Ala Ile Ser Ser Gln Met Val Ser Tyr Ser Ser Val Leu Thr
65                  70                  75                  80
Ala Ile Ser Lys Phe Asp Asp Phe Ser Arg Asp Leu Cys Val Gln Ala
                85                  90                  95
Leu Leu Asp Ile Met Asp Met Phe Cys Asp Arg Leu Ser Cys His Gly
            100                 105                 110
Lys Ala Glu Glu Cys Ile Gly Leu Cys Arg Ala Leu Leu Ser Ala Leu
        115                 120                 125
His Trp Leu Leu Arg Cys Thr Ala Ala Ser Ala Glu Arg Leu Arg Glu
    130                 135                 140
Gly Leu Glu Ala Gly Thr Pro Ala Ala Gly Glu Lys Gln Leu Ala Met
145                 150                 155                 160
Cys Leu Gln Arg Leu Glu Lys Thr Leu Ser Ser Thr Lys Asn Arg Ala
                165                 170                 175
Leu Leu His Ile Ala Lys Leu Glu Glu Ala Cys Pro His Gln Ala Leu
            180                 185                 190
Leu Val Gly Ser Lys Thr Ser Thr Ser Gln Thr Arg Lys Lys Leu Glu
        195                 200                 205
Asp Lys Thr Ser Thr Val Ser Ile Ile Val Phe Val Ser Met Leu Leu
    210                 215                 220
Ile Ala Trp Lys Gln Met Thr Leu Val Phe Glu Cys Tyr Leu Lys Cys
225                 230                 235                 240
Ser Ser Trp Thr Ala Ile Glu His Ser Leu Leu Lys Leu Gly Glu Ile
                245                 250                 255
Leu Thr Asn Leu Ser Asn Pro Gln Leu Arg Ser Gln Ala Glu Gln Cys
            260                 265                 270
Gly Thr Leu Ile Arg Ser Ile Pro Thr Met Leu Ser Val His Ala Glu
        275                 280                 285
Gln Met His Lys Thr Gly Phe Pro Thr Val His Ala Val Ile Leu Leu
    290                 295                 300
Glu Gly Thr Met Asn Leu Thr Gly Glu Thr Gln Ser Leu Val Glu Gln
305                 310                 315                 320
Leu Thr Met Val Lys Arg Met Gln His Ile Pro Thr Pro Leu Phe Val
                325                 330                 335
Leu Glu Ile Trp Lys Ala Cys Phe Val Gly Leu Ile Glu Ser Pro Glu
            340                 345                 350
Gly Thr Glu Glu Leu Lys Trp Thr Ala Phe Thr Phe Leu Lys Ile Pro
        355                 360                 365
Gln Val Leu Val Lys Leu Lys Tyr Ser His Gly Asp Lys Asp Phe
    370                 375                 380
Thr Glu Asp Val Asn Cys Ala Phe Glu Phe Leu Leu Lys Leu Thr Pro
385                 390                 395                 400
Leu Leu Asp Lys Ala Asp Gln Arg Cys Asn Cys Asp Cys Thr Asn Phe
```

```
                    405                 410                 415
Leu Leu Gln Glu Cys Gly Lys Gln Gly Leu Leu Ser Glu Ala Ser Val
                420                 425                 430

Asn Asn Leu Met Ala Lys Arg Lys Ala Asp Arg Glu His Ala Pro Gln
                435                 440                 445

Gln Lys Ser Gly Glu Asn Ala Asn Ile Gln Pro Asn Ile Gln Leu Ile
            450                 455                 460

Leu Arg Ala Glu Pro Thr Val Thr Asn Ile Leu Lys Thr Met Asp Ala
465                 470                 475                 480

Asp His Ser Lys Ser Pro Glu Gly Leu Leu Gly Val Leu Gly His Met
                485                 490                 495

Leu Ser Gly Lys Ser Leu Asp Leu Leu Leu Ala Ala Ala Ala Ala Thr
                500                 505                 510

Gly Lys Leu Lys Ser Phe Ala Arg Lys Phe Ile Asn Leu Asn Glu Phe
            515                 520                 525

Thr Thr Tyr Gly Ser Glu Glu Ser Thr Lys Pro Ala Ser Val Arg Ala
            530                 535                 540

Leu Leu Phe Asp Ile Ser Phe Leu Met Leu Cys His Val Ala Gln Thr
545                 550                 555                 560

Tyr Gly Ser Glu Val Ile Leu Ser Glu Ser Arg Thr Gly Ala Glu Val
                565                 570                 575

Pro Phe Phe Glu Thr Trp Met Gln Thr Cys Met Pro Glu Glu Gly Lys
                580                 585                 590

Ile Leu Asn Pro Asp His Pro Cys Phe Arg Pro Asp Ser Thr Lys Val
            595                 600                 605

Glu Ser Leu Val Ala Leu Leu Asn Asn Ser Ser Glu Met Lys Leu Val
            610                 615                 620

Gln Met Lys Trp His Glu Ala Cys Leu Ser Ile Ser Ala Ala Ile Leu
625                 630                 635                 640

Glu Ile Leu Asn Ala Trp Glu Asn Gly Val Leu Ala Phe Glu Ser Ile
                645                 650                 655

Gln Lys Ile Thr Asp Asn Ile Lys Gly Lys Val Cys Ser Leu Ala Val
            660                 665                 670

Cys Ala Val Ala Trp Leu Val Ala His Val Arg Met Leu Gly Leu Asp
            675                 680                 685

Glu Arg Glu Lys Ser Leu Gln Met Ile Arg Gln Leu Ala Gly Pro Leu
            690                 695                 700

Phe Ser Glu Asn Thr Leu Gln Phe Tyr Asn Glu Arg Val Val Ile Met
705                 710                 715                 720

Asn Ser Ile Leu Glu Arg Met Cys Ala Asp Val Leu Gln Gln Thr Ala
                725                 730                 735

Thr Gln Ile Lys Phe Pro Ser Thr Gly Val Asp Thr Met Pro Tyr Trp
            740                 745                 750

Asn Leu Leu Pro Pro Lys Arg Pro Ile Lys Glu Val Leu Thr Asp Ile
                755                 760                 765

Phe Ala Lys Val Leu Glu Lys Gly Trp Val Asp Ser Arg Ser Ile His
                770                 775                 780

Ile Phe Asp Thr Leu Leu His Met Gly Gly Val Tyr Trp Phe Cys Asn
785                 790                 795                 800

Asn Leu Ile Lys Glu Leu Leu Lys Glu Thr Arg Lys Glu His Thr Leu
                805                 810                 815

Arg Ala Val Glu Leu Leu Tyr Ser Ile Phe Cys Leu Asp Met Gln Gln
                820                 825                 830
```

Val Thr Leu Val Leu Leu Gly His Ile Leu Pro Gly Leu Leu Thr Asp
        835                 840                 845

Ser Ser Lys Trp His Ser Leu Met Asp Pro Pro Gly Thr Ala Leu Ala
    850                 855                 860

Lys Leu Ala Val Trp Cys Ala Leu Ser Ser Tyr Ser Ser His Lys Gly
865                 870                 875                 880

Gln Ala Ser Thr Arg Gln Lys Lys Arg His Arg Glu Asp Ile Glu Asp
                885                 890                 895

Tyr Ile Ser Leu Phe Pro Leu Asp Asp Val Gln Pro Ser Lys Leu Met
            900                 905                 910

Arg Leu Leu Ser Ser Asn Glu Asp Asp Ala Asn Ile Leu Ser Ser Pro
        915                 920                 925

Thr Asp Arg Ser Met Ser Ser Ser Leu Ser Ala Ser Gln Leu His Thr
    930                 935                 940

Val Asn Met Arg Asp Pro Leu Asn Arg Val Leu Ala Asn Leu Phe Leu
945                 950                 955                 960

Leu Ile Ser Ser Ile Leu Gly Ser Arg Thr Ala Gly Pro His Thr Gln
                965                 970                 975

Phe Val Gln Trp Phe Met Glu Glu Cys Val Asp Cys Leu Glu Gln Gly
            980                 985                 990

Gly Arg Gly Ser Val Leu Gln Phe Met Pro Phe Thr Thr Val Ser Glu
        995                 1000                1005

Leu Val Lys Val Ser Ala Met Ser Ser Pro Lys Val Val Leu Ala
    1010                1015                1020

Ile Thr Asp Leu Ser Leu Pro Leu Gly Arg Gln Val Ala Ala Lys
    1025                1030                1035

Ala Ile Ala Ala Leu
    1040

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
acttcctgtc tagagttgta gcs                                          23

<210> SEQ ID NO 15
<211> LENGTH: 24
<212> TYPE: DNA
<213> ORGANISM: Artificial sequence
<220> FEATURE:
<223> OTHER INFORMATION: primer

<400> SEQUENCE: 15
gtaagtcagc tatactaagt tctg                                         24

<210> SEQ ID NO 16
<211> LENGTH: 67
<212> TYPE: PRT
<213> ORGANISM: Artificial sequence
<220> FEATURE:
<223> OTHER INFORMATION: Primer

<400> SEQUENCE: 16

Met Ala Thr Ser Ser Glu Glu Val Leu Leu Ile Val Lys Lys Val Arg
1               5                   10                  15

Gln Lys Lys Gln Asp Gly Ala Leu Tyr Leu Met Ala Glu Arg Ile Ala

-continued

```
                    20                  25                  30
Trp Ala Pro Glu Gly Lys Asp Arg Phe Thr Ile Ser His Met Tyr Ala
             35                  40                  45
Asp Ile Lys Cys Lys Ser Ala Ile Leu Ser Ser Asp Val Phe Val Cys
 50                  55                  60
His Ser Cys
 65

<210> SEQ ID NO 17
<211> LENGTH: 548
<212> TYPE: PRT
<213> ORGANISM: Homo sapiens

<400> SEQUENCE: 17

Met Ala Thr Ser Ser Glu Glu Val Leu Leu Ile Val Lys Lys Val Arg
 1               5                  10                  15
Gln Lys Lys Gln Asp Gly Ala Leu Tyr Leu Met Ala Glu Arg Ile Ala
             20                  25                  30
Trp Ala Pro Glu Gly Lys Asp Arg Phe Thr Ile Ser His Met Tyr Ala
             35                  40                  45
Asp Ile Lys Cys Gln Lys Ile Ser Pro Glu Gly Lys Ala Lys Ile Gln
 50                  55                  60
Leu Gln Leu Val Leu His Ala Gly Asp Thr Thr Asn Phe His Phe Ser
 65                  70                  75                  80
Asn Glu Ser Thr Ala Val Lys Glu Arg Asp Ala Val Lys Asp Leu Leu
                 85                  90                  95
Gln Gln Leu Leu Pro Lys Phe Lys Arg Lys Ala Asn Lys Glu Leu Glu
            100                 105                 110
Glu Lys Asn Arg Met Leu Gln Glu Asp Pro Val Leu Phe Gln Leu Tyr
            115                 120                 125
Lys Asp Leu Val Val Ser Gln Val Ile Ser Ala Glu Glu Phe Trp Ala
        130                 135                 140
Asn Arg Leu Asn Val Asn Ala Thr Asp Ser Ser Ser Thr Ser Asn His
145                 150                 155                 160
Lys Gln Asp Val Gly Ile Ser Ala Ala Phe Leu Ala Asp Val Arg Pro
                165                 170                 175
Gln Thr Asp Gly Cys Asn Gly Leu Arg Tyr Asn Leu Thr Ser Asp Ile
            180                 185                 190
Ile Glu Ser Ile Phe Arg Thr Tyr Pro Ala Val Lys Met Lys Tyr Ala
        195                 200                 205
Glu Asn Val Pro His Asn Met Thr Glu Lys Glu Phe Trp Thr Arg Phe
    210                 215                 220
Phe Gln Ser His Tyr Phe His Arg Asp Arg Leu Asn Thr Gly Ser Lys
225                 230                 235                 240
Asp Leu Phe Ala Glu Cys Ala Lys Ile Asp Glu Lys Gly Leu Lys Thr
                245                 250                 255
Met Val Ser Leu Gly Val Lys Asn Pro Leu Leu Asp Leu Thr Ala Leu
            260                 265                 270
Glu Asp Lys Pro Leu Asp Glu Gly Tyr Gly Ile Ser Ser Val Pro Ser
        275                 280                 285
Ala Ser Asn Ser Lys Ser Ile Lys Glu Asn Ser Asn Ala Ala Ile Ile
    290                 295                 300
Lys Arg Phe Asn His His Ser Ala Met Val Leu Ala Ala Gly Leu Arg
305                 310                 315                 320
Lys Gln Glu Ala Gln Asn Glu Gln Thr Ser Glu Pro Ser Asn Met Asp
```

```
                    325                 330                 335
Gly Asn Ser Gly Asp Ala Asp Cys Phe Gln Pro Ala Val Lys Arg Ala
                340                 345                 350

Lys Leu Gln Glu Ser Ile Glu Tyr Glu Asp Leu Gly Lys Asn Asn Ser
            355                 360                 365

Val Lys Thr Ile Ala Leu Asn Leu Lys Lys Ser Asp Arg Tyr Tyr His
        370                 375                 380

Gly Pro Thr Pro Ile Gln Ser Leu Gln Tyr Ala Thr Ser Gln Asp Ile
385                 390                 395                 400

Ile Asn Ser Phe Gln Ser Ile Arg Gln Glu Met Glu Ala Tyr Thr Pro
                405                 410                 415

Lys Leu Thr Gln Val Leu Ser Ser Ser Ala Ala Ser Ser Thr Ile Thr
            420                 425                 430

Ala Leu Ser Pro Gly Gly Ala Leu Met Gln Gly Gly Thr Gln Gln Ala
        435                 440                 445

Ile Asn Gln Met Val Pro Asn Asp Ile Gln Ser Glu Leu Lys His Leu
    450                 455                 460

Tyr Val Ala Val Gly Glu Leu Leu Arg His Phe Trp Ser Cys Phe Pro
465                 470                 475                 480

Val Asn Thr Pro Phe Leu Glu Glu Lys Val Val Lys Met Lys Ser Asn
                485                 490                 495

Leu Glu Arg Phe Gln Val Thr Lys Leu Cys Pro Phe Gln Glu Lys Ile
            500                 505                 510

Arg Arg Gln Tyr Leu Ser Thr Asn Leu Val Ser His Ile Glu Glu Met
        515                 520                 525

Leu Gln Thr Ala Tyr Asn Lys Leu His Thr Trp Gln Ser Arg Arg Leu
    530                 535                 540

Met Lys Lys Thr
545

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
tttccggctg agagtccttc                                           20

<210> SEQ ID NO 19
<211> LENGTH: 21
<212> TYPE: DNA
<213> ORGANISM: Artificial sequence
<220> FEATURE:
<223> OTHER INFORMATION: Primer

<400> SEQUENCE: 19
cacatcactt cagcttaact c                                         21

<210> SEQ ID NO 20
<211> LENGTH: 165
<212> TYPE: PRT
<213> ORGANISM: Homo sapiens

<400> SEQUENCE: 20

Met Asp Glu Glu Pro Glu Arg Thr Lys Arg Trp Glu Gly Gly Tyr Glu
1               5                   10                  15

Arg Thr Trp Glu Ile Leu Lys Glu Asp Glu Ser Gly Ser Leu Lys Ala
```

```
                    20                  25                  30
Thr Ile Glu Asp Ile Leu Phe Lys Ala Lys Arg Lys Arg Val Phe Glu
                35                  40                  45

His His Gly Gln Val Arg Leu Gly Met Met Arg His Leu Tyr Val Val
            50                  55                  60

Val Asp Gly Ser Arg Thr Met Glu Asp Gln Asp Leu Lys Pro Asn Arg
65                  70                  75                  80

Leu Thr Cys Thr Leu Lys Leu Leu Glu Tyr Phe Val Glu Glu Tyr Phe
                85                  90                  95

Asp Gln Asn Pro Ile Ser Gln Ile Gly Ile Ile Val Thr Lys Ser Lys
            100                 105                 110

Arg Ala Glu Lys Leu Thr Glu Leu Ser Gly Asn Pro Arg Lys His Ile
        115                 120                 125

Thr Ser Leu Lys Lys Ala Val Asp Met Thr Cys His Gly Glu Pro Ser
    130                 135                 140

Leu Tyr Asn Ser Leu Ser Ile Ala Met Gln Thr Leu Lys Leu Val Leu
145                 150                 155                 160

Tyr Ile Met Tyr Asn
                165

<210> SEQ ID NO 21
<211> LENGTH: 395
<212> TYPE: PRT
<213> ORGANISM: Homo sapiens

<400> SEQUENCE: 21

Met Asp Glu Glu Pro Glu Arg Thr Lys Arg Trp Glu Gly Gly Tyr Glu
1               5                   10                  15

Arg Thr Trp Glu Ile Leu Lys Glu Asp Glu Ser Gly Ser Leu Lys Ala
                20                  25                  30

Thr Ile Glu Asp Ile Leu Phe Lys Ala Lys Arg Lys Arg Val Phe Glu
                35                  40                  45

His His Gly Gln Val Arg Leu Gly Met Met Arg His Leu Tyr Val Val
            50                  55                  60

Val Asp Gly Ser Arg Thr Met Glu Asp Gln Asp Leu Lys Pro Asn Arg
65                  70                  75                  80

Leu Thr Cys Thr Leu Lys Leu Leu Glu Tyr Phe Val Glu Glu Tyr Phe
                85                  90                  95

Asp Gln Asn Pro Ile Ser Gln Ile Gly Ile Ile Val Thr Lys Ser Lys
            100                 105                 110

Arg Ala Glu Lys Leu Thr Glu Leu Ser Gly Asn Pro Arg Lys His Ile
        115                 120                 125

Thr Ser Leu Lys Lys Ala Val Asp Met Thr Cys His Gly Glu Pro Ser
    130                 135                 140

Leu Tyr Asn Ser Leu Ser Ile Ala Met Gln Thr Leu Lys His Met Pro
145                 150                 155                 160

Gly His Thr Ser Arg Glu Val Leu Ile Ile Phe Ser Ser Leu Thr Thr
                165                 170                 175

Cys Asp Pro Ser Asn Ile Tyr Asp Leu Ile Lys Thr Leu Lys Ala Ala
            180                 185                 190

Lys Ile Arg Val Ser Val Ile Gly Leu Ser Ala Glu Val Arg Val Cys
        195                 200                 205

Thr Val Leu Ala Arg Glu Thr Gly Gly Thr Tyr His Val Ile Leu Asp
    210                 215                 220

Glu Ser His Tyr Lys Glu Leu Leu Thr His His Val Ser Pro Pro Pro
```

```
                225                 230                 235                 240
Ala Ser Ser Ser Glu Cys Ser Leu Ile Arg Met Gly Phe Pro Gln
                    245                 250                 255

His Thr Ile Ala Ser Leu Ser Asp Gln Asp Ala Lys Pro Ser Phe Ser
                260                 265                 270

Met Ala His Leu Asp Gly Asn Thr Glu Pro Gly Leu Thr Leu Gly Gly
            275                 280                 285

Tyr Phe Cys Pro Gln Cys Arg Ala Lys Tyr Cys Glu Leu Pro Val Glu
        290                 295                 300

Cys Lys Ile Cys Gly Leu Thr Leu Val Ser Ala Pro His Leu Ala Arg
305                 310                 315                 320

Ser Tyr His His Leu Phe Pro Leu Asp Ala Phe Gln Glu Ile Pro Leu
                325                 330                 335

Glu Glu Tyr Asn Gly Glu Arg Phe Cys Tyr Gly Cys Gln Gly Leu
            340                 345                 350

Lys Asp Gln His Val Tyr Val Cys Ala Val Cys Gln Asn Val Phe Cys
        355                 360                 365

Val Asp Cys Asp Val Phe Val His Asp Ser Leu His Cys Cys Pro Gly
    370                 375                 380

Cys Ile His Lys Ile Pro Ala Pro Ser Gly Val
385                 390                 395

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
gaggatgtga aggagcttgt gaag                                              24

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
caagtacagt gcaaacgcga ac                                                22

<210> SEQ ID NO 24
<211> LENGTH: 154
<212> TYPE: PRT
<213> ORGANISM: Homo sapiens

<400> SEQUENCE: 24

Met Arg His Leu Tyr Val Val Asp Gly Ser Arg Thr Met Glu Asp
1               5                   10                  15

Gln Asp Leu Lys Pro Asn Arg Leu Thr Cys Thr Leu Lys Leu Leu Glu
                20                  25                  30

Tyr Phe Val Glu Glu Tyr Phe Asp Gln Asn Pro Ile Ser Gln Ile Gly
            35                  40                  45

Ile Ile Val Thr Lys Ser Lys Arg Ala Glu Lys Leu Thr Glu Leu Ser
        50                  55                  60

Gly Asn Pro Arg Lys His Ile Thr Ser Leu Lys Lys Ala Val Asp Met
65                  70                  75                  80

Thr Cys His Gly Glu Pro Ser Leu Tyr Asn Ser Leu Ser Ile Ala Met
```

```
                    85                  90                  95

Gln Thr Leu Lys His Met Pro Gly His Thr Ser Arg Glu Val Leu Ile
                100                 105                 110

Ile Phe Ser Ser Leu Thr Thr Cys Asp Pro Ser Asn Ile Tyr Asp Leu
                115                 120                 125

Ile Lys Thr Leu Lys Ala Ala Lys Ile Arg Val Ser Val Ile Gly Leu
            130                 135                 140

Ser Ala Glu Val Arg Val Cys Thr Val Leu
145                 150

<210> SEQ ID NO 25
<211> LENGTH: 240
<212> TYPE: PRT
<213> ORGANISM: Homo sapiens

<400> SEQUENCE: 25

Met Asp Glu Glu Pro Glu Arg Thr Lys Arg Trp Glu Gly Gly Tyr Glu
1               5                   10                  15

Arg Thr Trp Glu Ile Leu Lys Glu Asp Glu Ser Gly Ser Leu Lys Ala
                20                  25                  30

Thr Ile Glu Asp Ile Leu Phe Lys Ala Lys Arg Lys Val Phe Glu
            35                  40                  45

His His Gly Gln Val Arg Leu Gly Met Met Arg His Leu Tyr Val Val
        50                  55                  60

Val Asp Gly Ser Arg Thr Met Glu Asp Gln Asp Leu Lys Pro Asn Arg
65                  70                  75                  80

Leu Thr Cys Thr Leu Lys Leu Glu Tyr Phe Val Glu Tyr Phe
                85                  90                  95

Asp Gln Asn Pro Ile Ser Gln Ile Gly Ile Val Thr Lys Ser Lys
                100                 105                 110

Arg Ala Glu Lys Leu Thr Glu Leu Ser Gly Asn Pro Arg Lys His Ile
            115                 120                 125

Thr Ser Leu Lys Lys Ala Val Asp Met Thr Cys His Gly Glu Pro Ser
        130                 135                 140

Leu Tyr Asn Ser Leu Ser Ile Ala Met Gln Thr Leu Lys His Met Pro
145                 150                 155                 160

Gly His Thr Ser Arg Glu Val Leu Ile Ile Phe Ser Ser Leu Thr Thr
                165                 170                 175

Cys Asp Pro Ser Asn Ile Tyr Asp Leu Ile Lys Thr Leu Lys Ala Ala
                180                 185                 190

Lys Ile Arg Val Ser Val Ile Gly Leu Ser Ala Glu Val Arg Val Cys
            195                 200                 205

Thr Val Leu Ala Arg Glu Thr Gly Gly Thr Tyr His Val Ile Leu Asp
        210                 215                 220

Glu Ser His Tyr Lys Glu Leu Leu Thr His His Val Ser Pro Pro
225                 230                 235                 240

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
gacagccatg gtttcagacg                                            20
```

<210> SEQ ID NO 27
<211> LENGTH: 21
<212> TYPE: DNA
<213> ORGANISM: Artificial sequence
<220> FEATURE:
<223> OTHER INFORMATION: Primer

<400> SEQUENCE: 27
cagaaacttt gctggcagga t                                              21

<210> SEQ ID NO 28
<211> LENGTH: 267
<212> TYPE: PRT
<213> ORGANISM: Homo sapiens

<400> SEQUENCE: 28

Met Val Leu Gly Asn Ser His Leu Phe Met Asn Arg Ser Asn Lys Leu
1               5                   10                  15

Ala Val Ile Ala Ser His Ile Gln Glu Ser Arg Phe Leu Tyr Pro Gly
            20                  25                  30

Lys Asn Gly Arg Leu Gly Asp Phe Phe Gly Asp Pro Gly Asn Pro Pro
        35                  40                  45

Glu Phe Asn Pro Ser Gly Ser Lys Asp Gly Lys Tyr Glu Leu Leu Thr
    50                  55                  60

Ser Ala Asn Glu Val Ile Val Glu Glu Ile Lys Asp Leu Met Thr Lys
65                  70                  75                  80

Ser Asp Ile Lys Gly Gln His Thr Glu Thr Leu Leu Ala Gly Ser Leu
                85                  90                  95

Ala Lys Ala Leu Cys Tyr Ile His Arg Met Asn Lys Glu Val Lys Asp
            100                 105                 110

Asn Gln Glu Met Lys Ser Arg Ile Leu Val Ile Lys Ala Ala Glu Asp
        115                 120                 125

Ser Ala Leu Gln Tyr Met Asn Phe Met Asn Val Ile Phe Ala Ala Gln
    130                 135                 140

Lys Gln Asn Ile Leu Ile Asp Ala Cys Val Leu Asp Ser Asp Ser Gly
145                 150                 155                 160

Leu Leu Gln Gln Ala Cys Asp Ile Thr Gly Gly Leu Tyr Leu Lys Val
                165                 170                 175

Pro Gln Met Pro Ser Leu Leu Gln Tyr Leu Leu Trp Val Phe Leu Pro
            180                 185                 190

Asp Gln Asp Gln Arg Ser Gln Leu Ile Leu Pro Pro Val His Val
        195                 200                 205

Asp Tyr Arg Ala Ala Cys Phe Cys His Arg Asn Leu Ile Glu Ile Gly
    210                 215                 220

Tyr Val Cys Ser Val Cys Leu Ser Ile Phe Cys Asn Phe Ser Pro Ile
225                 230                 235                 240

Cys Thr Thr Cys Glu Thr Ala Phe Lys Ile Ser Leu Pro Pro Val Leu
                245                 250                 255

Lys Ala Lys Lys Lys Lys Leu Lys Val Ser Ala
            260                 265

<210> SEQ ID NO 29
<211> LENGTH: 308
<212> TYPE: PRT
<213> ORGANISM: Homo sapiens

<400> SEQUENCE: 29

Met Val Ser Asp Glu Asp Glu Leu Asn Leu Leu Val Ile Val Val Asp
1               5                   10                  15

```
Ala Asn Pro Ile Trp Trp Gly Lys Gln Ala Leu Lys Glu Ser Gln Phe
             20                  25                  30

Thr Leu Ser Lys Cys Ile Asp Ala Val Met Val Leu Gly Asn Ser His
         35                  40                  45

Leu Phe Met Asn Arg Ser Asn Lys Leu Ala Val Ile Ala Ser His Ile
 50                  55                  60

Gln Glu Ser Arg Phe Leu Tyr Pro Gly Lys Asn Gly Arg Leu Gly Asp
 65                  70                  75                  80

Phe Phe Gly Asp Pro Gly Asn Pro Pro Glu Phe Asn Pro Ser Gly Ser
                 85                  90                  95

Lys Asp Gly Lys Tyr Glu Leu Leu Thr Ser Ala Asn Glu Val Ile Val
             100                 105                 110

Glu Glu Ile Lys Asp Leu Met Thr Lys Ser Asp Ile Lys Gly Gln His
             115                 120                 125

Thr Glu Thr Leu Leu Ala Gly Ser Leu Ala Lys Ala Leu Cys Tyr Ile
130                 135                 140

His Arg Met Asn Lys Glu Val Lys Asp Asn Gln Met Lys Ser Arg
145                 150                 155                 160

Ile Leu Val Ile Lys Ala Ala Glu Asp Ser Ala Leu Gln Tyr Met Asn
             165                 170                 175

Phe Met Asn Val Ile Phe Ala Ala Gln Lys Gln Asn Ile Leu Ile Asp
            180                 185                 190

Ala Cys Val Leu Asp Ser Asp Ser Gly Leu Leu Gln Gln Ala Cys Asp
             195                 200                 205

Ile Thr Gly Gly Leu Tyr Leu Lys Val Pro Gln Met Pro Ser Leu Leu
210                 215                 220

Gln Tyr Leu Leu Trp Val Phe Leu Pro Asp Gln Asp Gln Arg Ser Gln
225                 230                 235                 240

Leu Ile Leu Pro Pro Val His Val Asp Tyr Arg Ala Ala Cys Phe
             245                 250                 255

Cys His Arg Asn Leu Ile Glu Ile Gly Tyr Val Cys Ser Val Cys Leu
             260                 265                 270

Ser Ile Phe Cys Asn Phe Ser Pro Ile Cys Thr Thr Cys Glu Thr Ala
             275                 280                 285

Phe Lys Ile Ser Leu Pro Pro Val Leu Lys Ala Lys Lys Lys Lys Leu
             290                 295                 300

Lys Val Ser Ala
305

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
gacagccatg gtttcagacg                                                20

<210> SEQ ID NO 31
<211> LENGTH: 22
<212> TYPE: DNA
<213> ORGANISM: Artificial sequence
<220> FEATURE:
<223> OTHER INFORMATION: Primer

<400> SEQUENCE: 31
```
cgtggtgaaa acatggtgaa ac                                        22

<210> SEQ ID NO 32
<211> LENGTH: 34
<212> TYPE: PRT
<213> ORGANISM: Homo sapiens

<400> SEQUENCE: 32

Met Val Ser Asp Glu Asp Glu Leu Asn Leu Leu Val Ile Val Val Asp
1               5                   10                  15

Ala Asn Pro Ile Trp Trp Gly Lys Gln Ala Leu Lys Glu Ser Gln Pro
            20                  25                  30

Pro Lys

<210> SEQ ID NO 33
<211> LENGTH: 119
<212> TYPE: PRT
<213> ORGANISM: Homo sapiens

<400> SEQUENCE: 33

Met Val Ser Asp Glu Asp Glu Leu Asn Leu Leu Val Ile Val Val Asp
1               5                   10                  15

Ala Asn Pro Thr Trp Trp Gly Lys Gln Ala Leu Lys Glu Ser Gln Phe
            20                  25                  30

Thr Leu Ser Lys Cys Ile Asp Ala Val Met Val Leu Gly Asn Ser His
        35                  40                  45

Leu Phe Met Asn Arg Ser Asn Lys Leu Ala Val Ile Ala Ser His Ile
    50                  55                  60

Gln Glu Ser Arg Phe Leu Tyr Pro Gly Lys Asn Gly Arg Leu Gly Asp
65                  70                  75                  80

Phe Phe Gly Asp Pro Gly Asn Pro Pro Glu Phe Asn Pro Ser Gly Ser
                85                  90                  95

Lys Asp Gly Lys Tyr Glu Leu Leu Thr Ser Ala Ser Gly Val Ala Gly
            100                 105                 110

Ile Thr Thr Leu Leu Asn Pro
        115

<210> SEQ ID NO 34
<211> LENGTH: 109
<212> TYPE: PRT
<213> ORGANISM: Homo sapiens

<400> SEQUENCE: 34

Met Val Ser Asp Glu Asp Glu Leu Asn Leu Leu Val Ile Val Val Asp
1               5                   10                  15

Ala Asn Pro Ile Trp Trp Gly Lys Gln Ala Leu Lys Glu Ser Gln Phe
            20                  25                  30

Thr Leu Ser Lys Cys Ile Asp Ala Val Met Val Leu Gly Asn Ser His
        35                  40                  45

Leu Phe Met Asn Arg Ser Asn Lys Leu Ala Val Ile Ala Ser His Ile
    50                  55                  60

Gln Glu Ser Arg Phe Leu Tyr Pro Gly Phe Thr Pro Phe Ser Cys Leu
65                  70                  75                  80

Ser Leu Pro Ser Ser Trp Asp Tyr Tyr Ser Thr Glu Pro Met Arg Gln
                85                  90                  95

Lys Phe Glu Thr Ile Leu Pro Asn Val Val Lys Thr Trp
            100                 105

```
<210> SEQ ID NO 35
<211> LENGTH: 255
<212> TYPE: PRT
<213> ORGANISM: Homo sapiens

<400> SEQUENCE: 35

Met Val Leu Gly Asn Ser His Leu Phe Met Asn Arg Ser Asn Lys Leu
1               5                   10                  15

Ala Val Ile Ala Ser His Ile Gln Glu Ser Arg Phe Leu Tyr Pro Gly
            20                  25                  30

Lys Asn Gly Arg Leu Gly Asp Phe Phe Gly Asp Pro Gly Asn Pro Pro
        35                  40                  45

Glu Phe Asn Pro Ser Gly Ser Lys Asp Gly Lys Tyr Glu Leu Leu Thr
    50                  55                  60

Ser Ala Asn Glu Val Ile Val Glu Glu Ile Lys Asp Leu Met Thr Lys
65                  70                  75                  80

Ser Asp Ile Lys Gly Gln His Thr Glu Thr Leu Leu Ala Gly Ser Leu
                85                  90                  95

Ala Lys Ala Leu Cys Tyr Ile His Arg Met Asn Lys Glu Val Lys Asp
            100                 105                 110

Asn Gln Glu Met Lys Ser Arg Ile Leu Val Ile Lys Ala Ala Glu Asp
        115                 120                 125

Ser Ala Leu Gln Tyr Met Asn Phe Met Asn Val Ile Phe Ala Ala Gln
    130                 135                 140

Lys Gln Asn Ile Leu Ile Asp Ala Cys Val Leu Asp Ser Asp Ser Gly
145                 150                 155                 160

Leu Leu Gln Gln Ala Cys Asp Ile Thr Gly Gly Leu Tyr Leu Lys Val
                165                 170                 175

Pro Gln Met Pro Ser Leu Leu Gln Tyr Leu Leu Trp Val Phe Leu Pro
            180                 185                 190

Asp Gln Asp Gln Arg Ser Gln Leu Ile Leu Pro Pro Val His Val
        195                 200                 205

Asp Tyr Arg Ala Ala Cys Phe Cys His Arg Asn Leu Ile Glu Ile Gly
    210                 215                 220

Tyr Val Cys Ser Val Cys Leu Ser Ile Phe Cys Asn Phe Ser Pro Ile
225                 230                 235                 240

Cys Thr Thr Cys Glu Thr Ala Phe Lys Ile Ser Gln Pro Pro Lys
                245                 250                 255

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
gagactttgg ctccgattaa g                                        21

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
gaagtgctcc aaggaacagc                                          20
```

```
<210> SEQ ID NO 38
<211> LENGTH: 81
<212> TYPE: PRT
<213> ORGANISM: Homo sapiens

<400> SEQUENCE: 38

Met Glu Ser Thr Pro Ser Arg Gly Leu Asn Arg Val His Leu Gln Cys
1               5                   10                  15

Arg Asn Leu Gln Glu Phe Leu Gly Gly Leu Ser Pro Gly Val Leu Asp
            20                  25                  30

Arg Leu Tyr Gly His Pro Ala Thr Cys Leu Ala Val Phe Arg Glu Leu
        35                  40                  45

Pro Ser Leu Ala Lys Asn Trp Val Met Arg Met Leu Phe Leu Glu Gln
    50                  55                  60

Pro Leu Pro Gln Ala Ala Val Ala Leu Trp Val Lys Lys Glu Phe Ser
65                  70                  75                  80

Lys

<210> SEQ ID NO 39
<211> LENGTH: 462
<212> TYPE: PRT
<213> ORGANISM: Homo sapiens

<400> SEQUENCE: 39

Met Glu Ser Thr Pro Ser Arg Gly Leu Asn Arg Val His Leu Gln Cys
1               5                   10                  15

Arg Asn Leu Gln Glu Phe Leu Gly Gly Leu Ser Pro Gly Val Leu Asp
            20                  25                  30

Arg Leu Tyr Gly His Pro Ala Thr Cys Leu Ala Val Phe Arg Glu Leu
        35                  40                  45

Pro Ser Leu Ala Lys Asn Trp Val Met Arg Met Leu Phe Leu Glu Gln
    50                  55                  60

Pro Leu Pro Gln Ala Ala Val Ala Leu Trp Val Lys Lys Glu Phe Ser
65                  70                  75                  80

Lys Ala Gln Glu Glu Ser Thr Gly Leu Leu Ser Gly Leu Arg Ile Trp
                85                  90                  95

His Thr Gln Leu Leu Pro Gly Gly Leu Gln Gly Leu Ile Leu Asn Pro
            100                 105                 110

Ile Phe Arg Gln Asn Leu Arg Ile Ala Leu Leu Gly Gly Lys Ala
        115                 120                 125

Trp Ser Asp Asp Thr Ser Gln Leu Gly Pro Asp Lys His Ala Arg Asp
    130                 135                 140

Val Pro Ser Leu Asp Lys Tyr Ala Glu Glu Arg Trp Glu Val Val Leu
145                 150                 155                 160

His Phe Met Val Gly Ser Pro Ser Ala Ala Val Ser Gln Asp Leu Ala
                165                 170                 175

Gln Leu Leu Ser Gln Ala Gly Leu Met Lys Ser Thr Glu Pro Gly Glu
            180                 185                 190

Pro Pro Cys Ile Thr Ser Ala Gly Phe Gln Phe Leu Leu Leu Asp Thr
        195                 200                 205

Pro Ala Gln Leu Trp Tyr Phe Met Leu Gln Tyr Leu Gln Thr Ala Gln
    210                 215                 220

Ser Arg Gly Met Asp Leu Val Glu Ile Leu Ser Phe Leu Phe Gln Leu
225                 230                 235                 240

Ser Phe Ser Thr Leu Gly Lys Asp Tyr Ser Val Glu Gly Met Ser Asp
                245                 250                 255
```

```
Ser Leu Leu Asn Phe Leu Gln His Leu Arg Glu Phe Gly Leu Val Phe
            260                 265                 270
Gln Arg Lys Arg Lys Ser Arg Tyr Tyr Pro Thr Arg Leu Ala Ile
        275                 280                 285
Asn Leu Ser Ser Gly Val Ser Gly Ala Gly Gly Thr Val His Gln Pro
    290                 295                 300
Gly Phe Ile Val Val Glu Thr Asn Tyr Arg Leu Tyr Ala Tyr Thr Glu
305                 310                 315                 320
Ser Glu Leu Gln Ile Ala Leu Ile Ala Leu Phe Ser Glu Met Leu Tyr
                325                 330                 335
Arg Phe Pro Asn Met Val Val Ala Gln Val Thr Arg Glu Ser Val Gln
            340                 345                 350
Gln Ala Ile Ala Ser Gly Ile Thr Ala Gln Gln Ile Ile His Phe Leu
        355                 360                 365
Arg Thr Arg Ala His Pro Val Met Leu Lys Gly Thr Pro Val Leu Pro
    370                 375                 380
Pro Thr Ile Thr Asp Gln Ile Arg Leu Trp Glu Leu Glu Arg Asp Arg
385                 390                 395                 400
Leu Arg Phe Thr Glu Gly Val Leu Tyr Asn Gln Phe Leu Ser Gln Val
                405                 410                 415
Asp Phe Glu Leu Leu Leu Ala His Ala Arg Glu Leu Gly Val Leu Val
            420                 425                 430
Phe Glu Asn Ser Ala Lys Arg Leu Met Val Val Thr Pro Ala Gly His
        435                 440                 445
Ser Asp Val Lys Arg Phe Trp Lys Arg Gln Lys His Ser Ser
    450                 455                 460

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
gagactttgg ctccgattaa g                                         21

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
tgagcgagca tccgcatca                                            19

<210> SEQ ID NO 42
<211> LENGTH: 441
<212> TYPE: PRT
<213> ORGANISM: Homo sapiens

<400> SEQUENCE: 42

Met Glu Ser Thr Pro Ser Arg Gly Leu Asn Arg Val His Leu Gln Cys
1               5                   10                  15
Arg Asn Leu Gln Glu Phe Leu Gly Gly Leu Ser Pro Gly Val Leu Asp
            20                  25                  30
Arg Leu Tyr Gly His Pro Ala Thr Cys Leu Ala Val Phe Arg Glu Leu
        35                  40                  45
```

Pro Ser Leu Ala Lys Asn Trp Val Met Arg Met Leu Ala Gln Glu Glu
    50                  55                  60

Ser Thr Gly Leu Leu Ser Gly Leu Arg Ile Trp His Thr Gln Leu Leu
65                  70                  75                  80

Pro Gly Gly Leu Gln Gly Leu Ile Leu Asn Pro Ile Phe Arg Gln Asn
                85                  90                  95

Leu Arg Ile Ala Leu Leu Gly Gly Lys Ala Trp Ser Asp Asp Thr
            100                 105                 110

Ser Gln Leu Gly Pro Asp Lys His Ala Arg Asp Val Pro Ser Leu Asp
            115                 120                 125

Lys Tyr Ala Glu Glu Arg Trp Glu Val Val Leu His Phe Met Val Gly
    130                 135                 140

Ser Pro Ser Ala Ala Val Ser Gln Asp Leu Ala Gln Leu Leu Ser Gln
145                 150                 155                 160

Ala Gly Leu Met Lys Ser Thr Glu Pro Gly Glu Pro Pro Cys Ile Thr
                165                 170                 175

Ser Ala Gly Phe Gln Phe Leu Leu Leu Asp Thr Pro Ala Gln Leu Trp
            180                 185                 190

Tyr Phe Met Leu Gln Tyr Leu Gln Thr Ala Gln Ser Arg Gly Met Asp
    195                 200                 205

Leu Val Glu Ile Leu Ser Phe Leu Phe Gln Leu Ser Phe Ser Thr Leu
    210                 215                 220

Gly Lys Asp Tyr Ser Val Glu Gly Met Ser Asp Ser Leu Leu Asn Phe
225                 230                 235                 240

Leu Gln His Leu Arg Glu Phe Gly Leu Val Phe Gln Arg Lys Arg Lys
                245                 250                 255

Ser Arg Arg Tyr Tyr Pro Thr Arg Leu Ala Ile Asn Leu Ser Ser Gly
            260                 265                 270

Val Ser Gly Ala Gly Gly Thr Val His Gln Pro Gly Phe Ile Val Val
            275                 280                 285

Glu Thr Asn Tyr Arg Leu Tyr Ala Tyr Thr Glu Ser Glu Leu Gln Ile
    290                 295                 300

Ala Leu Ile Ala Leu Phe Ser Glu Met Leu Tyr Arg Phe Pro Asn Met
305                 310                 315                 320

Val Val Ala Gln Val Thr Arg Glu Ser Val Gln Gln Ala Ile Ala Ser
                325                 330                 335

Gly Ile Thr Ala Gln Gln Ile Ile His Phe Leu Arg Thr Arg Ala His
            340                 345                 350

Pro Val Met Leu Lys Gln Thr Pro Val Leu Pro Pro Thr Ile Thr Asp
    355                 360                 365

Gln Ile Arg Leu Trp Glu Leu Gly Arg Asp Arg Leu Arg Phe Thr Glu
    370                 375                 380

Gly Val Leu Tyr Asn Gln Phe Leu Ser Gln Val Asp Phe Glu Leu Leu
385                 390                 395                 400

Leu Ala His Ala Arg Glu Leu Gly Val Leu Val Phe Glu Asn Ser Ala
                405                 410                 415

Lys Arg Leu Met Val Val Thr Pro Ala Gly His Ser Asp Val Lys Arg
            420                 425                 430

Phe Trp Lys Arg Gln Lys His Ser Ser
            435                 440

<210> SEQ ID NO 43
<211> LENGTH: 462
<212> TYPE: PRT
<213> ORGANISM: Homo sapiens

<400> SEQUENCE: 43

```
Met Glu Ser Thr Pro Ser Arg Gly Leu Asn Arg Val His Leu Gln Cys
1               5                   10                  15
Arg Asn Leu Gln Glu Phe Leu Gly Gly Leu Ser Pro Gly Val Leu Asp
            20                  25                  30
Arg Leu Tyr Gly His Pro Ala Thr Cys Leu Ala Val Phe Arg Glu Leu
        35                  40                  45
Pro Ser Leu Ala Lys Asn Trp Val Met Arg Met Leu Phe Leu Glu Gln
    50                  55                  60
Pro Leu Pro Gln Ala Ala Val Ala Leu Trp Val Lys Lys Glu Phe Ser
65                  70                  75                  80
Lys Ala Gln Glu Glu Ser Thr Gly Leu Leu Ser Gly Leu Arg Ile Trp
                85                  90                  95
His Thr Gln Leu Leu Pro Gly Gly Leu Gln Gly Leu Ile Leu Asn Pro
            100                 105                 110
Ile Phe Arg Gln Asn Leu Arg Ile Ala Leu Leu Gly Gly Lys Ala
        115                 120                 125
Trp Ser Asp Asp Thr Ser Gln Leu Gly Pro Asp Lys His Ala Arg Asp
130                 135                 140
Val Pro Ser Leu Asp Lys Tyr Ala Glu Glu Arg Trp Glu Val Val Leu
145                 150                 155                 160
His Phe Met Val Gly Ser Pro Ser Ala Ala Val Ser Gln Asp Leu Ala
                165                 170                 175
Gln Leu Leu Ser Gln Ala Gly Leu Met Lys Ser Thr Glu Pro Gly Glu
            180                 185                 190
Pro Pro Cys Ile Thr Ser Ala Gly Phe Gln Phe Leu Leu Leu Asp Thr
        195                 200                 205
Pro Ala Gln Leu Trp Tyr Phe Met Leu Gln Tyr Leu Gln Thr Ala Gln
    210                 215                 220
Ser Arg Gly Met Asp Leu Val Glu Ile Leu Ser Phe Leu Phe Gln Leu
225                 230                 235                 240
Ser Phe Ser Thr Leu Gly Lys Asp Tyr Ser Val Glu Gly Met Ser Asp
                245                 250                 255
Ser Leu Leu Asn Phe Leu Gln His Leu Arg Glu Phe Gly Leu Val Phe
            260                 265                 270
Gln Arg Lys Arg Lys Ser Arg Arg Tyr Tyr Pro Thr Arg Leu Ala Ile
        275                 280                 285
Asn Leu Ser Ser Gly Val Ser Gly Ala Gly Thr Val His Gln Pro
    290                 295                 300
Gly Phe Ile Val Val Glu Thr Asn Tyr Arg Leu Tyr Ala Tyr Thr Glu
305                 310                 315                 320
Ser Glu Leu Gln Ile Ala Leu Ile Ala Leu Phe Ser Glu Met Leu Tyr
                325                 330                 335
Arg Phe Pro Asn Met Val Val Ala Gln Val Thr Arg Glu Ser Val Gln
            340                 345                 350
Gln Ala Ile Ala Ser Gly Ile Thr Ala Gln Gln Ile Ile His Phe Leu
        355                 360                 365
Arg Thr Arg Ala His Pro Val Met Leu Lys Gln Thr Pro Val Leu Pro
    370                 375                 380
Pro Thr Ile Thr Asp Gln Ile Arg Leu Trp Glu Leu Glu Arg Asp Arg
385                 390                 395                 400
Leu Arg Phe Thr Glu Gly Val Leu Tyr Asn Gln Phe Leu Ser Gln Val
                405                 410                 415
```

```
Asp Phe Glu Leu Leu Ala His Ala Arg Glu Leu Gly Val Leu Val
        420                 425                 430

Phe Glu Asn Ser Ala Lys Arg Leu Met Val Val Thr Pro Ala Gly His
        435                 440                 445

Ser Asp Val Lys Arg Phe Trp Lys Arg Gln Lys His Ser Ser
        450                 455                 460

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
tggggtcatc ggctcaacgt g                                          21

<210> SEQ ID NO 45
<211> LENGTH: 23
<212> TYPE: DNA
<213> ORGANISM: Artificial sequence
<220> FEATURE:
<223> OTHER INFORMATION: Primer

<400> SEQUENCE: 45
tcttgagcag tagatgagtt tgg                                        23

<210> SEQ ID NO 46
<211> LENGTH: 285
<212> TYPE: PRT
<213> ORGANISM: Homo sapiens

<400> SEQUENCE: 46

Met Arg Glu Leu Lys Arg Thr Leu Asp Ala Lys Gly His Gly Val Leu
1               5                   10                  15

Glu Met Pro Ser Gly Thr Gly Lys Thr Val Ser Leu Leu Ala Leu Ile
                20                  25                  30

Met Ala Tyr Gln Arg Ala Tyr Pro Leu Glu Val Thr Lys Leu Ile Tyr
        35                  40                  45

Cys Ser Arg Thr Val Pro Glu Ile Glu Lys Val Ile Glu Glu Leu Arg
    50                  55                  60

Lys Leu Leu Asn Phe Tyr Glu Lys Gln Glu Gly Glu Lys Leu Pro Phe
65                  70                  75                  80

Leu Gly Leu Ala Leu Ser Ser Arg Lys Asn Leu Cys Ile His Pro Glu
                85                  90                  95

Val Thr Pro Leu Arg Phe Gly Lys Asp Val Asp Gly Lys Cys His Ser
            100                 105                 110

Leu Thr Ala Ser Tyr Val Arg Ala Gln Tyr Gln His Asp Thr Ser Leu
        115                 120                 125

Pro His Cys Arg Phe Tyr Glu Glu Phe Asp Ala His Gly Arg Glu Val
    130                 135                 140

Pro Leu Pro Ala Gly Ile Tyr Asn Leu Asp Asp Leu Lys Ala Leu Gly
145                 150                 155                 160

Arg Arg Gln Gly Trp Cys Pro Tyr Phe Leu Ala Arg Tyr Ser Ile Leu
                165                 170                 175

His Ala Asn Val Val Val Tyr Ser Tyr His Tyr Leu Leu Asp Pro Lys
            180                 185                 190

Ile Ala Asp Leu Val Ser Lys Glu Leu Ala Arg Lys Ala Val Val Val
        195                 200                 205
```

```
Phe Asp Glu Ala His Asn Ile Asp Asn Val Cys Ile Asp Ser Met Ser
    210                 215                 220
Val Asn Leu Thr Arg Arg Thr Leu Asp Arg Cys Gln Gly Asn Leu Glu
225                 230                 235                 240
Thr Leu Gln Lys Thr Val Leu Arg Ile Lys Glu Thr Asp Glu Gln Arg
                245                 250                 255
Leu Arg Asp Glu Tyr Arg Arg Leu Val Glu Gly Leu Arg Glu Ala Ser
                260                 265                 270
Ala Ala Arg Glu Thr Asp Ala His Leu Ala Asn Pro Val
                275                 280                 285

<210> SEQ ID NO 47
<211> LENGTH: 300
<212> TYPE: PRT
<213> ORGANISM: Homo sapiens

<400> SEQUENCE: 47

Met Lys Leu Asn Val Asp Gly Leu Leu Val Tyr Phe Pro Tyr Asp Tyr
1               5                   10                  15
Ile Tyr Pro Glu Gln Phe Ser Tyr Met Arg Glu Leu Lys Arg Thr Leu
                20                  25                  30
Asp Ala Lys Gly His Gly Val Leu Glu Met Pro Ser Gly Thr Gly Lys
            35                  40                  45
Thr Val Ser Leu Leu Ala Leu Ile Met Ala Tyr Gln Arg Ala Tyr Pro
        50                  55                  60
Leu Glu Val Thr Lys Leu Ile Tyr Cys Ser Arg Thr Val Pro Glu Ile
65                  70                  75                  80
Glu Lys Val Ile Glu Glu Leu Arg Lys Leu Leu Asn Phe Tyr Glu Lys
                85                  90                  95
Gln Glu Gly Glu Lys Leu Pro Phe Leu Gly Leu Ala Leu Ser Ser Arg
                100                 105                 110
Lys Asn Leu Cys Ile His Pro Glu Val Thr Pro Leu Arg Phe Gly Lys
            115                 120                 125
Asp Val Asp Gly Lys Cys His Ser Leu Thr Ala Ser Tyr Val Arg Ala
        130                 135                 140
Gln Tyr Gln His Asp Thr Ser Leu Pro His Cys Arg Phe Tyr Glu Glu
145                 150                 155                 160
Phe Asp Ala His Gly Arg Glu Val Pro Leu Pro Ala Gly Ile Tyr Asn
                165                 170                 175
Leu Asp Asp Leu Lys Ala Leu Gly Arg Arg Gln Gly Trp Cys Pro Tyr
                180                 185                 190
Phe Leu Ala Arg Tyr Ser Ile Leu His Ala Asn Val Val Val Tyr Ser
            195                 200                 205
Tyr His Tyr Leu Leu Asp Pro Lys Ile Ala Asp Leu Val Ser Lys Glu
        210                 215                 220
Leu Ala Arg Lys Ala Val Val Phe Asp Glu Ala His Asn Ile Asp
225                 230                 235                 240
Asn Val Cys Ile Asp Ser Met Ser Val Asn Leu Thr Arg Arg Thr Leu
                245                 250                 255
Asp Arg Cys Gln Gly Asn Leu Glu Thr Leu Gln Lys Thr Val Leu Arg
            260                 265                 270
Ile Lys Glu Thr Asp Glu Gln Arg Leu Arg Asp Glu Tyr Arg Arg Leu
        275                 280                 285
Val Glu Gly Leu Arg Glu Ala Ser Ala Ala Arg Glu
    290                 295                 300
```

<210> SEQ ID NO 48
<211> LENGTH: 22
<212> TYPE: DNA
<213> ORGANISM: Artificial sequence
<220> FEATURE:
<223> OTHER INFORMATION: Primer

<400> SEQUENCE: 48
ggtcaacata tttcactggc ac                                        22

<210> SEQ ID NO 49
<211> LENGTH: 22
<212> TYPE: DNA
<213> ORGANISM: Artificial sequence
<220> FEATURE:
<223> OTHER INFORMATION: Primer

<400> SEQUENCE: 49
tccatcagat gaggcttatc gt                                        22

<210> SEQ ID NO 50
<211> LENGTH: 69
<212> TYPE: PRT
<213> ORGANISM: Homo sapiens

<400> SEQUENCE: 50

Met Gln Leu Glu Lys Pro Lys Pro Val Lys Pro Val Thr Phe Ser Thr
1               5                   10                  15

Gly Ile Lys Met Gly Gln His Ile Ser Leu Ala Pro Ile His Lys Leu
            20                  25                  30

Glu Glu Ala Leu Tyr Glu Tyr Gln Pro Leu Gln Ile Glu Thr Tyr Gly
        35                  40                  45

Pro His Val Pro Glu Leu Glu Met Leu Gly Arg Leu Gly Gly Phe Asp
    50                  55                  60

Thr Ile Ser Leu Ile
65

<210> SEQ ID NO 51
<211> LENGTH: 189
<212> TYPE: PRT
<213> ORGANISM: Homo sapiens

<400> SEQUENCE: 51

Lys Met Glu Ile Tyr Gln Lys Glu Asn Lys Asp Val Ile Gln Lys Asn
1               5                   10                  15

Lys Leu Lys Leu Thr Arg Glu Gln Glu Glu Leu Glu Glu Ala Leu Glu
            20                  25                  30

Val Glu Arg Gln Glu Asn Glu Gln Arg Leu Phe Ile Gln Lys Glu
        35                  40                  45

Glu Gln Leu Gln Gln Ile Leu Lys Arg Lys Asn Lys Gln Ala Phe Leu
        50                  55                  60

Asp Glu Leu Glu Ser Ser Asp Leu Pro Val Ala Leu Leu Ala Gln
65                  70                  75                  80

His Lys Asp Arg Ser Thr Gln Leu Glu Met Gln Leu Glu Lys Pro Lys
                85                  90                  95

Pro Val Lys Pro Val Thr Phe Ser Thr Gly Ile Lys Met Gly Gln His
            100                 105                 110

Ile Ser Leu Ala Pro Ile His Lys Leu Glu Glu Ala Leu Tyr Glu Tyr
        115                 120                 125

```
Gln Pro Leu Gln Ile Glu Thr Tyr Gly Pro His Val Pro Glu Leu Glu
        130                 135                 140

Met Leu Gly Arg Leu Gly Tyr Leu Asn His Val Arg Ala Ala Ser Pro
145                 150                 155                 160

Gln Asp Leu Ala Gly Gly Tyr Thr Ser Ser Leu Ala Cys His Arg Ala
                165                 170                 175

Leu Gln Asp Ala Phe Ser Gly Leu Phe Trp Gln Pro Ser
                180                 185

<210> SEQ ID NO 52
<211> LENGTH: 22
<212> TYPE: DNA
<213> ORGANISM: Artificial sequence
<220> FEATURE:
<223> OTHER INFORMATION: Primer

<400> SEQUENCE: 52
caaggccaga gataagaaca cc                                           22

<210> SEQ ID NO 53
<211> LENGTH: 22
<212> TYPE: DNA
<213> ORGANISM: Artificial sequence
<220> FEATURE:
<223> OTHER INFORMATION: Primer

<400> SEQUENCE: 53
gtaggctttg atgtgtgatg gt                                           22

<210> SEQ ID NO 54
<211> LENGTH: 94
<212> TYPE: PRT
<213> ORGANISM: Homo sapiens

<400> SEQUENCE: 54

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
                20                  25                  30

Asn Thr Asn Gln Ile Val Ala Ile Lys Lys Ile Lys Leu Gly His Arg
            35                  40                  45

Ser Glu Ala Lys Asp Gly Ile Asn Arg Thr Ala Leu Arg Glu Ile Lys
        50                  55                  60

Leu Leu Gln Glu Leu Ser His Pro Asn Ile Ile Gly Val Ile Ile Lys
65                  70                  75                  80

Asp Asn Ser Leu Val Leu Thr Pro Ser His Ile Lys Ala Tyr
                85                  90

<210> SEQ ID NO 55
<211> LENGTH: 120
<212> TYPE: PRT
<213> ORGANISM: Homo sapiens

<400> SEQUENCE: 55

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
                20                  25                  30

Asn Thr Asn Gln Ile Val Ala Ile Lys Lys Ile Lys Leu Gly His Arg
            35                  40                  45

Ser Glu Ala Lys Asp Gly Ile Asn Arg Thr Ala Leu Arg Glu Ile Lys
```

```
                    50                  55                  60
Leu Leu Gln Glu Leu Ser His Pro Asn Ile Ile Gly Leu Leu Asp Ala
 65                  70                  75                  80

Phe Gly His Lys Ser Asn Ile Ser Leu Val Phe Asp Phe Met Glu Thr
                 85                  90                  95

Asp Leu Glu Val Ile Ile Lys Asp Asn Ser Leu Val Leu Thr Pro Ser
                100                 105                 110

His Ile Lys Ala Tyr Met Leu Met
            115                 120
```

<210> SEQ ID NO 56
<211> LENGTH: 19
<212> TYPE: DNA
<213> ORGANISM: Artificial sequence
<220> FEATURE:
<223> OTHER INFORMATION: Primer

<400> SEQUENCE: 56
cttggacagg agaaggcac                                                    19

<210> SEQ ID NO 57
<211> LENGTH: 21
<212> TYPE: DNA
<213> ORGANISM: Artificial sequence
<220> FEATURE:
<223> OTHER INFORMATION: Primer

<400> SEQUENCE: 57
cagtatagtc acaccagaat g                                                 21

<210> SEQ ID NO 58
<211> LENGTH: 255
<212> TYPE: PRT
<213> ORGANISM: Homo sapiens

<400> SEQUENCE: 58

```
Met Pro Arg Ser Val Val Gly Thr Ala Cys Met Tyr Phe Lys Arg Phe
 1                   5                  10                  15

Tyr Leu Asn Asn Ser Val Met Glu Tyr His Pro Arg Ile Ile Met Leu
                 20                  25                  30

Thr Cys Ala Phe Leu Ala Cys Lys Val Asp Glu Phe Asn Val Ser Ser
             35                  40                  45

Pro Gln Phe Val Gly Asn Leu Arg Glu Ser Pro Leu Gly Gln Glu Lys
         50                  55                  60

Ala Leu Glu Gln Ile Leu Glu Tyr Glu Leu Leu Leu Ile Gln Gln Leu
 65                  70                  75                  80

Asn Phe His Leu Ile Val His Asn Pro Tyr Arg Pro Phe Glu Gly Phe
                 85                  90                  95

Leu Ile Asp Leu Lys Thr Arg Tyr Pro Ile Leu Glu Asn Pro Glu Ile
                100                 105                 110

Leu Arg Lys Thr Ala Asp Asp Phe Leu Asn Arg Ile Ala Leu Thr Asp
            115                 120                 125

Ala Tyr Leu Leu Tyr Thr Pro Ser Gln Ile Ala Leu Thr Ala Ile Leu
        130                 135                 140

Ser Ser Ala Ser Arg Ala Gly Ile Thr Met Glu Ser Tyr Leu Ser Glu
145                 150                 155                 160

Ser Leu Met Leu Lys Glu Asn Arg Thr Cys Leu Ser Gln Leu Leu Asp
                165                 170                 175

Ile Met Lys Ser Met Arg Asn Leu Val Lys Lys Tyr Glu Pro Pro Arg
```

```
              180                 185                 190
Ser Glu Glu Val Ala Val Leu Lys Gln Lys Leu Glu Arg Cys His Ser
            195                 200                 205

Ala Glu Leu Ala Leu Asn Val Ile Thr Lys Lys Arg Lys Gly Tyr Glu
            210                 215                 220

Asp Asp Asp Tyr Val Ser Lys Lys Ser Lys His Glu Glu Val Cys Phe
225                 230                 235                 240

Thr Pro Lys Met Asn Ser Lys Leu Phe Leu Leu Tyr Ile Leu Val
            245                 250                 255

<210> SEQ ID NO 59
<211> LENGTH: 323
<212> TYPE: PRT
<213> ORGANISM: Homo sapiens

<400> SEQUENCE: 59

Met Tyr His Asn Ser Ser Gln Lys Arg His Trp Thr Phe Ser Ser Glu
1               5                   10                  15

Glu Gln Leu Ala Arg Leu Arg Ala Asp Ala Asn Arg Lys Phe Arg Cys
                20                  25                  30

Lys Ala Val Ala Asn Gly Lys Val Leu Pro Asn Asp Pro Val Phe Leu
            35                  40                  45

Glu Pro His Glu Glu Met Thr Leu Cys Lys Tyr Tyr Glu Lys Arg Leu
        50                  55                  60

Leu Glu Phe Cys Ser Val Phe Lys Pro Ala Met Pro Arg Ser Val Val
65                  70                  75                  80

Gly Thr Ala Cys Met Tyr Phe Lys Arg Phe Tyr Leu Asn Asn Ser Val
                85                  90                  95

Met Glu Tyr His Pro Arg Ile Ile Met Leu Thr Cys Ala Phe Leu Ala
            100                 105                 110

Cys Lys Val Asp Glu Phe Asn Val Ser Ser Pro Gln Phe Val Gly Asn
        115                 120                 125

Leu Arg Glu Ser Pro Leu Gly Gln Glu Lys Ala Leu Glu Gln Ile Leu
130                 135                 140

Glu Tyr Glu Leu Leu Leu Ile Gln Gln Leu Asn Phe His Leu Ile Val
145                 150                 155                 160

His Asn Pro Tyr Arg Pro Phe Glu Gly Phe Leu Ile Asp Leu Lys Thr
                165                 170                 175

Arg Tyr Pro Ile Leu Glu Asn Pro Glu Ile Leu Arg Lys Thr Ala Asp
            180                 185                 190

Asp Phe Leu Asn Arg Ile Ala Leu Thr Asp Ala Tyr Leu Leu Tyr Thr
        195                 200                 205

Pro Ser Gln Ile Ala Leu Thr Ala Ile Leu Ser Ala Ser Arg Ala
    210                 215                 220

Gly Ile Thr Met Glu Ser Tyr Leu Ser Glu Ser Leu Met Leu Lys Glu
225                 230                 235                 240

Asn Arg Thr Cys Leu Ser Gln Leu Leu Asp Ile Met Lys Ser Met Arg
                245                 250                 255

Asn Leu Val Lys Lys Tyr Glu Pro Pro Arg Ser Glu Glu Val Ala Val
            260                 265                 270

Leu Lys Gln Lys Leu Glu Arg Cys His Ser Ala Glu Leu Ala Leu Asn
        275                 280                 285

Val Ile Thr Lys Lys Arg Lys Gly Tyr Glu Asp Asp Tyr Val Ser
    290                 295                 300

Lys Lys Ser Lys His Glu Glu Glu Glu Trp Thr Asp Asp Asp Leu Val
```

```
                305                 310                 315                 320
Glu Ser Leu

<210> SEQ ID NO 60
<211> LENGTH: 19
<212> TYPE: DNA
<213> ORGANISM: Artificial sequence
<220> FEATURE:
<223> OTHER INFORMATION: Primer

<400> SEQUENCE: 60
gctcggagga agttcaagg                                                      19

<210> SEQ ID NO 61
<211> LENGTH: 19
<212> TYPE: DNA
<213> ORGANISM: Artificial sequence
<220> FEATURE:
<223> OTHER INFORMATION: Primer

<400> SEQUENCE: 61
gtcctggtcc tgatccttg                                                      19

<210> SEQ ID NO 62
<211> LENGTH: 199
<212> TYPE: PRT
<213> ORGANISM: Homo sapiens

<400> SEQUENCE: 62

Met Ala Ala Leu Gly Pro Ser Ser Gln Asn Val Thr Glu Tyr Val Val
1               5                   10                  15

Arg Val Pro Lys Asn Thr Thr Lys Lys Tyr Asn Ile Met Ala Phe Asn
            20                  25                  30

Ala Ala Asp Lys Val Asn Phe Ala Thr Trp Asn Gln Ala Arg Leu Glu
        35                  40                  45

Arg Asp Leu Ser Asn Lys Lys Ile Tyr Gln Glu Glu Met Pro Glu
    50                  55                  60

Ser Gly Ala Gly Ser Glu Phe Asn Arg Lys Leu Arg Glu Glu Ala Arg
65                  70                  75                  80

Arg Lys Phe Lys Gly Ile Lys Lys Gly Val Thr Glu Asn Thr Ser
                85                  90                  95

Tyr Tyr Ile Phe Thr Gln Cys Pro Asp Gly Ala Phe Glu Ala Phe Pro
            100                 105                 110

Val His Asn Trp Tyr Asn Phe Thr Pro Leu Ala Arg His Arg Thr Leu
        115                 120                 125

Thr Ala Glu Glu Ala Glu Glu Trp Glu Arg Arg Asn Lys Val Leu
    130                 135                 140

Asn His Phe Ser Ile Met Gln Gln Arg Arg Leu Lys Asp Gln Asp Gln
145                 150                 155                 160

Asp Glu Asp Glu Glu Glu Lys Glu Lys Arg Gly Arg Lys Ala Ser
                165                 170                 175

Glu Leu Arg Ile His Asp Leu Asp Asp Leu Glu Met Ser Ser Asp
            180                 185                 190

Ala Ser Asp Ala Ser Gly Glu
        195

<210> SEQ ID NO 63
<211> LENGTH: 238
<212> TYPE: PRT
<213> ORGANISM: Homo sapiens
```

<400> SEQUENCE: 63

| | | | | | | | | | | | | | | |
|---|---|---|---|---|---|---|---|---|---|---|---|---|---|---|
| Met | Ala | Ala | Leu | Gly | Pro | Ser | Ser | Gln | Asn | Val | Thr | Glu | Tyr | Val |
| 1 | | | | 5 | | | | | 10 | | | | | 15 |
| Arg | Val | Pro | Lys | Asn | Thr | Thr | Lys | Lys | Tyr | Asn | Ile | Met | Ala | Phe | Asn |
| | | | 20 | | | | | 25 | | | | | 30 | | |
| Ala | Ala | Asp | Lys | Val | Asn | Phe | Ala | Thr | Trp | Asn | Gln | Ala | Arg | Leu | Glu |
| | | 35 | | | | | 40 | | | | | 45 | | | |
| Arg | Asp | Leu | Ser | Asn | Lys | Lys | Ile | Tyr | Gln | Glu | Glu | Met | Pro | Glu |
| | 50 | | | | | 55 | | | | | 60 | | | | |
| Ser | Gly | Ala | Gly | Ser | Glu | Phe | Asn | Arg | Lys | Leu | Arg | Glu | Glu | Ala | Arg |
| 65 | | | | | 70 | | | | | 75 | | | | | 80 |
| Arg | Lys | Lys | Tyr | Gly | Ile | Val | Leu | Lys | Glu | Phe | Arg | Pro | Glu | Asp | Gln |
| | | | | 85 | | | | | 90 | | | | | 95 | |
| Pro | Trp | Leu | Leu | Arg | Val | Asn | Gly | Lys | Ser | Gly | Arg | Lys | Phe | Lys | Gly |
| | | | 100 | | | | | 105 | | | | | 110 | | |
| Ile | Lys | Lys | Gly | Gly | Val | Thr | Glu | Asn | Thr | Ser | Tyr | Tyr | Ile | Phe | Thr |
| | | 115 | | | | | 120 | | | | | 125 | | | |
| Gln | Cys | Pro | Asp | Gly | Ala | Phe | Glu | Ala | Phe | Pro | Val | His | Asn | Trp | Tyr |
| | 130 | | | | | 135 | | | | | 140 | | | | |
| Asn | Phe | Thr | Pro | Leu | Ala | Arg | His | Arg | Thr | Leu | Thr | Ala | Glu | Glu | Ala |
| 145 | | | | | 150 | | | | | 155 | | | | | 160 |
| Glu | Glu | Glu | Trp | Glu | Arg | Arg | Asn | Lys | Val | Leu | Asn | His | Phe | Ser | Ile |
| | | | | 165 | | | | | 170 | | | | | 175 | |
| Met | Gln | Gln | Arg | Arg | Leu | Lys | Asp | Gln | Asp | Gln | Asp | Glu | Asp | Glu | Glu |
| | | | | 180 | | | | | 185 | | | | | 190 | |
| Glu | Lys | Glu | Lys | Arg | Gly | Arg | Arg | Lys | Ala | Ser | Glu | Leu | Arg | Ile | His |
| | | 195 | | | | | 200 | | | | | 205 | | | |
| Asp | Leu | Glu | Asp | Asp | Leu | Glu | Met | Ser | Ser | Asp | Ala | Ser | Asp | Ala | Ser |
| | 210 | | | | | 215 | | | | | 220 | | | | |
| Gly | Glu | Glu | Gly | Gly | Arg | Val | Pro | Lys | Ala | Lys | Lys | Ala |
| 225 | | | | | 230 | | | | | 235 | | |

<210> SEQ ID NO 64
<211> LENGTH: 19
<212> TYPE: DNA
<213> ORGANISM: Artificial sequence
<220> FEATURE:
<223> OTHER INFORMATION: Primer

<400> SEQUENCE: 64
aggcctgggc gtctgtttg                                                    19

<210> SEQ ID NO 65
<211> LENGTH: 19
<212> TYPE: DNA
<213> ORGANISM: Artificial sequence
<220> FEATURE:
<223> OTHER INFORMATION: Primer

<400> SEQUENCE: 65
gcacggcatc ctcagtcac                                                    19

<210> SEQ ID NO 66
<211> LENGTH: 437
<212> TYPE: PRT
<213> ORGANISM: Homo sapiens

<400> SEQUENCE: 66

-continued

```
Met Ala Ala Leu Gly Pro Ser Gln Asn Val Thr Glu Tyr Val Val
1               5                   10                  15

Arg Val Pro Lys Asn Thr Thr Lys Lys Tyr Asn Ile Met Ala Phe Asn
                20                  25                  30

Ala Ala Asp Lys Val Asn Phe Ala Thr Trp Asn Gln Ala Arg Leu Glu
            35                  40                  45

Arg Asp Leu Ser Asn Lys Lys Ile Tyr Gln Glu Glu Met Pro Glu
    50                  55                  60

Ser Gly Ala Gly Ser Glu Phe Asn Arg Lys Leu Arg Glu Glu Ala Arg
65                  70                  75                  80

Arg Lys Lys Tyr Gly Ile Val Leu Lys Glu Phe Arg Pro Glu Asp Gln
                85                  90                  95

Pro Trp Leu Leu Arg Val Asn Gly Lys Ser Gly Arg Lys Phe Lys Gly
                100                 105                 110

Ile Lys Lys Gly Gly Val Thr Glu Asn Thr Ser Tyr Tyr Ile Phe Thr
                115                 120                 125

Gln Cys Pro Asp Gly Ala Phe Glu Ala Phe Pro Val His Asn Trp Tyr
        130                 135                 140

Asn Phe Thr Pro Leu Ala Arg His Arg Thr Leu Thr Ala Glu Glu Ala
145                 150                 155                 160

Glu Glu Glu Trp Glu Arg Arg Asn Lys Val Leu Asn His Phe Ser Ile
                165                 170                 175

Met Gln Gln Arg Arg Leu Lys Asp Gln Asp Gln Glu Asp Glu Glu
        180                 185                 190

Glu Lys Glu Lys Arg Gly Arg Arg Lys Ala Ser Glu Leu Arg Ile His
    195                 200                 205

Asp Leu Glu Asp Asp Leu Glu Met Ser Ser Asp Ala Ser Asp Ala Ser
    210                 215                 220

Gly Glu Glu Gly Gly Arg Val Pro Lys Ala Lys Lys Ala Pro Leu
225                 230                 235                 240

Ala Lys Gly Gly Arg Lys Lys Lys Lys Lys Gly Ser Asp Glu
            245                 250                 255

Ala Phe Glu Asp Ser Asp Gly Asp Phe Glu Gly Gln Glu Val Asp
        260                 265                 270

Tyr Met Ser Asp Gly Ser Ser Ser Gln Glu Glu Pro Glu Ser Lys
    275                 280                 285

Ala Lys Ala Pro Gln Gln Glu Glu Gly Pro Lys Gly Val Asp Glu Gln
    290                 295                 300

Ser Asp Ser Ser Glu Glu Ser Glu Glu Glu Lys Pro Pro Glu Glu Asp
305                 310                 315                 320

Lys Glu Glu Glu Glu Glu Lys Lys Ala Pro Thr Pro Gln Glu Lys Lys
                325                 330                 335

Arg Arg Lys Asp Ser Ser Glu Glu Ser Asp Ser Ser Glu Glu Ser Asp
                340                 345                 350

Ile Asp Ser Glu Ala Ser Ser Ala Leu Phe Met Ala Val Arg Pro Ser
        355                 360                 365

Pro Val Ala Gly Glu Ala Trp Ala Ser Val Cys Arg Leu Thr His Leu
    370                 375                 380

Pro Thr Leu Thr Ser Ala Glu Glu Asp Ala Thr Gln Glu Arg Ala
385                 390                 395                 400

Glu Ala Val Gly Arg Glu Leu Lys Gly Gln Gln Pro Pro Arg His Ala
                405                 410                 415

Gln Arg Arg Gly Trp Gln His Leu Leu His Pro Ala Gly Gly Cys Gln
            420                 425                 430
```

Gln Thr Arg Ala Arg
        435

<210> SEQ ID NO 67
<211> LENGTH: 480
<212> TYPE: PRT
<213> ORGANISM: Homo sapiens

<400> SEQUENCE: 67

Met Ala Ala Leu Gly Pro Ser Ser Gln Asn Val Thr Glu Tyr Val Val
1               5                   10                  15

Arg Val Pro Lys Asn Thr Thr Lys Lys Tyr Asn Ile Met Ala Phe Asn
            20                  25                  30

Ala Ala Asp Lys Val Asn Phe Ala Thr Trp Asn Gln Ala Arg Leu Glu
        35                  40                  45

Arg Asp Leu Ser Asn Lys Lys Ile Tyr Gln Glu Glu Met Pro Glu
    50                  55                  60

Ser Gly Ala Gly Ser Glu Phe Asn Arg Lys Leu Arg Glu Glu Ala Arg
65                  70                  75                  80

Arg Lys Lys Tyr Gly Ile Val Leu Lys Glu Phe Arg Pro Glu Asp Gln
                85                  90                  95

Pro Trp Leu Leu Arg Val Asn Gly Lys Ser Gly Arg Lys Phe Lys Gly
            100                 105                 110

Ile Lys Lys Gly Gly Val Thr Glu Asn Thr Ser Tyr Tyr Ile Phe Thr
        115                 120                 125

Gln Cys Pro Asp Gly Ala Phe Glu Ala Phe Pro Val His Asn Trp Tyr
    130                 135                 140

Asn Phe Thr Pro Leu Ala Arg His Arg Thr Leu Thr Ala Glu Glu Ala
145                 150                 155                 160

Glu Glu Glu Trp Glu Arg Arg Asn Lys Val Leu Asn His Phe Ser Ile
                165                 170                 175

Met Gln Gln Arg Arg Leu Lys Asp Gln Asp Gln Asp Glu Asp Glu Glu
            180                 185                 190

Glu Lys Glu Lys Arg Gly Arg Arg Lys Ala Ser Glu Leu Arg Ile His
        195                 200                 205

Asp Leu Glu Asp Asp Leu Glu Met Ser Ser Asp Ala Ser Asp Ala Ser
    210                 215                 220

Gly Glu Glu Gly Gly Arg Val Pro Lys Ala Lys Lys Ala Pro Leu
225                 230                 235                 240

Ala Lys Gly Gly Arg Lys Lys Lys Lys Gly Ser Asp Asp Glu
                245                 250                 255

Ala Phe Glu Asp Ser Asp Asp Gly Asp Phe Glu Gly Gln Glu Val Asp
            260                 265                 270

Tyr Met Ser Asp Gly Ser Ser Ser Gln Glu Glu Pro Glu Ser Lys
        275                 280                 285

Ala Lys Ala Pro Gln Gln Glu Glu Gly Pro Lys Gly Val Asp Glu Gln
    290                 295                 300

Ser Asp Ser Ser Glu Glu Ser Glu Glu Glu Lys Pro Pro Glu Glu Asp
305                 310                 315                 320

Lys Glu Glu Glu Glu Lys Lys Ala Pro Thr Pro Gln Glu Lys Lys
                325                 330                 335

Arg Arg Lys Asp Ser Ser Glu Glu Ser Asp Ser Ser Glu Glu Ser Asp
            340                 345                 350

Ile Asp Ser Glu Ala Ser Ser Ala Leu Phe Met Ala Lys Lys Lys Thr
        355                 360                 365

```
Pro Pro Lys Arg Glu Arg Lys Pro Ser Gly Gly Ser Ser Arg Gly Asn
    370                 375                 380

Ser Arg Pro Gly Thr Pro Ser Ala Glu Gly Gly Ser Thr Ser Ser Thr
385                 390                 395                 400

Leu Arg Ala Ala Ala Ser Lys Leu Glu Gln Gly Lys Arg Val Ser Glu
                405                 410                 415

Met Pro Ala Ala Lys Arg Leu Arg Leu Asp Thr Gly Pro Gln Ser Leu
            420                 425                 430

Ser Gly Lys Ser Thr Pro Gln Pro Pro Ser Gly Lys Thr Thr Pro Asn
            435                 440                 445

Ser Gly Asp Val Gln Val Thr Glu Asp Ala Val Arg Arg Tyr Leu Thr
            450                 455                 460

Arg Lys Pro Met Thr Thr Lys Asp Leu Leu Lys Lys Phe Gln Thr Lys
465                 470                 475                 480
```

<210> SEQ ID NO 68
<211> LENGTH: 481
<212> TYPE: PRT
<213> ORGANISM: Homo sapiens

<400> SEQUENCE: 68

```
Met Ala Ala Leu Gly Pro Ser Ser Gln Asn Val Thr Glu Tyr Val Val
1               5                   10                  15

Arg Val Pro Lys Asn Thr Thr Lys Lys Tyr Asn Ile Met Ala Phe Asn
                20                  25                  30

Ala Ala Asp Lys Val Asn Phe Ala Thr Trp Asn Gln Ala Arg Leu Glu
            35                  40                  45

Arg Asp Leu Ser Asn Lys Lys Ile Tyr Gln Glu Glu Met Pro Glu
    50                  55                  60

Ser Gly Ala Gly Ser Glu Phe Asn Arg Lys Leu Arg Glu Glu Ala Arg
65              70                  75                  80

Arg Lys Lys Tyr Gly Ile Val Leu Lys Glu Phe Arg Pro Glu Asp Gln
                85                  90                  95

Pro Trp Leu Leu Arg Val Asn Gly Lys Ser Gly Arg Lys Phe Lys Gly
            100                 105                 110

Ile Lys Lys Gly Gly Val Thr Glu Asn Thr Ser Tyr Tyr Ile Phe Thr
        115                 120                 125

Gln Cys Pro Asp Gly Ala Phe Glu Ala Phe Pro Val His Asn Trp Tyr
    130                 135                 140

Asn Phe Thr Pro Leu Ala Arg His Arg Thr Leu Thr Ala Glu Glu Ala
145                 150                 155                 160

Glu Glu Glu Trp Glu Arg Arg Asn Lys Val Leu Asn His Phe Ser Ile
                165                 170                 175

Met Gln Gln Arg Arg Leu Lys Asp Gln Asp Gln Asp Glu Asp Glu Glu
            180                 185                 190

Glu Lys Glu Lys Arg Gly Arg Arg Lys Ala Ser Glu Leu Arg Ile His
        195                 200                 205

Asp Leu Glu Asp Leu Glu Met Ser Ser Ala Ser Asp Ala Ser
    210                 215                 220

Gly Glu Glu Gly Gly Arg Val Pro Lys Ala Lys Lys Ala Pro Leu
225             230                 235                 240

Ala Lys Gly Gly Arg Lys Lys Lys Lys Lys Gly Ser Asp Glu
                245                 250                 255

Ala Phe Glu Asp Ser Asp Asp Gly Asp Phe Glu Gly Gln Glu Val Asp
                260                 265                 270
```

-continued

```
Tyr Met Ser Asp Gly Ser Ser Ser Gln Glu Glu Pro Glu Ser Lys
            275                 280                 285

Ala Lys Ala Pro Gln Gln Glu Glu Gly Pro Lys Gly Val Asp Glu Gln
        290                 295                 300

Ser Asp Ser Ser Glu Glu Ser Glu Glu Glu Lys Pro Pro Glu Glu Asp
305                 310                 315                 320

Lys Glu Glu Glu Glu Lys Lys Ala Pro Thr Pro Gln Glu Lys Lys
                325                 330                 335

Arg Arg Lys Asp Ser Ser Glu Glu Ser Asp Ser Ser Glu Glu Ser Asp
            340                 345                 350

Ile Asp Ser Glu Ala Ser Ser Ala Phe Phe Met Ala Val Arg Pro Ser
        355                 360                 365

Pro Val Ala Gly Glu Ala Trp Ala Ser Val Cys Arg Leu Thr His Leu
370                 375                 380

Pro Thr Leu Thr Ser Ala Glu Glu Glu Asp Ala Thr Gln Glu Arg Ala
385                 390                 395                 400

Glu Ala Val Gly Arg Glu Leu Lys Gly Gln Gln Pro Pro Arg His Ala
                405                 410                 415

Gln Arg Arg Gly Trp Gln His Leu Leu His Pro Ala Gly Gly Cys Gln
            420                 425                 430

Gln Thr Arg Ala Arg Glu Ala Gly Glu Arg Asp Ala Cys Ser Gln Ala
        435                 440                 445

Val Ala Ala Gly His Gly Thr Pro Glu Pro Val Trp Glu Val Asp Thr
    450                 455                 460

Pro Ala Thr Ile Arg Gln Asp Asn Thr Gln Gln Arg Arg Arg Ala Gly
465                 470                 475                 480

Asp

<210> SEQ ID NO 69
<211> LENGTH: 217
<212> TYPE: PRT
<213> ORGANISM: Homo sapiens

<400> SEQUENCE: 69

Val Asp Glu Gln Ser Asp Ser Ser Glu Glu Ser Glu Glu Glu Lys Pro
1               5                   10                  15

Pro Glu Glu Asp Lys Glu Glu Glu Glu Lys Lys Ala Pro Thr Pro
            20                  25                  30

Gln Glu Lys Lys Arg Arg Lys Asp Ser Ser Glu Glu Ser Asp Ser Ser
        35                  40                  45

Glu Glu Ser Asp Ile Asp Ser Glu Ala Ser Ser Ala Leu Phe Met Ala
    50                  55                  60

Lys Lys Lys Thr Pro Pro Lys Arg Glu Arg Lys Pro Ser Gly Gly Ser
65                  70                  75                  80

Ser Arg Gly Asn Ser Arg Pro Gly Thr Pro Ser Ala Glu Gly Gly Ser
                85                  90                  95

Thr Ser Ser Thr Leu Arg Ala Ala Ala Ser Lys Leu Glu Gln Gly Lys
            100                 105                 110

Arg Val Ser Glu Met Pro Ala Ala Lys Arg Leu Arg Leu Asp Thr Gly
        115                 120                 125

Pro Gln Ser Leu Ser Gly Lys Ser Thr Pro Gln Pro Pro Ser Gly Lys
    130                 135                 140

Thr Thr Pro Asn Ser Gly Asp Val Gln Val Thr Glu Asp Ala Val Arg
145                 150                 155                 160
```

```
Arg Tyr Leu Thr Arg Lys Pro Met Thr Thr Lys Asp Leu Leu Lys Lys
                165                 170                 175

Phe Gln Thr Lys Lys Thr Gly Leu Ser Ser Glu Gln Thr Val Asn Val
            180                 185                 190

Leu Ala Gln Ile Leu Lys Arg Leu Asn Pro Glu Arg Lys Met Ile Asn
        195                 200                 205

Asp Lys Met His Phe Ser Leu Lys Glu
    210                 215

<210> SEQ ID NO 70
<211> LENGTH: 21
<212> TYPE: DNA
<213> ORGANISM: Artificial sequence
<220> FEATURE:
<223> OTHER INFORMATION: Primer

<400> SEQUENCE: 70
taccaagagg aggagaagga g                                           21

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
tcctctgagc tgtccgactc                                             20

<210> SEQ ID NO 72
<211> LENGTH: 178
<212> TYPE: PRT
<213> ORGANISM: Homo sapiens

<400> SEQUENCE: 72

Met Ala Ala Leu Gly Pro Ser Ser Gln Asn Val Thr Glu Tyr Val Val
1               5                   10                  15

Arg Val Pro Lys Asn Thr Thr Lys Lys Tyr Asn Ile Met Ala Phe Asn
            20                  25                  30

Ala Ala Asp Lys Val Asn Phe Ala Thr Trp Asn Gln Ala Arg Leu Glu
        35                  40                  45

Arg Asp Leu Ser Asn Lys Lys Ile Tyr Gln Glu Glu Lys Glu Lys
    50                  55                  60

Arg Gly Arg Arg Lys Ala Ser Glu Leu Arg Ile His Asp Leu Glu Asp
65                  70                  75                  80

Asp Leu Glu Met Ser Ser Asp Ala Ser Asp Ala Ser Gly Glu Glu Gly
                85                  90                  95

Gly Arg Val Pro Lys Ala Lys Lys Lys Ala Pro Leu Ala Lys Gly Gly
            100                 105                 110

Arg Lys Lys Lys Lys Lys Gly Ser Asp Glu Ala Phe Glu Asp
        115                 120                 125

Ser Asp Asp Gly Asp Phe Glu Gly Gln Glu Val Asp Tyr Met Ser Asp
    130                 135                 140

Gly Ser Ser Ser Gln Glu Glu Pro Glu Ser Lys Ala Lys Ala Pro
145                 150                 155                 160

Gln Gln Glu Glu Gly Pro Lys Gly Val Asp Gln Ser Asp Ser Ser
                165                 170                 175

Glu Glu
```

```
<210> SEQ ID NO 73
<211> LENGTH: 358
<212> TYPE: PRT
<213> ORGANISM: Homo sapiens

<400> SEQUENCE: 73

Met Ala Ala Leu Gly Pro Ser Ser Gln Asn Val Thr Glu Tyr Val Val
1               5                   10                  15

Arg Val Pro Lys Asn Thr Thr Lys Lys Tyr Asn Ile Met Ala Phe Asn
            20                  25                  30

Ala Ala Asp Lys Val Asn Phe Ala Thr Trp Asn Gln Ala Arg Leu Glu
        35                  40                  45

Arg Asp Leu Ser Asn Lys Lys Ile Tyr Gln Glu Glu Glu Met Pro Glu
    50                  55                  60

Ser Gly Ala Gly Ser Glu Phe Asn Arg Lys Leu Arg Glu Glu Ala Arg
65                  70                  75                  80

Arg Lys Lys Tyr Gly Ile Val Leu Lys Glu Phe Arg Pro Glu Asp Gln
                85                  90                  95

Pro Trp Leu Leu Arg Val Asn Gly Lys Ser Gly Arg Lys Phe Lys Gly
            100                 105                 110

Ile Lys Lys Gly Gly Val Thr Glu Asn Thr Ser Tyr Tyr Ile Phe Thr
        115                 120                 125

Gln Cys Pro Asp Gly Ala Phe Glu Ala Phe Pro Val His Asn Trp Tyr
    130                 135                 140

Asn Phe Thr Pro Leu Ala Arg His Arg Thr Leu Thr Ala Glu Ala
145                 150                 155                 160

Glu Glu Glu Trp Glu Arg Arg Asn Lys Val Leu Asn His Phe Ser Ile
                165                 170                 175

Met Gln Gln Arg Arg Leu Lys Asp Gln Asp Gln Asp Glu Asp Glu Glu
            180                 185                 190

Glu Lys Glu Lys Arg Gly Arg Arg Lys Ala Ser Glu Leu Arg Ile His
        195                 200                 205

Asp Leu Glu Asp Asp Leu Glu Met Ser Ser Asp Ala Ser Asp Ala Ser
    210                 215                 220

Gly Glu Glu Gly Gly Arg Val Pro Lys Ala Lys Lys Ala Pro Leu
225                 230                 235                 240

Ala Lys Gly Gly Arg Lys Lys Lys Lys Lys Gly Ser Asp Asp Glu
                245                 250                 255

Ala Phe Glu Asp Ser Asp Asp Gly Asp Phe Glu Gly Gln Glu Val Asp
            260                 265                 270

Tyr Met Ser Asp Gly Ser Ser Ser Gln Glu Glu Pro Glu Ser Lys
    275                 280                 285

Ala Lys Ala Pro Gln Gln Glu Glu Gly Pro Lys Gly Val Asp Glu Gln
    290                 295                 300

Ser Asp Ser Ser Glu Glu Ser Glu Glu Glu Lys Pro Pro Glu Glu Asp
305                 310                 315                 320

Lys Glu Glu Glu Glu Lys Lys Ala Pro Thr Pro Gln Glu Lys Lys
                325                 330                 335

Arg Arg Lys Asp Ser Ser Glu Glu Ser Asp Ser Ser Glu Glu Ser Asp
            340                 345                 350

Ile Asp Ser Glu Ala Ser
        355

<210> SEQ ID NO 74
<211> LENGTH: 20
<212> TYPE: DNA
```

```
<213> ORGANISM: Artificial sequence
<220> FEATURE:
<223> OTHER INFORMATION: Primer

<400> SEQUENCE: 74
cagagaacac gtcctactac                                                   20

<210> SEQ ID NO 75
<211> LENGTH: 19
<212> TYPE: DNA
<213> ORGANISM: Artificial sequence
<220> FEATURE:
<223> OTHER INFORMATION: Primer

<400> SEQUENCE: 75
cagagaacac gtcctacta                                                    19

<210> SEQ ID NO 76
<211> LENGTH: 183
<212> TYPE: PRT
<213> ORGANISM: Homo sapiens

<400> SEQUENCE: 76

Met Gln Gln Arg Arg Leu Lys Asp Gln Asp Gln Asp Glu Asp Glu Glu
1               5                  10                  15

Glu Lys Glu Lys Arg Gly Arg Arg Lys Ala Ser Glu Leu Arg Ile His
            20                  25                  30

Asp Leu Glu Asp Asp Leu Glu Met Ser Ser Asp Ala Ser Asp Ala Ser
        35                  40                  45

Gly Glu Glu Gly Gly Arg Val Pro Lys Ala Lys Lys Ala Pro Leu
    50                  55                  60

Ala Lys Gly Gly Arg Lys Lys Lys Lys Lys Gly Ser Asp Asp Glu
65                  70                  75                  80

Ala Phe Glu Asp Ser Asp Asp Gly Asp Phe Glu Gly Gln Glu Val Asp
                85                  90                  95

Tyr Met Ser Asp Gly Ser Ser Ser Gln Glu Glu Pro Glu Ser Lys
            100                 105                 110

Ala Lys Ala Pro Gln Gln Glu Glu Gly Pro Lys Gly Val Asp Glu Gln
        115                 120                 125

Ser Asp Ser Ser Glu Glu Ser Glu Glu Lys Pro Pro Glu Lys Pro
    130                 135                 140

Pro Pro Gly Ser Ala Ser Leu Thr Leu Thr Lys Gly Leu Cys Cys Pro
145                 150                 155                 160

Leu Gly Asn Phe Tyr Ser Ser Pro Phe His Phe Pro Lys Ser Leu Phe
                165                 170                 175

Ser Cys Asp Leu Ser Thr Thr
            180

<210> SEQ ID NO 77
<211> LENGTH: 240
<212> TYPE: PRT
<213> ORGANISM: Homo sapiens

<400> SEQUENCE: 77

Asn Thr Ser Tyr Tyr Ile Phe Thr Gln Cys Pro Asp Gly Ala Phe Glu
1               5                  10                  15

Ala Phe Pro Val His Asn Trp Tyr Asn Phe Thr Pro Leu Ala Arg His
            20                  25                  30

Arg Thr Leu Thr Ala Glu Glu Ala Glu Glu Glu Trp Glu Arg Arg Asn
        35                  40                  45
```

-continued

Lys Val Leu Asn His Phe Ser Ile Met Gln Gln Arg Arg Leu Lys Asp
            50                  55                  60

Gln Asp Gln Asp Glu Asp Glu Glu Lys Glu Lys Arg Gly Arg Arg
 65                  70                  75                  80

Lys Ala Ser Glu Leu Arg Ile His Asp Leu Asp Asp Leu Glu Met
                85                  90                  95

Ser Ser Asp Ala Ser Asp Ala Ser Gly Glu Glu Gly Gly Arg Val Pro
               100                 105                 110

Lys Ala Lys Lys Lys Ala Pro Leu Ala Lys Gly Gly Arg Lys Lys Lys
               115                 120                 125

Lys Lys Lys Gly Ser Asp Asp Glu Ala Phe Glu Asp Ser Asp Asp Gly
       130                 135                 140

Asp Phe Glu Gly Gln Glu Val Asp Tyr Met Ser Asp Gly Ser Ser Ser
145                 150                 155                 160

Ser Gln Glu Glu Pro Glu Ser Lys Ala Lys Ala Pro Gln Gln Glu Glu
               165                 170                 175

Gly Pro Lys Gly Val Asp Glu Gln Ser Asp Ser Ser Glu Glu Ser Glu
               180                 185                 190

Glu Glu Lys Pro Pro Glu Glu Asp Lys Glu Glu Glu Glu Lys Lys
               195                 200                 205

Ala Pro Thr Pro Gln Lys Lys Arg Arg Lys Asp Ser Ser Glu Glu
210                 215                 220

Ser Asp Ser Ser Glu Glu Ser Asp Ile Asp Ser Glu Ala Ser Ala
225                 230                 235                 240

<210> SEQ ID NO 78
<211> LENGTH: 19
<212> TYPE: DNA
<213> ORGANISM: Artificial sequence
<220> FEATURE:
<223> OTHER INFORMATION: Primer

<400> SEQUENCE: 78
agacacggac agcgacgaa                                                19

<210> SEQ ID NO 79
<211> LENGTH: 19
<212> TYPE: DNA
<213> ORGANISM: Artificial sequence
<220> FEATURE:
<223> OTHER INFORMATION: Primer

<400> SEQUENCE: 79
accacctgaa gcttgcctc                                                19

<210> SEQ ID NO 80
<211> LENGTH: 153
<212> TYPE: PRT
<213> ORGANISM: Homo sapiens

<400> SEQUENCE: 80

Met Glu Gly Glu Ser Val Leu Asp Asp Glu Cys Lys Lys His Leu Ala
 1               5                  10                  15

Gly Leu Gly Ala Leu Gly Leu Gly Ser Leu Ile Thr Glu Leu Thr Ala
                20                  25                  30

Asn Glu Glu Leu Thr Gly Thr Asp Gly Ala Leu Val Asn Asp Glu Gly
            35                  40                  45

Trp Val Arg Ser Thr Glu Val Lys Asp Pro Trp Asn Leu Ser Asn Asp
        50                  55                  60

-continued

```
Glu Tyr Tyr Tyr Pro Lys Gln Gln Gly Leu Arg Gly Thr Phe Gly Gly
 65                  70                  75                  80

Asn Ile Ile Gln His Ser Ile Pro Ala Val Glu Leu Arg Gln Pro Phe
                 85                  90                  95

Phe Pro Thr His Met Gly Pro Ile Lys Leu Arg Gln Phe His Arg Pro
            100                 105                 110

Pro Leu Lys Lys Tyr Ser Phe Gly Ala Leu Ser Gln Pro Gly Pro His
        115                 120                 125

Ser Val Gln Pro Leu Leu Lys His Ile Lys Lys Lys Ala Glu Met Arg
    130                 135                 140

Glu Gln Glu Arg Gln Ala Ser Gly Gly
145                 150

<210> SEQ ID NO 81
<211> LENGTH: 660
<212> TYPE: PRT
<213> ORGANISM: Homo sapiens

<400> SEQUENCE: 81

Met Gly Pro Gly Cys Asp Leu Leu Leu Arg Thr Ala Ala Thr Ile Thr
  1               5                  10                  15

Ala Ala Ala Ile Met Ser Asp Thr Asp Ser Asp Glu Asp Ser Ala Gly
             20                  25                  30

Gly Gly Pro Phe Ser Leu Ala Gly Phe Leu Phe Gly Asn Ile Asn Gly
         35                  40                  45

Ala Gly Gln Leu Glu Gly Glu Ser Val Leu Asp Asp Glu Cys Lys Lys
     50                  55                  60

His Leu Ala Gly Leu Gly Ala Leu Gly Leu Gly Ser Leu Ile Thr Glu
 65                  70                  75                  80

Leu Thr Ala Asn Glu Glu Leu Thr Gly Thr Asp Gly Ala Leu Val Asn
                 85                  90                  95

Asp Glu Gly Trp Val Arg Ser Thr Glu Asp Ala Val Asp Tyr Ser Asp
            100                 105                 110

Ile Asn Glu Val Ala Glu Asp Glu Ser Arg Arg Tyr Gln Gln Thr Met
        115                 120                 125

Gly Ser Leu Gln Pro Leu Cys His Ser Asp Tyr Asp Glu Asp Asp Tyr
    130                 135                 140

Asp Ala Asp Cys Glu Asp Ile Asp Cys Lys Leu Met Pro Pro Pro Pro
145                 150                 155                 160

Pro Pro Pro Gly Pro Met Lys Lys Asp Lys Asp Gln Asp Ser Ile Thr
                165                 170                 175

Gly Glu Lys Val Asp Phe Ser Ser Ser Asp Ser Glu Ser Glu Met Gly
            180                 185                 190

Gly Pro Gln Glu Ala Thr Gln Ala Glu Ser Glu Asp Gly Lys Leu Thr
        195                 200                 205

Leu Pro Leu Ala Gly Ile Met Gln His Asp Ala Thr Lys Leu Leu Pro
    210                 215                 220

Ser Val Thr Glu Leu Phe Pro Glu Phe Arg Pro Gly Lys Val Leu Arg
225                 230                 235                 240

Phe Leu Arg Leu Phe Gly Pro Gly Lys Asn Val Pro Ser Val Trp Arg
                245                 250                 255

Ser Ala Arg Arg Lys Arg Lys Lys Lys His Arg Glu Leu Ile Gln Glu
            260                 265                 270

Glu Gln Ile Gln Glu Val Glu Cys Ser Val Glu Ser Glu Val Ser Gln
        275                 280                 285
```

```
Lys Ser Leu Trp Asn Tyr Asp Tyr Ala Pro Pro Pro Glu Gln
    290                 295                 300

Cys Leu Ser Asp Asp Glu Ile Thr Met Met Ala Pro Val Glu Ser Lys
305                 310                 315                 320

Phe Ser Gln Ser Thr Gly Asp Ile Asp Lys Val Thr Asp Thr Lys Pro
                325                 330                 335

Arg Val Ala Glu Trp Arg Tyr Gly Pro Ala Arg Leu Trp Tyr Asp Met
            340                 345                 350

Leu Gly Val Pro Glu Asp Gly Ser Gly Phe Asp Tyr Gly Phe Lys Leu
        355                 360                 365

Arg Lys Thr Glu His Glu Pro Val Ile Lys Ser Arg Met Ile Glu Glu
    370                 375                 380

Phe Arg Lys Leu Glu Glu Asn Asn Gly Thr Asp Leu Leu Ala Asp Glu
385                 390                 395                 400

Asn Phe Leu Met Val Thr Gln Leu His Trp Glu Asp Asp Ile Ile Trp
                405                 410                 415

Asp Gly Glu Asp Val Lys His Lys Gly Thr Lys Pro Gln Arg Ala Ser
            420                 425                 430

Leu Ala Gly Trp Leu Pro Ser Ser Met Thr Arg Asn Ala Met Ala Tyr
        435                 440                 445

Asn Val Gln Gln Gly Phe Ala Ala Thr Leu Asp Asp Asp Lys Pro Trp
    450                 455                 460

Tyr Ser Ile Phe Pro Ile Asp Asn Glu Asp Leu Val Tyr Gly Arg Trp
465                 470                 475                 480

Glu Asp Asn Ile Ile Trp Asp Ala Gln Ala Met Pro Arg Leu Leu Glu
                485                 490                 495

Pro Pro Val Leu Thr Leu Asp Pro Asn Asp Glu Asn Leu Ile Leu Glu
            500                 505                 510

Ile Pro Asp Glu Lys Glu Glu Ala Thr Ser Asn Ser Pro Ser Lys Glu
        515                 520                 525

Ser Lys Lys Glu Ser Ser Leu Lys Lys Ser Arg Ile Leu Leu Gly Lys
    530                 535                 540

Thr Gly Val Ile Lys Glu Glu Pro Gln Gln Asn Met Ser Gln Pro Glu
545                 550                 555                 560

Val Lys Asp Pro Trp Asn Leu Ser Asn Asp Glu Tyr Tyr Tyr Pro Lys
                565                 570                 575

Gln Gln Gly Leu Arg Gly Thr Phe Gly Gly Asn Ile Ile Gln His Ser
            580                 585                 590

Ile Pro Ala Val Glu Leu Arg Gln Pro Phe Phe Pro Thr His Met Gly
        595                 600                 605

Pro Ile Lys Leu Arg Gln Phe His Arg Pro Pro Leu Lys Lys Tyr Ser
    610                 615                 620

Phe Gly Ala Leu Ser Gln Pro Gly Pro His Ser Val Gln Pro Leu Leu
625                 630                 635                 640

Lys His Ile Lys Lys Lys Ala Lys Met Arg Glu Gln Glu Arg Gln Ala
                645                 650                 655

Ser Gly Gly Gly
        660

<210> SEQ ID NO 82
<211> LENGTH: 153
<212> TYPE: PRT
<213> ORGANISM: Homo sapiens

<400> SEQUENCE: 82
```

```
Leu Glu Gly Glu Ser Val Leu Asp Asp Glu Cys Lys Lys His Leu Ala
1               5                   10                  15

Gly Leu Gly Ala Leu Gly Leu Gly Ser Leu Ile Thr Glu Leu Thr Ala
                20                  25                  30

Asn Glu Glu Leu Thr Gly Thr Asp Gly Ala Leu Val Asn Asp Glu Gly
                35                  40                  45

Trp Val Arg Ser Thr Glu Val Lys Asp Pro Trp Asn Leu Ser Asn Asp
50                  55                  60

Glu Tyr Tyr Tyr Pro Lys Gln Gln Gly Leu Arg Gly Thr Phe Gly Gly
65                  70                  75                  80

Asn Ile Ile Gln His Ser Ile Pro Ala Val Glu Leu Arg Gln Pro Phe
                85                  90                  95

Phe Pro Thr His Met Gly Pro Ile Lys Leu Arg Gln Phe His Arg Pro
                100                 105                 110

Pro Leu Lys Lys Tyr Ser Phe Gly Ala Leu Ser Gln Pro Gly Pro His
                115                 120                 125

Ser Val Gln Pro Leu Leu Lys His Ile Lys Lys Ala Glu Met Arg
                130                 135                 140

Glu Gln Glu Arg Gln Ala Ser Gly Gly
145                 150

<210> SEQ ID NO 83
<211> LENGTH: 111
<212> TYPE: PRT
<213> ORGANISM: Homo sapiens

<400> SEQUENCE: 83

Met Glu Gly Glu Ser Val Leu Asp Asp Glu Cys Lys Lys His Leu Ala
1               5                   10                  15

Gly Leu Gly Ala Leu Gly Leu Gly Ser Leu Ile Thr Glu Leu Thr Ala
                20                  25                  30

Asn Glu Glu Leu Thr Gly Thr Asp Gly Ala Leu Val Asn Asp Glu Gly
                35                  40                  45

Trp Val Arg Ser Thr Glu Asp Ala Val Asp Tyr Ser Asp Ile Lys Leu
50                  55                  60

Arg Gln Phe His Arg Pro Leu Lys Lys Tyr Ser Phe Gly Ala Leu
65                  70                  75                  80

Ser Gln Pro Gly Pro His Ser Val Gln Pro Leu Leu Lys His Ile Lys
                85                  90                  95

Lys Lys Ala Lys Met Arg Glu Gln Glu Arg Gln Ala Ser Gly Gly
                100                 105                 110

<210> SEQ ID NO 84
<211> LENGTH: 77
<212> TYPE: PRT
<213> ORGANISM: Homo sapiens

<400> SEQUENCE: 84

Met Glu Gly Glu Ser Val Leu Asp Asp Glu Cys Lys Lys His Leu Ala
1               5                   10                  15

Gly Leu Gly Ala Leu Gly Leu Gly Ser Leu Ile Thr Glu Leu Arg Gln
                20                  25                  30

Phe His Arg Pro Pro Leu Lys Lys Tyr Ser Phe Gly Ala Leu Ser Gln
                35                  40                  45

Pro Gly Pro His Ser Val Gln Pro Leu Leu Lys His Ile Lys Lys Lys
50                  55                  60
```

Ala Lys Met Arg Glu Gln Glu Arg Gln Ala Ser Gly Gly
 65                  70                  75

<210> SEQ ID NO 85
<211> LENGTH: 22
<212> TYPE: DNA
<213> ORGANISM: Artificial sequence
<220> FEATURE:
<223> OTHER INFORMATION: Primer

<400> SEQUENCE: 85
gagctttctg gatgatgtaa ac                                              22

<210> SEQ ID NO 86
<211> LENGTH: 21
<212> TYPE: DNA
<213> ORGANISM: Artificial sequence
<220> FEATURE:
<223> OTHER INFORMATION: Primer

<400> SEQUENCE: 86
ctcctcatca tcatacccTt c                                               21

<210> SEQ ID NO 87
<211> LENGTH: 205
<212> TYPE: PRT
<213> ORGANISM: Homo sapiens

<400> SEQUENCE: 87

Met Asp Asp Val Asn Leu Ile Leu Ala Asn Ser Val Lys Tyr Asn Gly
 1               5                  10                  15

Pro Glu Ser Gln Tyr Thr Lys Thr Ala Gln Glu Ile Val Asn Val Cys
             20                  25                  30

Tyr Gln Thr Leu Thr Glu Tyr Asp Glu His Leu Thr Gln Leu Glu Lys
         35                  40                  45

Asp Ile Cys Thr Ala Lys Glu Ala Ala Leu Glu Glu Ala Glu Leu Glu
     50                  55                  60

Ser Leu Asp Pro Met Thr Pro Gly Pro Tyr Thr Pro Gln Pro Pro Asp
 65                  70                  75                  80

Leu Tyr Asp Thr Asn Thr Ser Leu Ser Met Ser Arg Asp Ala Ser Val
                 85                  90                  95

Phe Gln Asp Glu Ser Asn Met Ser Val Leu Asp Ile Pro Ser Ala Thr
            100                 105                 110

Pro Glu Lys Gln Val Thr Gln Met Arg Gln Gly Arg Gly Arg Leu Gly
        115                 120                 125

Glu Glu Asp Ser Asp Val Asp Ile Glu Gly Tyr Asp Asp Glu Glu Glu
    130                 135                 140

Asp Gly Lys Pro Lys Thr Pro Ala Pro Glu Gly Glu Asp Gly Asp Gly
145                 150                 155                 160

Asp Leu Ala Asp Glu Glu Glu Gly Thr Val Gln Gln Pro Gln Ala Ser
                165                 170                 175

Val Leu Tyr Glu Asp Leu Leu Met Ser Glu Gly Glu Asp Asp Glu Glu
            180                 185                 190

Asp Ala Gly Ser Asp Glu Glu Gly Asp Asn Pro Phe Ser
        195                 200                 205

<210> SEQ ID NO 88
<211> LENGTH: 206
<212> TYPE: PRT
<213> ORGANISM: Homo sapiens

```
<400> SEQUENCE: 88

Lys Tyr Gln Ser Arg Glu Ser Phe Leu Asp Asp Val Asn Leu Ile Leu
1               5                   10                  15

Ala Asn Ser Val Lys Tyr Asn Gly Pro Glu Ser Gln Tyr Thr Lys Thr
            20                  25                  30

Ala Gln Glu Ile Val Asn Val Cys Tyr Gln Thr Leu Thr Glu Tyr Asp
        35                  40                  45

Glu His Leu Thr Gln Leu Glu Lys Asp Ile Cys Thr Ala Lys Glu Ala
    50                  55                  60

Ala Leu Glu Glu Ala Glu Leu Glu Ser Leu Asp Pro Met Thr Pro Gly
65                  70                  75                  80

Pro Tyr Thr Pro Gln Pro Pro Asp Leu Tyr Asp Thr Asn Thr Ser Leu
                85                  90                  95

Ser Met Ser Arg Asp Ala Ser Val Phe Gln Asp Glu Ser Asn Met Ser
            100                 105                 110

Val Leu Asp Ile Pro Ser Ala Thr Pro Glu Lys Gln Val Thr Gln Glu
        115                 120                 125

Gly Glu Asp Gly Asp Gly Asp Leu Ala Asp Glu Glu Gly Thr Val
    130                 135                 140

Gln Gln Pro Gln Ala Ser Val Leu Tyr Glu Asp Leu Leu Met Ser Glu
145                 150                 155                 160

Gly Glu Asp Asp Glu Gly Asp Ala Gly Ser Glu Glu Gly Asp Asn
                165                 170                 175

Pro Phe Ser Ala Ile Gln Leu Ser Glu Ser Gly Ser Asp Ser Asp Val
            180                 185                 190

Gly Ser Gly Gly Ile Arg Pro Lys Gln Pro Arg Met Leu Gln
        195                 200                 205

<210> SEQ ID NO 89
<211> LENGTH: 22
<212> TYPE: DNA
<213> ORGANISM: Artificial sequence
<220> FEATURE:
<223> OTHER INFORMATION: Primer

<400> SEQUENCE: 89
gagctttctg gatgatgtaa ac                                              22

<210> SEQ ID NO 90
<211> LENGTH: 21
<212> TYPE: DNA
<213> ORGANISM: Artificial sequence
<220> FEATURE:
<223> OTHER INFORMATION: Primer

<400> SEQUENCE: 90
ctcctcatca tcatacccctt c                                              21

<210> SEQ ID NO 91
<211> LENGTH: 1466
<212> TYPE: PRT
<213> ORGANISM: Homo sapiens

<400> SEQUENCE: 91

Met Gly Pro Gly Cys Asp Leu Leu Leu Arg Thr Ala Thr Ile Thr
1               5                   10                  15

Ala Ala Ala Ile Met Ser Asp Thr Asp Ser Asp Glu Asp Ser Ala Gly
            20                  25                  30

Gly Gly Pro Phe Ser Leu Ala Gly Phe Leu Phe Gly Asn Ile Asn Gly
```

```
            35                  40                  45
Ala Gly Gln Leu Glu Gly Glu Ser Val Leu Asp Asp Glu Cys Lys Lys
 50                  55                  60
His Leu Ala Gly Leu Gly Ala Leu Gly Leu Gly Ser Leu Ile Thr Glu
 65                  70                  75                  80
Leu Thr Ala Asn Glu Glu Leu Thr Gly Thr Asp Gly Ala Leu Val Asn
                 85                  90                  95
Asp Glu Gly Trp Val Arg Ser Thr Glu Asp Ala Val Asp Tyr Ser Asp
                100                 105                 110
Ile Asn Glu Val Ala Glu Asp Glu Ser Arg Arg Tyr Gln Gln Thr Met
            115                 120                 125
Gly Ser Leu Gln Pro Leu Cys His Ser Asp Tyr Asp Glu Asp Asp Tyr
130                 135                 140
Asp Ala Asp Cys Glu Asp Ile Asp Cys Lys Leu Met Pro Pro Pro Pro
145                 150                 155                 160
Pro Pro Pro Gly Pro Met Lys Lys Asp Lys Asp Gln Asp Ser Ile Thr
                165                 170                 175
Gly Glu Lys Val Asp Phe Ser Ser Ser Asp Ser Glu Ser Glu Met
                180                 185                 190
Gly Pro Gln Glu Ala Thr Gln Ala Glu Ser Glu Asp Gly Lys Leu Thr
            195                 200                 205
Leu Pro Leu Ala Gly Ile Met Gln His Asp Ala Thr Lys Leu Leu Pro
210                 215                 220
Ser Val Thr Glu Leu Phe Pro Glu Phe Arg Pro Gly Lys Val Leu Arg
225                 230                 235                 240
Phe Leu Arg Leu Phe Gly Pro Gly Lys Asn Val Pro Ser Val Trp Arg
                245                 250                 255
Ser Ala Arg Arg Lys Arg Lys Lys His Arg Glu Leu Ile Gln Glu
                260                 265                 270
Glu Gln Ile Gln Glu Val Glu Cys Ser Val Ser Glu Val Ser Gln
            275                 280                 285
Lys Ser Leu Trp Asn Tyr Asp Tyr Ala Pro Pro Pro Pro Glu Gln
290                 295                 300
Cys Leu Ser Asp Asp Glu Ile Thr Met Met Ala Pro Val Glu Ser Lys
305                 310                 315                 320
Phe Ser Gln Ser Thr Gly Asp Ile Asp Lys Val Thr Asp Thr Lys Pro
                325                 330                 335
Arg Val Ala Glu Trp Arg Tyr Gly Pro Ala Arg Leu Trp Tyr Asp Met
            340                 345                 350
Leu Gly Val Pro Glu Asp Gly Ser Gly Phe Asp Tyr Gly Phe Lys Leu
            355                 360                 365
Arg Lys Thr Glu His Glu Pro Val Ile Lys Ser Arg Met Ile Glu Glu
            370                 375                 380
Phe Arg Lys Leu Glu Glu Asn Asn Gly Thr Asp Leu Leu Ala Asp Glu
385                 390                 395                 400
Asn Phe Leu Met Val Thr Gln Leu His Trp Glu Asp Asp Ile Ile Trp
                405                 410                 415
Asp Gly Glu Asp Val Lys His Lys Gly Thr Lys Pro Gln Arg Ala Ser
            420                 425                 430
Leu Ala Gly Trp Leu Pro Ser Ser Met Thr Arg Asn Ala Met Ala Tyr
            435                 440                 445
Asn Val Gln Gln Gly Phe Ala Ala Thr Leu Asp Asp Lys Pro Trp
450                 455                 460
```

```
Tyr Ser Ile Phe Pro Ile Asp Asn Glu Asp Leu Val Tyr Gly Arg Trp
465                 470                 475                 480

Glu Asp Asn Ile Ile Trp Asp Ala Gln Ala Met Pro Arg Leu Leu Glu
            485                 490                 495

Pro Pro Val Leu Thr Leu Asp Pro Asn Asp Glu Asn Leu Ile Leu Glu
        500                 505                 510

Ile Pro Asp Glu Lys Glu Ala Thr Ser Asn Ser Pro Ser Lys Glu
        515                 520                 525

Ser Lys Lys Glu Ser Ser Leu Lys Lys Ser Arg Ile Leu Leu Gly Lys
        530                 535                 540

Thr Gly Val Ile Lys Glu Pro Gln Gln Asn Met Ser Gln Pro Glu
545                 550                 555                 560

Val Lys Asp Pro Trp Asn Leu Ser Asn Asp Glu Tyr Tyr Pro Lys
                565                 570                 575

Gln Gln Gly Leu Arg Gly Thr Phe Gly Gly Asn Ile Ile Gln His Ser
            580                 585                 590

Ile Pro Ala Val Glu Leu Arg Gln Pro Phe Phe Pro Thr His Met Gly
        595                 600                 605

Pro Ile Lys Leu Arg Gln Phe His Arg Pro Pro Leu Lys Lys Tyr Ser
        610                 615                 620

Phe Gly Ala Leu Ser Gln Pro Gly Pro His Ser Val Gln Pro Leu Leu
625                 630                 635                 640

Lys His Ile Lys Lys Lys Ala Lys Met Arg Glu Gln Glu Arg Gln Ala
                645                 650                 655

Ser Gly Gly Gly Glu Met Phe Phe Met Arg Thr Pro Gln Asp Leu Thr
                660                 665                 670

Gly Lys Asp Gly Asp Leu Ile Leu Ala Glu Tyr Ser Glu Glu Asn Gly
        675                 680                 685

Pro Leu Met Met Gln Val Gly Met Ala Thr Lys Ile Lys Asn Tyr Tyr
        690                 695                 700

Lys Arg Lys Pro Gly Lys Asp Pro Gly Ala Pro Asp Cys Lys Tyr Gly
705                 710                 715                 720

Glu Thr Val Tyr Cys His Thr Ser Pro Phe Leu Gly Ser Leu His Pro
                725                 730                 735

Gly Gln Leu Leu Gln Ala Phe Glu Asn Asn Leu Phe Arg Ala Pro Ile
            740                 745                 750

Tyr Leu His Lys Met Pro Glu Thr Asp Phe Leu Ile Ile Arg Thr Arg
        755                 760                 765

Gln Gly Tyr Tyr Ile Arg Glu Leu Val Asp Ile Phe Val Val Gly Gln
        770                 775                 780

Gln Cys Pro Leu Phe Glu Val Pro Gly Pro Asn Ser Lys Arg Ala Asn
785                 790                 795                 800

Thr His Ile Arg Asp Phe Leu Gln Val Phe Ile Tyr Arg Leu Phe Trp
        805                 810                 815

Lys Ser Lys Asp Arg Pro Arg Arg Ile Arg Met Glu Asp Ile Lys Lys
                820                 825                 830

Ala Phe Pro Ser His Ser Glu Ser Ser Ile Arg Lys Arg Leu Lys Leu
        835                 840                 845

Cys Ala Asp Phe Lys Arg Thr Gly Met Asp Ser Asn Trp Trp Val Leu
850                 855                 860

Lys Ser Asp Phe Arg Leu Pro Thr Glu Glu Ile Arg Ala Met Val
865                 870                 875                 880

Ser Pro Glu Gln Cys Cys Ala Tyr Tyr Ser Met Ile Ala Ala Glu Gln
                885                 890                 895
```

```
Arg Leu Lys Asp Ala Gly Tyr Gly Glu Lys Ser Phe Ala Pro Glu
         900                 905                 910
Glu Glu Asn Glu Glu Asp Phe Gln Met Lys Ile Asp Asp Glu Val Arg
         915                 920                 925
Thr Ala Pro Trp Asn Thr Thr Arg Ala Phe Ile Ala Ala Met Lys Gly
         930                 935                 940
Lys Cys Leu Leu Glu Val Thr Gly Val Ala Asp Pro Thr Gly Cys Gly
945                 950                 955                 960
Glu Gly Phe Ser Tyr Val Lys Ile Pro Asn Lys Pro Thr Gln Gln Lys
                 965                 970                 975
Asp Lys Glu Pro Gln Pro Val Lys Lys Thr Val Thr Gly Thr Asp
         980                 985                 990
Ala Asp Leu Arg Arg Leu Ser Leu Lys Asn Ala Lys Gln Leu Leu Arg
         995                 1000                1005
Lys Phe Gly Val Pro Glu Glu Ile Lys Lys Leu Ser Arg Trp
    1010                1015                1020
Glu Val Ile Asp Val Val Arg Thr Met Ser Thr Glu Gln Ala Arg
    1025                1030                1035
Ser Gly Glu Gly Pro Met Ser Lys Phe Ala Arg Gly Ser Arg Phe
    1040                1045                1050
Ser Val Ala Glu His Gln Glu Arg Tyr Lys Glu Cys Gln Arg
    1055                1060                1065
Ile Phe Asp Leu Gln Asn Lys Val Leu Ser Ser Thr Glu Val Leu
    1070                1075                1080
Ser Thr Asp Thr Asp Ser Ser Ala Glu Asp Ser Asp Phe Glu
    1085                1090                1095
Glu Met Gly Lys Asn Ile Glu Asn Met Leu Gln Asn Lys Lys Thr
    1100                1105                1110
Ser Ser Gln Leu Ser Arg Glu Arg Glu Gln Glu Arg Lys Glu
    1115                1120                1125
Leu Gln Arg Met Leu Leu Ala Ala Gly Ser Ala Ala Ser Gly Asn
    1130                1135                1140
Asn His Arg Asp Asp Asp Thr Ala Ser Val Thr Ser Leu Asn Ser
    1145                1150                1155
Ser Ala Thr Gly Arg Cys Leu Lys Ile Tyr Arg Thr Phe Arg Asp
    1160                1165                1170
Glu Glu Gly Lys Glu Tyr Val Arg Cys Glu Thr Val Arg Lys Pro
    1175                1180                1185
Ala Val Ile Asp Ala Tyr Val Arg Ile Arg Thr Thr Lys Asp Glu
    1190                1195                1200
Glu Phe Ile Arg Lys Phe Ala Leu Phe Asp Glu Gln His Arg Glu
    1205                1210                1215
Glu Met Arg Lys Glu Arg Arg Arg Ile Gln Glu Gln Leu Arg Arg
    1220                1225                1230
Leu Lys Arg Asn Gln Glu Lys Glu Lys Leu Lys Gly Pro Pro Glu
    1235                1240                1245
Lys Lys Pro Lys Lys Met Lys Glu Arg Pro Asp Leu Lys Leu Lys
    1250                1255                1260
Cys Gly Ala Cys Gly Ala Ile Gly His Met Arg Thr Asn Lys Phe
    1265                1270                1275
Cys Pro Leu Tyr Tyr Gln Thr Asn Ala Pro Pro Ser Asn Pro Val
    1280                1285                1290
Ala Met Thr Glu Glu Gln Glu Glu Glu Leu Glu Lys Thr Val Ile
```

```
                1295                1300                1305
His Asn Asp Asn Glu Glu Leu Ile Lys Val Glu Gly Thr Lys Ile
    1310                1315                1320
Val Leu Gly Lys Gln Leu Ile Glu Ser Ala Asp Glu Val Arg Arg
    1325                1330                1335
Lys Ser Leu Val Leu Lys Phe Pro Lys Gln Gln Leu Pro Pro Lys
    1340                1345                1350
Lys Lys Arg Arg Val Gly Thr Thr Val His Cys Asp Tyr Leu Asn
    1355                1360                1365
Arg Pro His Lys Ser Ile His Arg Arg Thr Asp Pro Met Val
    1370                1375                1380
Thr Leu Ser Ser Ile Leu Glu Ser Ile Ile Asn Asp Met Arg Asp
    1385                1390                1395
Leu Pro Asn Thr Tyr Pro Phe His Thr Pro Val Asn Ala Lys Val
    1400                1405                1410
Val Lys Asp Tyr Tyr Lys Ile Ile Thr Arg Pro Met Asp Leu Gln
    1415                1420                1425
Thr Leu Arg Glu Asn Val Arg Lys Arg Leu Tyr Pro Ser Arg Glu
    1430                1435                1440
Glu Phe Arg Glu His Leu Glu Leu Ile Val Lys Asn Ser Ala Thr
    1445                1450                1455
Tyr Asn Ala Gly Ser Phe Ser Ile
    1460                1465

<210> SEQ ID NO 92
<211> LENGTH: 1872
<212> TYPE: PRT
<213> ORGANISM: Homo sapiens

<400> SEQUENCE: 92

Met Gly Pro Gly Cys Asp Leu Leu Arg Thr Ala Ala Thr Ile Thr
1               5                   10                  15
Ala Ala Ala Ile Met Ser Asp Thr Asp Ser Asp Glu Asp Ser Ala Gly
            20                  25                  30
Gly Gly Pro Phe Ser Leu Ala Gly Phe Leu Phe Gly Asn Ile Asn Gly
        35                  40                  45
Ala Gly Gln Leu Glu Gly Glu Ser Val Leu Asp Asp Glu Cys Lys Lys
    50                  55                  60
His Leu Ala Gly Leu Gly Ala Leu Gly Leu Gly Ser Leu Ile Thr Glu
65                  70                  75                  80
Leu Thr Ala Asn Glu Glu Leu Thr Gly Thr Asp Gly Ala Leu Val Asn
                85                  90                  95
Asp Glu Gly Trp Val Arg Ser Thr Glu Asp Ala Val Asp Tyr Ser Asp
            100                 105                 110
Ile Asn Glu Val Ala Glu Asp Glu Ser Arg Arg Tyr Gln Gln Thr Met
        115                 120                 125
Gly Ser Leu Gln Pro Leu Cys His Ser Asp Tyr Asp Glu Asp Tyr
    130                 135                 140
Asp Ala Asp Cys Glu Asp Ile Asp Cys Lys Leu Met Pro Pro Pro
145                 150                 155                 160
Pro Pro Pro Gly Pro Met Lys Lys Asp Lys Asp Gln Asp Ser Ile Thr
                165                 170                 175
Gly Glu Lys Val Asp Phe Ser Ser Ser Ser Asp Ser Glu Ser Glu Met
            180                 185                 190
Gly Pro Gln Glu Ala Thr Gln Ala Glu Ser Glu Asp Gly Lys Leu Thr
```

-continued

```
            195                 200                 205
Leu Pro Leu Ala Gly Ile Met Gln His Asp Ala Thr Lys Leu Leu Pro
    210                 215                 220

Ser Val Thr Glu Leu Phe Pro Glu Phe Arg Pro Gly Lys Val Leu Arg
225                 230                 235                 240

Phe Leu Arg Leu Phe Gly Pro Gly Lys Asn Val Pro Ser Val Trp Arg
                245                 250                 255

Ser Ala Arg Arg Lys Arg Lys Lys Lys His Arg Glu Leu Ile Gln Glu
                260                 265                 270

Glu Gln Ile Gln Glu Val Glu Cys Ser Val Glu Ser Glu Val Ser Gln
            275                 280                 285

Lys Ser Leu Trp Asn Tyr Asp Tyr Ala Pro Pro Pro Pro Glu Gln
    290                 295                 300

Cys Leu Ser Asp Asp Glu Ile Thr Met Met Ala Pro Val Glu Ser Lys
305                 310                 315                 320

Phe Ser Gln Ser Thr Gly Asp Ile Asp Lys Val Thr Asp Thr Lys Pro
                325                 330                 335

Arg Val Ala Glu Trp Arg Tyr Gly Pro Ala Arg Leu Trp Tyr Asp Met
                340                 345                 350

Leu Gly Val Pro Glu Asp Gly Ser Gly Phe Asp Tyr Gly Phe Lys Leu
            355                 360                 365

Arg Lys Thr Glu His Glu Pro Val Ile Lys Ser Arg Met Ile Glu Glu
    370                 375                 380

Phe Arg Lys Leu Glu Glu Asn Asn Gly Thr Asp Leu Leu Ala Asp Glu
385                 390                 395                 400

Asn Phe Leu Met Val Thr Gln Leu His Trp Glu Asp Asp Ile Ile Trp
                405                 410                 415

Asp Gly Glu Asp Val Lys His Lys Gly Thr Lys Pro Gln Arg Ala Ser
                420                 425                 430

Leu Ala Gly Trp Leu Pro Ser Ser Met Thr Arg Asn Ala Met Ala Tyr
            435                 440                 445

Asn Val Gln Gln Gly Phe Ala Ala Thr Leu Asp Asp Lys Pro Trp
    450                 455                 460

Tyr Ser Ile Phe Pro Ile Asp Asn Glu Asp Leu Val Tyr Gly Arg Trp
465                 470                 475                 480

Glu Asp Asn Ile Ile Trp Asp Ala Gln Ala Met Pro Arg Leu Leu Glu
                485                 490                 495

Pro Pro Val Leu Thr Leu Asp Pro Asn Asp Glu Asn Leu Ile Leu Glu
                500                 505                 510

Ile Pro Asp Glu Lys Glu Glu Ala Thr Ser Asn Ser Pro Ser Lys Glu
    515                 520                 525

Ser Lys Lys Glu Ser Ser Leu Lys Lys Ser Arg Ile Leu Leu Gly Lys
530                 535                 540

Thr Gly Val Ile Lys Glu Glu Pro Gln Gln Asn Met Ser Gln Pro Glu
545                 550                 555                 560

Val Lys Asp Pro Trp Asn Leu Ser Asn Asp Glu Tyr Tyr Pro Lys
                565                 570                 575

Gln Gln Gly Leu Arg Gly Thr Phe Gly Gly Asn Ile Ile Gln His Ser
                580                 585                 590

Ile Pro Ala Val Glu Leu Arg Gln Pro Phe Pro Thr His Met Gly
            595                 600                 605

Pro Ile Lys Leu Arg Gln Phe His Arg Pro Pro Leu Lys Lys Tyr Ser
    610                 615                 620
```

-continued

```
Phe Gly Ala Leu Ser Gln Pro Gly Pro His Ser Val Gln Pro Leu Leu
625                 630                 635                 640

Lys His Ile Lys Lys Ala Lys Met Arg Glu Gln Glu Arg Gln Ala
            645                 650                 655

Ser Gly Gly Gly Glu Met Phe Phe Met Arg Thr Pro Gln Asp Leu Thr
                660                 665                 670

Gly Lys Asp Gly Asp Leu Ile Leu Ala Glu Tyr Ser Glu Glu Asn Gly
            675                 680                 685

Pro Leu Met Met Gln Val Gly Met Ala Thr Lys Ile Lys Asn Tyr Tyr
690                 695                 700

Lys Arg Lys Pro Gly Lys Asp Pro Gly Ala Pro Asp Cys Lys Tyr Gly
705                 710                 715                 720

Glu Thr Val Tyr Cys His Thr Ser Pro Phe Leu Gly Ser Leu His Pro
                725                 730                 735

Gly Gln Leu Leu Gln Ala Phe Glu Asn Asn Leu Phe Arg Ala Pro Ile
            740                 745                 750

Tyr Leu His Lys Met Pro Glu Thr Asp Phe Leu Ile Ile Arg Thr Arg
            755                 760                 765

Gln Gly Tyr Tyr Ile Arg Glu Leu Val Asp Ile Phe Val Val Gly Gln
770                 775                 780

Gln Cys Pro Leu Phe Glu Val Pro Gly Pro Asn Ser Lys Arg Ala Asn
785                 790                 795                 800

Thr His Ile Arg Asp Phe Leu Gln Val Phe Ile Tyr Arg Leu Phe Trp
                805                 810                 815

Lys Ser Lys Asp Arg Pro Arg Arg Ile Arg Met Glu Asp Ile Lys Lys
            820                 825                 830

Ala Phe Pro Ser His Ser Glu Ser Ser Ile Arg Lys Arg Leu Lys Leu
            835                 840                 845

Cys Ala Asp Phe Lys Arg Thr Gly Met Asp Ser Asn Trp Trp Val Leu
850                 855                 860

Lys Ser Asp Phe Arg Leu Pro Thr Glu Glu Glu Ile Arg Ala Met Val
865                 870                 875                 880

Ser Pro Glu Gln Cys Cys Ala Tyr Tyr Ser Met Ile Ala Ala Glu Gln
                885                 890                 895

Arg Leu Lys Asp Ala Gly Tyr Gly Glu Lys Ser Phe Phe Ala Pro Glu
            900                 905                 910

Glu Glu Asn Glu Glu Asp Phe Gln Met Lys Ile Asp Asp Glu Val Arg
            915                 920                 925

Thr Ala Pro Trp Asn Thr Thr Arg Ala Phe Ile Ala Ala Met Lys Gly
930                 935                 940

Lys Cys Leu Leu Glu Val Thr Gly Val Ala Asp Pro Thr Gly Cys Gly
945                 950                 955                 960

Glu Gly Phe Ser Tyr Val Lys Ile Pro Asn Lys Pro Thr Gln Gln Lys
                965                 970                 975

Asp Asp Lys Glu Pro Gln Pro Val Lys Lys Thr Val Thr Gly Thr Asp
            980                 985                 990

Ala Asp Leu Arg Arg Leu Ser Leu Lys Asn Ala Lys Gln Leu Leu Arg
            995                 1000                1005

Lys Phe Gly Val Pro Glu Glu Glu Ile Lys Lys Leu Ser Arg Trp
    1010                1015                1020

Glu Val Ile Asp Val Val Arg Thr Met Ser Thr Glu Gln Ala Arg
    1025                1030                1035

Ser Gly Glu Gly Pro Met Ser Lys Phe Ala Arg Gly Ser Arg Phe
    1040                1045                1050
```

```
Ser Val Ala Glu His Gln Glu Arg Tyr Lys Glu Cys Gln Arg
1055                1060                1065

Ile Phe Asp Leu Gln Asn Lys Val Leu Ser Ser Thr Glu Val Leu
1070                1075                1080

Ser Thr Asp Thr Asp Ser Ser Ser Ala Glu Asp Ser Asp Phe Glu
1085                1090                1095

Glu Met Gly Lys Asn Ile Glu Asn Met Leu Gln Asn Lys Lys Thr
1100                1105                1110

Ser Ser Gln Leu Ser Arg Glu Arg Glu Gln Glu Arg Lys Glu
1115                1120                1125

Leu Gln Arg Met Leu Leu Ala Ala Gly Ser Ala Ala Ser Gly Asn
1130                1135                1140

Asn His Arg Asp Asp Asp Thr Ala Ser Val Thr Ser Leu Asn Ser
1145                1150                1155

Ser Ala Thr Gly Arg Cys Leu Lys Ile Tyr Arg Thr Phe Arg Asp
1160                1165                1170

Glu Glu Gly Lys Glu Tyr Val Arg Cys Glu Thr Val Arg Lys Pro
1175                1180                1185

Ala Val Ile Asp Ala Tyr Val Arg Ile Arg Thr Thr Lys Asp Glu
1190                1195                1200

Glu Phe Ile Arg Lys Phe Ala Leu Phe Asp Glu Gln His Arg Glu
1205                1210                1215

Glu Met Arg Lys Glu Arg Arg Arg Ile Gln Glu Gln Leu Arg Arg
1220                1225                1230

Leu Lys Arg Asn Gln Glu Lys Glu Lys Leu Lys Gly Pro Pro Glu
1235                1240                1245

Lys Lys Pro Lys Lys Met Lys Glu Arg Pro Asp Leu Lys Leu Lys
1250                1255                1260

Cys Gly Ala Cys Gly Ala Ile Gly His Met Arg Thr Asn Lys Phe
1265                1270                1275

Cys Pro Leu Tyr Tyr Gln Thr Asn Ala Pro Pro Ser Asn Pro Val
1280                1285                1290

Ala Met Thr Glu Glu Gln Glu Glu Leu Glu Lys Thr Val Ile
1295                1300                1305

His Asn Asp Asn Glu Glu Leu Ile Lys Val Glu Gly Thr Lys Ile
1310                1315                1320

Val Leu Gly Lys Gln Leu Ile Glu Ser Ala Asp Glu Val Arg Arg
1325                1330                1335

Lys Ser Leu Val Leu Lys Phe Pro Lys Gln Gln Leu Pro Pro Lys
1340                1345                1350

Lys Lys Arg Arg Val Gly Thr Thr Val His Cys Asp Tyr Leu Asn
1355                1360                1365

Arg Pro His Lys Ser Ile His Arg Arg Arg Thr Asp Pro Met Val
1370                1375                1380

Thr Leu Ser Ser Ile Leu Glu Ser Ile Ile Asn Asp Met Arg Asp
1385                1390                1395

Leu Pro Asn Thr Tyr Pro Phe His Thr Pro Val Asn Ala Lys Val
1400                1405                1410

Val Lys Asp Tyr Tyr Lys Ile Ile Thr Arg Pro Met Asp Leu Gln
1415                1420                1425

Thr Leu Arg Glu Asn Val Arg Lys Arg Leu Tyr Pro Ser Arg Glu
1430                1435                1440

Glu Phe Arg Glu His Leu Glu Leu Ile Val Lys Asn Ser Ala Thr
```

-continued

|  |  |  |
|---|---|---|
| 1445 | 1450 | 1455 |

Tyr Asn Gly Pro Lys His Ser Leu Thr Gln Ile Ser Gln Ser Met
1460        1465            1470

Leu Asp Leu Cys Asp Glu Lys Leu Lys Glu Lys Glu Asp Lys Leu
1475        1480            1485

Ala Arg Leu Glu Lys Ala Ile Asn Pro Leu Leu Asp Asp Asp Asp
1490        1495            1500

Gln Val Ala Phe Ser Phe Ile Leu Asp Asn Ile Val Thr Gln Lys
1505        1510            1515

Met Met Ala Val Pro Asp Ser Trp Pro Phe His His Pro Val Asn
1520        1525            1530

Lys Lys Phe Val Pro Asp Tyr Tyr Lys Val Ile Val Asn Pro Met
1535        1540            1545

Asp Leu Glu Thr Ile Arg Lys Asn Ile Ser Lys His Lys Tyr Gln
1550        1555            1560

Ser Arg Glu Ser Phe Leu Asp Asp Val Asn Leu Ile Leu Ala Asn
1565        1570            1575

Ser Val Lys Tyr Asn Gly Pro Glu Ser Gln Tyr Thr Lys Thr Ala
1580        1585            1590

Gln Glu Ile Val Asn Val Cys Tyr Gln Thr Leu Thr Glu Tyr Asp
1595        1600            1605

Glu His Leu Thr Gln Leu Glu Lys Asp Ile Cys Thr Ala Lys Glu
1610        1615            1620

Ala Ala Leu Glu Glu Ala Glu Leu Glu Ser Leu Asp Pro Met Thr
1625        1630            1635

Pro Gly Pro Tyr Thr Pro Gln Pro Pro Asp Leu Tyr Asp Thr Asn
1640        1645            1650

Thr Ser Leu Ser Met Ser Arg Asp Ala Ser Val Phe Gln Asp Glu
1655        1660            1665

Ser Asn Met Ser Val Leu Asp Ile Pro Ser Ala Thr Pro Glu Lys
1670        1675            1680

Gln Val Thr Gln Glu Gly Glu Asp Gly Asp Gly Asp Leu Ala Asp
1685        1690            1695

Glu Glu Glu Gly Thr Val Gln Gln Pro Gln Ala Ser Val Leu Tyr
1700        1705            1710

Glu Asp Leu Leu Met Ser Glu Gly Glu Asp Asp Glu Glu Asp Ala
1715        1720            1725

Gly Ser Asp Glu Glu Gly Asp Asn Pro Phe Ser Ala Ile Gln Leu
1730        1735            1740

Ser Glu Ser Gly Ser Asp Ser Asp Val Gly Ser Gly Gly Ile Arg
1745        1750            1755

Pro Lys Gln Pro Arg Met Leu Gln Glu Asn Thr Arg Met Asp Met
1760        1765            1770

Glu Asn Glu Glu Ser Met Met Ser Tyr Glu Gly Asp Gly Gly Glu
1775        1780            1785

Ala Ser His Gly Leu Glu Asp Ser Asn Ile Ser Tyr Gly Ser Tyr
1790        1795            1800

Glu Glu Pro Asp Pro Lys Ser Asn Thr Gln Asp Thr Ser Phe Ser
1805        1810            1815

Ser Ile Gly Gly Tyr Glu Val Ser Glu Glu Glu Asp Glu Glu
1820        1825            1830

Glu Glu Glu Gln Arg Ser Gly Pro Ser Val Leu Ser Gln Val His
1835        1840            1845

Leu Ser Glu Asp Glu Glu Asp Ser Glu Asp Phe His Ser Ile Ala
    1850                1855                1860

Gly Asp Ser Asp Leu Asp Ser Asp Glu
    1865                1870

<210> SEQ ID NO 93
<211> LENGTH: 1488
<212> TYPE: PRT
<213> ORGANISM: Homo sapiens

<400> SEQUENCE: 93

Met Gly Pro Gly Cys Asp Leu Leu Arg Thr Ala Ala Thr Ile Thr
1               5                   10                  15

Ala Ala Ala Ile Met Ser Asp Thr Asp Ser Asp Glu Asp Ser Ala Gly
                20              25                  30

Gly Gly Pro Phe Ser Leu Ala Gly Phe Leu Phe Gly Asn Ile Asn Gly
            35              40                  45

Ala Gly Gln Leu Glu Gly Glu Ser Val Leu Asp Asp Glu Cys Lys Lys
    50              55                  60

His Leu Ala Gly Leu Gly Ala Leu Gly Leu Gly Ser Leu Ile Thr Glu
65              70                  75                  80

Leu Thr Ala Asn Glu Glu Leu Thr Gly Thr Asp Gly Ala Leu Val Asn
                85                  90                  95

Asp Glu Gly Trp Val Arg Ser Thr Glu Asp Ala Val Asp Tyr Ser Asp
                100                 105                 110

Ile Asn Glu Val Ala Glu Asp Glu Ser Arg Arg Tyr Gln Gln Thr Met
            115                 120                 125

Gly Ser Leu Gln Pro Leu Cys His Ser Asp Tyr Asp Glu Asp Asp Tyr
    130                 135                 140

Asp Ala Asp Cys Glu Asp Ile Asp Cys Lys Leu Met Pro Pro Pro Pro
145                 150                 155                 160

Pro Pro Pro Gly Pro Met Lys Lys Asp Lys Asp Gln Asp Ser Ile Thr
                165                 170                 175

Gly Glu Lys Val Asp Phe Ser Ser Ser Asp Ser Glu Ser Glu Met
            180                 185                 190

Gly Pro Gln Glu Ala Thr Gln Ala Glu Ser Glu Asp Gly Lys Leu Thr
    195                 200                 205

Leu Pro Leu Ala Gly Ile Met Gln His Asp Ala Thr Lys Leu Leu Pro
    210                 215                 220

Ser Val Thr Glu Leu Phe Pro Glu Phe Arg Pro Gly Lys Val Leu Arg
225                 230                 235                 240

Phe Leu Arg Leu Phe Gly Pro Gly Lys Asn Val Pro Ser Val Trp Arg
                245                 250                 255

Ser Ala Arg Arg Lys Arg Lys Lys Lys His Arg Glu Leu Ile Gln Glu
            260                 265                 270

Glu Gln Ile Gln Glu Val Glu Cys Ser Val Ser Glu Val Ser Gln
    275                 280                 285

Lys Ser Leu Trp Asn Tyr Asp Tyr Ala Pro Pro Pro Pro Glu Gln
    290                 295                 300

Cys Leu Ser Asp Asp Glu Ile Thr Met Met Ala Pro Val Glu Ser Lys
305                 310                 315                 320

Phe Ser Gln Ser Thr Gly Asp Ile Asp Lys Val Thr Thr Lys Pro
                325                 330                 335

Arg Val Ala Glu Trp Arg Tyr Gly Pro Ala Arg Leu Trp Tyr Asp Met
            340                 345                 350

```
Leu Gly Val Pro Glu Asp Gly Ser Gly Phe Asp Tyr Gly Phe Lys Leu
            355                 360                 365

Arg Lys Thr Glu His Glu Pro Val Ile Lys Ser Arg Met Ile Glu Glu
        370                 375                 380

Phe Arg Lys Leu Glu Glu Asn Asn Gly Thr Asp Leu Leu Ala Asp Glu
385                 390                 395                 400

Asn Phe Leu Met Val Thr Gln Leu His Trp Glu Asp Asp Ile Ile Trp
                405                 410                 415

Asp Gly Glu Asp Val Lys His Lys Gly Thr Lys Pro Gln Arg Ala Ser
                420                 425                 430

Leu Ala Gly Trp Leu Pro Ser Ser Met Thr Arg Asn Ala Met Ala Tyr
            435                 440                 445

Asn Val Gln Gln Gly Phe Ala Ala Thr Leu Asp Asp Asp Lys Pro Trp
        450                 455                 460

Tyr Ser Ile Phe Pro Ile Asp Asn Glu Asp Leu Val Tyr Gly Arg Trp
465                 470                 475                 480

Glu Asp Asn Ile Ile Trp Asp Ala Gln Ala Met Pro Arg Leu Leu Glu
                485                 490                 495

Pro Pro Val Leu Thr Leu Asp Pro Asn Asp Glu Asn Leu Ile Leu Glu
            500                 505                 510

Ile Pro Asp Glu Lys Glu Ala Thr Ser Asn Ser Pro Ser Lys Glu
        515                 520                 525

Ser Lys Lys Glu Ser Ser Leu Lys Lys Ser Arg Ile Leu Leu Gly Lys
530                 535                 540

Thr Gly Val Ile Lys Glu Pro Gln Gln Asn Met Ser Gln Pro Glu
545                 550                 555                 560

Val Lys Asp Pro Trp Asn Leu Ser Asn Asp Glu Tyr Tyr Pro Lys
                565                 570                 575

Gln Gln Gly Leu Arg Gly Thr Phe Gly Gly Asn Ile Ile Gln His Ser
            580                 585                 590

Ile Pro Ala Val Glu Leu Arg Gln Pro Phe Phe Pro Thr His Met Gly
        595                 600                 605

Pro Ile Lys Leu Arg Gln Phe His Arg Pro Pro Leu Lys Lys Tyr Ser
    610                 615                 620

Phe Gly Ala Leu Ser Gln Pro Gly Pro His Ser Val Gln Pro Leu Leu
625                 630                 635                 640

Lys His Ile Lys Lys Lys Ala Lys Met Arg Glu Gln Glu Arg Gln Ala
                645                 650                 655

Ser Gly Gly Gly Glu Met Phe Phe Met Arg Thr Pro Gln Asp Leu Thr
            660                 665                 670

Gly Lys Asp Gly Asp Leu Ile Leu Ala Glu Tyr Ser Glu Glu Asn Gly
        675                 680                 685

Pro Leu Met Met Gln Val Gly Met Ala Thr Lys Ile Lys Asn Tyr Tyr
    690                 695                 700

Lys Arg Lys Pro Gly Lys Asp Pro Gly Ala Pro Asp Cys Lys Tyr Gly
705                 710                 715                 720

Glu Thr Val Tyr Cys His Thr Ser Pro Phe Leu Gly Ser Leu His Pro
                725                 730                 735

Gly Gln Leu Leu Gln Ala Phe Glu Asn Asn Leu Phe Arg Ala Pro Ile
            740                 745                 750

Tyr Leu His Lys Met Pro Glu Thr Asp Phe Leu Ile Ile Arg Thr Arg
        755                 760                 765

Gln Gly Tyr Tyr Ile Arg Glu Leu Val Asp Ile Phe Val Val Gly Gln
    770                 775                 780
```

```
Gln Cys Pro Leu Phe Glu Val Pro Gly Pro Asn Ser Lys Arg Ala Asn
785                 790                 795                 800

Thr His Ile Arg Asp Phe Leu Gln Val Phe Ile Tyr Arg Leu Phe Trp
            805                 810                 815

Lys Ser Lys Asp Arg Pro Arg Ile Arg Met Glu Asp Ile Lys Lys
        820                 825                 830

Ala Phe Pro Ser His Ser Glu Ser Ser Ile Arg Lys Arg Leu Lys Leu
            835                 840                 845

Cys Ala Asp Phe Lys Arg Thr Gly Met Asp Ser Asn Trp Trp Val Leu
        850                 855                 860

Lys Ser Asp Phe Arg Leu Pro Thr Glu Glu Glu Ile Arg Ala Met Val
865                 870                 875                 880

Ser Pro Glu Gln Cys Cys Ala Tyr Tyr Ser Met Ile Ala Ala Glu Gln
                885                 890                 895

Arg Leu Lys Asp Ala Gly Tyr Gly Glu Lys Ser Phe Phe Ala Pro Glu
                900                 905                 910

Glu Glu Asn Glu Glu Asp Phe Gln Met Lys Ile Asp Asp Glu Val Arg
            915                 920                 925

Thr Ala Pro Trp Asn Thr Thr Arg Ala Phe Ile Ala Ala Met Lys Gly
    930                 935                 940

Lys Cys Leu Leu Glu Val Thr Gly Val Ala Asp Pro Thr Gly Cys Gly
945                 950                 955                 960

Glu Gly Phe Ser Tyr Val Lys Ile Pro Asn Lys Pro Thr Gln Gln Lys
                965                 970                 975

Asp Asp Lys Glu Pro Gln Pro Val Lys Lys Thr Val Thr Gly Thr Asp
                980                 985                 990

Ala Asp Leu Arg Arg Leu Ser Leu Lys Asn Ala Lys Gln Leu Leu Arg
            995                 1000                1005

Lys Phe Gly Val Pro Glu Glu Glu Ile Lys Lys Leu Ser Arg Trp
    1010                1015                1020

Glu Val Ile Asp Val Val Arg Thr Met Ser Thr Glu Gln Ala Arg
    1025                1030                1035

Ser Gly Glu Gly Pro Met Ser Lys Phe Ala Arg Gly Ser Arg Phe
    1040                1045                1050

Ser Val Ala Glu His Gln Glu Arg Tyr Lys Glu Glu Cys Gln Arg
    1055                1060                1065

Ile Phe Asp Leu Gln Asn Lys Val Leu Ser Ser Thr Glu Val Leu
    1070                1075                1080

Ser Thr Asp Thr Asp Ser Ser Ala Glu Asp Ser Asp Phe Glu
    1085                1090                1095

Glu Met Gly Lys Asn Ile Glu Asn Met Leu Gln Asn Lys Lys Thr
    1100                1105                1110

Ser Ser Gln Leu Ser Arg Glu Arg Glu Glu Gln Glu Arg Lys Glu
    1115                1120                1125

Leu Gln Arg Met Leu Leu Ala Ala Gly Ser Ala Ala Ser Gly Asn
    1130                1135                1140

Asn His Arg Asp Asp Asp Thr Ala Ser Val Thr Ser Leu Asn Ser
    1145                1150                1155

Ser Ala Thr Gly Arg Cys Leu Lys Ile Tyr Arg Thr Phe Arg Asp
    1160                1165                1170

Glu Glu Gly Lys Glu Tyr Val Arg Cys Glu Thr Val Arg Lys Pro
    1175                1180                1185

Ala Val Ile Asp Ala Tyr Val Arg Ile Arg Thr Thr Lys Asp Glu
```

-continued

```
               1190                1195                1200

Glu Phe Ile Arg Lys Phe Ala  Leu Phe Asp Glu Gln  His Arg Glu
    1205                1210                1215

Glu Met Arg Lys Glu Arg Arg  Arg Ile Gln Glu Gln  Leu Arg Arg
    1220                1225                1230

Leu Lys Arg Asn Gln Glu Lys  Glu Lys Leu Lys Gly  Pro Pro Glu
    1235                1240                1245

Lys Lys Pro Lys Lys Met Lys  Glu Arg Pro Asp Leu  Lys Leu Lys
    1250                1255                1260

Cys Gly Ala Cys Gly Ala Ile  Gly His Met Arg Thr  Asn Lys Phe
    1265                1270                1275

Cys Pro Leu Tyr Tyr Gln Thr  Asn Ala Pro Pro Ser  Asn Pro Val
    1280                1285                1290

Ala Met Thr Glu Glu Gln Glu  Glu Leu Glu Lys Thr  Val Ile
    1295                1300                1305

His Asn Asp Asn Glu Glu Leu  Ile Lys Val Glu Gly  Thr Lys Ile
    1310                1315                1320

Val Leu Gly Lys Gln Leu Ile  Glu Ser Ala Asp Glu  Val Arg Arg
    1325                1330                1335

Lys Ser Leu Val Leu Lys Phe  Pro Lys Gln Gln Leu  Pro Pro Lys
    1340                1345                1350

Lys Lys Arg Arg Val Gly Thr  Thr Val His Cys Asp  Tyr Leu Asn
    1355                1360                1365

Arg Pro His Lys Ser Ile His  Arg Arg Arg Thr Asp  Pro Met Val
    1370                1375                1380

Thr Leu Ser Ser Ile Leu Glu  Ser Ile Ile Asn Asp  Met Arg Asp
    1385                1390                1395

Leu Pro Asn Thr Tyr Pro Phe  His Thr Pro Val Asn  Ala Lys Val
    1400                1405                1410

Val Lys Asp Tyr Tyr Lys Ile  Ile Thr Arg Pro Met  Asp Leu Gln
    1415                1420                1425

Thr Leu Arg Glu Asn Val Arg  Lys Arg Leu Tyr Pro  Ser Arg Glu
    1430                1435                1440

Glu Phe Arg Glu His Leu Asp  Asp Arg Trp Arg Pro  Cys Leu Lys
    1445                1450                1455

Lys Lys Lys Lys Glu Glu Glu  Thr Trp Leu Ser Glu  Tyr Ala Phe
    1460                1465                1470

His Lys Pro Thr Arg Gly Cys  Ser Leu Pro Thr Gln  Ser Gln Phe
    1475                1480                1485

<210> SEQ ID NO 94
<211> LENGTH: 104
<212> TYPE: PRT
<213> ORGANISM: Homo sapiens

<400> SEQUENCE: 94

Met Val Thr Leu Ser Ser Ile Leu Glu Ser Ile Ile Asn Asp Met Arg
1               5                   10                  15

Asp Leu Pro Asn Thr Tyr Pro Phe His Thr Pro Val Asn Ala Lys Val
                20                  25                  30

Val Lys Asp Tyr Tyr Lys Ile Ile Thr Arg Pro Met Asp Leu Gln Thr
            35                  40                  45

Leu Arg Glu Asn Val Arg Lys Arg Leu Tyr Pro Ser Arg Glu Glu Phe
        50                  55                  60

Arg Glu His Leu Glu Leu Ile Val Lys Asn Ser Ala Thr Tyr Asn Gly
```

```
                65                  70                  75                  80
Lys Asn Gln Met Phe Arg Asp Cys Lys Gly His Cys Ser Asp Pro Tyr
                    85                  90                  95

Ser Leu Leu Ala Leu Asn Ser Asp
                100

<210> SEQ ID NO 95
<211> LENGTH: 552
<212> TYPE: PRT
<213> ORGANISM: Homo sapiens

<400> SEQUENCE: 95

Thr Lys Ile Val Leu Gly Lys Gln Leu Ile Glu Ser Ala Asp Glu Val
1               5                   10                  15

Arg Arg Lys Ser Leu Val Leu Lys Phe Pro Lys Gln Gln Leu Pro Pro
                20                  25                  30

Lys Lys Lys Arg Arg Val Gly Thr Thr Val His Cys Asp Tyr Leu Asn
                35                  40                  45

Arg Pro His Lys Ser Ile His Arg Arg Thr Asp Pro Met Val Thr
    50                  55                  60

Leu Ser Ser Ile Leu Glu Ser Ile Ile Asn Asp Met Arg Asp Leu Pro
65                  70                  75                  80

Asn Thr Tyr Pro Phe His Thr Pro Val Asn Ala Lys Val Val Lys Asp
                85                  90                  95

Tyr Tyr Lys Ile Ile Thr Arg Pro Met Asp Leu Gln Thr Leu Arg Glu
                100                 105                 110

Asn Val Arg Lys Arg Leu Tyr Pro Ser Arg Glu Glu Phe Arg Glu His
                115                 120                 125

Leu Glu Leu Ile Val Lys Asn Ser Ala Thr Tyr Asn Gly Pro Lys His
            130                 135                 140

Ser Leu Thr Gln Ile Ser Gln Ser Met Leu Asp Leu Cys Asp Glu Lys
145                 150                 155                 160

Leu Lys Glu Lys Glu Asp Lys Leu Ala Arg Leu Glu Lys Ala Ile Asn
                165                 170                 175

Pro Leu Leu Asp Asp Asp Asp Gln Val Ala Phe Ser Phe Ile Leu Asp
                180                 185                 190

Asn Ile Val Thr Gln Lys Met Met Ala Val Pro Asp Ser Trp Pro Phe
            195                 200                 205

His His Pro Val Asn Lys Lys Phe Val Pro Asp Tyr Tyr Lys Val Ile
    210                 215                 220

Val Asn Pro Met Asp Leu Glu Thr Ile Arg Lys Asn Ile Ser Lys His
225                 230                 235                 240

Lys Tyr Gln Ser Arg Glu Ser Phe Leu Asp Asp Val Asn Leu Ile Leu
                245                 250                 255

Ala Asn Ser Val Lys Tyr Asn Gly Pro Glu Ser Gln Tyr Thr Lys Thr
                260                 265                 270

Ala Gln Glu Ile Val Asn Val Cys Tyr Gln Thr Leu Thr Glu Tyr Asp
            275                 280                 285

Glu His Leu Thr Gln Leu Glu Lys Asp Ile Cys Thr Ala Lys Glu Ala
    290                 295                 300

Ala Leu Glu Glu Ala Glu Leu Glu Ser Leu Asp Pro Met Thr Pro Gly
305                 310                 315                 320

Pro Tyr Thr Pro Gln Pro Pro Asp Leu Tyr Asp Thr Asn Thr Ser Leu
                325                 330                 335

Ser Met Ser Arg Asp Ala Ser Val Phe Gln Asp Glu Ser Asn Met Ser
```

```
                340                 345                 350
Val Leu Asp Ile Pro Ser Ala Thr Pro Glu Lys Gln Val Thr Gln Glu
            355                 360                 365
Gly Glu Asp Gly Asp Gly Asp Leu Ala Asp Glu Glu Gly Thr Val
        370                 375                 380
Gln Gln Pro Gln Ala Ser Val Leu Tyr Glu Asp Leu Leu Met Ser Glu
385                 390                 395                 400
Gly Glu Asp Asp Glu Glu Asp Ala Gly Ser Glu Glu Gly Asp Asn
                405                 410                 415
Pro Phe Ser Ala Ile Gln Leu Ser Glu Ser Gly Ser Asp Ser Asp Val
                420                 425                 430
Gly Ser Gly Gly Ile Arg Pro Lys Gln Pro Arg Met Leu Gln Glu Asn
            435                 440                 445
Thr Arg Met Asp Met Glu Asn Glu Glu Ser Met Met Ser Tyr Glu Gly
        450                 455                 460
Asp Gly Gly Glu Ala Ser His Gly Leu Glu Asp Ser Asn Ile Ser Tyr
465                 470                 475                 480
Gly Ser Tyr Glu Glu Pro Asp Pro Lys Ser Asn Thr Gln Asp Thr Ser
                485                 490                 495
Phe Ser Ser Ile Gly Gly Tyr Glu Val Ser Glu Glu Glu Asp Glu
                500                 505                 510
Glu Glu Glu Glu Gln Arg Ser Gly Pro Ser Val Leu Ser Gln Val His
            515                 520                 525
Leu Ser Glu Asp Glu Asp Ser Glu Asp Phe His Ser Ile Ala Gly
        530                 535                 540
Asp Ser Asp Leu Asp Ser Asp Glu
545                 550

<210> SEQ ID NO 96
<211> LENGTH: 1460
<212> TYPE: PRT
<213> ORGANISM: Homo sapiens

<400> SEQUENCE: 96

Met Gly Pro Gly Cys Asp Leu Leu Leu Arg Thr Ala Ala Thr Ile Thr
1               5                   10                  15
Ala Ala Ile Met Ser Asp Thr Asp Ser Asp Glu Asp Ser Ala Gly
            20                  25                  30
Gly Gly Pro Phe Ser Leu Ala Gly Phe Leu Phe Gly Asn Ile Asn Gly
        35                  40                  45
Ala Gly Gln Leu Glu Gly Glu Ser Val Leu Asp Asp Glu Cys Lys Lys
    50                  55                  60
His Leu Ala Gly Leu Gly Ala Leu Gly Leu Gly Ser Leu Ile Thr Glu
65                  70                  75                  80
Leu Thr Ala Asn Glu Glu Leu Thr Gly Thr Asp Gly Ala Leu Val Asn
                85                  90                  95
Asp Glu Gly Trp Val Arg Ser Thr Glu Asp Ala Val Asp Tyr Ser Asp
                100                 105                 110
Ile Asn Glu Val Ala Glu Asp Glu Ser Arg Arg Tyr Gln Gln Thr Met
            115                 120                 125
Gly Ser Leu Gln Pro Leu Cys His Ser Asp Tyr Asp Glu Asp Tyr
        130                 135                 140
Asp Ala Asp Cys Glu Asp Ile Asp Cys Lys Leu Met Pro Pro Pro Pro
145                 150                 155                 160
Pro Pro Pro Gly Pro Met Lys Lys Asp Lys Asp Gln Asp Ser Ile Thr
```

```
                     165                 170                 175
Gly Glu Lys Val Asp Phe Ser Ser Ser Asp Ser Glu Ser Glu Met
                180                 185                 190
Gly Pro Gln Glu Ala Thr Gln Ala Glu Ser Glu Asp Gly Lys Leu Thr
                195                 200                 205
Leu Pro Leu Ala Gly Ile Met Gln His Asp Ala Thr Lys Leu Leu Pro
    210                 215                 220
Ser Val Thr Glu Leu Phe Pro Glu Phe Arg Pro Gly Lys Val Leu Arg
225                 230                 235                 240
Phe Leu Arg Leu Phe Gly Pro Gly Lys Asn Val Pro Ser Val Trp Arg
                245                 250                 255
Ser Ala Arg Arg Lys Arg Lys Lys His Arg Glu Leu Ile Gln Glu
            260                 265                 270
Glu Gln Ile Gln Glu Val Glu Cys Ser Val Glu Ser Glu Val Ser Gln
        275                 280                 285
Lys Ser Leu Trp Asn Tyr Asp Tyr Ala Pro Pro Pro Glu Gln
    290                 295                 300
Cys Leu Ser Asp Asp Glu Ile Thr Met Met Ala Pro Val Glu Ser Lys
305                 310                 315                 320
Phe Ser Gln Ser Thr Gly Asp Ile Asp Lys Val Thr Asp Thr Lys Pro
                325                 330                 335
Arg Val Ala Glu Trp Arg Tyr Gly Pro Ala Arg Leu Trp Tyr Asp Met
                340                 345                 350
Leu Gly Val Pro Glu Asp Gly Ser Gly Phe Asp Tyr Gly Phe Lys Leu
                355                 360                 365
Arg Lys Thr Glu His Glu Pro Val Ile Lys Ser Arg Met Ile Glu Glu
            370                 375                 380
Phe Arg Lys Leu Glu Glu Asn Asn Gly Thr Asp Leu Leu Ala Asp Glu
385                 390                 395                 400
Asn Phe Leu Met Val Thr Gln Leu His Trp Glu Asp Asp Ile Ile Trp
                405                 410                 415
Asp Gly Glu Asp Val Lys His Lys Gly Thr Lys Pro Gln Arg Ala Ser
                420                 425                 430
Leu Ala Gly Trp Leu Pro Ser Ser Met Thr Arg Asn Ala Met Ala Tyr
                435                 440                 445
Asn Val Gln Gln Gly Phe Ala Ala Thr Leu Asp Asp Lys Pro Trp
    450                 455                 460
Tyr Ser Ile Phe Pro Ile Asp Asn Glu Asp Leu Val Tyr Gly Arg Trp
465                 470                 475                 480
Glu Asp Asn Ile Ile Trp Asp Ala Gln Ala Met Pro Arg Leu Leu Glu
                485                 490                 495
Pro Pro Val Leu Thr Leu Asp Pro Asn Asp Glu Asn Leu Ile Leu Glu
            500                 505                 510
Ile Pro Asp Glu Lys Glu Glu Ala Thr Ser Asn Ser Pro Ser Lys Glu
        515                 520                 525
Ser Lys Lys Glu Ser Ser Leu Lys Lys Ser Arg Ile Leu Leu Gly Lys
    530                 535                 540
Thr Gly Val Ile Lys Glu Glu Pro Gln Gln Asn Met Ser Gln Pro Glu
545                 550                 555                 560
Val Lys Asp Pro Trp Asn Leu Ser Asn Asp Glu Tyr Tyr Tyr Pro Lys
                565                 570                 575
Gln Gln Gly Leu Arg Gly Thr Phe Gly Gly Asn Ile Ile Gln His Ser
            580                 585                 590
```

-continued

```
Ile Pro Ala Val Glu Leu Arg Gln Pro Phe Phe Pro Thr His Met Gly
    595                 600                 605
Pro Ile Lys Leu Arg Gln Phe His Arg Pro Pro Leu Lys Lys Tyr Ser
    610                 615                 620
Phe Gly Ala Leu Ser Gln Pro Gly Pro His Ser Val Gln Pro Leu Leu
625                 630                 635                 640
Lys His Ile Lys Lys Ala Lys Met Arg Glu Gln Glu Arg Gln Ala
            645                 650                 655
Ser Gly Gly Glu Met Phe Phe Met Arg Thr Pro Gln Asp Leu Thr
                660                 665                 670
Gly Lys Asp Gly Asp Leu Ile Leu Ala Glu Tyr Ser Glu Glu Asn Gly
            675                 680                 685
Pro Leu Met Met Gln Val Gly Met Ala Thr Lys Ile Lys Asn Tyr Tyr
    690                 695                 700
Lys Arg Lys Pro Gly Lys Asp Pro Gly Ala Pro Asp Cys Lys Tyr Gly
705                 710                 715                 720
Glu Thr Val Tyr Cys His Thr Ser Pro Phe Leu Gly Ser Leu His Pro
                725                 730                 735
Gly Gln Leu Leu Gln Ala Phe Glu Asn Asn Leu Phe Arg Ala Pro Ile
            740                 745                 750
Tyr Leu His Lys Met Pro Glu Thr Asp Phe Leu Ile Ile Arg Thr Arg
        755                 760                 765
Gln Gly Tyr Tyr Ile Arg Glu Leu Val Asp Ile Phe Val Val Gly Gln
    770                 775                 780
Gln Cys Pro Leu Phe Glu Val Pro Gly Pro Asn Ser Lys Arg Ala Asn
785                 790                 795                 800
Thr His Ile Arg Asp Phe Leu Gln Val Phe Ile Tyr Arg Leu Phe Trp
                805                 810                 815
Lys Ser Lys Asp Arg Pro Arg Arg Ile Arg Met Glu Asp Ile Lys Lys
            820                 825                 830
Ala Phe Pro Ser His Ser Glu Ser Ser Ile Arg Lys Arg Leu Lys Leu
        835                 840                 845
Cys Ala Asp Phe Lys Arg Thr Gly Met Asp Ser Asn Trp Trp Val Leu
    850                 855                 860
Lys Ser Asp Phe Arg Leu Pro Thr Glu Glu Ile Arg Ala Met Val
865                 870                 875                 880
Ser Pro Glu Gln Cys Cys Ala Tyr Tyr Ser Met Ile Ala Ala Glu Gln
                885                 890                 895
Arg Leu Lys Asp Ala Gly Tyr Gly Glu Lys Ser Phe Phe Ala Pro Glu
            900                 905                 910
Glu Glu Asn Glu Glu Asp Phe Gln Met Lys Ile Asp Asp Glu Val Arg
        915                 920                 925
Thr Ala Pro Trp Asn Thr Thr Arg Ala Phe Ile Ala Ala Met Lys Gly
    930                 935                 940
Lys Cys Leu Leu Glu Val Thr Gly Val Ala Asp Pro Thr Gly Cys Gly
945                 950                 955                 960
Glu Gly Phe Ser Tyr Val Lys Ile Pro Asn Lys Pro Thr Gln Gln Lys
                965                 970                 975
Asp Asp Lys Glu Pro Gln Pro Val Lys Lys Thr Val Thr Gly Thr Asp
            980                 985                 990
Ala Asp Leu Arg Arg Leu Ser Leu  Lys Asn Ala Lys Gln  Leu Leu Arg
        995                 1000                 1005
Lys Phe  Gly Val Pro Glu Glu  Glu Ile Lys Lys Leu  Ser Arg Trp
    1010                  1015                 1020
```

-continued

```
Glu Val Ile Asp Val Val Arg Thr Met Ser Thr Glu Gln Ala Arg
    1025                1030                1035

Ser Gly Glu Gly Pro Met Ser Lys Phe Ala Arg Gly Ser Arg Phe
    1040                1045                1050

Ser Val Ala Glu His Gln Glu Arg Tyr Lys Glu Glu Cys Gln Arg
    1055                1060                1065

Ile Phe Asp Leu Gln Asn Lys Val Leu Ser Ser Thr Glu Val Leu
    1070                1075                1080

Ser Thr Asp Thr Asp Ser Ser Ser Ala Glu Asp Ser Asp Phe Glu
    1085                1090                1095

Glu Met Gly Lys Asn Ile Glu Asn Met Leu Gln Asn Lys Lys Thr
    1100                1105                1110

Ser Ser Gln Leu Ser Arg Glu Arg Glu Gln Glu Arg Lys Glu
    1115                1120                1125

Leu Gln Arg Met Leu Leu Ala Ala Gly Ser Ala Ala Ser Gly Asn
    1130                1135                1140

Asn His Arg Asp Asp Asp Thr Ala Ser Val Thr Ser Leu Asn Ser
    1145                1150                1155

Ser Ala Thr Gly Arg Cys Leu Lys Ile Tyr Arg Thr Phe Arg Asp
    1160                1165                1170

Glu Glu Gly Lys Glu Tyr Val Arg Cys Glu Thr Val Arg Lys Pro
    1175                1180                1185

Ala Val Ile Asp Ala Tyr Val Arg Ile Arg Thr Thr Lys Asp Glu
    1190                1195                1200

Glu Phe Ile Arg Lys Phe Ala Leu Phe Asp Glu Gln His Arg Glu
    1205                1210                1215

Glu Met Arg Lys Glu Arg Arg Arg Ile Gln Glu Gln Leu Arg Arg
    1220                1225                1230

Leu Lys Arg Asn Gln Glu Lys Glu Lys Leu Lys Gly Pro Pro Glu
    1235                1240                1245

Lys Lys Pro Lys Lys Met Lys Glu Arg Pro Asp Leu Lys Leu Lys
    1250                1255                1260

Cys Gly Ala Cys Gly Ala Ile Gly His Met Arg Thr Asn Lys Phe
    1265                1270                1275

Cys Pro Leu Tyr Tyr Gln Thr Asn Ala Pro Pro Ser Asn Pro Val
    1280                1285                1290

Ala Met Thr Glu Glu Gln Glu Glu Glu Leu Glu Lys Thr Val Ile
    1295                1300                1305

His Asn Asp Asn Glu Glu Leu Ile Lys Val Glu Gly Thr Lys Ile
    1310                1315                1320

Val Leu Gly Lys Gln Leu Ile Glu Ser Ala Asp Glu Val Arg Arg
    1325                1330                1335

Lys Ser Leu Val Leu Lys Phe Pro Lys Gln Gln Leu Pro Pro Lys
    1340                1345                1350

Lys Lys Arg Arg Val Gly Thr Thr Val His Cys Asp Tyr Leu Asn
    1355                1360                1365

Arg Pro His Lys Ser Ile His Arg Arg Arg Thr Asp Pro Met Val
    1370                1375                1380

Thr Leu Ser Ser Ile Leu Glu Ser Ile Ile Asn Asp Met Arg Asp
    1385                1390                1395

Leu Pro Asn Thr Tyr Pro Phe His Thr Pro Ala Trp Met Thr Asp
    1400                1405                1410

Gly Asp Pro Val Ser Lys Arg Lys Lys Lys Lys Lys Lys Arg Gly
```

-continued

```
                1415                1420                1425

Phe Gln Ser Met Leu Ser Thr Ser Pro Leu Gly Val Ala Leu Cys
            1430                1435                1440

Pro His Arg Ala Asn Ser Glu Trp Arg Gly Leu Pro Pro Arg Ser
    1445                1450                1455

Leu Leu
    1460

<210> SEQ ID NO 97
<211> LENGTH: 1485
<212> TYPE: PRT
<213> ORGANISM: Homo sapiens

<400> SEQUENCE: 97

Met Gly Pro Gly Cys Asp Leu Leu Leu Arg Thr Ala Ala Ile Thr
1               5                   10                  15

Ala Ala Ala Ile Met Ser Asp Thr Asp Ser Asp Glu Asp Ser Ala Gly
                20                  25                  30

Gly Gly Pro Phe Ser Leu Ala Gly Phe Leu Phe Gly Asn Ile Asn Gly
            35                  40                  45

Ala Gly Gln Leu Glu Gly Glu Ser Val Leu Asp Asp Glu Cys Lys Lys
50                  55                  60

His Leu Ala Gly Leu Gly Ala Leu Gly Leu Gly Ser Leu Ile Thr Glu
65                  70                  75                  80

Leu Thr Ala Asn Glu Glu Leu Thr Gly Thr Asp Gly Ala Leu Val Asn
                85                  90                  95

Asp Glu Gly Trp Val Arg Ser Thr Glu Asp Ala Val Asp Tyr Ser Asp
            100                 105                 110

Ile Asn Glu Val Ala Glu Asp Glu Ser Arg Arg Tyr Gln Gln Thr Met
        115                 120                 125

Gly Ser Leu Gln Pro Leu Cys His Ser Asp Tyr Asp Glu Asp Asp Tyr
    130                 135                 140

Asp Ala Asp Cys Glu Asp Ile Asp Cys Lys Leu Met Pro Pro Pro Pro
145                 150                 155                 160

Pro Pro Pro Gly Pro Met Lys Lys Asp Lys Asp Gln Asp Ser Ile Thr
                165                 170                 175

Gly Glu Lys Val Asp Phe Ser Ser Ser Asp Ser Glu Ser Glu Met
            180                 185                 190

Gly Pro Gln Glu Ala Thr Gln Ala Glu Ser Glu Asp Gly Lys Leu Thr
        195                 200                 205

Leu Pro Leu Ala Gly Ile Met Gln His Asp Ala Thr Lys Leu Leu Pro
    210                 215                 220

Ser Val Thr Glu Leu Phe Pro Glu Phe Arg Pro Gly Lys Val Leu Arg
225                 230                 235                 240

Phe Leu Arg Leu Phe Gly Pro Gly Lys Asn Val Pro Ser Val Trp Arg
                245                 250                 255

Ser Ala Arg Arg Lys Arg Lys Lys His Arg Glu Leu Ile Gln Glu
            260                 265                 270

Glu Gln Ile Gln Glu Val Glu Cys Ser Val Glu Ser Glu Val Ser Gln
        275                 280                 285

Lys Ser Leu Trp Asn Tyr Asp Tyr Ala Pro Pro Pro Pro Glu Gln
    290                 295                 300

Cys Leu Ser Asp Asp Glu Ile Thr Met Met Ala Pro Val Glu Ser Lys
305                 310                 315                 320

Phe Ser Gln Ser Thr Gly Asp Ile Asp Lys Val Thr Asp Thr Lys Pro
```

```
                     325                 330                 335
Arg Val Ala Glu Trp Arg Tyr Gly Pro Ala Arg Leu Trp Tyr Asp Met
                340                 345                 350

Leu Gly Val Pro Glu Asp Gly Ser Gly Phe Asp Tyr Gly Phe Lys Leu
                355                 360                 365

Arg Lys Thr Glu His Glu Pro Val Ile Lys Ser Arg Met Ile Glu Glu
            370                 375                 380

Phe Arg Lys Leu Glu Glu Asn Asn Gly Thr Asp Leu Leu Ala Asp Glu
385                 390                 395                 400

Asn Phe Leu Met Val Thr Gln Leu His Trp Glu Asp Ile Ile Trp
                    405                 410                 415

Asp Gly Glu Asp Val Lys His Lys Gly Thr Lys Pro Gln Arg Ala Ser
                420                 425                 430

Leu Ala Gly Trp Leu Pro Ser Met Thr Arg Asn Ala Met Ala Tyr
                435                 440                 445

Asn Val Gln Gln Gly Phe Ala Ala Thr Leu Asp Asp Lys Pro Trp
            450                 455                 460

Tyr Ser Ile Phe Pro Ile Asp Asn Glu Asp Leu Val Tyr Gly Arg Trp
465                 470                 475                 480

Glu Asp Asn Ile Ile Trp Asp Ala Gln Ala Met Pro Arg Leu Leu Glu
                    485                 490                 495

Pro Pro Val Leu Thr Leu Asp Pro Asn Asp Glu Asn Leu Ile Leu Glu
                500                 505                 510

Ile Pro Asp Glu Lys Glu Glu Ala Thr Ser Asn Ser Pro Ser Lys Glu
            515                 520                 525

Ser Lys Lys Glu Ser Ser Leu Lys Lys Ser Arg Ile Leu Leu Gly Lys
        530                 535                 540

Thr Gly Val Ile Lys Glu Glu Pro Gln Gln Asn Met Ser Gln Pro Glu
545                 550                 555                 560

Val Lys Asp Pro Trp Asn Leu Ser Asn Asp Glu Tyr Tyr Tyr Pro Lys
                565                 570                 575

Gln Gln Gly Leu Arg Gly Thr Phe Gly Gly Asn Ile Ile Gln His Ser
                580                 585                 590

Ile Pro Ala Val Glu Leu Arg Gln Pro Phe Phe Pro Thr His Met Gly
            595                 600                 605

Pro Ile Lys Leu Arg Gln Phe His Arg Pro Pro Leu Lys Lys Tyr Ser
            610                 615                 620

Phe Gly Ala Leu Ser Gln Pro Gly Pro His Ser Val Gln Pro Leu Leu
625                 630                 635                 640

Lys His Ile Lys Lys Lys Ala Lys Met Arg Glu Gln Glu Arg Gln Ala
                    645                 650                 655

Ser Gly Gly Gly Glu Met Phe Phe Met Arg Thr Pro Gln Asp Leu Thr
                660                 665                 670

Gly Lys Asp Gly Asp Leu Ile Leu Ala Glu Tyr Ser Glu Glu Asn Gly
            675                 680                 685

Pro Leu Met Met Gln Val Gly Met Ala Thr Lys Ile Lys Asn Tyr Tyr
            690                 695                 700

Lys Arg Lys Pro Gly Lys Asp Pro Gly Ala Pro Asp Cys Lys Tyr Gly
705                 710                 715                 720

Glu Thr Val Tyr Cys His Thr Ser Pro Phe Leu Gly Ser Leu His Pro
                    725                 730                 735

Gly Gln Leu Leu Gln Ala Phe Glu Asn Asn Leu Phe Arg Ala Pro Ile
                740                 745                 750
```

```
Tyr Leu His Lys Met Pro Glu Thr Asp Phe Leu Ile Ile Arg Thr Arg
        755                 760                 765

Gln Gly Tyr Tyr Ile Arg Glu Leu Val Asp Ile Phe Val Val Gly Gln
        770                 775                 780

Gln Cys Pro Leu Phe Glu Val Pro Gly Pro Asn Ser Lys Arg Ala Asn
785                 790                 795                 800

Thr His Ile Arg Asp Phe Leu Gln Val Phe Ile Tyr Arg Leu Phe Trp
                805                 810                 815

Lys Ser Lys Asp Arg Pro Arg Arg Ile Arg Met Glu Asp Ile Lys Lys
                820                 825                 830

Ala Phe Pro Ser His Ser Glu Ser Ser Ile Arg Lys Arg Leu Lys Leu
                835                 840                 845

Cys Ala Asp Phe Lys Arg Thr Gly Met Asp Ser Asn Trp Trp Val Leu
850                 855                 860

Lys Ser Asp Phe Arg Leu Pro Thr Glu Glu Ile Arg Ala Met Val
865                 870                 875                 880

Ser Pro Glu Gln Cys Ala Tyr Tyr Ser Met Ile Ala Ala Glu Gln
                885                 890                 895

Arg Leu Lys Asp Ala Gly Tyr Gly Lys Ser Phe Phe Ala Pro Glu
                900                 905                 910

Glu Glu Asn Glu Glu Asp Phe Gln Met Lys Ile Asp Asp Glu Val Arg
                915                 920                 925

Thr Ala Pro Trp Asn Thr Thr Arg Ala Phe Ile Ala Ala Met Lys Gly
930                 935                 940

Lys Cys Leu Leu Glu Val Thr Gly Val Ala Asp Pro Thr Gly Cys Gly
945                 950                 955                 960

Glu Gly Phe Ser Tyr Val Lys Ile Pro Asn Lys Pro Thr Gln Gln Lys
                965                 970                 975

Asp Asp Lys Glu Pro Gln Pro Val Lys Lys Thr Val Thr Gly Thr Asp
                980                 985                 990

Ala Asp Leu Arg Arg Leu Ser Leu  Lys Asn Ala Lys Gln  Leu Leu Arg
                995                 1000                1005

Lys Phe  Gly Val Pro Glu Glu  Glu Ile Lys Lys Leu  Ser Arg Trp
        1010                1015                1020

Glu Val  Ile Asp Val Val Arg  Thr Met Ser Thr Glu  Gln Ala Arg
        1025                1030                1035

Ser Gly  Glu Gly Pro Met Ser  Lys Phe Ala Arg Gly  Ser Arg Phe
        1040                1045                1050

Ser Val  Ala Glu His Gln Glu  Arg Tyr Lys Glu Glu  Cys Gln Arg
        1055                1060                1065

Ile Phe  Asp Leu Gln Asn Lys  Val Leu Ser Ser Thr  Glu Val Leu
        1070                1075                1080

Ser Thr  Asp Thr Asp Ser Ser  Ala Glu Asp Ser  Asp Phe Glu
        1085                1090                1095

Glu Met  Gly Lys Asn Ile Glu  Asn Met Leu Gln Asn  Lys Lys Thr
        1100                1105                1110

Ser Ser  Gln Leu Ser Arg Glu  Arg Glu Glu Gln Glu  Arg Lys Glu
        1115                1120                1125

Leu Gln  Arg Met Leu Leu Ala  Ala Gly Ser Ala Ala  Ser Gly Asn
        1130                1135                1140

Asn His  Arg Asp Asp Asp Thr  Ala Ser Val Thr Ser  Leu Asn Ser
        1145                1150                1155

Ser Ala  Thr Gly Arg Cys Leu  Lys Ile Tyr Arg Thr  Phe Arg Asp
        1160                1165                1170
```

-continued

| | | | | | | | | | |
|---|---|---|---|---|---|---|---|---|---|
|Glu|Glu|Gly|Lys|Glu|Tyr|Val|Arg|Cys|Glu|Thr|Val|Arg|Lys|Pro|
|1175| | | | |1180| | | | |1185| | | | |

Glu Glu Gly Lys Glu Tyr Val Arg Cys Glu Thr Val Arg Lys Pro
    1175                1180                1185

Ala Val Ile Asp Ala Tyr Val Arg Ile Arg Thr Thr Lys Asp Glu
    1190                1195                1200

Glu Phe Ile Arg Lys Phe Ala Leu Phe Asp Glu Gln His Arg Glu
    1205                1210                1215

Glu Met Arg Lys Glu Arg Arg Ile Gln Glu Gln Leu Arg Arg
    1220                1225                1230

Leu Lys Arg Asn Gln Glu Lys Glu Lys Leu Lys Gly Pro Pro Glu
    1235                1240                1245

Lys Lys Pro Lys Lys Met Lys Glu Arg Pro Asp Leu Lys Leu Lys
    1250                1255                1260

Cys Gly Ala Cys Gly Ala Ile Gly His Met Arg Thr Asn Lys Phe
    1265                1270                1275

Cys Pro Leu Tyr Tyr Gln Thr Asn Ala Pro Pro Ser Asn Pro Val
    1280                1285                1290

Ala Met Thr Glu Glu Gln Glu Glu Leu Glu Lys Thr Val Ile
    1295                1300                1305

His Asn Asp Asn Glu Glu Leu Ile Lys Val Glu Gly Thr Lys Ile
    1310                1315                1320

Val Leu Gly Lys Gln Leu Ile Glu Ser Ala Asp Glu Val Arg Arg
    1325                1330                1335

Lys Ser Leu Val Leu Lys Phe Pro Lys Gln Gln Leu Pro Pro Lys
    1340                1345                1350

Lys Lys Arg Arg Val Gly Thr Thr Val His Cys Asp Tyr Leu Asn
    1355                1360                1365

Arg Pro His Lys Ser Ile His Arg Arg Arg Thr Asp Pro Met Val
    1370                1375                1380

Thr Leu Ser Ser Ile Leu Glu Ser Ile Ile Asn Asp Met Arg Asp
    1385                1390                1395

Leu Pro Asn Thr Tyr Pro Phe His Thr Pro Val Asn Ala Lys Val
    1400                1405                1410

Val Lys Asp Tyr Tyr Lys Ile Ile Thr Arg Pro Met Asp Leu Gln
    1415                1420                1425

Thr Leu Arg Glu Asn Val Arg Lys Arg Leu Tyr Pro Ser Arg Glu
    1430                1435                1440

Glu Phe Arg Glu His Leu Glu Leu Ile Val Lys Asn Ser Ala Thr
    1445                1450                1455

Tyr Asn Gly Lys Asn Gln Met Phe Arg Asp Cys Lys Gly His Cys
    1460                1465                1470

Ser Asp Pro Tyr Ser Leu Leu Ala Leu Asn Ser Asp
    1475                1480                1485

<210> SEQ ID NO 98
<211> LENGTH: 22
<212> TYPE: DNA
<213> ORGANISM: Artificial sequence
<220> FEATURE:
<223> OTHER INFORMATION: Primer

<400> SEQUENCE: 98
ccactagaac ctggtcaaat ac                                              22

<210> SEQ ID NO 99
<211> LENGTH: 20
<212> TYPE: DNA

<213> ORGANISM: Artificial sequence
<220> FEATURE:
<223> OTHER INFORMATION: Primer

<400> SEQUENCE: 99
gactgagagt ggagcgcttg                                                   20

<210> SEQ ID NO 100
<211> LENGTH: 271
<212> TYPE: PRT
<213> ORGANISM: Homo sapiens

<400> SEQUENCE: 100

Leu Ser Arg Pro Ser Cys Leu Pro Leu Pro Glu Leu Gly Leu Val Leu
1               5                   10                  15

Asn Leu Lys Glu Lys Lys Ala Val Leu Asn Pro Thr Ile Ile Pro Glu
            20                  25                  30

Ser Val Ala Gly Asn Gln Glu Ala Ala Asn Asn Pro Ser Ser His Pro
        35                  40                  45

Gln Leu Val Gly Phe Gln Asn Pro Glu Asp Asp His Leu Ala Lys Glu
    50                  55                  60

Ala Ser Cys Asn Ile Ser Ala His Gln Gln Gly Val Lys Arg Lys Ser
65                  70                  75                  80

Asp Thr Pro Leu Gly Ser Pro Leu Glu Pro Gly Gln Ile Leu Glu Lys
                85                  90                  95

Asn Glu Asp Ser Ser Lys Val Lys Leu Lys Ile Arg Phe Ser Ser Ser
            100                 105                 110

Gln Asp Glu Glu Glu Ile Asp Met Asp Thr Val His Asp Ser Gln Ala
        115                 120                 125

Phe Ile Ser His His Leu Asn Met Leu Glu Arg Pro Ser Thr Pro Gly
    130                 135                 140

Leu Ser Lys Tyr Arg Pro Ala Ser Ser Arg Ser Ala Leu Ile Pro Gln
145                 150                 155                 160

His Ser Ala Gly Cys Asp Ser Thr Pro Thr Thr Lys Pro Gln Trp Ser
                165                 170                 175

Leu Glu Leu Ala Arg Lys Gly Thr Gly Lys Glu Gln Ala Pro Leu Glu
            180                 185                 190

Met Ser Met His Pro Ala Ala Ser Ala Pro Leu Ser Val Phe Thr Lys
        195                 200                 205

Glu Ser Thr Ala Ser Lys His Ser Asp His His His His His His
    210                 215                 220

Glu His Lys Lys Lys Lys Lys His Lys His Lys His Lys His Lys
225                 230                 235                 240

His Lys His Asp Ser Lys Glu Lys Asp Lys Glu Pro Phe Thr Phe Ser
                245                 250                 255

Ser Pro Ala Ser Gly Arg Ser Ile Arg Ser Pro Ser Leu Ser Asp
            260                 265                 270

<210> SEQ ID NO 101
<211> LENGTH: 239
<212> TYPE: PRT
<213> ORGANISM: Homo sapiens

<400> SEQUENCE: 101

Thr Ser His Asp Trp Arg Leu Arg Cys Gly Ala Val Asp Leu Tyr Phe
1               5                   10                  15

Thr Leu Phe Gly Leu Ser Arg Pro Ser Cys Leu Pro Leu Pro Glu Leu
            20                  25                  30

-continued

Gly Leu Val Leu Asn Leu Lys Glu Lys Ala Val Leu Asn Pro Thr
                35                  40                  45

Ile Ile Pro Glu Ser Val Ala Gly Asn Gln Glu Ala Ala Asn Asn Pro
 50                  55                  60

Ser Ser His Pro Gln Leu Val Gly Phe Gln Asn Pro Phe Ser Ser Ser
 65                  70                  75                  80

Gln Asp Glu Glu Ile Asp Met Asp Thr Val His Asp Ser Gln Ala
                85                  90                  95

Phe Ile Ser His His Leu Asn Met Leu Glu Arg Pro Ser Thr Pro Gly
                100                 105                 110

Leu Ser Lys Tyr Arg Pro Ala Ser Ser Arg Ser Ala Leu Ile Pro Gln
                115                 120                 125

His Ser Ala Gly Cys Asp Ser Thr Pro Thr Thr Lys Pro Gln Trp Ser
    130                 135                 140

Leu Glu Leu Ala Arg Lys Gly Thr Gly Lys Glu Gln Ala Pro Leu Glu
145                 150                 155                 160

Met Ser Met His Pro Ala Ala Ser Ala Pro Leu Ser Val Phe Thr Lys
                165                 170                 175

Glu Ser Thr Ala Ser Lys His Ser Asp His His His His His His
                180                 185                 190

Glu His Lys Lys Lys Lys Lys His Lys His Lys His Lys His Lys
            195                 200                 205

His Lys His Asp Ser Lys Glu Lys Asp Lys Glu Pro Phe Thr Phe Ser
    210                 215                 220

Ser Pro Ala Ser Gly Arg Ser Ile Arg Ser Pro Ser Leu Ser Asp
225                 230                 235

<210> SEQ ID NO 102
<211> LENGTH: 21
<212> TYPE: DNA
<213> ORGANISM: Artificial sequence
<220> FEATURE:
<223> OTHER INFORMATION: Primer

<400> SEQUENCE: 102
atctgctgga cgaggtcttc t                                           21

<210> SEQ ID NO 103
<211> LENGTH: 21
<212> TYPE: DNA
<213> ORGANISM: Artificial sequence
<220> FEATURE:
<223> OTHER INFORMATION: Primer

<400> SEQUENCE: 103
tatggtagtt ggggtcacct g                                           21

<210> SEQ ID NO 104
<211> LENGTH: 653
<212> TYPE: PRT
<213> ORGANISM: Homo sapiens

<400> SEQUENCE: 104

Met Ala Ala Gly Ser Asp Leu Leu Asp Glu Val Phe Phe Asn Ser Glu
 1               5                  10                  15

Val Asp Glu Lys Val Gly Met Val Leu Val Arg Ser Glu Asn Gly Gln
                20                  25                  30

Leu Leu Met Ile Pro Gln Gln Ala Leu Ala Gln Met Gln Ala Gln Ala
                35                  40                  45

```
His Ala Gln Pro Gln Thr Thr Met Ala Pro Arg Pro Ala Thr Pro Thr
    50                  55                  60

Ser Ala Pro Pro Val Gln Ile Ser Thr Val Gln Ala Pro Gly Thr Pro
65                  70                  75                  80

Ile Ile Ala Arg Gln Val Thr Pro Thr Thr Ile Lys Gln Val Ser
                85                  90                  95

Gln Ala Gln Thr Thr Val Gln Pro Ser Ala Thr Leu Gln Arg Ser Pro
            100                 105                 110

Gly Val Gln Pro Gln Leu Val Leu Gly Gly Ala Ala Gln Thr Ala Ser
        115                 120                 125

Leu Gly Thr Ala Thr Ala Val Gln Thr Gly Thr Pro Gln Arg Thr Val
    130                 135                 140

Pro Gly Ala Thr Thr Thr Ser Ser Ala Ala Thr Glu Thr Met Glu Asn
145                 150                 155                 160

Val Lys Lys Cys Lys Asn Phe Leu Ser Thr Leu Ile Lys Leu Ala Ser
                165                 170                 175

Ser Gly Lys Gln Ser Thr Glu Thr Ala Ala Asn Val Lys Glu Leu Val
            180                 185                 190

Gln Asn Leu Leu Asp Gly Lys Ile Glu Ala Glu Asp Phe Thr Ser Arg
        195                 200                 205

Leu Tyr Arg Glu Leu Asn Ser Ser Pro Gln Pro Tyr Leu Val Pro Phe
    210                 215                 220

Leu Lys Arg Ser Leu Pro Ala Leu Arg Gln Leu Thr Pro Asp Ser Ala
225                 230                 235                 240

Ala Phe Ile Gln Gln Ser Gln Gln Pro Pro Pro Thr Ser Gln
                245                 250                 255

Ala Thr Thr Ala Leu Thr Ala Val Val Leu Ser Ser Val Gln Arg
            260                 265                 270

Thr Ala Gly Lys Thr Ala Ala Thr Val Thr Ser Ala Leu Gln Pro Pro
        275                 280                 285

Val Leu Ser Leu Thr Gln Pro Thr Gln Val Gly Val Gly Lys Gln Gly
    290                 295                 300

Gln Pro Thr Pro Leu Val Ile Gln Gln Pro Lys Pro Gly Ala Leu
305                 310                 315                 320

Ile Arg Pro Pro Gln Val Thr Leu Thr Gln Thr Pro Met Val Ala Leu
                325                 330                 335

Arg Gln Pro His Asn Arg Ile Met Leu Thr Thr Pro Gln Gln Ile Gln
            340                 345                 350

Leu Asn Pro Leu Gln Pro Val Pro Val Lys Pro Ala Val Leu Pro
        355                 360                 365

Gly Thr Lys Ala Leu Ser Ala Val Ser Ala Gln Ala Ala Ala Gln
    370                 375                 380

Lys Asn Lys Leu Lys Glu Pro Gly Gly Ser Phe Arg Asp Asp Asp
385                 390                 395                 400

Asp Ile Asn Asp Val Ala Ser Met Ala Gly Val Asn Leu Ser Glu Glu
                405                 410                 415

Ser Ala Arg Ile Leu Ala Thr Asn Ser Glu Leu Val Gly Thr Leu Thr
            420                 425                 430

Arg Ser Cys Lys Asp Glu Thr Phe Leu Leu Gln Ala Pro Leu Gln Arg
        435                 440                 445

Arg Ile Leu Glu Ile Gly Lys Lys His Gly Ile Thr Glu Leu His Pro
    450                 455                 460

Asp Val Val Ser Tyr Val Ser His Ala Thr Gln Gln Arg Leu Gln Asn
```

```
                465                 470                 475                 480
Leu Val Glu Lys Ile Ser Glu Thr Ala Gln Gln Lys Asn Phe Ser Tyr
                    485                 490                 495

Lys Asp Asp Arg Tyr Glu Gln Ala Ser Asp Val Arg Ala Gln Leu
                500                 505                 510

Lys Phe Phe Glu Gln Leu Asp Gln Ile Glu Lys Gln Arg Lys Asp Glu
                515                 520                 525

Gln Glu Arg Glu Ile Leu Met Arg Ala Lys Ser Arg Ser Arg Gln
                530                 535                 540

Glu Asp Pro Glu Gln Leu Arg Leu Lys Gln Lys Ala Lys Glu Met Gln
545                 550                 555                 560

Gln Gln Glu Leu Ala Gln Met Arg Gln Arg Asp Ala Asn Leu Thr Ala
                565                 570                 575

Leu Ala Ala Ile Gly Pro Arg Lys Arg Lys Val Asp Cys Pro Gly
                580                 585                 590

Pro Gly Ser Gly Ala Glu Gly Ser Gly Pro Gly Ser Val Val Pro Gly
                595                 600                 605

Ser Ser Gly Val Gly Thr Pro Arg Gln Phe Thr Arg Gln Arg Ile Thr
    610                 615                 620

Arg Val Asn Leu Arg Asp Leu Ile Phe Cys Leu Glu Asn Glu Arg Glu
625                 630                 635                 640

Thr Ser His Ser Leu Leu Leu Tyr Lys Ala Phe Leu Lys
                    645                 650

<210> SEQ ID NO 105
<211> LENGTH: 1085
<212> TYPE: PRT
<213> ORGANISM: Homo sapiens

<400> SEQUENCE: 105

Met Ala Ala Gly Ser Asp Leu Leu Asp Glu Val Phe Phe Asn Ser Glu
1               5                   10                  15

Val Asp Glu Lys Val Val Ser Asp Leu Val Gly Ser Leu Glu Ser Gln
                20                  25                  30

Leu Ala Ala Ser Ala Ala His His His Leu Ala Pro Arg Thr Pro
                35                  40                  45

Glu Val Arg Ala Ala Ala Gly Ala Leu Gly Asn His Val Val Ser
    50                  55                  60

Gly Ser Pro Ala Gly Ala Ala Gly Ala Gly Pro Ala Ala Pro Ala Glu
65                  70                  75                  80

Gly Ala Pro Gly Ala Ala Pro Glu Pro Pro Ala Gly Arg Ala Arg
                85                  90                  95

Pro Gly Gly Gly Gly Pro Gln Arg Pro Gly Pro Pro Ser Pro Arg Arg
                100                 105                 110

Pro Leu Val Pro Ala Gly Pro Ala Pro Ala Ala Lys Leu Arg Pro
                115                 120                 125

Pro Pro Glu Gly Ser Ala Gly Ser Cys Ala Pro Val Pro Ala Ala Ala
                130                 135                 140

Ala Val Ala Ala Gly Pro Glu Pro Ala Pro Ala Gly Pro Ala Lys Pro
145                 150                 155                 160

Ala Gly Pro Ala Ala Leu Ala Ala Arg Ala Gly Pro Gly Pro Gly Pro
                165                 170                 175

Gly Pro Gly Pro Gly Pro Gly Pro Gly Lys Pro Ala Gly Pro
                180                 185                 190

Gly Ala Ala Gln Thr Leu Asn Gly Ser Ala Ala Leu Leu Asn Ser His
```

```
                195                 200                 205
His Ala Ala Ala Pro Ala Val Ser Leu Val Asn Asn Gly Pro Ala Ala
    210                 215                 220
Leu Leu Pro Leu Pro Lys Pro Ala Ala Pro Gly Thr Val Ile Gln Thr
225                 230                 235                 240
Pro Pro Phe Val Gly Ala Ala Pro Pro Ala Pro Ala Ala Pro Ser
            245                 250                 255
Pro Pro Ala Ala Pro Ala Pro Ala Pro Ala Ala Ala Pro Pro
        260                 265                 270
Pro Pro Pro Ala Pro Ala Thr Leu Ala Arg Pro Pro Gly His Pro Ala
    275                 280                 285
Gly Pro Pro Thr Ala Ala Pro Ala Val Pro Pro Ala Ala Ala Gln
    290                 295                 300
Asn Gly Gly Ser Ala Gly Ala Ala Pro Ala Pro Ala Pro Ala Ala Gly
305                 310                 315                 320
Gly Pro Ala Gly Val Ser Gly Gln Pro Gly Pro Gly Ala Ala Ala Ala
            325                 330                 335
Ala Pro Ala Pro Gly Val Lys Ala Glu Ser Pro Lys Arg Val Val Gln
        340                 345                 350
Ala Ala Pro Pro Ala Ala Gln Thr Leu Ala Ala Ser Gly Pro Ala Ser
        355                 360                 365
Thr Ala Ala Ser Met Val Ile Gly Pro Thr Met Gln Gly Ala Leu Pro
    370                 375                 380
Ser Pro Ala Ala Val Pro Pro Ala Pro Gly Thr Pro Thr Gly Leu
385                 390                 395                 400
Pro Lys Gly Ala Ala Gly Ala Val Thr Gln Ser Leu Ser Arg Thr Pro
            405                 410                 415
Thr Ala Thr Thr Ser Gly Ile Arg Ala Thr Leu Thr Pro Thr Val Leu
        420                 425                 430
Ala Pro Arg Leu Pro Gln Pro Pro Gln Asn Pro Thr Asn Ile Gln Asn
        435                 440                 445
Phe Gln Leu Pro Pro Gly Met Val Leu Val Arg Ser Glu Asn Gly Gln
    450                 455                 460
Leu Leu Met Ile Pro Gln Gln Ala Leu Ala Gln Met Gln Ala Gln Ala
465                 470                 475                 480
His Ala Gln Pro Gln Thr Thr Met Ala Pro Arg Pro Ala Thr Pro Thr
            485                 490                 495
Ser Ala Pro Pro Val Gln Ile Ser Thr Val Gln Ala Pro Gly Thr Pro
        500                 505                 510
Ile Ile Ala Arg Gln Val Thr Pro Thr Thr Ile Ile Lys Gln Val Ser
        515                 520                 525
Gln Ala Gln Thr Thr Val Gln Pro Ser Ala Thr Leu Gln Arg Ser Pro
    530                 535                 540
Gly Val Gln Pro Gln Leu Val Leu Gly Gly Ala Ala Gln Thr Ala Ser
545                 550                 555                 560
Leu Gly Thr Ala Thr Ala Val Gln Thr Gly Thr Pro Gln Arg Thr Val
            565                 570                 575
Pro Gly Ala Thr Thr Thr Ser Ser Ala Ala Thr Glu Thr Met Glu Asn
        580                 585                 590
Val Lys Lys Cys Lys Asn Phe Leu Ser Thr Leu Ile Lys Leu Ala Ser
        595                 600                 605
Ser Gly Lys Gln Ser Thr Glu Thr Ala Ala Asn Val Lys Glu Leu Val
    610                 615                 620
```

-continued

Gln Asn Leu Leu Asp Gly Lys Ile Glu Ala Glu Asp Phe Thr Ser Arg
625                 630                 635                 640

Leu Tyr Arg Glu Leu Asn Ser Ser Pro Gln Pro Tyr Leu Val Pro Phe
            645                 650                 655

Leu Lys Arg Ser Leu Pro Ala Leu Arg Gln Leu Thr Pro Asp Ser Ala
            660                 665                 670

Ala Phe Ile Gln Gln Ser Gln Gln Pro Pro Pro Thr Ser Gln
            675                 680                 685

Ala Thr Thr Ala Leu Thr Ala Val Leu Ser Ser Val Gln Arg
690                 695                 700

Thr Ala Gly Lys Thr Ala Ala Thr Val Thr Ser Ala Leu Gln Pro Pro
705                 710                 715                 720

Val Leu Ser Leu Thr Gln Pro Thr Gln Val Gly Val Gly Lys Gln Gly
            725                 730                 735

Gln Pro Thr Pro Leu Val Ile Gln Gln Pro Lys Pro Gly Ala Leu
            740                 745                 750

Ile Arg Pro Pro Gln Val Thr Leu Thr Gln Thr Pro Met Val Ala Leu
            755                 760                 765

Arg Gln Pro His Asn Arg Ile Met Leu Thr Thr Pro Gln Gln Ile Gln
770                 775                 780

Leu Asn Pro Leu Gln Pro Val Pro Val Lys Pro Ala Val Leu Pro
785                 790                 795                 800

Gly Thr Lys Ala Leu Ser Ala Val Ser Ala Gln Ala Ala Ala Gln
            805                 810                 815

Lys Asn Lys Leu Lys Glu Pro Gly Gly Gly Ser Phe Arg Asp Asp Asp
            820                 825                 830

Asp Ile Asn Asp Val Ala Ser Met Ala Gly Val Asn Leu Ser Glu Glu
            835                 840                 845

Ser Ala Arg Ile Leu Ala Thr Asn Ser Glu Leu Val Gly Thr Leu Thr
850                 855                 860

Arg Ser Cys Lys Asp Glu Thr Phe Leu Leu Gln Ala Pro Leu Gln Arg
865                 870                 875                 880

Arg Ile Leu Glu Ile Gly Lys Lys His Gly Ile Thr Glu Leu His Pro
            885                 890                 895

Asp Val Val Ser Tyr Val Ser His Ala Thr Gln Gln Arg Leu Gln Asn
            900                 905                 910

Leu Val Glu Lys Ile Ser Glu Thr Ala Gln Gln Lys Asn Phe Ser Tyr
            915                 920                 925

Lys Asp Asp Asp Arg Tyr Glu Gln Ala Ser Asp Val Arg Ala Gln Leu
            930                 935                 940

Lys Phe Phe Glu Gln Leu Asp Gln Ile Glu Lys Gln Arg Lys Asp Glu
945                 950                 955                 960

Gln Glu Arg Glu Ile Leu Met Arg Ala Ala Lys Ser Arg Ser Arg Gln
            965                 970                 975

Glu Asp Pro Glu Gln Leu Arg Leu Lys Gln Lys Ala Lys Glu Met Gln
            980                 985                 990

Gln Gln Glu Leu Ala Gln Met Arg Gln Arg Asp Ala Asn Leu Thr Ala
            995                 1000                1005

Leu Ala Ala Ile Gly Pro Arg Lys Lys Arg Lys Val Asp Cys Pro
            1010                1015                1020

Gly Pro Gly Ser Gly Ala Glu Gly Ser Gly Pro Gly Ser Val Val
            1025                1030                1035

Pro Gly Ser Ser Gly Val Gly Thr Pro Arg Gln Phe Thr Arg Gln
            1040                1045                1050

Arg Ile Thr Arg Val Asn Leu Arg Asp Leu Ile Phe Cys Leu Glu
    1055                1060                1065

Asn Glu Arg Glu Thr Ser His Ser Leu Leu Leu Tyr Lys Ala Phe
    1070                1075                1080

Leu Lys
    1085

<210> SEQ ID NO 106
<211> LENGTH: 21
<212> TYPE: DNA
<213> ORGANISM: Artificial sequence
<220> FEATURE:
<223> OTHER INFORMATION: Primer

<400> SEQUENCE: 106
cagtcatgaa acgagtgcgt a                                              21

<210> SEQ ID NO 107
<211> LENGTH: 22
<212> TYPE: DNA
<213> ORGANISM: Artificial sequence
<220> FEATURE:
<223> OTHER INFORMATION: Primer

<400> SEQUENCE: 107
gaatctctca tctacagaca ac                                             22

<210> SEQ ID NO 108
<211> LENGTH: 85
<212> TYPE: PRT
<213> ORGANISM: Homo sapiens

<400> SEQUENCE: 108

Met Lys Arg Val Arg Thr Glu Gln Ile Gln Met Ala Val Ser Cys Tyr
1               5                   10                  15

Leu Lys Arg Arg Gln Tyr Val Asp Ser Asp Gly Pro Leu Lys Gln Gly
            20                  25                  30

Leu Arg Leu Ser Gln Thr Ala Glu Glu Met Ala Ala Asn Leu Thr Val
        35                  40                  45

Gln Ser Glu Ser Gly Cys Ala Asn Ile Val Ser Ala Ala Pro Cys Gln
    50                  55                  60

Ala Glu Pro Gln Gln Tyr Glu Val Gln Phe Gly Arg Leu Arg Asn Phe
65                  70                  75                  80

Leu Thr Gly Cys Leu
            85

<210> SEQ ID NO 109
<211> LENGTH: 120
<212> TYPE: PRT
<213> ORGANISM: Homo sapiens

<400> SEQUENCE: 109

Met Lys Arg Val Arg Thr Glu Gln Ile Gln Met Ala Val Ser Cys Tyr
1               5                   10                  15

Leu Lys Arg Arg Gln Tyr Val Asp Ser Asp Gly Pro Leu Lys Gln Gly
            20                  25                  30

Leu Arg Leu Ser Gln Thr Ala Glu Glu Met Ala Ala Asn Leu Thr Val
        35                  40                  45

Gln Ser Glu Ser Gly Cys Ala Asn Ile Val Ser Ala Ala Pro Cys Gln
    50                  55                  60

```
Ala Glu Pro Gln Gln Tyr Glu Val Gln Phe Gly Arg Leu Arg Asn Phe
 65                  70                  75                  80

Leu Thr Asp Ser Asp Ser Gln His Ser His Glu Val Met Pro Leu Leu
                 85                  90                  95

Tyr Pro Leu Phe Val Tyr Leu His Leu Asn Leu Val Gln Asn Ser Pro
            100                 105                 110

Lys Ser Thr Val Glu Ser Phe Tyr
        115                 120

<210> SEQ ID NO 110
<211> LENGTH: 21
<212> TYPE: DNA
<213> ORGANISM: Artificial sequence
<220> FEATURE:
<223> OTHER INFORMATION: Primer

<400> SEQUENCE: 110
cctatttcgt aatccgcacc t                                        21

<210> SEQ ID NO 111
<211> LENGTH: 21
<212> TYPE: DNA
<213> ORGANISM: Artificial sequence
<220> FEATURE:
<223> OTHER INFORMATION: Primer

<400> SEQUENCE: 111
actgactcag agcggcaagt a                                        21

<210> SEQ ID NO 112
<211> LENGTH: 265
<212> TYPE: PRT
<213> ORGANISM: Homo sapiens

<400> SEQUENCE: 112

Met Cys Leu Gly Pro Tyr Val Arg Cys Leu Val Gly Ser Val Leu Tyr
  1               5                  10                  15

Cys Val Leu Glu Pro Leu Ala Ala Ser Ile Asn Pro Leu Asn Asp His
                 20                  25                  30

Trp Thr Leu Arg Asp Gly Ala Ala Leu Leu Leu Ser His Ile Phe Trp
             35                  40                  45

Thr His Gly Asp Leu Val Ser Gly Leu Tyr Gln His Ile Leu Leu Ser
         50                  55                  60

Leu Gln Lys Ile Leu Ala Asp Pro Val Arg Pro Leu Cys Cys His Tyr
 65                  70                  75                  80

Gly Ala Val Val Gly Leu His Ala Leu Gly Trp Lys Ala Val Glu Arg
                 85                  90                  95

Val Leu Tyr Pro His Leu Ser Thr Tyr Trp Thr Asn Leu Gln Ala Val
            100                 105                 110

Leu Asp Asp Tyr Ser Val Ser Asn Ala Gln Val Lys Ala Asp Gly His
        115                 120                 125

Lys Val Tyr Gly Ala Ile Leu Val Ala Val Glu Arg Leu Leu Lys Met
130                 135                 140

Lys Ala Gln Ala Ala Glu Pro Asn Arg Gly Gly Pro Gly Gly Arg Gly
145                 150                 155                 160

Cys Arg Arg Leu Asp Asp Leu Pro Trp Asp Ser Leu Leu Phe Gln Glu
                165                 170                 175

Ser Ser Ser Gly Gly Gly Ala Glu Pro Ser Phe Gly Ser Gly Leu Pro
            180                 185                 190
```

```
Leu Pro Pro Gly Gly Ala Gly Pro Glu Asp Pro Ser Leu Ser Val Thr
        195                 200                 205
Leu Ala Asp Ile Tyr Arg Glu Leu Tyr Ala Phe Phe Gly Asp Ser Leu
        210                 215                 220
Ala Thr Arg Phe Gly Thr Gly Leu Ala Leu Arg Ala Glu Thr Ala His
225                 230                 235                 240
Asp Arg Pro Tyr Gln Pro Pro Arg Pro Pro Val Gly Ala Leu Gly Leu
                    245                 250                 255
Leu Ala Val Leu Ala Ala Leu Ser Gln
            260                 265

<210> SEQ ID NO 113
<211> LENGTH: 360
<212> TYPE: PRT
<213> ORGANISM: Homo sapiens

<400> SEQUENCE: 113

Gln Asp Leu Gln Thr Asn Ser Lys Ile Gly Ala Leu Leu Pro Tyr Phe
1               5                   10                  15
Val Tyr Val Val Ser Gly Val Lys Ser Val Ser His Asp Leu Glu Gln
                20                  25                  30
Leu His Arg Leu Leu Gln Val Ala Arg Ser Leu Phe Arg Asn Pro His
            35                  40                  45
Leu Cys Leu Gly Pro Tyr Val Arg Cys Leu Val Gly Ser Val Leu Tyr
    50                  55                  60
Cys Val Leu Glu Pro Leu Ala Ala Ser Ile Asn Pro Leu Asn Asp His
65                  70                  75                  80
Trp Thr Leu Arg Asp Gly Ala Ala Leu Leu Ser His Ile Phe Trp
                85                  90                  95
Thr His Gly Asp Leu Val Ser Gly Leu Tyr Gln His Ile Leu Leu Ser
                100                 105                 110
Leu Gln Lys Ile Leu Ala Asp Pro Val Arg Pro Leu Cys Cys His Tyr
            115                 120                 125
Gly Ala Val Val Gly Leu His Ala Leu Gly Trp Lys Ala Val Glu Arg
    130                 135                 140
Val Leu Tyr Pro His Leu Ser Thr Tyr Trp Thr Asn Leu Gln Ala Val
145                 150                 155                 160
Leu Asp Asp Tyr Ser Val Ser Asn Ala Gln Val Lys Ala Asp Gly His
                165                 170                 175
Lys Val Tyr Gly Ala Ile Leu Val Ala Val Glu Arg Leu Leu Lys Met
                180                 185                 190
Lys Ala Gln Ala Ala Glu Pro Asn Arg Gly Gly Pro Gly Gly Arg Gly
            195                 200                 205
Cys Arg Arg Leu Asp Asp Leu Pro Trp Asp Ser Leu Leu Phe Gln Glu
    210                 215                 220
Ser Ser Ser Gly Gly Gly Ala Glu Pro Ser Phe Gly Ser Gly Leu Pro
225                 230                 235                 240
Leu Pro Pro Gly Gly Ala Gly Pro Glu Asp Pro Ser Leu Ser Val Thr
                245                 250                 255
Leu Ala Asp Ile Tyr Arg Glu Leu Tyr Ala Phe Phe Gly Asp Ser Leu
                260                 265                 270
Ala Thr Arg Phe Gly Thr Gly Gln Pro Ala Pro Thr Ala Pro Arg Pro
            275                 280                 285
Pro Gly Asp Lys Lys Glu Pro Ala Ala Ala Pro Asp Ser Val Arg Lys
    290                 295                 300
```

```
Met Pro Gln Leu Thr Ala Ser Ala Ile Val Ser Pro His Gly Asp Glu
305                 310                 315                 320

Ser Pro Arg Gly Ser Gly Gly Gly Pro Ala Ser Ala Ser Gly Pro
            325                 330                 335

Ala Ala Ser Glu Ser Arg Pro Leu Pro Arg Val His Arg Ala Arg Gly
                340                 345                 350

Ala Pro Arg Gln Gln Gly Pro Gly
            355                 360
```

<210> SEQ ID NO 114
<211> LENGTH: 21
<212> TYPE: DNA
<213> ORGANISM: Artificial sequence
<220> FEATURE:
<223> OTHER INFORMATION: Primer

<400> SEQUENCE: 114
agacatgagt gaaagccagg a                                           21

<210> SEQ ID NO 115
<211> LENGTH: 21
<212> TYPE: DNA
<213> ORGANISM: Artificial sequence
<220> FEATURE:
<223> OTHER INFORMATION: Primer

<400> SEQUENCE: 115
cataaggcaa ctgaagggac a                                           21

<210> SEQ ID NO 116
<211> LENGTH: 302
<212> TYPE: PRT
<213> ORGANISM: Homo sapiens

<400> SEQUENCE: 116

```
Met Ser Glu Ser Gln Asp Glu Val Pro Asp Glu Val Glu Asn Gln Phe
1               5                   10                  15

Ile Leu Arg Leu Pro Leu Glu His Ala Cys Thr Val Arg Asn Leu Ala
                20                  25                  30

Arg Ser Gln Ser Val Lys Met Lys Asp Lys Leu Lys Ile Asp Leu Leu
            35                  40                  45

Pro Asp Gly Arg His Ala Val Glu Val Glu Asp Val Pro Leu Ala
    50                  55                  60

Ala Lys Leu Val Asp Leu Pro Cys Val Ile Glu Ser Leu Arg Thr Leu
65                  70                  75                  80

Asp Lys Lys Thr Phe Tyr Lys Thr Ala Asp Ile Ser Gln Met Leu Val
                85                  90                  95

Cys Thr Ala Asp Gly Asp Ile His Leu Ser Pro Glu Glu Pro Ala Ala
                100                 105                 110

Ser Thr Asp Pro Asn Ile Val Arg Lys Glu Arg Gly Arg Glu Glu
            115                 120                 125

Lys Cys Val Trp Lys His Gly Ile Thr Pro Pro Leu Lys Asn Val Arg
    130                 135                 140

Lys Lys Arg Phe Arg Lys Thr Gln Lys Val Pro Asp Val Lys Glu
145                 150                 155                 160

Met Glu Lys Ser Ser Phe Thr Glu Tyr Ile Glu Ser Pro Asp Val Glu
                165                 170                 175

Asn Glu Val Lys Arg Leu Leu Arg Ser Asp Ala Glu Ala Val Ser Thr
                180                 185                 190
```

```
Arg Trp Glu Val Ile Ala Glu Asp Gly Thr Lys Glu Ile Glu Ser Gln
            195                 200                 205

Gly Ser Ile Pro Gly Phe Leu Ile Ser Ser Gly Met Ser Ser His Lys
    210                 215                 220

Gln Gly His Thr Ser Ser Val Met Glu Ile Gln Lys Gln Ile Glu Lys
225                 230                 235                 240

Lys Glu Lys Lys Leu His Lys Ile Gln Asn Lys Ala Gln Arg Gln Lys
                245                 250                 255

Asp Leu Ile Met Lys Val Glu Asn Leu Thr Leu Lys Asn His Phe Gln
            260                 265                 270

Ser Val Leu Glu Gln Leu Glu Leu Gln Glu Lys Gln Lys Asn Glu Lys
        275                 280                 285

Leu Ile Ser Leu Gln Glu Gln Leu Gln Arg Phe Leu Lys Lys
        290                 295                 300

<210> SEQ ID NO 117
<211> LENGTH: 376
<212> TYPE: PRT
<213> ORGANISM: Homo sapiens

<400> SEQUENCE: 117

Met Ser Glu Ser Gln Asp Glu Val Pro Asp Glu Val Glu Asn Gln Phe
1               5                   10                  15

Ile Leu Arg Leu Pro Leu Glu His Ala Cys Thr Val Arg Asn Leu Ala
            20                  25                  30

Arg Ser Gln Ser Val Lys Met Lys Asp Lys Leu Lys Ile Asp Leu Leu
        35                  40                  45

Pro Asp Gly Arg His Ala Val Val Glu Val Glu Asp Val Pro Leu Ala
    50                  55                  60

Ala Lys Leu Val Asp Leu Pro Cys Val Ile Glu Ser Leu Arg Thr Leu
65                  70                  75                  80

Asp Lys Lys Thr Phe Tyr Lys Thr Ala Asp Ile Ser Gln Met Leu Val
                85                  90                  95

Cys Thr Ala Asp Gly Asp Ile His Leu Ser Pro Glu Glu Pro Ala Ala
            100                 105                 110

Ser Thr Asp Pro Asn Ile Val Arg Lys Lys Glu Arg Gly Arg Glu Glu
        115                 120                 125

Lys Cys Val Trp Lys His Gly Ile Thr Pro Pro Leu Lys Asn Val Arg
130                 135                 140

Lys Lys Arg Phe Arg Lys Thr Gln Lys Lys Val Pro Asp Val Lys Glu
145                 150                 155                 160

Met Glu Lys Ser Ser Phe Thr Glu Tyr Ile Glu Ser Pro Asp Val Glu
                165                 170                 175

Asn Glu Val Lys Arg Leu Leu Arg Ser Asp Ala Glu Ala Val Ser Thr
            180                 185                 190

Arg Trp Glu Val Ile Ala Glu Asp Gly Thr Lys Glu Ile Glu Ser Gln
        195                 200                 205

Gly Ser Ile Pro Gly Phe Leu Ile Ser Ser Gly Met Ser Ser His Lys
    210                 215                 220

Gln Gly His Thr Ser Ser Glu Tyr Asp Met Leu Arg Glu Met Phe Ser
225                 230                 235                 240

Asp Ser Arg Ser Asn Asn Asp Asp Glu Asp Glu Asp Glu
                245                 250                 255

Glu Asp Glu Asp Glu Asp Glu Asp Glu Asp Lys Glu Glu
            260                 265                 270
```

```
Glu Glu Asp Cys Ser Glu Glu Tyr Leu Glu Arg Gln Leu Gln Ala Glu
        275                 280                 285

Phe Ile Glu Ser Gly Gln Tyr Arg Ala Asn Glu Gly Thr Ser Ser Ile
290                 295                 300

Val Met Glu Ile Gln Lys Gln Ile Glu Lys Lys Glu Lys Lys Leu His
305                 310                 315                 320

Lys Ile Gln Asn Lys Ala Gln Arg Gln Lys Asp Leu Ile Met Lys Val
                325                 330                 335

Glu Asn Leu Thr Leu Lys Asn His Phe Gln Ser Val Leu Glu Gln Leu
                340                 345                 350

Glu Leu Gln Glu Lys Gln Lys Asn Glu Lys Leu Ile Ser Leu Gln Glu
            355                 360                 365

Gln Leu Gln Arg Phe Leu Lys Lys
        370                 375

<210> SEQ ID NO 118
<211> LENGTH: 21
<212> TYPE: DNA
<213> ORGANISM: Artificial sequence
<220> FEATURE:
<223> OTHER INFORMATION: Primer

<400> SEQUENCE: 118
cactacgcca gaacaagatg g                                            21

<210> SEQ ID NO 119
<211> LENGTH: 21
<212> TYPE: DNA
<213> ORGANISM: Artificial sequence
<220> FEATURE:
<223> OTHER INFORMATION: Primer

<400> SEQUENCE: 119
gtttgcttcc gtgtgtgtct t                                            21

<210> SEQ ID NO 120
<211> LENGTH: 214
<212> TYPE: PRT
<213> ORGANISM: Homo sapiens

<400> SEQUENCE: 120

Met Ala Asp Ala Ala Ala Thr Ala Gly Ala Gly Gly Ser Gly Thr Arg
1               5                   10                  15

Ser Gly Ser Lys Gln Ser Thr Asn Pro Ala Asp Asn Tyr His Leu Ala
                20                  25                  30

Arg Arg Arg Thr Leu Gln Val Val Ser Ser Leu Leu Thr Glu Ala
            35                  40                  45

Gly Phe Glu Ser Ala Glu Lys Ala Ser Val Glu Thr Leu Thr Glu Met
50                  55                  60

Leu Gln Ser Tyr Ile Ser Glu Ile Gly Arg Ser Ala Lys Ser Tyr Cys
65                  70                  75                  80

Glu His Thr Ala Arg Thr Gln Pro Thr Leu Ser Asp Ile Val Val Thr
                85                  90                  95

Leu Val Glu Met Gly Phe Asn Val Asp Thr Leu Pro Ala Tyr Ala Lys
                100                 105                 110

Arg Ser Gln Arg Met Val Ile Thr Ala Pro Pro Val Thr Asn Gln Pro
            115                 120                 125

Val Thr Pro Lys Ala Leu Thr Ala Gly Gln Asn Arg Pro His Pro Pro
130                 135                 140
```

```
His Ile Pro Ser His Phe Pro Glu Phe Pro Asp Pro His Thr Tyr Ile
145                 150                 155                 160

Lys Thr Pro Glu Asp Ser Gly Ala Glu Lys Glu Asn Thr Ser Val Leu
            165                 170                 175

Gln Gln Asn Pro Ser Leu Ser Gly Ser Arg Asn Gly Glu Glu Asn Ile
        180                 185                 190

Ile Asp Asn Pro Tyr Leu Arg Pro Val Lys Lys Pro Lys Ile Arg Arg
        195                 200                 205

Lys Lys Pro Asp Thr Phe
        210

<210> SEQ ID NO 121
<211> LENGTH: 338
<212> TYPE: PRT
<213> ORGANISM: Homo sapiens

<400> SEQUENCE: 121

Met Ala Asp Ala Ala Thr Ala Gly Ala Gly Gly Ser Gly Thr Arg
1               5                   10                  15

Ser Gly Ser Lys Gln Ser Thr Asn Pro Ala Asp Asn Tyr His Leu Ala
            20                  25                  30

Arg Arg Arg Thr Leu Gln Val Val Ser Ser Leu Leu Thr Glu Ala
            35                  40                  45

Gly Phe Glu Ser Ala Glu Lys Ala Ser Val Glu Thr Leu Thr Glu Met
50                  55                  60

Leu Gln Ser Tyr Ile Ser Glu Ile Gly Arg Ser Ala Lys Ser Tyr Cys
65                  70                  75                  80

Glu His Thr Ala Arg Thr Gln Pro Thr Leu Ser Asp Ile Val Val Thr
                85                  90                  95

Leu Val Glu Met Gly Phe Asn Val Asp Thr Leu Pro Ala Tyr Ala Lys
            100                 105                 110

Arg Ser Gln Arg Met Val Ile Thr Ala Pro Pro Val Thr Asn Gln Pro
            115                 120                 125

Val Thr Pro Lys Ala Leu Thr Ala Gly Gln Asn Arg Pro His Pro Pro
130                 135                 140

His Ile Pro Ser His Phe Pro Glu Phe Pro Asp Pro His Thr Tyr Ile
145                 150                 155                 160

Lys Thr Pro Thr Tyr Arg Glu Pro Val Ser Asp Tyr Gln Val Leu Arg
            165                 170                 175

Glu Lys Ala Ala Ser Gln Arg Arg Asp Val Glu Arg Ala Leu Thr Arg
            180                 185                 190

Phe Met Ala Lys Thr Gly Glu Thr Gln Ser Leu Phe Lys Asp Asp Val
        195                 200                 205

Ser Thr Phe Pro Leu Ile Ala Ala Arg Pro Phe Thr Ile Pro Tyr Leu
        210                 215                 220

Thr Ala Leu Leu Pro Ser Glu Leu Glu Met Gln Gln Met Glu Glu Thr
225                 230                 235                 240

Asp Ser Ser Glu Gln Asp Glu Gln Thr Asp Thr Glu Asn Leu Ala Leu
                245                 250                 255

His Ile Ser Met Ile Glu Ser Arg Ser Val Thr Gln Ala Gly Val Gln
            260                 265                 270

Trp Gln Asp Leu Gly Ser Leu Gln Pro Pro Pro Gly Phe Lys Arg
        275                 280                 285

Phe Ser Ser Leu Ser Leu Leu Ser Ser Trp Asn Tyr Arg Arg Ile Leu
290                 295                 300
```

```
Glu Pro Arg Arg Arg Thr Pro Leu Ser Cys Ser Arg Thr Pro Pro Cys
305                 310                 315                 320

Arg Val Ala Gly Met Gly Arg Thr Ser Ser Ile Thr Leu Ile Cys
            325                 330                 335

Gly Arg
```

<210> SEQ ID NO 122
<211> LENGTH: 21
<212> TYPE: DNA
<213> ORGANISM: Artificial sequence
<220> FEATURE:
<223> OTHER INFORMATION: Primer

<400> SEQUENCE: 122
ttgatgaccc tccttcagct a                                           21

<210> SEQ ID NO 123
<211> LENGTH: 21
<212> TYPE: DNA
<213> ORGANISM: Artificial sequence
<220> FEATURE:
<223> OTHER INFORMATION: Primer

<400> SEQUENCE: 123
gcaaaactct ggcaatttca c                                           21

<210> SEQ ID NO 124
<211> LENGTH: 457
<212> TYPE: PRT
<213> ORGANISM: Homo sapiens

<400> SEQUENCE: 124

```
Met Ser Asp Ser Gly Ser Tyr Gly Gln Ser Gly Gly Glu Gln Gln Ser
1               5                   10                  15

Tyr Ser Thr Tyr Gly Asn Pro Gly Ser Gln Gly Tyr Gly Gln Ala Ser
            20                  25                  30

Gln Ser Tyr Ser Gly Tyr Gly Gln Thr Thr Asp Ser Ser Tyr Gly Gln
        35                  40                  45

Asn Tyr Ser Gly Tyr Ser Ser Tyr Gly Gln Ser Gln Ser Gly Tyr Ser
    50                  55                  60

Gln Ser Tyr Gly Gly Tyr Glu Asn Gln Lys Gln Ser Ser Tyr Ser Gln
65                  70                  75                  80

Gln Pro Tyr Asn Asn Gln Gly Gln Gln Gln Asn Met Glu Ser Ser Gly
                85                  90                  95

Ser Gln Gly Gly Arg Ala Pro Ser Tyr Asp Gln Pro Asp Tyr Gly Gln
            100                 105                 110

Gln Asp Ser Tyr Asp Gln Ser Gly Tyr Asp Gln His Gln Gly Ser
        115                 120                 125

Tyr Asp Glu Gln Ser Asn Tyr Asp Gln His Asp Ser Tyr Ser Gln
    130                 135                 140

Asn Gln Gln Ser Tyr His Ser Gln Arg Glu Asn Tyr Ser His His Thr
145                 150                 155                 160

Gln Asp Asp Arg Arg Asp Val Ser Arg Tyr Gly Glu Asp Asn Arg Gly
                165                 170                 175

Tyr Gly Gly Ser Gln Gly Gly Arg Gly Arg Gly Tyr Asp Lys
            180                 185                 190

Asp Gly Arg Gly Pro Met Thr Gly Ser Ser Gly Gly Asp Arg Gly Gly
        195                 200                 205

Phe Lys Asn Phe Gly Gly His Arg Asp Tyr Gly Pro Arg Thr Asp Ala
```

```
              210                 215                 220
Asp Ser Glu Ser Asp Asn Ser Asp Asn Thr Ile Phe Val Gln Gly
225                 230                 235                 240

Leu Gly Glu Gly Val Ser Thr Asp Gln Val Gly Glu Phe Phe Lys Gln
                245                 250                 255

Ile Gly Ile Ile Lys Thr Asn Lys Lys Thr Gly Lys Pro Met Ile Asn
                260                 265                 270

Leu Tyr Thr Asp Lys Asp Thr Gly Lys Pro Lys Gly Glu Ala Thr Val
                275                 280                 285

Ser Phe Asp Asp Pro Pro Ser Ala Lys Ala Ala Ile Asp Trp Phe Asp
290                 295                 300

Gly Lys Glu Phe His Gly Asn Ile Ile Lys Val Ser Phe Ala Thr Arg
305                 310                 315                 320

Arg Pro Glu Phe Met Arg Gly Gly Gly Ser Gly Gly Arg Arg Gly
                325                 330                 335

Arg Gly Gly Tyr Arg Gly Arg Gly Gly Phe Gln Gly Arg Gly Gly Asp
                340                 345                 350

Pro Lys Ser Gly Asp Trp Val Cys Pro Asn Pro Ser Cys Gly Asn Met
                355                 360                 365

Asn Phe Ala Arg Arg Asn Ser Cys Asn Gln Cys Asn Glu Pro Arg Pro
                370                 375                 380

Glu Asp Ser Arg Pro Ser Gly Gly Glu Thr Thr Thr Glu Met Ile Ser
385                 390                 395                 400

Ala Thr Asp His Thr Asp Asp Cys Phe Glu Cys Ser Phe Val Ser Asp
                405                 410                 415

Met Ile His Ser Glu Ile Ala Arg Val Leu Pro Ala Ala Phe Leu Val
                420                 425                 430

Ala Ser Ser Trp Val Val Lys Leu Ser Asp Ile Trp Ile Phe Ile Trp
                435                 440                 445

Val Gly Gly Leu Gly Gln Phe Phe Phe
                450                 455

<210> SEQ ID NO 125
<211> LENGTH: 592
<212> TYPE: PRT
<213> ORGANISM: Homo sapiens

<400> SEQUENCE: 125

Met Ser Asp Ser Gly Ser Tyr Gly Gln Ser Gly Gly Glu Gln Gln Ser
1               5                   10                  15

Tyr Ser Thr Tyr Gly Asn Pro Gly Ser Gln Gly Tyr Gly Gln Ala Ser
                20                  25                  30

Gln Ser Tyr Ser Gly Tyr Gly Gln Thr Thr Asp Ser Ser Tyr Gly Gln
                35                  40                  45

Asn Tyr Ser Gly Tyr Ser Ser Tyr Gly Gln Ser Gln Ser Gly Tyr Ser
                50                  55                  60

Gln Ser Tyr Gly Gly Tyr Glu Asn Gln Lys Gln Ser Ser Tyr Ser Gln
65                  70                  75                  80

Gln Pro Tyr Asn Asn Gln Gly Gln Gln Asn Met Glu Ser Ser Gly
                85                  90                  95

Ser Gln Gly Gly Arg Ala Pro Ser Tyr Asp Gln Pro Asp Tyr Gly Gln
                100                 105                 110

Gln Asp Ser Tyr Asp Gln Gln Ser Gly Tyr Asp Gln His Gln Gly Ser
                115                 120                 125

Tyr Asp Glu Gln Ser Asn Tyr Asp Gln Gln His Asp Ser Tyr Ser Gln
```

-continued

```
                130                 135                 140
Asn Gln Gln Ser Tyr His Ser Gln Arg Glu Asn Tyr Ser His His Thr
145                 150                 155                 160
Gln Asp Asp Arg Arg Asp Val Ser Arg Tyr Gly Glu Asp Asn Arg Gly
                165                 170                 175
Tyr Gly Gly Ser Gln Gly Gly Arg Gly Arg Gly Gly Tyr Asp Lys
                180                 185                 190
Asp Gly Arg Gly Pro Met Thr Gly Ser Ser Gly Asp Arg Gly Gly
                195                 200                 205
Phe Lys Asn Phe Gly Gly His Arg Asp Tyr Gly Pro Arg Thr Asp Ala
210                 215                 220
Asp Ser Glu Ser Asp Asn Ser Asp Asn Asn Thr Ile Phe Val Gln Gly
225                 230                 235                 240
Leu Gly Glu Gly Val Ser Thr Asp Gln Val Gly Glu Phe Phe Lys Gln
                245                 250                 255
Ile Gly Ile Ile Lys Thr Asn Lys Lys Thr Gly Lys Pro Met Ile Asn
                260                 265                 270
Leu Tyr Thr Asp Lys Asp Thr Gly Lys Pro Lys Gly Glu Ala Thr Val
                275                 280                 285
Ser Phe Asp Asp Pro Pro Ser Ala Lys Ala Ala Ile Asp Trp Phe Asp
290                 295                 300
Gly Lys Glu Phe His Gly Asn Ile Ile Lys Val Ser Phe Ala Thr Arg
305                 310                 315                 320
Arg Pro Glu Phe Met Arg Gly Gly Ser Gly Gly Arg Arg Gly
                325                 330                 335
Arg Gly Gly Tyr Arg Gly Arg Gly Gly Phe Gln Gly Arg Gly Gly Asp
                340                 345                 350
Pro Lys Ser Gly Asp Trp Val Cys Pro Asn Pro Ser Cys Gly Asn Met
                355                 360                 365
Asn Phe Ala Arg Arg Asn Ser Cys Asn Gln Cys Asn Glu Pro Arg Pro
                370                 375                 380
Glu Asp Ser Arg Pro Ser Gly Gly Asp Phe Arg Gly Arg Gly Tyr Gly
385                 390                 395                 400
Gly Glu Arg Gly Tyr Arg Gly Arg Gly Gly Arg Gly Asp Arg Gly
                405                 410                 415
Gly Tyr Gly Gly Asp Arg Ser Gly Gly Gly Tyr Gly Gly Asp Arg Ser
                420                 425                 430
Ser Gly Gly Gly Tyr Ser Gly Asp Arg Ser Gly Gly Tyr Gly Gly
                435                 440                 445
Asp Arg Ser Gly Gly Gly Tyr Gly Gly Asp Arg Gly Gly Tyr Gly
450                 455                 460
Gly Asp Arg Gly Gly Gly Tyr Gly Gly Asp Arg Gly Gly Tyr Gly
465                 470                 475                 480
Gly Asp Arg Gly Gly Tyr Gly Gly Asp Arg Gly Gly Tyr Gly Gly
                485                 490                 495
Asp Arg Gly Gly Tyr Gly Gly Asp Arg Gly Gly Tyr Gly Gly Asp Arg
                500                 505                 510
Gly Gly Tyr Gly Gly Asp Arg Gly Gly Tyr Gly Gly Asp Arg Ser Arg
                515                 520                 525
Gly Gly Tyr Gly Gly Asp Arg Gly Gly Gly Ser Gly Tyr Gly Gly Asp
                530                 535                 540
Arg Ser Gly Gly Tyr Gly Gly Asp Arg Ser Gly Gly Tyr Gly Gly
545                 550                 555                 560
```

```
Asp Arg Gly Gly Gly Tyr Gly Asp Arg Gly Gly Tyr Gly Gly Lys
            565                 570                 575

Met Gly Gly Arg Asn Asp Tyr Arg Asn Asp Gln Arg Asn Arg Pro Tyr
            580                 585                 590
```

<210> SEQ ID NO 126
<211> LENGTH: 19
<212> TYPE: DNA
<213> ORGANISM: Artificial sequence
<220> FEATURE:
<223> OTHER INFORMATION: Primer

<400> SEQUENCE: 126
gaaaatggct gcgtcttcg                                              19

<210> SEQ ID NO 127
<211> LENGTH: 21
<212> TYPE: DNA
<213> ORGANISM: Artificial sequence
<220> FEATURE:
<223> OTHER INFORMATION: Primer

<400> SEQUENCE: 127
ctcatctcta aatcagttgg g                                           21

<210> SEQ ID NO 128
<211> LENGTH: 136
<212> TYPE: PRT
<213> ORGANISM: Homo sapiens

<400> SEQUENCE: 128

```
Met Leu Ala Ile Ser Arg Asn Gln Lys Leu Leu Gln Ala Gly Glu Glu
1               5                   10                  15

Asn Gln Val Leu Glu Leu Leu Ile His Arg Asp Gly Glu Phe Gln Glu
            20                  25                  30

Leu Met Lys Leu Ala Leu Asn Gln Gly Lys Ile His His Glu Met Gln
        35                  40                  45

Val Leu Glu Lys Glu Val Glu Lys Arg Asp Ser Asp Ile Gln Gln Leu
    50                  55                  60

Gln Lys Gln Leu Lys Glu Ala Glu Gln Ile Leu Ala Thr Ala Val Tyr
65                  70                  75                  80

Gln Ala Lys Glu Lys Leu Lys Ser Ile Glu Lys Ala Arg Lys Gly Ala
                85                  90                  95

Ile Ser Ser Glu Glu Ile Ile Lys Tyr Ala His Arg Ile Ser Ala Ser
            100                 105                 110

Asn Ala Val Cys Ala Pro Leu Thr Trp Val Pro Gly Asp Pro Arg Arg
        115                 120                 125

Pro Tyr Pro Thr Asp Leu Glu Met
    130                 135
```

<210> SEQ ID NO 129
<211> LENGTH: 270
<212> TYPE: PRT
<213> ORGANISM: Homo sapiens

<400> SEQUENCE: 129

```
Met Ala Ala Ser Ser Ser Gly Glu Lys Glu Lys Glu Arg Leu Gly Gly
1               5                   10                  15

Gly Leu Gly Val Ala Gly Gly Asn Ser Thr Arg Glu Arg Leu Leu Ser
            20                  25                  30

Ala Leu Glu Asp Leu Glu Val Leu Ser Arg Glu Leu Ile Glu Met Leu
```

-continued

```
                35                  40                  45

Ala Ile Ser Arg Asn Gln Lys Leu Leu Gln Ala Gly Glu Glu Asn Gln
 50                  55                  60

Val Leu Glu Leu Leu Ile His Arg Asp Gly Glu Phe Gln Glu Leu Met
 65                  70                  75                  80

Lys Leu Ala Leu Asn Gln Gly Lys Ile His His Glu Met Gln Val Leu
                 85                  90                  95

Glu Lys Glu Val Glu Lys Arg Asp Ser Asp Ile Gln Gln Leu Gln Lys
            100                 105                 110

Gln Leu Lys Glu Ala Glu Gln Ile Leu Ala Thr Ala Val Tyr Gln Ala
        115                 120                 125

Lys Glu Lys Leu Lys Ser Ile Glu Lys Ala Arg Lys Gly Ala Ile Ser
130                 135                 140

Ser Glu Glu Ile Ile Lys Tyr Ala His Arg Ile Ser Ala Ser Asn Ala
145                 150                 155                 160

Val Cys Ala Pro Leu Thr Trp Val Pro Gly Asp Pro Arg Arg Pro Tyr
                165                 170                 175

Pro Thr Asp Leu Glu Met Arg Ser Gly Leu Leu Gly Gln Met Asn Asn
            180                 185                 190

Pro Ser Thr Asn Gly Val Asn Gly His Leu Pro Gly Asp Ala Leu Ala
        195                 200                 205

Ala Gly Arg Leu Pro Asp Val Leu Ala Pro Gln Tyr Pro Trp Gln Ser
    210                 215                 220

Asn Asp Met Ser Met Asn Met Leu Pro Pro Asn His Ser Ser Asp Phe
225                 230                 235                 240

Leu Leu Glu Pro Pro Gly His Asn Lys Glu Asn Glu Asp Asp Val Glu
                245                 250                 255

Ile Met Ser Thr Asp Ser Ser Ser Ser Ser Glu Ser Asp
            260                 265                 270

<210> SEQ ID NO 130
<211> LENGTH: 19
<212> TYPE: DNA
<213> ORGANISM: Artificial sequence
<220> FEATURE:
<223> OTHER INFORMATION: Primer

<400> SEQUENCE: 130
caaatggctc aggcaggtc                                                  19

<210> SEQ ID NO 131
<211> LENGTH: 22
<212> TYPE: DNA
<213> ORGANISM: Artificial sequence
<220> FEATURE:
<223> OTHER INFORMATION: Primer

<400> SEQUENCE: 131
tgtagacaat catgaagcca cg                                              22

<210> SEQ ID NO 132
<211> LENGTH: 164
<212> TYPE: PRT
<213> ORGANISM: Homo sapiens

<400> SEQUENCE: 132

Met Arg Gln Thr Glu Gly Arg Val Pro Val Phe Ser His Glu Val Val
 1               5                  10                  15

Pro Asp His Leu Arg Thr Lys Pro Asp Pro Glu Val Glu Glu Gln Glu
```

```
                    20                  25                  30
Lys Gln Leu Thr Thr Asp Ala Ala Arg Ile Gly Ala Asp Ala Ala Gln
            35                  40                  45

Lys Gln Ile Gln Ser Leu Asn Lys Met Cys Ser Asn Leu Leu Glu Lys
        50                  55                  60

Ile Ser Lys Glu Glu Arg Glu Ser Glu Ser Gly Gly Leu Arg Pro Asn
65                  70                  75                  80

Lys Gln Thr Phe Asn Pro Thr Asp Thr Asn Ala Leu Val Ala Ala Val
                85                  90                  95

Ala Phe Gly Lys Gly Leu Ser Asn Trp Arg Pro Ser Gly Ser Ser Gly
            100                 105                 110

Pro Gly Gln Ala Gly Gln Pro Gly Ala Gly Thr Ile Leu Ala Gly Thr
        115                 120                 125

Ser Gly Leu Gln Gln Val Gln Met Ala Gly Ala Pro Ser Gln Gln Gln
    130                 135                 140

Pro Met Leu Ser Gly Val Gln Met Ala Gln Ala Gly Gln Pro Gly Lys
145                 150                 155                 160

Cys Gln Val Glu

<210> SEQ ID NO 133
<211> LENGTH: 179
<212> TYPE: PRT
<213> ORGANISM: Homo sapiens

<400> SEQUENCE: 133

Met Arg Gln Thr Glu Gly Arg Val Pro Val Phe Ser His Glu Val Val
1               5                   10                  15

Pro Asp His Leu Arg Thr Lys Pro Asp Pro Glu Val Glu Glu Gln Glu
            20                  25                  30

Lys Gln Leu Thr Thr Asp Ala Ala Arg Ile Gly Ala Asp Ala Ala Gln
        35                  40                  45

Lys Gln Ile Gln Ser Leu Asn Lys Met Cys Ser Asn Leu Leu Glu Lys
    50                  55                  60

Ile Ser Lys Glu Glu Arg Glu Ser Glu Ser Gly Gly Leu Arg Pro Asn
65                  70                  75                  80

Lys Gln Thr Phe Asn Pro Thr Asp Thr Asn Ala Leu Val Ala Ala Val
                85                  90                  95

Ala Phe Gly Lys Gly Leu Ser Asn Trp Arg Pro Ser Gly Ser Ser Gly
            100                 105                 110

Pro Gly Gln Ala Gly Gln Pro Gly Ala Gly Thr Ile Leu Ala Gly Thr
        115                 120                 125

Ser Gly Leu Gln Gln Val Gln Met Ala Gly Ala Pro Ser Gln Gln Gln
    130                 135                 140

Pro Met Leu Ser Gly Val Gln Met Ala Gln Ala Gly Gln Pro Gly Lys
145                 150                 155                 160

Met Pro Ser Gly Ile Lys Thr Asn Ile Lys Ser Ala Ser Met His Pro
                165                 170                 175

Tyr Gln Arg

<210> SEQ ID NO 134
<211> LENGTH: 21
<212> TYPE: DNA
<213> ORGANISM: Artificial sequence
<220> FEATURE:
<223> OTHER INFORMATION: Primer

<400> SEQUENCE: 134
```

-continued

```
tcaggatgct cgaagaaggt c                                          21

<210> SEQ ID NO 135
<211> LENGTH: 21
<212> TYPE: DNA
<213> ORGANISM: Artificial sequence
<220> FEATURE:
<223> OTHER INFORMATION: Primer

<400> SEQUENCE: 135
cagacacttg aggagatcct g                                          21

<210> SEQ ID NO 136
<211> LENGTH: 112
<212> TYPE: PRT
<213> ORGANISM: Homo sapiens

<400> SEQUENCE: 136

Met Asn Met Phe Val Asp Ser Asn Gln Asp Ala Arg Arg Arg Ser Val
1               5                   10                  15

Asn Glu Asp Asp Asn Pro Pro Ser Pro Ile Gly Gly Asp Met Met Asp
            20                  25                  30

Ser Leu Ile Ser Gln Leu Gln Pro Pro Gln Gln Gln Pro Phe Pro
        35                  40                  45

Lys Gln Pro Gly Thr Ser Gly Ala Tyr Pro Leu Thr Ser Pro Pro Thr
    50                  55                  60

Ser Tyr His Ser Thr Val Asn Gln Ser Pro Ser Met Met His Thr Gln
65                  70                  75                  80

Ser Pro Gly Thr Leu Asp Pro Ser Ser Pro Tyr Thr Met Val Ser Pro
                85                  90                  95

Ser Gly Arg Ala Gly Asn Trp Pro Gly Ser Pro Gln Val Ser Gly Pro
            100                 105                 110

<210> SEQ ID NO 137
<211> LENGTH: 462
<212> TYPE: PRT
<213> ORGANISM: Homo sapiens

<400> SEQUENCE: 137

Leu Glu Phe Ala Arg Ser Leu Pro Asp Ile Pro Ala His Leu Asn Ile
1               5                   10                  15

Phe Ser Glu Val Arg Val Tyr Asn Tyr Arg Lys Leu Ile Leu Cys Tyr
            20                  25                  30

Gly Thr Thr Lys Gly Ser Ser Ile Ser Ile Gln Trp Asn Ser Ile His
        35                  40                  45

Gln Lys Phe His Ile Ser Leu Gly Thr Val Gly Pro Asn Ser Gly Cys
    50                  55                  60

Ser Asn Cys His Asn Thr Ile Leu His Gln Leu Gln Glu Met Phe Asn
65                  70                  75                  80

Lys Thr Pro Asn Val Val Gln Leu Leu Gln Val Leu Phe Asp Thr Gln
                85                  90                  95

Ala Pro Leu Asn Ala Ile Asn Lys Leu Pro Thr Val Pro Met Leu Gly
            100                 105                 110

Leu Thr Gln Arg Thr Asn Thr Ala Tyr Gln Cys Phe Ser Ile Leu Pro
        115                 120                 125

Gln Ser Ser Thr His Ile Arg Leu Ala Phe Arg Asn Met Tyr Cys Ile
    130                 135                 140

Asp Ile Tyr Cys Arg Ser Arg Gly Val Val Ala Ile Arg Asp Gly Ala
```

```
            145                 150                 155                 160
Tyr Ser Leu Phe Asp Asn Ser Lys Leu Val Glu Gly Phe Tyr Pro Ala
                165                 170                 175

Pro Gly Leu Lys Thr Phe Leu Asn Met Phe Val Asp Ser Asn Gln Asp
            180                 185                 190

Ala Arg Arg Arg Ser Val Asn Glu Asp Asn Pro Pro Ser Pro Ile
        195                 200                 205

Gly Gly Asp Met Met Asp Ser Leu Ile Ser Gln Leu Gln Pro Pro
    210                 215                 220

Gln Gln Gln Pro Phe Pro Lys Gln Pro Gly Thr Ser Gly Ala Tyr Pro
225                 230                 235                 240

Leu Thr Ser Pro Pro Thr Ser Tyr His Ser Thr Val Asn Gln Ser Pro
                245                 250                 255

Ser Met Met His Thr Gln Ser Pro Gly Asn Leu His Ala Ala Ser Ser
            260                 265                 270

Pro Ser Gly Ala Leu Arg Ala Pro Ser Pro Ala Ser Phe Val Pro Thr
        275                 280                 285

Pro Pro Pro Ser Ser His Gly Ile Ser Ile Gly Pro Gly Ala Ser Phe
    290                 295                 300

Ala Ser Pro His Gly Thr Leu Asp Pro Ser Ser Pro Tyr Thr Met Val
305                 310                 315                 320

Ser Pro Ser Gly Arg Ala Gly Asn Trp Pro Gly Ser Pro Gln Val Ser
                325                 330                 335

Gly Pro Ser Pro Ala Ala Arg Met Pro Gly Met Ser Pro Ala Asn Pro
            340                 345                 350

Ser Leu His Ser Pro Val Pro Asp Ala Ser His Ser Pro Arg Ala Gly
        355                 360                 365

Thr Ser Ser Gln Thr Met Pro Thr Asn Met Pro Pro Pro Arg Lys Leu
    370                 375                 380

Pro Gln Arg Ser Trp Ala Ala Ser Ile Pro Thr Ile Leu Thr His Ser
385                 390                 395                 400

Ala Leu Asn Ile Leu Leu Leu Pro Ser Pro Thr Pro Gly Leu Val Pro
                405                 410                 415

Gly Leu Ala Gly Ser Tyr Leu Cys Ser Pro Leu Glu Arg Phe Leu Gly
            420                 425                 430

Ser Val Ile Met Arg Arg His Leu Gln Arg Ile Ile Gln Gln Glu Thr
        435                 440                 445

Leu Gln Leu Ile Asn Ser Asn Glu Pro Gly Val Ile Met Phe
    450                 455                 460

<210> SEQ ID NO 138
<211> LENGTH: 19
<212> TYPE: DNA
<213> ORGANISM: Artificial sequence
<220> FEATURE:
<223> OTHER INFORMATION: Primer

<400> SEQUENCE: 138
gctctgccga tcgacttcc                                                    19

<210> SEQ ID NO 139
<211> LENGTH: 20
<212> TYPE: DNA
<213> ORGANISM: Artificial sequence
<220> FEATURE:
<223> OTHER INFORMATION: Primer

<400> SEQUENCE: 139
```

```
aggcgatcag cagtgtccac                                                  20
```

<210> SEQ ID NO 140
<211> LENGTH: 217
<212> TYPE: PRT
<213> ORGANISM: Homo sapiens

<400> SEQUENCE: 140

```
Met Pro Arg Lys Ser Asp Val Glu Arg Lys Ile Glu Ile Val Gln Phe
1               5                   10                  15

Ala Ser Arg Thr Arg Gln Leu Phe Val Arg Leu Leu Ala Leu Val Lys
            20                  25                  30

Trp Ala Asn Asn Ala Gly Lys Val Glu Lys Cys Ala Met Ile Ser Ser
        35                  40                  45

Phe Leu Asp Gln Gln Ala Ile Leu Phe Val Asp Thr Ala Asp Arg Leu
    50                  55                  60

Ala Ser Leu Ala Arg Asp Ala Leu Val His Ala Arg Leu Pro Ser Phe
65                  70                  75                  80

Ala Ile Pro Tyr Ala Ile Asp Val Leu Thr Thr Gly Ser Tyr Pro Arg
                85                  90                  95

Leu Pro Thr Cys Ile Arg Asp Lys Ile Ile Pro Pro Asp Pro Ile Thr
            100                 105                 110

Lys Ile Glu Lys Gln Ala Thr Leu His Gln Leu Asn Gln Ile Leu Arg
        115                 120                 125

His Arg Leu Val Thr Thr Asp Leu Pro Pro Gln Leu Ala Asn Leu Thr
    130                 135                 140

Val Ala Asn Gly Arg Val Lys Phe Arg Val Glu Gly Glu Phe Glu Ala
145                 150                 155                 160

Thr Leu Thr Val Met Gly Asp Pro Asp Val Pro Trp Arg Leu Leu
                165                 170                 175

Lys Leu Glu Ile Leu Val Glu Asp Lys Glu Thr Gly Asp Gly Arg Ala
            180                 185                 190

Leu Val His Ser Met Gln Ile Ser Phe Ile His Gln Leu Val Gln Ser
        195                 200                 205

Arg Leu Phe Ala Asp Glu Lys Pro Leu
    210                 215
```

<210> SEQ ID NO 141
<211> LENGTH: 420
<212> TYPE: PRT
<213> ORGANISM: Homo sapiens

<400> SEQUENCE: 141

```
Met Ala Pro Val Gln Leu Glu Asn His Gln Leu Val Pro Pro Gly Gly
1               5                   10                  15

Gly Gly Gly Gly Ser Gly Gly Pro Pro Ser Ala Pro Ala Pro Pro
            20                  25                  30

Pro Gly Ala Ala Val Ala Ala Ala Ala Ala Ala Ser Pro Gly
        35                  40                  45

Tyr Arg Leu Ser Thr Leu Ile Glu Phe Leu Leu His Arg Ala Tyr Ser
    50                  55                  60

Glu Leu Met Val Leu Thr Asp Leu Leu Pro Arg Lys Ser Asp Val Glu
65                  70                  75                  80

Arg Lys Ile Glu Ile Val Gln Phe Ala Ser Arg Thr Arg Gln Leu Phe
                85                  90                  95

Val Arg Leu Leu Ala Leu Val Lys Trp Ala Asn Asn Ala Gly Lys Val
```

```
            100                 105                 110
Glu Lys Cys Ala Met Ile Ser Ser Phe Leu Asp Gln Gln Ala Ile Leu
        115                 120                 125

Phe Val Asp Thr Ala Asp Arg Leu Ala Ser Leu Ala Arg Asp Ala Leu
    130                 135                 140

Val His Ala Arg Leu Pro Ser Phe Ala Ile Pro Tyr Ala Ile Asp Val
145                 150                 155                 160

Leu Thr Thr Gly Ser Tyr Pro Arg Leu Pro Thr Cys Ile Arg Asp Lys
                165                 170                 175

Ile Ile Pro Pro Asp Pro Ile Thr Lys Ile Glu Lys Gln Ala Thr Leu
                180                 185                 190

His Gln Leu Asn Gln Ile Leu Arg His Arg Leu Val Thr Thr Asp Leu
            195                 200                 205

Pro Pro Gln Leu Ala Asn Leu Thr Val Ala Asn Gly Arg Val Lys Phe
        210                 215                 220

Arg Val Glu Gly Glu Phe Glu Ala Thr Leu Thr Val Met Gly Asp Asp
225                 230                 235                 240

Pro Asp Val Pro Trp Arg Leu Leu Lys Leu Glu Ile Leu Val Glu Asp
                245                 250                 255

Lys Glu Thr Gly Asp Gly Arg Ala Leu Val His Ser Met Gln Ile Ser
                260                 265                 270

Phe Ile His Gln Leu Val Gln Ser Arg Leu Phe Ala Asp Glu Lys Pro
            275                 280                 285

Leu Gln Asp Met Tyr Asn Cys Leu His Ser Phe Cys Leu Ser Leu Gln
        290                 295                 300

Leu Glu Val Leu His Ser Gln Thr Leu Met Leu Ile Arg Glu Arg Trp
305                 310                 315                 320

Gly Asp Leu Val Gln Val Glu Arg Tyr His Ala Gly Lys Cys Leu Ser
                325                 330                 335

Leu Ser Val Trp Asn Gln Gln Val Leu Gly Arg Lys Thr Gly Thr Ala
                340                 345                 350

Ser Val His Lys Val Thr Ile Lys Ile Asp Glu Asn Asp Val Ser Lys
            355                 360                 365

Pro Leu Gln Ile Phe His Asp Pro Pro Leu Pro Ala Ser Asp Ser Lys
        370                 375                 380

Leu Val Glu Arg Ala Met Lys Ile Asp His Leu Ser Ile Glu Lys Leu
385                 390                 395                 400

Leu Ile Asp Ser Val His Ala Arg Ala His Gln Lys Leu Gln Glu Leu
                405                 410                 415

Lys Ala Ile Leu
        420

<210> SEQ ID NO 142
<211> LENGTH: 21
<212> TYPE: DNA
<213> ORGANISM: Artificial sequence
<220> FEATURE:
<223> OTHER INFORMATION: Primer

<400> SEQUENCE: 142
tggatgtaag atgagattgg g                                        21

<210> SEQ ID NO 143
<211> LENGTH: 19
<212> TYPE: DNA
<213> ORGANISM: Artificial sequence
<220> FEATURE:
```

<223> OTHER INFORMATION: Primer

<400> SEQUENCE: 143
aatgagcctg gccacgaga                                                19

<210> SEQ ID NO 144
<211> LENGTH: 90
<212> TYPE: PRT
<213> ORGANISM: Homo sapiens

<400> SEQUENCE: 144

Met Arg Lys Ala Gly Val Ala His Ser Lys Ser Ser Lys Asp Met Glu
1               5                   10                  15

Ser His Val Phe Leu Lys Ala Lys Thr Arg Asp Glu Tyr Leu Ser Leu
            20                  25                  30

Val Ala Arg Leu Ile Ile His Phe Arg Asp Ile His Asn Lys Lys Ser
        35                  40                  45

Gln Ala Ser Val Ser Asp Pro Met Asn Ala Leu Gln Ser Leu Thr Gly
    50                  55                  60

Gly Pro Ala Ala Gly Ala Ala Gly Ile Gly Met Pro Pro Arg Gly Pro
65                  70                  75                  80

Gly Gln Ser Leu Gly Gly Met Gly Ser Leu
                85                  90

<210> SEQ ID NO 145
<211> LENGTH: 180
<212> TYPE: PRT
<213> ORGANISM: Homo sapiens

<400> SEQUENCE: 145

Met Asp Val Ser Gly Gln Glu Thr Asp Trp Arg Ser Thr Ala Phe Arg
1               5                   10                  15

Gln Lys Leu Val Ser Gln Ile Glu Asp Ala Met Arg Lys Ala Gly Val
            20                  25                  30

Ala His Ser Lys Ser Ser Lys Asp Met Glu Ser His Val Phe Leu Lys
        35                  40                  45

Ala Lys Thr Arg Asp Glu Tyr Leu Ser Leu Val Ala Arg Leu Ile Ile
    50                  55                  60

His Phe Arg Asp Ile His Asn Lys Lys Ser Gln Ala Ser Val Ser Asp
65                  70                  75                  80

Pro Met Asn Ala Leu Gln Ser Leu Thr Gly Gly Pro Ala Ala Gly Ala
                85                  90                  95

Ala Gly Ile Gly Met Pro Pro Arg Gly Pro Gly Gln Ser Leu Gly Gly
            100                 105                 110

Met Gly Ser Leu Gly Ala Met Gly Gln Pro Met Ser Leu Ser Gly Gln
        115                 120                 125

Pro Pro Pro Gly Thr Ser Gly Met Ala Pro His Ser Met Ala Val Val
    130                 135                 140

Ser Thr Ala Thr Pro Gln Thr Gln Leu Gln Leu Gln Gln Val Ala Leu
145                 150                 155                 160

Gln Gln Gln Gln Gln Gln Gln Phe Gln Gln Gln Gln Ala Ala
                165                 170                 175

Leu Gln Gln Gln
        180

<210> SEQ ID NO 146
<211> LENGTH: 22
<212> TYPE: DNA

```
<213> ORGANISM: Artificial sequence
<220> FEATURE:
<223> OTHER INFORMATION: Primer

<400> SEQUENCE: 146
cacgaatctg atcacacact ac                                            22

<210> SEQ ID NO 147
<211> LENGTH: 19
<212> TYPE: DNA
<213> ORGANISM: Artificial sequence
<220> FEATURE:
<223> OTHER INFORMATION: Primer

<400> SEQUENCE: 147
ctgggtggtc tggactatg                                                19

<210> SEQ ID NO 148
<211> LENGTH: 244
<212> TYPE: PRT
<213> ORGANISM: Homo sapiens

<400> SEQUENCE: 148
```

Met Glu Asn Phe Thr Ala Leu Phe Gly Ala Gln Ala Asp Pro Pro Pro
1               5                   10                  15

Pro Pro Thr Ala Leu Gly Phe Gly Pro Gly Lys Pro Pro Pro Pro Pro
            20                  25                  30

Pro Pro Pro Ala Gly Gly Gly Pro Gly Thr Ala Pro Pro Pro Thr Ala
        35                  40                  45

Ala Thr Ala Pro Pro Gly Ala Asp Lys Ser Gly Ala Gly Cys Gly Pro
    50                  55                  60

Phe Tyr Leu Met Arg Glu Leu Pro Gly Ser Thr Glu Leu Thr Gly Ser
65                  70                  75                  80

Thr Asn Leu Ile Thr His Tyr Asn Leu Glu Gln Ala Tyr Asn Lys Phe
                85                  90                  95

Cys Gly Lys Lys Val Lys Glu Lys Leu Ser Asn Phe Leu Pro Asp Leu
            100                 105                 110

Pro Gly Met Ile Asp Leu Pro Gly Ser His Asp Asn Ser Ser Leu Arg
        115                 120                 125

Ser Leu Ile Glu Lys Pro Pro Ile Leu Ser Ser Phe Asn Pro Ile
    130                 135                 140

Thr Gly Thr Met Leu Ala Gly Phe Arg Leu His Thr Gly Pro Leu Pro
145                 150                 155                 160

Glu Gln Cys Arg Leu Met His Ile Gln Pro Pro Lys Lys Asn Lys
                165                 170                 175

His Lys His Lys Gln Ser Arg Thr Gln Asp Pro Val Pro Pro Glu Thr
            180                 185                 190

Pro Ser Asp Ser Asp His Lys Lys Lys Lys Lys Lys Glu Glu Asp
        195                 200                 205

Pro Glu Arg Lys Arg Lys Lys Glu Lys Lys Lys Lys Asn Arg
    210                 215                 220

His Ser Pro Asp His Pro Gly Met Gly Ser Ser Gln Ala Ser Ser Ser
225                 230                 235                 240

Ser Ser Leu Arg

```
<210> SEQ ID NO 149
<211> LENGTH: 74
<212> TYPE: PRT
<213> ORGANISM: Homo sapiens
```

<400> SEQUENCE: 149

Ser His Asp Asn Ser Ser Leu Arg Ser Leu Ile Glu Lys Pro Pro Ile
1               5                   10                  15

Leu Ser Ser Ser Phe Asn Pro Ile Thr Gly Thr Met Leu Ala Gly Phe
            20                  25                  30

Arg Leu His Thr Gly Pro Leu Pro Glu Gln Cys Arg Leu Met His Ile
        35                  40                  45

Gln Pro Pro Lys Lys Asn Lys His Lys Gln Ser Arg Thr
    50              55                  60

Gln Asp Pro Val Pro Pro Gly Lys Pro Ser
65                  70

<210> SEQ ID NO 150
<211> LENGTH: 124
<212> TYPE: PRT
<213> ORGANISM: Homo sapiens

<400> SEQUENCE: 150

Ser His Asp Asn Ser Ser Leu Arg Ser Leu Ile Glu Lys Pro Pro Ile
1               5                   10                  15

Leu Ser Ser Ser Phe Asn Pro Ile Thr Gly Thr Met Leu Ala Gly Phe
            20                  25                  30

Arg Leu His Thr Gly Pro Leu Pro Glu Gln Cys Arg Leu Met His Ile
        35                  40                  45

Gln Pro Pro Lys Lys Asn Lys His Lys Gln Ser Arg Thr
    50              55                  60

Gln Asp Pro Val Pro Pro Glu Thr Pro Ser Asp Ser Asp His Lys Lys
65                  70                  75                  80

Lys Lys Lys Lys Lys Glu Glu Asp Pro Glu Arg Lys Arg Lys Lys Lys
                85                  90                  95

Glu Lys Lys Lys Lys Asn Arg His Ser Pro Asp His Pro Gly Met
            100                 105                 110

Gly Ser Ser Gln Ala Ser Ser Ser Ser Leu Arg
        115                 120

<210> SEQ ID NO 151
<211> LENGTH: 20
<212> TYPE: DNA
<213> ORGANISM: Artificial sequence
<220> FEATURE:
<223> OTHER INFORMATION: Primer

<400> SEQUENCE: 151
cgttactaga gcaggccatg                                           20

<210> SEQ ID NO 152
<211> LENGTH: 21
<212> TYPE: DNA
<213> ORGANISM: Artificial sequence
<220> FEATURE:
<223> OTHER INFORMATION: Primer

<400> SEQUENCE: 152
taccctcggg agactcaatg a                                         21

<210> SEQ ID NO 153
<211> LENGTH: 268
<212> TYPE: PRT
<213> ORGANISM: Homo sapiens -continued

<400> SEQUENCE: 153

| | | | | | | | | | | | | | | |
|---|---|---|---|---|---|---|---|---|---|---|---|---|---|---|
|Met|Ile|Gly|Pro|Ser|Pro|Asn|Pro|Leu|Ile|Leu|Ser|Tyr|Leu|Lys|Tyr|
|1| | | |5| | | | |10| | | | |15| |

Ala Ile Ser Ser Gln Met Val Ser Tyr Ser Val Leu Thr Ala Ile
            20                  25                  30

Ser Lys Phe Asp Asp Phe Ser Arg Asp Leu Cys Val Gln Ala Leu Leu
        35                  40                  45

Asp Ile Met Asp Met Phe Cys Asp Arg Leu Ser Cys His Gly Lys Ala
    50                  55                  60

Glu Glu Cys Ile Gly Leu Cys Arg Ala Leu Leu Ser Ala Leu His Trp
65                  70                  75                  80

Leu Leu Arg Cys Thr Ala Ala Ser Ala Glu Arg Leu Arg Glu Gly Leu
            85                  90                  95

Glu Ala Gly Thr Pro Ala Ala Gly Glu Lys Gln Leu Ala Met Cys Leu
        100                 105                 110

Gln Arg Leu Glu Lys Thr Leu Ser Ser Thr Lys Asn Arg Ala Leu Leu
    115                 120                 125

His Ile Ala Lys Leu Glu Glu Ala Ser Leu His Thr Ser Gln Gly Leu
130                 135                 140

Gly Gln Gly Gly Thr Arg Ala Asn Gln Pro Thr Ala Ser Trp Thr Ala
145                 150                 155                 160

Ile Glu His Ser Leu Leu Lys Leu Gly Glu Ile Leu Ala Asn Leu Ser
            165                 170                 175

Asn Pro Gln Leu Arg Ser Gln Ala Glu Gln Cys Gly Thr Leu Ile Arg
        180                 185                 190

Ser Ile Pro Thr Met Leu Ser Val His Ala Glu Gln Met His Lys Thr
    195                 200                 205

Gly Phe Pro Thr Val His Ala Val Ile Leu Leu Glu Gly Thr Met Asn
210                 215                 220

Leu Thr Gly Glu Thr Gln Ser Leu Val Glu Gln Leu Thr Met Val Lys
225                 230                 235                 240

Arg Met Gln His Ile Pro Thr Pro Leu Phe Val Leu Glu Ile Trp Lys
            245                 250                 255

Ala Cys Phe Val Gly Leu Ile Glu Ser Pro Glu Gly
        260                 265

<210> SEQ ID NO 154
<211> LENGTH: 341
<212> TYPE: PRT
<213> ORGANISM: Homo sapiens

<400> SEQUENCE: 154

Met Lys Val Val Asn Leu Lys Gln Ala Ile Leu Gln Ala Trp Lys Glu
1               5                   10                  15

Arg Trp Ser Asp Tyr Gln Trp Ala Ile Asn Met Lys Lys Phe Phe Pro
            20                  25                  30

Lys Gly Ala Thr Trp Asp Ile Leu Asn Leu Ala Asp Ala Leu Leu Glu
        35                  40                  45

Gln Ala Met Ile Gly Pro Ser Pro Asn Pro Leu Ile Leu Ser Tyr Leu
    50                  55                  60

Lys Tyr Ala Ile Ser Ser Gln Met Val Ser Tyr Ser Val Leu Thr
65                  70                  75                  80

Ala Ile Ser Lys Phe Asp Asp Phe Ser Arg Asp Leu Cys Val Gln Ala
            85                  90                  95

Leu Leu Asp Ile Met Asp Met Phe Cys Asp Arg Leu Ser Cys His Gly

```
                   100                 105                 110
Lys Ala Glu Glu Cys Ile Gly Leu Cys Arg Ala Leu Leu Ser Ala Leu
            115                 120                 125

His Trp Leu Leu Arg Cys Thr Ala Ala Ser Ala Glu Arg Leu Arg Glu
130                 135                 140

Gly Leu Glu Ala Gly Thr Pro Ala Ala Gly Glu Lys Gln Leu Ala Met
145                 150                 155                 160

Cys Leu Gln Arg Leu Glu Lys Thr Leu Ser Ser Thr Lys Asn Arg Ala
            165                 170                 175

Leu Leu His Ile Ala Lys Leu Glu Glu Ala Ser Ser Trp Thr Ala Ile
            180                 185                 190

Glu His Ser Leu Leu Lys Leu Gly Glu Ile Leu Ala Asn Leu Ser Asn
            195                 200                 205

Pro Gln Leu Arg Ser Gln Ala Glu Gln Cys Gly Thr Leu Ile Arg Ser
            210                 215                 220

Ile Pro Thr Met Leu Ser Val His Ala Glu Gln Met His Lys Thr Gly
225                 230                 235                 240

Phe Pro Thr Val His Ala Val Ile Leu Leu Glu Gly Thr Met Asn Leu
            245                 250                 255

Thr Gly Glu Thr Gln Ser Leu Val Glu Gln Leu Thr Met Val Lys Arg
            260                 265                 270

Met Gln His Ile Pro Thr Pro Leu Phe Val Leu Glu Ile Trp Lys Ala
            275                 280                 285

Cys Phe Val Gly Leu Ile Glu Ser Pro Glu Gly Thr Glu Leu Lys
            290                 295                 300

Trp Thr Ala Phe Thr Phe Leu Lys Ile Pro Gln Val Leu Val Lys Leu
305                 310                 315                 320

Lys Lys Tyr Ser His Gly Asp Lys Asp Phe Thr Glu Asp Val Asn Cys
            325                 330                 335

Ala Phe Glu Phe Leu
            340

<210> SEQ ID NO 155
<211> LENGTH: 21
<212> TYPE: DNA
<213> ORGANISM: Artificial sequence
<220> FEATURE:
<223> OTHER INFORMATION: Primer

<400> SEQUENCE: 155
agatgactcg cttgctggat a                                               21

<210> SEQ ID NO 156
<211> LENGTH: 21
<212> TYPE: DNA
<213> ORGANISM: Artificial sequence
<220> FEATURE:
<223> OTHER INFORMATION: Primer

<400> SEQUENCE: 156
aggttaattc cgagacctcc a                                               21

<210> SEQ ID NO 157
<211> LENGTH: 950
<212> TYPE: PRT
<213> ORGANISM: Homo sapiens

<400> SEQUENCE: 157

Met Asp Pro Glu Tyr Glu Glu Lys Met Lys Ala Asp Arg Ala Lys Arg
```

-continued

```
1               5                   10                  15
Phe Glu Phe Leu Leu Lys Gln Thr Glu Leu Phe Ala His Phe Ile Gln
                20                  25                  30

Pro Ser Ala Gln Lys Ser Pro Thr Ser Pro Leu Asn Met Lys Leu Gly
                35                  40                  45

Arg Pro Arg Ile Lys Lys Asp Glu Lys Gln Ser Leu Ile Ser Ala Gly
 50                  55                  60

Asp Tyr Arg His Arg Arg Thr Glu Gln Glu Asp Glu Glu Leu Leu
 65              70                  75                  80

Ser Glu Ser Arg Lys Thr Ser Asn Val Cys Ile Arg Phe Glu Val Ser
                85                  90                  95

Pro Ser Tyr Val Lys Gly Gly Pro Leu Arg Asp Tyr Gln Ile Arg Gly
                100                 105                 110

Leu Asn Trp Leu Ile Ser Leu Tyr Glu Asn Gly Val Asn Gly Ile Leu
            115                 120                 125

Ala Asp Glu Met Gly Leu Gly Lys Thr Leu Gln Thr Ile Ala Leu Leu
            130                 135                 140

Gly Tyr Leu Lys His Tyr Arg Asn Ile Pro Gly Pro His Met Val Leu
145                 150                 155                 160

Val Pro Lys Ser Thr Leu His Asn Trp Met Asn Glu Phe Lys Arg Trp
                165                 170                 175

Val Pro Ser Leu Arg Val Ile Cys Phe Val Gly Asp Lys Asp Ala Arg
                180                 185                 190

Ala Ala Phe Ile Arg Asp Glu Met Met Pro Gly Glu Trp Asp Val Cys
            195                 200                 205

Val Thr Ser Tyr Glu Met Val Ile Lys Glu Lys Ser Val Phe Lys Lys
            210                 215                 220

Phe His Trp Arg Tyr Leu Val Ile Asp Glu Ala His Arg Ile Lys Asn
225                 230                 235                 240

Glu Lys Ser Lys Leu Ser Glu Ile Val Arg Glu Phe Lys Ser Thr Asn
                245                 250                 255

Arg Leu Leu Leu Thr Gly Thr Pro Leu Gln Asn Asn Leu His Glu Leu
                260                 265                 270

Trp Ala Leu Leu Asn Phe Leu Leu Pro Asp Val Phe Asn Ser Ala Asp
            275                 280                 285

Asp Phe Asp Ser Trp Phe Asp Thr Lys Asn Cys Leu Gly Asp Gln Lys
            290                 295                 300

Leu Val Glu Arg Leu His Ala Val Leu Lys Pro Phe Leu Leu Arg Arg
305                 310                 315                 320

Ile Lys Thr Asp Val Glu Lys Ser Leu Pro Pro Lys Lys Glu Ile Lys
                325                 330                 335

Ile Tyr Leu Gly Leu Ser Lys Met Gln Arg Glu Trp Tyr Thr Lys Ile
            340                 345                 350

Leu Met Lys Asp Ile Asp Val Leu Asn Ser Ser Gly Lys Met Asp Lys
            355                 360                 365

Met Arg Leu Leu Asn Ile Leu Met Gln Leu Arg Lys Cys Cys Asn His
370                 375                 380

Pro Tyr Leu Phe Asp Gly Ala Glu Pro Gly Pro Pro Tyr Thr Thr Asp
385                 390                 395                 400

Glu His Ile Val Ser Asn Ser Gly Lys Met Val Val Leu Asp Lys Leu
                405                 410                 415

Leu Ala Lys Leu Lys Glu Gln Gly Ser Arg Val Leu Ile Phe Ser Gln
                420                 425                 430
```

```
Met Thr Arg Leu Leu Asp Ile Leu Glu Asp Tyr Cys Met Trp Arg Gly
        435                 440                 445

Tyr Glu Tyr Cys Arg Leu Asp Gly Gln Thr Pro His Glu Glu Arg Glu
    450                 455                 460

Glu Ala Ile Glu Ala Phe Asn Ala Pro Asn Ser Ser Lys Phe Ile Phe
465                 470                 475                 480

Met Leu Ser Thr Arg Ala Gly Gly Leu Gly Ile Asn Leu Ala Ser Ala
            485                 490                 495

Asp Val Val Ile Leu Tyr Asp Ser Asp Trp Asn Pro Gln Val Asp Leu
                500                 505                 510

Gln Ala Met Asp Arg Ala His Arg Ile Gly Gln Lys Lys Pro Val Arg
            515                 520                 525

Val Phe Arg Leu Ile Thr Asp Asn Thr Val Glu Glu Arg Ile Val Glu
        530                 535                 540

Arg Ala Glu Ile Lys Leu Arg Leu Asp Ser Ile Val Ile Gln Gln Gly
545                 550                 555                 560

Arg Leu Ile Asp Gln Gln Ser Asn Lys Leu Ala Lys Glu Glu Met Leu
                565                 570                 575

Gln Met Ile Arg His Gly Ala Thr His Val Phe Ala Ser Lys Glu Ser
            580                 585                 590

Glu Leu Thr Asp Glu Asp Ile Thr Thr Ile Leu Glu Arg Gly Glu Lys
        595                 600                 605

Lys Thr Ala Glu Met Asn Glu Arg Leu Gln Lys Met Gly Glu Ser Ser
610                 615                 620

Leu Arg Asn Phe Arg Met Asp Ile Glu Gln Ser Leu Tyr Lys Phe Glu
625                 630                 635                 640

Gly Glu Asp Tyr Arg Glu Lys Gln Lys Leu Gly Met Val Glu Trp Ile
                645                 650                 655

Glu Pro Pro Lys Arg Glu Arg Lys Ala Asn Tyr Ala Val Asp Ala Tyr
            660                 665                 670

Phe Arg Glu Ala Leu Arg Val Ser Glu Pro Lys Ile Pro Lys Ala Pro
        675                 680                 685

Arg Pro Pro Lys Gln Pro Asn Val Gln Asp Phe Gln Phe Pro Pro
690                 695                 700

Arg Leu Phe Glu Leu Leu Glu Lys Glu Ile Leu Tyr Tyr Arg Lys Thr
705                 710                 715                 720

Ile Gly Tyr Lys Val Pro Arg Asn Pro Asp Ile Pro Asn Pro Ala Leu
                725                 730                 735

Ala Gln Arg Glu Gln Lys Lys Ile Asp Gly Ala Glu Pro Leu Thr
            740                 745                 750

Pro Glu Glu Thr Glu Lys Glu Lys Leu Leu Thr Gln Gly Phe Thr
        755                 760                 765

Asn Trp Thr Lys Arg Asp Phe Asn Gln Phe Ile Lys Ala Asn Glu Lys
770                 775                 780

Tyr Gly Arg Asp Asp Ile Asp Asn Ile Ala Arg Glu Val Glu Gly Lys
785                 790                 795                 800

Ser Pro Glu Glu Val Met Glu Tyr Ser Ala Val Phe Trp Glu Arg Cys
                805                 810                 815

Asn Glu Leu Gln Asp Ile Glu Lys Ile Met Ala Gln Ile Glu Arg Gly
            820                 825                 830

Glu Ala Arg Ile Gln Arg Arg Ile Ser Ile Lys Lys Ala Leu Asp Ala
        835                 840                 845

Lys Ile Ala Arg Tyr Lys Ala Pro Phe His Gln Leu Arg Ile Gln Tyr
850                 855                 860
```

```
Gly Thr Ser Lys Gly Lys Asn Tyr Thr Glu Glu Asp Arg Phe Leu
865                 870                 875                 880

Ile Cys Met Leu His Lys Met Gly Phe Asp Arg Glu Asn Val Tyr Glu
                885                 890                 895

Glu Leu Arg Gln Cys Val Arg Asn Ala Pro Gln Phe Arg Phe Asp Trp
            900                 905                 910

Phe Ile Lys Ser Arg Thr Ala Met Glu Phe Gln Arg Arg Cys Asn Thr
            915                 920                 925

Leu Ile Ser Leu Ile Glu Lys Glu Asn Met Glu Ile Glu Glu Arg Glu
            930                 935                 940

Arg Ala Lys Lys Lys Lys
945             950
```

<210> SEQ ID NO 158
<211> LENGTH: 180
<212> TYPE: PRT
<213> ORGANISM: Homo sapiens

<400> SEQUENCE: 158

```
Asn Ser Ser Gly Lys Met Asp Lys Met Arg Leu Leu Asn Ile Leu Met
1               5                   10                  15

Gln Leu Arg Lys Cys Cys Asn His Pro Tyr Leu Phe Asp Gly Ala Glu
            20                  25                  30

Pro Gly Pro Pro Tyr Thr Thr Asp Glu His Ile Val Ser Asn Ser Gly
        35                  40                  45

Lys Met Val Val Leu Asp Lys Leu Leu Ala Lys Leu Lys Glu Gln Gly
    50                  55                  60

Ser Arg Val Leu Ile Phe Ser Gln Met Thr Arg Leu Leu Asp Ile Leu
65                  70                  75                  80

Glu Asp Tyr Cys Met Trp Arg Gly Tyr Glu Tyr Cys Arg Leu Asp Gly
                85                  90                  95

Gln Thr Pro His Glu Glu Arg Glu Asp Lys Phe Leu Glu Val Glu Phe
            100                 105                 110

Leu Gly Gln Arg Glu Ala Ile Glu Ala Phe Asn Ala Pro Asn Ser Ser
        115                 120                 125

Lys Phe Ile Phe Met Leu Ser Thr Arg Ala Gly Gly Leu Gly Ile Asn
    130                 135                 140

Leu Ala Ser Ala Asp Val Val Ile Leu Tyr Asp Ser Asp Trp Asn Pro
145                 150                 155                 160

Gln Val Asp Leu Gln Ala Met Asp Arg Ala His Arg Ile Gly Gln Lys
                165                 170                 175

Lys Pro Val Arg
            180
```

<210> SEQ ID NO 159
<211> LENGTH: 168
<212> TYPE: PRT
<213> ORGANISM: Homo sapiens

<400> SEQUENCE: 159

```
Asn Ser Ser Gly Lys Met Asp Lys Met Arg Leu Leu Asn Ile Leu Met
1               5                   10                  15

Gln Leu Arg Lys Cys Cys Asn His Pro Tyr Leu Phe Asp Gly Ala Glu
            20                  25                  30

Pro Gly Pro Pro Tyr Thr Thr Asp Glu His Ile Val Ser Asn Ser Gly
        35                  40                  45
```

```
Lys Met Val Val Leu Asp Lys Leu Leu Ala Lys Leu Lys Glu Gln Gly
        50                  55                  60

Ser Arg Val Leu Ile Phe Ser Gln Met Thr Arg Leu Leu Asp Ile Leu
65                  70                  75                  80

Glu Asp Tyr Cys Met Trp Arg Gly Tyr Glu Tyr Cys Arg Leu Asp Gly
                85                  90                  95

Gln Thr Pro His Glu Glu Arg Glu Ala Ile Glu Ala Phe Asn Ala
            100                 105                 110

Pro Asn Ser Ser Lys Phe Ile Phe Met Leu Ser Thr Arg Ala Gly Gly
                115                 120                 125

Leu Gly Ile Asn Leu Ala Ser Ala Asp Val Val Ile Leu Tyr Asp Ser
        130                 135                 140

Asp Trp Asn Pro Gln Val Asp Leu Gln Ala Met Asp Arg Ala His Arg
145                 150                 155                 160

Ile Gly Gln Lys Lys Pro Val Arg
                165
```

```
<210> SEQ ID NO 160
<211> LENGTH: 21
<212> TYPE: DNA
<213> ORGANISM: Artificial sequence
<220> FEATURE:
<223> OTHER INFORMATION: Primer

<400> SEQUENCE: 160
atcatggcct acaagatgct g                                              21

<210> SEQ ID NO 161
<211> LENGTH: 21
<212> TYPE: DNA
<213> ORGANISM: Artificial sequence
<220> FEATURE:
<223> OTHER INFORMATION: Primer

<400> SEQUENCE: 161
atccgctcgt tctctttctt c                                              21

<210> SEQ ID NO 162
<211> LENGTH: 128
<212> TYPE: PRT
<213> ORGANISM: Homo sapiens

<400> SEQUENCE: 162

Met Ala Tyr Lys Met Leu Ala Arg Gly Gln Pro Leu Pro Asp His Leu
1               5                   10                  15

Leu Asn Phe Gln Arg Gln Leu Arg Gln Glu Val Val Val Cys Met Arg
                20                  25                  30

Arg Asp Thr Ala Leu Glu Thr Ala Leu Asn Ala Lys Ala Tyr Lys Arg
            35                  40                  45

Ser Lys Arg Gln Ser Leu Arg Glu Ala Arg Ile Thr Glu Lys Leu Glu
        50                  55                  60

Lys Gln Gln Lys Ile Glu Gln Glu Arg Lys Arg Gln Lys His Gln
65                  70                  75                  80

Glu Tyr Leu Asn Ser Ile Leu Gln His Ala Lys Asp Phe Lys Glu Tyr
                85                  90                  95

His Arg Ser Val Thr Gly Lys Ile Gln Lys Leu Thr Lys Ala Val Ala
            100                 105                 110

Thr Tyr His Ala Asn Thr Glu Arg Glu Gln Lys Lys Glu Asn Glu Arg
        115                 120                 125
```

-continued

```
<210> SEQ ID NO 163
<211> LENGTH: 420
<212> TYPE: PRT
<213> ORGANISM: Homo sapiens

<400> SEQUENCE: 163
```

Pro Leu Gly Gly Ser Glu His Ala Ser Ser Pro Val Pro Ala Ser Gly
1               5                   10                  15

Pro Ser Ser Gly Pro Gln Met Ser Gly Pro Gly Gly Ala Pro Leu
            20                  25                  30

Asp Gly Ala Asp Pro Gln Ala Leu Gly Gln Gln Asn Arg Gly Pro Thr
            35                  40                  45

Pro Phe Asn Gln Asn Gln Leu His Gln Leu Arg Ala Gln Ile Met Ala
    50                  55                  60

Tyr Lys Met Leu Ala Arg Gly Gln Pro Leu Pro Asp His Leu Gln Met
65                  70                  75                  80

Ala Val Gln Gly Lys Arg Pro Met Pro Gly Met Gln Gln Gln Met Pro
                85                  90                  95

Thr Leu Pro Pro Pro Ser Val Ser Ala Thr Gly Pro Gly Pro Gly Pro
            100                 105                 110

Gly Pro Gly Pro Gly Pro Gly Pro Ala Pro Asn Tyr Ser
        115                 120                 125

Arg Pro His Gly Met Gly Gly Pro Asn Met Pro Pro Gly Pro Ser
    130                 135                 140

Gly Val Pro Pro Gly Met Pro Gly Gln Pro Pro Gly Gly Pro Pro Lys
145                 150                 155                 160

Pro Trp Pro Glu Gly Pro Met Ala Asn Ala Ala Ala Pro Thr Ser Thr
                165                 170                 175

Pro Gln Lys Leu Ile Pro Pro Gln Pro Thr Gly Arg Pro Ser Pro Ala
            180                 185                 190

Pro Pro Ala Val Pro Ala Ala Ser Pro Val Met Pro Pro Gln Thr
        195                 200                 205

Gln Ser Pro Gly Gln Pro Ala Gln Pro Ala Pro Met Val Pro Leu His
    210                 215                 220

Gln Lys Gln Ser Arg Ile Thr Pro Ile Gln Lys Pro Arg Gly Leu Asp
225                 230                 235                 240

Pro Val Glu Ile Leu Gln Glu Arg Glu Tyr Arg Leu Gln Ala Arg Ile
                245                 250                 255

Ala His Arg Ile Gln Glu Leu Glu Asn Leu Pro Gly Ser Leu Ala Gly
            260                 265                 270

Asp Leu Arg Thr Lys Ala Thr Ile Glu Leu Lys Ala Leu Arg Leu Leu
        275                 280                 285

Asn Phe Gln Arg Gln Leu Arg Gln Glu Val Val Val Cys Met Arg Arg
    290                 295                 300

Asp Thr Ala Leu Glu Thr Ala Leu Asn Ala Lys Ala Tyr Lys Arg Ser
305                 310                 315                 320

Lys Arg Gln Ser Leu Arg Glu Ala Arg Ile Thr Glu Lys Leu Glu Lys
                325                 330                 335

Gln Gln Lys Ile Glu Gln Glu Arg Lys Arg Arg Gln Lys His Gln Glu
            340                 345                 350

Tyr Leu Asn Ser Ile Leu Gln His Ala Lys Asp Phe Lys Glu Tyr His
        355                 360                 365

Arg Ser Val Thr Gly Lys Ile Gln Lys Leu Thr Lys Ala Val Ala Thr
    370                 375                 380

```
Tyr His Ala Asn Thr Glu Arg Glu Gln Lys Lys Glu Asn Glu Arg Ile
385                 390                 395                 400

Glu Lys Glu Arg Met Arg Arg Leu Met Ala Asp Glu Glu Gly Tyr
            405                 410                 415

Arg Lys Leu Ile
            420

<210> SEQ ID NO 164
<211> LENGTH: 78
<212> TYPE: PRT
<213> ORGANISM: Homo sapiens

<400> SEQUENCE: 164

Met Ala Tyr Lys Met Leu Ala Arg Gly Gln Pro Leu Pro Asp His Leu
1               5                   10                  15

Gln Met Ala Val Gln Glu Arg Lys Arg Gln Lys His Gln Glu Tyr
            20                  25                  30

Leu Asn Ser Ile Leu Gln His Ala Lys Asp Phe Lys Glu Tyr His Arg
        35                  40                  45

Ser Val Thr Gly Lys Ile Gln Lys Leu Thr Lys Ala Val Ala Thr Tyr
    50                  55                  60

His Ala Asn Thr Glu Arg Glu Gln Lys Lys Glu Asn Glu Arg
65                  70                  75

<210> SEQ ID NO 165
<211> LENGTH: 360
<212> TYPE: PRT
<213> ORGANISM: Homo sapiens

<400> SEQUENCE: 165

Gln Ile Met Ala Tyr Lys Met Leu Ala Arg Gly Gln Pro Leu Pro Asp
1               5                   10                  15

His Leu Gln Met Ala Val Gln Gly Lys Arg Pro Met Pro Gly Met Gln
            20                  25                  30

Gln Gln Met Pro Thr Leu Pro Pro Ser Val Ser Ala Thr Gly Pro
        35                  40                  45

Gly Pro Gly Pro Gly Pro Gly Pro Gly Pro Gly Pro Ala Pro
    50                  55                  60

Pro Asn Tyr Ser Arg Pro His Gly Met Gly Gly Pro Asn Met Pro Pro
65                  70                  75                  80

Pro Gly Pro Ser Gly Val Pro Pro Gly Met Pro Gly Gln Pro Pro Gly
            85                  90                  95

Gly Pro Pro Lys Pro Trp Pro Glu Gly Pro Met Ala Asn Ala Ala Ala
        100                 105                 110

Pro Thr Ser Thr Pro Gln Lys Leu Ile Pro Pro Gln Pro Thr Gly Arg
            115                 120                 125

Pro Ser Pro Ala Pro Pro Ala Val Pro Pro Ala Ala Ser Pro Val Met
    130                 135                 140

Pro Pro Gln Thr Gln Ser Pro Gly Gln Pro Ala Gln Pro Ala Pro Met
145                 150                 155                 160

Val Pro Leu His Gln Lys Gln Ser Arg Ile Thr Pro Ile Gln Lys Pro
            165                 170                 175

Arg Gly Leu Asp Pro Val Glu Ile Leu Gln Glu Arg Glu Tyr Arg Leu
        180                 185                 190

Gln Ala Arg Ile Ala His Arg Ile Gln Glu Leu Glu Asn Leu Pro Gly
    195                 200                 205

Ser Leu Ala Gly Asp Leu Arg Thr Lys Ala Thr Ile Glu Leu Lys Ala
```

```
                210                 215                 220
Leu Arg Leu Leu Asn Phe Gln Arg Gln Leu Arg Gln Glu Val Val
225                 230                 235                 240

Cys Met Arg Arg Asp Thr Ala Leu Glu Thr Ala Leu Asn Ala Lys Ala
                245                 250                 255

Tyr Lys Arg Ser Lys Arg Gln Ser Leu Arg Glu Ala Arg Ile Thr Glu
                260                 265                 270

Lys Leu Glu Lys Gln Gln Lys Ile Glu Gln Glu Arg Lys Arg Gln
                275                 280                 285

Lys His Gln Glu Tyr Leu Asn Ser Ile Leu Gln His Ala Lys Asp Phe
290                 295                 300

Lys Glu Tyr His Arg Ser Val Thr Gly Lys Ile Gln Lys Leu Thr Lys
305                 310                 315                 320

Ala Val Ala Thr Tyr His Ala Asn Thr Glu Arg Glu Gln Lys Lys Glu
                325                 330                 335

Asn Glu Arg Ile Glu Lys Glu Arg Met Arg Arg Leu Met Ala Glu Asp
                340                 345                 350

Glu Glu Gly Tyr Arg Lys Leu Ile
                355                 360
```

<210> SEQ ID NO 166
<211> LENGTH: 21
<212> TYPE: DNA
<213> ORGANISM: Artificial sequence
<220> FEATURE:
<223> OTHER INFORMATION: Primer

<400> SEQUENCE: 166
gctcggcaag aactacaaga a        21

<210> SEQ ID NO 167
<211> LENGTH: 21
<212> TYPE: DNA
<213> ORGANISM: Artificial sequence
<220> FEATURE:
<223> OTHER INFORMATION: Primer

<400> SEQUENCE: 167
cggacacttt gttccagtca t        21

<210> SEQ ID NO 168
<211> LENGTH: 130
<212> TYPE: PRT
<213> ORGANISM: Homo sapiens

<400> SEQUENCE: 168

```
Met Leu Gly Lys Asn Tyr Lys Lys Tyr Ile Gln Ala Glu Pro Pro Thr
1               5                   10                  15

Asn Lys Ser Leu Ser Ser Leu Val Val Gln Leu Leu Gln Phe Gln Glu
                20                  25                  30

Glu Val Phe Gly Lys His Val Leu Ala Asp Thr Pro Ser Gly Leu Val
                35                  40                  45

Pro Leu Gln Pro Lys Thr Pro Gln Gln Thr Ser Ala Ser Gln Gln Met
                50                  55                  60

Leu Asn Phe Pro Asp Lys Gly Lys Glu Lys Pro Thr Asp Met Gln Asn
65                  70                  75                  80

Phe Gly Leu Arg Thr Asp Met Tyr Thr Lys Lys Asn Val Pro Ser Lys
                85                  90                  95

Ser Lys Ala Ala Ala Ser Ala Thr Arg Glu Trp Thr Glu Gln Glu Thr
```

```
                  100                 105                 110
Leu Leu Leu Leu Glu Ala Leu Glu Met Tyr Lys Asp Asp Trp Asn Lys
        115                 120                 125
Val Ser
    130

<210> SEQ ID NO 169
<211> LENGTH: 660
<212> TYPE: PRT
<213> ORGANISM: Homo sapiens

<400> SEQUENCE: 169

Met Ala Val Arg Lys Asp Gly Gly Pro Asn Val Lys Tyr Tyr Glu
1               5                   10                  15

Ala Ala Asp Thr Val Thr Gln Phe Asp Asn Val Arg Leu Trp Leu Gly
                20                  25                  30

Lys Asn Tyr Lys Lys Tyr Ile Gln Ala Glu Pro Pro Thr Asn Lys Ser
            35                  40                  45

Leu Ser Ser Leu Val Val Gln Leu Leu Gln Phe Gln Glu Glu Val Phe
        50                  55                  60

Gly Lys His Val Ser Asn Ala Pro Leu Thr Lys Leu Pro Ile Lys Cys
65                  70                  75                  80

Phe Leu Asp Phe Lys Ala Gly Gly Ser Leu Cys His Ile Leu Ala Ala
                85                  90                  95

Ala Tyr Lys Phe Lys Ser Asp Gln Gly Trp Arg Arg Tyr Asp Phe Gln
                100                 105                 110

Asn Pro Ser Arg Met Asp Arg Asn Val Glu Met Phe Met Thr Ile Glu
            115                 120                 125

Lys Ser Leu Val Gln Asn Asn Cys Leu Ser Arg Pro Asn Ile Phe Leu
        130                 135                 140

Cys Pro Glu Ile Glu Pro Lys Leu Leu Gly Lys Leu Lys Asp Ile Ile
145                 150                 155                 160

Lys Arg His Gln Gly Thr Val Thr Glu Asp Lys Asn Asn Ala Ser His
                165                 170                 175

Val Val Tyr Pro Val Pro Gly Asn Leu Glu Glu Glu Trp Val Arg
            180                 185                 190

Pro Val Met Lys Arg Asp Lys Gln Val Leu Leu His Trp Gly Tyr Tyr
        195                 200                 205

Pro Asp Ser Tyr Asp Thr Trp Ile Pro Ala Ser Glu Ile Glu Ala Ser
    210                 215                 220

Val Glu Asp Ala Pro Thr Pro Glu Lys Pro Arg Lys Val His Ala Lys
225                 230                 235                 240

Trp Ile Leu Asp Thr Asp Thr Phe Asn Glu Trp Met Asn Glu Glu Asp
                245                 250                 255

Tyr Glu Val Asn Asp Asp Lys Asn Pro Val Ser Arg Arg Lys Lys Ile
                260                 265                 270

Ser Ala Lys Thr Leu Thr Asp Glu Val Asn Ser Pro Asp Ser Asp Arg
            275                 280                 285

Arg Asp Lys Lys Gly Gly Asn Tyr Lys Lys Arg Lys Arg Ser Pro Ser
        290                 295                 300

Pro Ser Pro Thr Pro Glu Ala Lys Lys Asn Ala Lys Lys Gly Pro
305                 310                 315                 320

Ser Thr Pro Tyr Thr Lys Ser Lys Arg Gly His Arg Glu Glu Gln
                325                 330                 335

Glu Asp Leu Thr Lys Asp Met Asp Glu Pro Ser Pro Val Pro Asn Val
```

-continued

```
                340                 345                 350
Glu Glu Val Thr Leu Pro Lys Thr Val Asn Thr Lys Lys Asp Ser Glu
            355                 360                 365
Ser Ala Pro Val Lys Gly Gly Thr Met Thr Asp Leu Asp Glu Gln Glu
        370                 375                 380
Asp Glu Ser Met Glu Thr Thr Gly Lys Asp Glu Asp Glu Asn Ser Thr
385                 390                 395                 400
Gly Asn Lys Gly Glu Gln Thr Lys Asn Pro Asp Leu His Glu Asp Asn
                405                 410                 415
Val Thr Glu Gln Thr His His Ile Ile Ile Pro Ser Tyr Ala Ala Trp
            420                 425                 430
Phe Asp Tyr Asn Ser Val His Ala Ile Glu Arg Arg Ala Leu Pro Glu
        435                 440                 445
Phe Phe Asn Gly Lys Asn Lys Ser Lys Thr Pro Glu Ile Tyr Leu Ala
    450                 455                 460
Tyr Arg Asn Phe Met Ile Asp Thr Tyr Arg Leu Asn Pro Gln Glu Tyr
465                 470                 475                 480
Leu Thr Ser Thr Ala Cys Arg Arg Asn Leu Ala Gly Asp Val Cys Ala
                485                 490                 495
Ile Met Arg Val His Ala Phe Leu Glu Gln Trp Gly Leu Ile Asn Tyr
            500                 505                 510
Gln Val Asp Ala Glu Ser Arg Pro Thr Pro Met Gly Pro Pro Pro Thr
        515                 520                 525
Ser His Phe His Val Leu Ala Asp Thr Pro Ser Gly Leu Val Pro Leu
    530                 535                 540
Gln Pro Lys Thr Pro Gln Gln Thr Ser Ala Ser Gln Gln Met Leu Asn
545                 550                 555                 560
Phe Pro Asp Lys Gly Lys Glu Lys Pro Thr Asp Met Gln Asn Phe Gly
                565                 570                 575
Leu Arg Thr Asp Met Tyr Thr Lys Lys Asn Val Pro Ser Lys Ser Lys
            580                 585                 590
Ala Ala Ala Ser Ala Thr Arg Glu Trp Thr Glu Gln Glu Thr Leu Leu
        595                 600                 605
Leu Leu Glu Ala Leu Glu Met Tyr Lys Asp Asp Trp Asn Lys Val Ser
    610                 615                 620
Glu His Val Gly Ser Arg Thr Gln Asp Glu Cys Ile Leu His Phe Leu
625                 630                 635                 640
Arg Leu Pro Ile Glu Asp Pro Tyr Leu Glu Asp Ser Glu Ala Ser Leu
                645                 650                 655
Gly Pro Leu Ala
        660

<210> SEQ ID NO 170
<211> LENGTH: 208
<212> TYPE: PRT
<213> ORGANISM: Homo sapiens

<400> SEQUENCE: 170

Ser Ser Leu Val Val Gln Leu Leu Gln Phe Gln Glu Glu Val Phe Gly
1               5                   10                  15
Lys His Val Ser Asn Ala Pro Leu Thr Lys Leu Pro Ile Lys Cys Phe
            20                  25                  30
Leu Asp Phe Lys Ala Gly Gly Ser Leu Cys His Ile Leu Ala Ala Ala
        35                  40                  45
Tyr Arg Asn Phe Met Ile Asp Thr Tyr Arg Leu Asn Pro Gln Glu Tyr
```

```
Leu Thr Ser Thr Ala Cys Arg Arg Asn Leu Ala Gly Asp Val Cys Ala
 65                  70                  75                  80

Ile Met Arg Val His Ala Phe Leu Glu Gln Trp Gly Leu Ile Asn Tyr
                 85                  90                  95

Gln Val Asp Ala Glu Ser Arg Pro Thr Pro Met Gly Pro Pro Pro Thr
            100                 105                 110

Ser His Phe His Val Leu Ala Asp Thr Pro Ser Gly Leu Val Pro Leu
        115                 120                 125

Gln Pro Lys Thr Pro Gln Gln Thr Ser Ala Ser Gln Gln Met Leu Asn
    130                 135                 140

Phe Pro Asp Lys Gly Lys Glu Lys Pro Thr Asp Met Gln Asn Phe Gly
145                 150                 155                 160

Leu Arg Thr Asp Met Tyr Thr Lys Lys Asn Val Pro Ser Lys Ser Lys
                165                 170                 175

Ala Ala Ala Ser Ala Thr Arg Glu Trp Thr Glu Gln Glu Thr Leu Leu
            180                 185                 190

Leu Leu Glu Ala Leu Glu Met Tyr Lys Asp Asp Trp Asn Lys Val Ser
        195                 200                 205

<210> SEQ ID NO 171
<211> LENGTH: 96
<212> TYPE: PRT
<213> ORGANISM: Homo sapiens

<400> SEQUENCE: 171

Met Ser Ser Leu Val Val Gln Leu Leu Gln Phe Gln Glu Glu Val Phe
  1               5                  10                  15

Gly Lys His Val Ser Asn Ala Pro Leu Thr Lys Leu Pro Ile Lys Cys
                 20                  25                  30

Phe Leu Asp Lys Gly Lys Glu Lys Pro Thr Asp Met Gln Asn Phe Gly
            35                  40                  45

Leu Arg Thr Asp Met Tyr Thr Lys Lys Asn Val Pro Ser Lys Ser Lys
         50                  55                  60

Ala Ala Ala Ser Ala Thr Arg Glu Trp Thr Glu Gln Glu Thr Leu Leu
 65                  70                  75                  80

Leu Leu Glu Ala Leu Glu Met Tyr Lys Asp Asp Trp Asn Lys Val Ser
                 85                  90                  95

<210> SEQ ID NO 172
<211> LENGTH: 20
<212> TYPE: DNA
<213> ORGANISM: Artificial sequence
<220> FEATURE:
<223> OTHER INFORMATION: Primer

<400> SEQUENCE: 172
gcggtgtctc agattcattc                                           20

<210> SEQ ID NO 173
<211> LENGTH: 22
<212> TYPE: DNA
<213> ORGANISM: Artificial sequence
<220> FEATURE:
<223> OTHER INFORMATION: Primer

<400> SEQUENCE: 173
ttgccggatg ctgtaatagt tg                                        22
```

```
<210> SEQ ID NO 174
<211> LENGTH: 77
<212> TYPE: PRT
<213> ORGANISM: Homo sapiens

<400> SEQUENCE: 174

Met Ser Lys Arg Pro Ser Tyr Ala Pro Pro Thr Pro Ala Pro Ala
1               5                  10                  15

Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Val Gly Glu Ser Thr Ile Thr Ala Ser Gly Lys Gln
    50                  55                  60

Leu Glu Leu Thr Arg Asn Ala Phe Arg Ile Arg Ser Phe
65                  70                  75

<210> SEQ ID NO 175
<211> LENGTH: 180
<212> TYPE: PRT
<213> ORGANISM: Homo sapiens

<400> SEQUENCE: 175

Met Ser Lys Arg Pro Ser Tyr Ala Pro Pro Thr Pro Ala Pro Ala
1               5                  10                  15

Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Ala Ser Ser Gly Ile Thr Ile Pro Lys Pro Lys
    50                  55                  60

Pro Pro Asp Lys Pro Leu Met Pro Tyr Met Arg Tyr Ser Arg Lys Val
65                  70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Glu Lys
                100                 105                 110

Gln Glu Tyr Leu Asn Glu Tyr Glu Ala Glu Lys Ile Glu Tyr Asn Glu
            115                 120                 125

Ser Met Lys Ala Tyr His Asn Ser Pro Ala Tyr Leu Ala Tyr Ile Asn
    130                 135                 140

Ala Lys Ser Arg Ala Glu Ala Ala Leu Glu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp
            180
```

COMPOSITIONS AND METHODS FOR TARGETING CANCER-SPECIFIC TRANSCRIPTION COMPLEXES

TECHNICAL FIELD OF THE INVENTION

The present invention relates generally to detection and therapy of cancer. The invention is more specifically related to novel molecules directed against cancer-specific transcription complexes. The molecules of the invention can be used in vaccines and pharmaceutical compositions for the treatment of various cancers expressing the targeted transcription complexes, as well as in methods of detecting and assessing the malignancy of such cancers.

BACKGROUND OF THE INVENTION

Cancer remains a significant health problem throughout the world. Current therapies, which are generally based on a combination of chemotherapy or surgery and radiation, continue to prove inadequate in many patients.

Among cancers, melanoma is well known both for its rapidly increasing incidence and its resistance to virtually all but surgical therapies. Melanoma arises from melanocytes, neural crest derived pigment cells in the skin and eye. During melanoma carcinogenesis, many of the normal markers of the melanocyte lineage become lost. Gene expression patterns in melanoma cells and melanocytes have significant differences that reflect the cancerous nature of melanoma. In general, gene expression is regulated by two types of factors—DNA binding transcription factors and co-regulators which form cell type specific complexes including mediator complex and chromatin remodeling complex that control activity of RNA polymerase two (pol II). Cofactor complexes integrate signals from DNA binding transcription factors as well as from different signaling systems to control RNA synthesis. Cofactor complexes are highly cell- and stimulus-specific, and vary from one physiological stage to another. Cancer cells express transcriptional co-factors with modified structure that is a result of mutations, post-translational modifications, alternative splicing, fusion of different fragments of different proteins to name but a few.

Transcriptional Control of Melanoma and Melanocyte Development

Despite altered gene expression patterns, most, if not all, melanomas retain expression of the basic/helix-loop-helix/leucine-zipper (bHLHzip) transcription factor Microphthalmia-associated transcription factor (MITF) (King et al., 1999) that is characteristic for melanocytes. Published data suggests a role for MITF in the commitment, proliferation, and survival of melanocytes before and/or during neural crest cell migration (Opdecamp et al, 1997). Numerous studies also suggest that MITF, in addition to its role in differentiation pathways such as pigmentation, may have an important role in the proliferation and/or survival of developing melanocytes. The retention of MITF expression in the vast majority of human primary melanomas, including nonpigmented tumors, is consistent with this possibility and has also led to the widespread use of MITF as a diagnostic marker in this malignancy (King et al., 1999; Salti et al. 2000; Chang and Folpe, 2001; Miettinen et al., 2001). Wnt signaling pathway and beta-catenin are significant regulators of melanoma cell growth, with MITF as a critical downstream target. Importantly, disruption of the canonical Wnt pathway abrogates growth of melanoma cells, and constitutive overexpression of MITF rescues the growth suppression.

The invention disclosed herein arises from a search for MITF target genes, which influence cell cycle progression, to examine the possibility that MITF contributes to maintenance of the cell cycle machinery while perhaps not directly participating in the mitogenic response. Cell cycle targets of Wnt signaling such as c-Myc, Cyclin D1 (He et al., 1998; Tetsu and McCormick, 1999; Shtutman et al., 1999), and others may more directly mediate beta-catenin's mitogenic effects. In addition, it has been shown that MITF serves as an upstream regulator of a variety of proliferation related genes such as CDK2: p21 (Cip1): INK4A. MITF interacts with several transcription factors (TEs) including Rb, TFEB, ITF2, PIAS3 and STAT3, to regulate a network of downstream genes that are related to different aspects of melanocyte and melanoma development.

In addition to the MITF pathway, several other signaling pathways have been reported to be associated with melanoma cells, including NOTCH, interferon, nuclear hormone receptor and immune modulatory pathways. Some differentially expressed genes reside on chromosomal regions displaying common loss or gain in melanomas or are known to be regulated by CpG promoter methylation. Several data also indicate that transcription cofactors are differentially expressed in melanomas compared to melanocytes, Goldberg et al. (2003) reported that tumor suppressor genes TXNIP and KISS1, which are down-regulated in metastatic melanomas, are controlled by transcriptional factor DRIP130CRSP3. DRIP130/CRSP3 is located in chromosome 6 in the region that is frequently deleted in melanomas.

Transcriptional Control

Precise temporal and spatial regulation of the transcription of protein-encoding genes by RNA polymerase II (pol II) is vital to the execution of complex gene expression programs in response to growth, developmental and homeostatic signals. The molecular circuitry that enables coordinated gene expression is largely based on DNA-binding transcription factors (TFs) that bring regulatory information to the target genes. As a rule, DNA binding TFs do not interact directly with pol II and other basal transcriptional complex components. Group of factors called co-regulators including co-activators, co-repressors and a mediator complex have emerged as central players in the process of transcription. These co-regulators mediate DNA binding TFs and pol II complex to control transcriptional activity of specific genes.

Although it has been realized that co-regulators are universally required for the expression of almost all genes, the full implications of a requirement for a multi-subunit co-regulator complex are not yet readily apparent. By inserting itself between the DNA binding TFs and the basal transcriptional machinery, the mediator complex probably affords additional opportunities to control the diverse regulatory inputs received both from the DNA-binding factors and, most likely, from other signals and to present an appropriately calibrated output to the pol II machinery. In its capacity as a processor of diverse signals in the form of activators and repressors that impinge on it, and its location at the interface of pol II and general transcription factors (GTFs), the mediator represents a final check-point before pol II transcription actually commences. The central role of co-regulator complexes in transcriptional control makes them an attractive drug target. Interference at this point of transcription machinery could enable researchers and clinicians to control or correct expression of a large number of genes. Transcriptional complex that contains 70-80 subunits has a different composition in different cell types and on different promoters. This cell specific variability of transcriptional complex assures specificity of potential treatments that target transcriptional machinery.

There remains a need for molecules useful in the treatment of cancer. The invention disclosed herein meets this need by providing isoforms of transcription factors and molecules that specifically target the transcription complexes found in cancer.

SUMMARY OF THE INVENTION

The present invention identifies cancer specific transcriptional complexes (CSTCs) that contain isoforms of individual cofactors in melanoma cells. The melanoma specific isoform related transcriptional complexes (TFCs) have altered function compared to wild type TFCs and are part of the molecular machinery that is responsible for malignant transformation. Therefore, melanoma specific TFCs represent attractive drug targets for treatment of melanoma. In addition, these specific TFCs can be used as diagnostic and prognostic biomarkers. Since individual melanomas express different sets of cofactors and TFCs, the efficacy of many current and novel drugs likely depend on composition of TFCs. Modified TECs provide tools for theranostics, i.e., to select patients who will have favorable response to specific treatments. Moreover, the cancer-specific isoforms of transcriptional co-regulators described herein are expressed in a variety of other cancers, extending the usefulness of the disclosed molecules and methods beyond melanoma.

The invention provides molecules that target cancer-specific transcription complexes (CSTCs) compositions and kits comprising CSTC-targeting molecules, and methods of using CSTC-targeting molecules for the treatment and detection of cancer. In one embodiment the invention provides an expression vector comprising a nucleic acid molecule that encodes a CSTC-targeting molecule operably linked to an expression control sequence. In another embodiment, the invention provides an oligonucleotide that encodes a CGSTC-targeting molecule. The nucleic acid molecule may encode the CSTC-targeting molecule in a sense or anti-sense orientation, depending on the intended use. Also provided are host cells containing such expression vectors, which can be used for the production of CSTC-targeting molecules. In some embodiments, the nucleic acid molecule is labeled with a detectable marker, or provided in a composition with a pharmaceutically acceptable carrier.

The invention additionally provides CSTC-targeting peptides and small molecules, including peptides that target transcription complexes modified by cancer-specific isoforms of transcriptional co-regulators. More specifically, the CSTC-targeting molecules of the invention include molecules that modulate the activity of a cancer-specific mediator complex, containing MED24/TRAP100 and isoforms thereof, and a cancer-specific chromatin modifying complex, containing BAF57 and isoforms thereof. The CSTC-targeting molecule may be provided in a variety of forms, as appropriate for a particular use, including, for example, in a soluble form, immobilized on a substrate, or in combination with a pharmaceutically acceptable carrier. In some embodiments, the CSTC-targeting molecule is labeled with a detectable marker, or provided in a composition with a pharmaceutically acceptable carrier.

The methods provided by the invention include a method for inhibiting proliferation of cancer cells comprising contacting a cancer cell with a CSTC-targeting molecule of the invention. Typically, the molecule comprises a peptide, oligonucleotide (e.g. siRNA) or small molecule that modulates the activity of a cancer-specific mediator complex containing MED24/TRAP100 and its isoforms, and a cancer-specific chromatin modifying complex containing BAF57 and its isoforms. In one embodiment, the peptide comprises the amino acid sequence PQMQQNVFQYPGAGMVPQGEANF (SEQ ID NO: 1) or NDRLSDGDSKYSQTSHKLVQLL (SEQ ID NO: 2), that interfere with the function of cancer-specific isoforms of TRAP100 and BAF57, respectively. In a typical embodiment, the peptide further comprises additional sequence selected to facilitate delivery into cells and into nuclei. For example, a cell penetrating peptide (CPP) can be added, such as the following amino acid sequence: RRRRRRR (SEQ ID NO: 3). An example of a peptide that facilitates nuclear delivery is the nucleus localizing signal (NLS) having the amino acid sequence PKKRKV (SEQ ID NO: 4). A peptide of the invention is exemplified by the peptide having the amino acid sequence of PKKRKVR-RRRRRRPQMQQNVFQYPGAGMVPQGEANF (TRAP100 P05, SEQ ID NO: 5) or PKKRKVRRRRRRRN-DRLSDGDSKYSQTSHKLVQLL (BAF57 P12; SEQ ID NO. 6).

Other methods provided include a method for treating cancer in a subject by administering to the subject a CSTC-targeting molecule of the invention, a method of inhibiting tumor growth, a method for detecting cancer, and a method for inducing apoptosis. The method for inhibiting tumor growth and the method for inducing apoptosis, comprises contacting a tumor or cancer cell with a CSTC-targeting molecule. The method for detecting cancer comprises contacting a tissue specimen with a detectable molecule that specifically binds a CSTC and detecting binding of the detectable molecule. Binding of the detectable molecule is indicative of cancer. Examples of a detectable molecule include a peptide antibody or other molecule that specifically binds to a CSTC. Typically, the cancer is melanoma.

DETAILED DESCRIPTION OF THE INVENTION

The present invention is based on the discovery of cancer-specific transcription complexes (CSTCs) that contain isoforms of transcriptional co-regulators specific to human cancers. These molecules provide novel targets for treatment and detection of cancer. Moreover, the data described herein show that molecules directed against the CSTC of the invention are effective in inhibiting proliferation of cancer cells, inducing apoptosis and inhibiting tumor growth. This invention thus provides CSTC-targeting molecules as diagnostic and therapeutic agents for the detection, monitoring and treatment of various cancers.

Transcriptional Complexes as Novel Promising Drug Targets

Transcriptional regulators determine regulatory networks that control gene-specific transcription. The misregulation of these networks is correlated with a growing number of human diseases that are characterized by altered gene expression patterns. This has spurred intense efforts toward the development of artificial transcriptional regulators and/or molecules that modify TFCs to correct and restore "normal" expression of affected genes. Numerous research groups and companies are focusing on development of treatment strategies that target signaling systems mostly kinases and phosphatases, and cell surface molecules that control gene expression and regulate cell division and differentiation. All potential treatments that target signaling and cell surface molecules have one critical problem—cell type specificity. To be effective with minimal side effects, treatments have to affect only diseased cells. Signaling systems and surface molecules are expressed and function in a wide variety of cell populations that makes achieving localized/restricted effects extremely difficult.

It is well known that transcriptional control of individual genes is cell type specific and that different transcription factor complexes are responsible for this specificity. We propose to use the cell type specificity of TFCs to control expression of proteins that are critical for cancer development. Achieving this goal will allow us to manipulate growth and apoptosis of cancer cells. For a long time TFs have been considered to be difficult targets for effective drug development. Recently numerous reports show that small molecules can be developed that interact with specific TFs and control activity of specific TFCs.

Peptide Drugs—Targeting Transcription Complexes

The ultimate action of TFs on target genes, after site-specific DNA binding, is to enhance the recruitment and/or function of the general transcription machinery (RNA polymerase II and general transcription factors TFII-A, -B, -D, -E, -F, and -H; Roeder 1996) on cognate core promoter elements. Recent studies have implicated a large multisubunit coactivator complex, a mediator, as the main pathway for direct communication between DNA binding TFs and the general transcription machinery (reviewed in Malik and Roeder, 2000). Large number of protein/protein interactions determines specificity and function of mediator complex. Peptides that represent interaction surfaces of different transcription factors have been designed and used to manipulate expression of target genes (Kalinichenko et al., 2004, Chinmay et al., 2005, Gail et al., 2005) and control disease.

Prediction of the structures of multi molecular complexes has largely not been addressed, probably due to the magnitude of the combinatorial complexity of the problem. Docking applications have traditionally been used to predict pair-wise interactions between molecules. Several algorithms that extend the application of docking to multimolecular assemblies have been developed. We apply these algorithms to predict quaternary structures of both oligomers and multi-protein complexes. These algorithms have predicted well a near-native arrangement of the subunits of mediator complexes. We have used these computational tools to design a small library of peptides that interact with a cancer specific mediator complex and a cancer specific chromatin modifying complex containing cancer specific isoforms of MED24/TRAP100 and BAF57 respectively. Screening of these libraries has identified peptides that affect growth and apoptosis of melanoma cells.

Another critical issue is delivery of therapeutic peptides to cell nucleus where transcription factor complexes are localized and where they perform their function. Cell membranes act as protective walls to exclude peptides that are not actively imported by living cells in order to overcome this barrier for effective delivery of membrane-impermeable peptides, several chemical and physical methods have been developed including electroporation and cationic lipids/liposomes. These methods have been shown to be effective for delivering hydrophobic macromolecules. The drawbacks of these harsh methods are, primarily, the unwanted cellular effects exerted by them, and, secondly, their limitation to in vitro applications. The last decade's discovery of cell-penetrating peptides (CPP) translocating themselves across cell membranes of various cell lines, along with a cargo 100-fold their own size, via a seemingly energy independent process, opens up the possibility for efficient delivery of proteins, peptides and small molecules into cells both in vitro and in vivo. The only consistently found feature present in all CPPs is the high content of basic amino acids, resulting in a positive net charge. Rothbard et al. (2000) showed that cyclosporin A was efficiently delivered into dermal T lymphocytes and inhibited inflammation by linking to a hepta-arginine segment suggesting that positive charge is the required feature for cellular translocation. CPPs possess an appealing set of desirable features for cellular targeting, such as effective delivery in vivo, targeting of the nucleus, applicability to all cell types, no apparent size constraint of cargo and seemingly no immunogenic, antigenic or inflammatory properties.

As delivery vectors, cell-penetrating peptides definitely have proven their value. Their ability to effectively deliver hydrophobic macromolecules into practically all types of cells in vitro, as well as in vivo, without marked levels of cytotoxicity, is impressive.

Combining CPP and TFC interfering peptides opens a new and more effective approach to the targeting of transcriptional complexes with therapeutic peptides.

Cancer and Transcriptional Control

Cancer is a disease of enormous complexity. To date, thousands of genes representing virtually every sub-group of genes have been implicated in cancer. Currently, cancer is thought to develop from proliferating stem or progenitor cells with either mutated genes or rearranged chromosomes. As a result of these genetic alterations tumor cells also possess an altered gene and protein expression compared with non-malignant cells. Whole-genome analysis of gene expression clearly shows specific differences between normal and cancerous cells as well as between cancer types. This suggests that regulatory networks determining the expression of specific genes are different in malignant and non-malignant cells.

Cancer patients have a highly variable clinical course and outcome. Intrinsic genetic heterogeneity of the primary tumor has been suggested to play a role in this variability and may explain it in part (Chang, et al. 2003). Pathological and clinical factors are insufficient to capture the complex cascade of events that drive the clinical behavior of tumors. Extensive analyses of gene expression patterns of a variety of tumors have resulted in an understanding that histologically similar tumors have different gene expression patterns. Oligonucleotide and cDNA microarray techniques have identified molecular subgroups of specific types of cancer (Perou et al., 2000, Hedenfalk et al., 2001, West et al., 2001, Zajchowski et al., 2001). Molecular profiling of tumors has also been used to predict survival of patients and to select patients for adjuvant therapy (van't Veer et al., 2002, van de Vijever et al., 2002).

Cancer Specific TFCs—Novel Drug targets with High Specificity

Well-known characteristics of cancer cells are mutations in variety of regulatory molecules including transcription factors, misexpression of transcription factors, expression of mRNA splice variants encoding specific isoforms of proteins and presence of posttranslational modifications that are not present in normal cells. Mutations and expression of fusion proteins are described in almost every single type of cancer (Leroy H, Roumier C, Huyghe P, Biggio V, Fenaux P, Preudhomme C., CEBPA point mutations in hematological malignancies. Leukemia. 2005 March; 19(3), 329-34, Xia and Barr, Chromosome translocations in sarcomas and the emergence of oncogenic transcription factors. Eur J Cancer. 2005 November; 41(16): 2513-27). Large number of papers report identification of cancer specific or enriched mRNA alternative splice variants. For example, a genome-wide computational screening of 11014 genes using 3,471,822 human expressed sequence tag (EST) sequences identified 26,258 alternatively spliced transcripts/mRNAs of which 845 were significantly associated with cancer (Wang et al., 2003). Several of the gene-specific splice variants have been shown to have a prognostic value. Patients with a high expression of the alternative splice variant of helix-loop-helix transcription factor ARNT have a worse relapse-free and overall survival than patients with a low expression (Qin et al. 2001). As a rule the expression of cancer-specific or enriched alternatively spliced mRNAs is not related to the mutations in splice donor or acceptor sites but due to the changes in the expression of splicing factors.

Our in silico analysis using variety of gene expression and EST databases has revealed a large number of alternative splice variants of transcriptional coactivators including mediator complex that have cell type and diseases specific expression. Not all of these splice variants result in protein isoforms with altered function but represent a cryptic splicing that leads to degradation of mRNAs. However, a number of splice variants become translated into functional proteins that will become part of cancer specific TFCs. These changed TFCs may contribute to the development of cancer. We have generated peptides that affect specifically MED24/TRAP100 and BAF57 isoform containing TFCs and block proliferation and induce apoptosis of melanoma cells.

Therapeutic Approach

Our therapeutic approach is based on identification of cancer specific transcription factor complexes (TFC) that contain mutated and/or altered by posttranslational modifications, and/or alternative splicing, and/or TFC components that are modified by a genomic rearrangement. These cancer specific TFCs have structure and function that are different from structure and function of TFCs in normal, non-cancerous cells.

As an example of our approach, we have specifically identified a number of novel isoforms of transcriptional co-regulators that are components of cancer specific TFCs, including but not limited to mediator complex and chromatin remodeling complex. We have focused on two of these altered complexes:

1. Mediator complex that contains cancer specific isoform of MED24/RAP100.
2. Chromatin modifying complex that contains cancer specific isoform of BAF57.

Using different modeling tools and current understanding of composition, structure and function of mediator and chromatin remodeling complexes we identified potential interactions that are unique in complexes that contain cancer specific isoforms of MED24 and BAF57 and identified potential therapeutic peptides. These peptides interact with a MED and chromatin remodeling complexes and alter the function of transcriptional machinery that results in apoptosis and growth arrest of melanoma cells.

MED24 Isoform Containing Complex

Mediator complex consists of approximately 30 proteins that have different functions and participate in different signaling pathways to respond variety of regulatory signals. MED24 is a part of a MED complex "tail" subunit that is present in specific MED complexes. MED 24 co-precipitates with MED16, MED23 and MED25 that are other subunits of "tail" module. Incorporation of MED24 isoform into "tail" subunit modifies interactions of subunit components and opens opportunity to design interfering molecules that target MED24 isoform specific complex. Therapeutic peptide TRAP100 P05 likely interacts with a "tail" complex structure that is composed of MED16, MED23, MED24 and MED25.

Based on these potential interactions, we have designed a small library of peptides that interact with a cancer specific mediator complex "tail" unit containing cancer specific isoform of MED24/TRAP100. Screening of these libraries has identified a peptide that affects growth and apoptosis of melanoma cells. This peptide does not have a sequence of MED24 isoform and was found to affect transcription via binding to altered structure of "tail" subunit of MED complex.

Chromatin Modifying Complex

Chromatin modifying complex consists of a large number of SWI/SNF/SMARC/BAF proteins, histone acetylases (HAT) and histone deacetylases (HDAC). BAF 57, a specific member of BAF complex and it interacts directly with BAF155, BAF170, steroid hormone receptor co-activators and several HDAC proteins, BAF57 melanoma specific isoform modifies structure and function of a chromatin modifying complex. We have used modeling tools to predict changes in the structure and interactions of chromatin modifying complex containing isoform of BAF571. Based on this information, we have designed a peptide library and screening of this library resulted in the identification of peptides that affect growth and apoptosis of melanoma cells. Specifically, therapeutic peptide which we denoted as BAF57 P12 likely interacts with a chromatin modifying complex subunit that contains BAF155, BAF170 and one or more different HDAC molecules.

Definitions

All scientific and technical terms used in this application have meanings commonly used in the art unless otherwise specified. As used in this application, the following words or phrases have the meanings specified.

As used herein, "peptide" or "polypeptide" includes fragments of proteins, and peptides, whether isolated from natural sources, produced by recombinant techniques or chemically synthesized. Polypeptides (and peptides) of the invention typically comprise at least about 6 amino acids.

As used herein, "CSTC-targeting molecule" includes CSTC-targeting peptides, polynucleotides encoding CSTC-targeting peptides, polynucleotides complementary to those encoding CSTC-targeting peptides, antibodies that specifically recognize and bind CSTCs, and other small molecules exhibiting the same targeting activity.

A "small molecule" means a molecule having a molecular weight of less than 2000 daltons, in some embodiments less than 1000 daltons, and in still other embodiments less than 500 daltons or less. Such molecules include, for example, heterocyclic compounds, carboxylic compounds, sterols, amino acids, lipids, and nucleic acids.

As used herein, "CSTC-targeting" refers to the specific binding of a CSTC-targeting molecule to a cancer-specific transcription complex, wherein the specificity is such that the CSTC-targeting molecule essentially does not bind normal or native transcription complex.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "tumor protein" is a protein that is expressed by tumor cells. A tumor protein is tumor specific if it is not expressed in non-tumor cells.

As used herein, "pharmaceutically acceptable carrier" includes any material which, when combined with an active ingredient, allows the ingredient to retain biological activity and is non-reactive with the subjects immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein. "a" or "an" means at least one, unless clearly indicated otherwise CSTC-Targeting Peptides CSTC-targeting peptides and polypeptides as described herein may be of any length. Additional sequences derived from the native protein and/or heterologous sequences may be present, and such sequences retain the ability to modulate transcription complex. Preferred peptides comprise the amino acid sequence PQMQQNVFQYPGAGMVP QGEANF (SEQ ID NO: 1) or NDRLSDGDSKYSQTSH-KLVQLL (SEQ ID NO: 2), peptides that interfere with function of CSTCs containing cancer-specific isoforms of TRAP100 P05 and BAF57, respectively. In a typical embodiment, the peptide further comprises additional sequence selected to facilitate delivery into cells and into nuclei. For example, a cell penetrating peptide (CPP) can be added, such as the following amino acid sequence: RRRRRRR (SEQ ID NO: 3). Those skilled in the art are aware of other CPPs that can be suitable for use with the invention, such as those described in Ulo Langel, ed., *Cell-Penetrating Peptides: Processes and Applications*, Culinary & Hospitality Industry Publications Services (CHIPS), Weimar, Tex., 2002. An example of a peptide that facilitates nuclear delivery is a nuclear localizing signal (NLS). Typically, this signal consists of a few short sequences of positively charged lysines or arginines, such as PPKKRKV (SEQ ID NO: 9). In one embodiment, the NLS has the amino acid sequence PKKRKV (SEQ ID NO: 4). A peptide of the invention is exemplified by the peptide having the amino acid sequence of PKKRKVRRRRRRRPQMQQNVFQ YPGAGM-VPQGEANF (TRAP100 P05; SEQ ID NO: 5) or PKKRKVRRRRRRR NDRLSDGDSKYSQTSHKLVQLL (BAF57 P12; SEQ ID NO: 6).

Those skilled in the art will appreciate that certain variants thereof will be useful in the treatment and detection of cancer. A peptide "variant," as used herein, is a peptide that differs from a native CSTC-targeting peptide in one or more substitutions, deletions, additions and/or insertions, such that the transcription complex targeting activity of the peptide is not substantially diminished. In other words, the ability of a variant to bind the transcription complex may be enhanced or unchanged, relative to the native peptide, or may be diminished by less than 50%, and preferably less than 20%, relative to the native peptide. Such variants may generally be identified by modifying one of the above peptide sequences and evaluating the binding of the modified peptide with the targeted transcription complex as described herein. Peptide variants preferably exhibit at least about 70%, more preferably at least about 90% and most preferably at least about 95% identity (determined as described above) to the identified peptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine, and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant peptides differ from a native sequence by substitution, deletion or addition of five amino acids or fewer.

Specifically, amino acid residues of the peptides of the invention can be varied as follows:

```
Variant Residues for MED24 P05
                                        (SEQ ID NO: 7)
PQ(N)MQ(N)Q(N)N(Q)VFQ(N)YPG(A)A(G)G(A)MV(L)PQ(N)GE
(D)A(G)N(Q)F;

Variant Residues for BAF57 P12
                                        (SEQ ID NO: 8)
ND(E)R(K)L(V)SD(E)GD(E)SK(R)YSQ(N)TSHK(R)L(V)V(L)Q
L(V)L(V);
``` wherein each indicated native residue that is followed by an alternative in parentheses can optionally be substituted with that alternative residue. One or more of the indicated alternatives can be employed in a given variant peptide. Such variant peptides are referred to herein as "conservatively modified variants".

Recombinant peptides encoded by DNA sequences as described herein may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant peptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or peptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant peptide.

Portions and other variants having fewer than about 100 amino acids and generally fewer than about 50 amino acids, may also be generated by synthetic means, using techniques well known to those of ordinary skill in the art. For example, such peptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of peptides is commercially available from suppliers such as Perkin Elmer/Applied BioSystems Division (Foster City, Calif.), and may be operated according to the manufacturer's instructions.

Peptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation: binding to an immobilized surface, or labeling of the peptide. Cleavage of the peptides from the solid support may be carried out using the following cleavage mixture, trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

In general, peptides (including fusion proteins) and polynucleotides as described herein are isolated. An "isolated" peptide or polynucleotide is one that is removed from its original environment. For example, a naturally occurring protein is isolated if it is separated from some or all of the coexisting materials in the natural system. Preferably, such peptides are at least about 90% pure, more preferably at least about 95% pure and most preferably at least about 99% pure. A polynucleotide is considered to be isolated if for example, it is cloned into a vector that is not a part of the natural environment.

Polynucleotides of the Invention

The invention provides polynucleotides that encode one or more CSTC-targeting peptides, as described above. Preferred polynucleotides comprise at least 15 consecutive nucleotides: preferably at least 30 consecutive nucleotides and more preferably 35 consecutive nucleotides, that encode a CSTC-targeting peptide. Polynucleotides that are fully complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules: which do not contain introns. Additional coding or non-coding sequences may, but need not, be present within a polynucleotide of the present invention, and a polynucleotide may, but need not, be linked to other molecules and/or support materials. Portions of such CSTC-targeting polynucleotides can be useful as primers and probes for the amplification and detection of CSTC-targeting molecules.

Polynucleotides may comprise a native sequence (i.e., a sequence that encodes a CSTC-targeting peptide as described above or a portion thereof) or may comprise a variant of such a sequence. Polynucleotide variants contain one or more substitutions, additions, deletions and/or insertions such that the specific CSTC binding of the encoded peptide is not diminished, relative to a native peptide. Variants preferably exhibit at least about 70% identity, more preferably at least about 80% identity and most preferably at least about 90% identity to a polynucleotide sequence that encodes a native CSTC-targeting peptide or a portion thereof.

Two polynucleotide or peptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. C. and Sharp, P. M. (1989) CABIOS S.151-153; Myers, E .W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or peptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1%, sodium dodecyl sulfate at 50° C.; (2) employ during hybridization a denaturing agent, such as formamide, for example: 50% (v/v)

formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a peptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art, including, for example, oligonucleotide synthesis. Libraries can be screened with probes designed to identify the gene of interest or the peptide encoded by it. Screening the cDNA or other library with the selected probe may be conducted using standard procedures, such as those described in Sambrook et al., *Molecular Cloning: A Laboratory Manual* (New York: Cold Spring Harbor Laboratory Press, 1989).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a CSTC-targeting peptide, or portion thereof, provided that the DNA is incorporated into a vector with a suitable RNA polymerase promoter (such as T7 or SP6). Certain portions may be used to prepare an encoded peptide, as described herein. In addition, or alternatively, a portion may be administered to a patient such that the encoded peptide is generated in vivo (e.g., by transfecting antigen-presenting cells, such as dendritic cells, with a cDNA construct encoding a CSTC-targeting peptide, and administering the transfected cells to the patient).

Any polynucleotide may be further modified to increase stability in vivo. Possible modifications include, but are not limited to, the addition of flanking sequences at the 5' and/or 3' ends, the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. Some embodiments of the peptides of the invention have been described herein with a cell penetrating peptide (CPP) incorporated into the peptide for facilitation of entry into a cell.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antisense and Inhibitory Nucleic Acid Molecules

The antisense molecules of the present invention comprise a sequence substantially complementary, or preferably fully complementary, to all or a fragment of a nucleic acid molecule that encodes a CSTC-targeting peptide and/or a cancer-specific isoform of a transcription modulator as described herein. Included are fragments of oligonucleotides within a coding sequence, and inhibitory nucleotides that inhibit the expression of CSTCs and/or cancer-specific isoforms of transcription modulators. Antisense oligonucleotides of DNA or RNA complementary to sequences at the boundary between introns and exons can be employed to prevent the maturation of newly-generated nuclear RNA transcripts of specific genes into mRNA for transcription. Antisense RNA, including siRNA, complementary to specific genes can hybridize with the mRNA for that gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds. Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures include, but are not limited to, U.S. Pat. Nos.: 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990. Formation of the triple helix would interrupt the ability of the specific gene to undergo transcription by RNA polymerase. Triple helix formation using myc-specific oligonucleotides has been observed. See: Cooney, M, et al. Science 241:456-459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in, Antisense Research and Applications, Crooke, S. and B. Lebleu, eds. CRC Press, Inc. Boca Raton Fla. 1993, Nucleic Acids in Chemistry and Biology Blackburn, G. and M. J. Gait, eds. IRL Press at Oxford University Press, Inc. New York 1990; and Oligonucleotides and Analogues; A Practical Approach Eckstein, F. ed. IRL Press at Oxford University Press, Inc. New York 1991, which are each hereby incorporated herein by reference including all references cited therein which are hereby incorporated herein by reference.

Pharmaceutical Compositions and Vaccines

The invention provides CSTC-targeting peptides, cancer-specific isoforms of transcription modulators, polynucleotides, T cells and/or antigen presenting cells that are incorporated into pharmaceutical compositions Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition can contain DNA encoding one or more of the peptides as described above, such that the peptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci, USA 86:317-321, 1989; Flexner et al., Ann. N.Y. Aced Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-

434, 1991; Kolls et al., Proc. Natl. Acad. Sci. USA 91:215-219, 1994; Kass-Eisler et al., Proc. Natl Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993.

The uptake of naked DNA may be increased by coating the DNA onto biodegradable beads. which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the delivered molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortedella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines: see Mosmann and Coffman, Ann. Rev. Immunol. 7:145-173, 1989.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a peptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as peptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumorinfiltrating lymphocytes), killer cells (such as Natural Killer cells and lymphokine-activated killer cells). B cells and antigen-presenting cells (such as dendritic cells and macrophages) expressing a peptide provided herein. In a preferred embodiment, dendritic cells are modified in vitro to present the peptide, and these modified ARCs are administered to the subject. T cell receptors and antibody receptors specific for the peptides recited herein may be cloned, expressed and transferred into other vectors or effector cells for adoptive immunotherapy. The peptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to alleviate, reduce, cure or at least partially arrest symptoms and/or complications from the disease and/or to elicit an effective immune response to the specific antigens. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intraperitoneal, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart. In another embodiment, a dose is administered daily or once every 2 or 3 days over an extended period, such as weeks or months.

A suitable dose is an amount of a compound that, when administered as described above, is capable of promoting an anti-tumor response, and is at least 10-50% above the basal (i.e., untreated) level. Such response can be monitored, for example, by measuring reduction in tumor size or the level of anti-tumor antibodies in a patient or by vaccine-dependent generation of cytolytic effector cells capable of killing the patient's tumor cells in vitro. Such therapies should also be capable of causing a response that leads to an improved clinical outcome (e.g., more frequent remissions, complete or partial or longer disease-free survival) in patients as compared to untreated patients. In general, for pharmaceutical compositions and vaccines comprising one or more peptides, the amount of each peptide present in a dose ranges from about 100 µg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Diagnostic Methods

The invention provides a method for detecting cancer in a tissue comprising contacting the tissue with a molecule that recognizes and binds a CSTC or cancer-specific isoform of a transcription modulator described herein. The molecule can be, for example, a CSTC-targeting peptide, an antibody directed against a CSTC or cancer-specific isoform of a transcription modulator, or an oligonucleotide probe or antisense molecule directed against a cancer-specific molecule. The tissue can be from a mammal, such as human, bovine, equine, canine, feline, porcine, and ovine tissue. The tissue is preferably a human. The tissue can comprise a tumor specimen, cerebrospinal fluid, or other suitable specimen. In one embodiment, the method comprises use of an ELISA type assay. Those skilled in the art will appreciate additional variations suitable for the method of detecting cancer in tissue through detection of a cancer-specific molecule in a specimen. This method can also be used to monitor levels of the cancer-specific molecule in tissue of a patent undergoing treatment for cancer. The suitability of a CSTC-targeted therapeutic regimen for initial or continued treatment can be determined by monitoring such levels using this method.

The invention additionally provides a method for identifying a molecule that inhibits proliferation of cancer cells. The method comprises contacting a candidate molecule with a CSTC and determining whether the candidate molecule disrupts the biological activity of the CSTC. Disruption of the biological activity of the CSTC is indicative of a molecule that inhibits proliferation of cancer cells. Representative molecules include antibodies, proteins, peptides and nucleotides.

Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for a cancer-specific molecule of the invention. The kit can also include containers containing nucleotide(s) for amplification of a target nucleic acid sequence and/or a container comprising a reporter-means, such as a biotin-binding protein, e.g., avidin or streptavidin, bound to a detectable label, e.g., an enzymatic, florescent, or radioisotope label. The kit can include all or part of an amino acid sequence of the sequences described herein, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Identification of Isoforms of Transcriptional Co-Regulators

This example demonstrates the results of an extensive in silico analysis of components of transcriptional co-regulators and use of PCR primers designed to identify novel isoforms with altered activity.

MATERIAL & METHODS

Primary Tumors

Surgical specimens were obtained from human patients undergoing surgery for melanoma. Specimens were trypsinized and prepared for analysis using conventional techniques. RNA isolation was performed as described below.

Cell Culture

Human melanoma cell lines SK-MEL-28 and WM-266-4 were obtained from the American Type Culture Collection (ATCC; Manassas, Va.; SK-MEL-28 deposited by T. Takehashi and subject to release terms set by The Memorial Sloan-Kettering Cancer Center; WM-266-4 deposited by M. Herlyn). Cells were cultured according to recommendations of ATCC (DMEM, 10% FCS, penicillin+streptomycin) and used in experiments after two passages in the laboratory. Cells were grown in 24 well plates, each treatment in triplicates. Cells were plated 16 hours prior treatments started. Peptides were added to the media, and media was changed every day during 7 day experiment. CPP concentration was 10 µM.

For cell counting, cells were trypsinized (0.25% Trypsin, 2 mM EDTA) in Ca+2, Mg+2 free PBS. Cells were precipitated and resuspended in 100 µl of PBS, and 5 µl were removed for counting Apoptosis was analyzed using Biovision Annexin V-Cy3 Apoptosis Kit according to manufacturer's protocols.

Identification of Isoforms of Transcriptional Co-Regulators in Melanoma Cells

RNA was isolated from human melanoma cell lines SK-MEL-28 and WM 266-4 and primary tumors using RNA isolation KIT (Qiagen). RT-PCR was used to identify isoforms of co-regulators. Primers used to analyze isoforms are presented in Table 1.

First strand cDNAs were synthesized with reverse transcriptase (SuperscriptII, Life Technologies Inc.) using 5-10 µg of mRNA from different cell lines as a template. PCR reactions were performed in the volume of 25 µl containing one tenth of RT reaction as a template and GC-Rich PCR System or the Expand™. Long Distance PCR System kit (Roche) according to manufacturer's instructions. All amplified PCR products were sequenced and sequences analyzed to identify novel functional isoforms of transcriptional co-regulators.

TABLE 1

Oligonucleotide primers used to isolate and characterize isoforms of transcriptional co-regulators in human melanoma cells.

1. GTF2H1 (NM 005316) (GTF = general transcription factor)
Product amplified with primers: ACTTCCTGTCTAGAGTTGTAGC (S; SEQ ID NO: 14) and GTAAGTCAGCIATACTAAGTTCTG (AS3; SEQ ID NO: 15)
67 aa: shorter protein (different sequence after 52 aa)

MATSSEEVLLIVKKVRQKKQDGALYLMAERIAWAPEGKDPFTISHMYADIKCKSAILSSDVFVCHSC*
(SEQ ID NO: 16)

Alignment with P32780 (548 aa; SEQ ID NO: 16 and 17)

```
  1  MATSSEEVLLIVKKVRQKKQDGALYLMAERIAWAPEGKDRFTISHMYADIKCQKISPEGK
     ||||||||||||||||||||||||||||||||||||||||||||||||||.
  1  MATSSEEVLLIVKKVRQKKQDGALYLMAERIAWAPEGKDRFTISHMYADIKCKSAILSSD

61  AKIQLQLVLHAGDTTNFHFSNESTAVKERDAVKDLLQQLLPKFKRKANKELEEKNRMLQE
     :
 61  VFVCHSC.....................................................

121  DPVLFQLYKDLVVSQVISAEEFWANRLNVNATDSSSTSNHKQDVGISAAFLADVRPQTDG

68  ............................................................

181  CNGLRYNLTSDIIESIFRTYPAVKMKYAENVPHNMTEKEFWTRFFQSHYFHRDRLNTGSK

68  ............................................................

241  DLFAECAKIDEKGLKTMVSLGVKNPLLDLTALEDKPLDEGYGISSVPSASNSKSIKENSN

68  ............................................................

301  AAIIKRFNHHSAMVLAAGLRKQEAQNEQTSEPSNMDGNSGDADCFQPAVKRAKLQESIEY

68  ............................................................
```

TABLE 1-continued

Oligonucleotide primers used to isolate and characterize isoforms of transcriptional co-regulators in human melanoma cells.

```
361  EDLGKNNSVKTIALNLKKSDRYYBGPTPIQSLQYATSQDIINSFQSIRQSMEAYTPKLTQ

68  ...........................................................

421  VLSSSAASSTITALSPGGALMQGGTQQAINQMVPNDIQSELKHLYVAVGELLRHFWSCFP

68  ...........................................................

481  VNTPFLEEKVVKMKSNLERFQVTKLCPFQEKIRRQYLSTNLVSHIEEMLQTAYNKLHTWQ

68  ...........................................................

541  SRRLMKKT

68  ........
```

2. GTF2H2 (NM_001515)
1. Product amplified with primers TTTCCGGCTRGAGAGTCCTTC (S1; SEQ ID
NO: 18) and CACATCACTTCAGCTTAACTC (AS1; SEQ ID NO: 19)
165 aa: 230 aa shorter C-term, different 8 aa of C-term;

MDEEPERTKRWEGGYERTWEILKEDESGSLKATIEDILFKAKRKRVFEHHGQVRLGMMRHLYVVVDGSRT
MEDQDLKFNRLTCTLKLLEYFVEEYFDQNPISQIGIIVTKSKRAEKLTELSGNPRKHITSLKKAVDMTCH
GEPSLYNSLSIAMQTLKLVLYIMYN\* (SEQ ID NO: 20)

Alignment with Q13888 (395 aa; SEQ ID NO: 20 and 21):

```
  1  MDEEPERTKRWEGGYERTWEILKEDESGSLKATIEDILFKAKRKRVFEHHGQVRLGMMRH
     |||||||||||||||||||||||||||||||||||||||||||||||||||||||||||
  1  MDEEPERTKRWEGGYERTWEILKEDESGSLKATIEDILFKAKRKRVFEHHGQVRLGMMRH

61  LYVVVDGSRTMEDQDLKPNRLTCTLKLLEYFVEEYFDQNPISQIGIIVTKSKRAEKLTEL
     |||||||||||||||||||||||||||||||||||||||||||||||||||||||||||
 61  LYVVVDGSRTMEDQDLKPNRLTCTLKLLEYFVEEYFDQNPISQIGIIVTKSKRAEKLTEL

121  SGNPRKHITSLKKAVDMTCHGEPSLYNSLSIAMQTLKLVLYIMYN...............
     ||||||||||||||||||||||||||||||||||||||    .
121  SGNPRKHITSLKKAVDMTCHGEPSLYNSLSIAMQTLKHMPGHTSREVLIIFSSLTTCDPS

166  ...........................................................

181  NIYDLIKTLKAAKIRVSVIGLSAEVRVCTVLARETGGTYHVILDESHYKELLTHHVSPPP

166  ...........................................................

241  ASSSSECSLIRMGFPQHTIASLSDQDAKPSFSMAHLDGNTEPGLTLGGYFCPQCRAKYCE

166  ...........................................................

301  LPVECKICGLTLVSAPHLARSYHHLFPLDAFQEIPLEEYNGERFCYGCQGELKDQHVYVC

166  ...........................................................

361  AVCQNVRCVDCDVFVHDSLHCCPGCIHKIPAPSGV
```

2. Product amplified with primers AGGATGTGAAGGAGCTTGTGAAG (S2; SEQ ID
NO: 22) and CAAGTACAGTGOAARCGCGAAC (AS5; SEQ ID NO: 23)
338 aa: 57 aa shorter N-terminus (or NMD?), same as 5G82327

MRHLYVVVDGSRTMEDQDLKPNRLTCTLKLLEYFVEEYFDQNPISQIGIIVTKSKRAEKLTELSGNPRKH
ITSLKKAVDMTCHGEPSLYNSLSIAMQTLKHMPGHTSREVLIIFSSLTTCDPSNIYDLIKTLKAAKIRVS
VIGLSAEVRVCTVL... (SEQ ID NO: 24)

Alignment with q13888 (395 aa; SEQ ID NO: 24 and 25):

```
  1  MDEEPERTKRWEGGYERTWEILKEDESGSLKATIEDILFKAKRKRVFEHHGQVRLGMMRH
                                                              |||
  1  .........................................................MRH

61  LYVVVDGSRTMEDQDLKPNRLTCTLKLLEYFVEEYFDQNPISQIGIIVTKSKRAEKLTEL
     |||||||||||||||||||||||||||||||||||||||||||||||||||||||||||
  4  LYVVVDGSRTMEDQDLKPNRLTCTLKLLEYFVEEYFDQNPISQIGIIVTKSKRAEKLTEL
```

TABLE 1-continued

Oligonucleotide primers used to isolate and characterize isoforms of transcriptional co-regulators in human melanoma cells.

```
121 SGNPRKHITSLKKAVDMTCHGEPSLYNSLSIAMQTLKHMPGHTSREVLIIFSSLTTCDPS
    ||||||||||||||||||||||||||||||||||||||||||||||||||||||||||||
 64 SGNPRKHITSLKKAVDMTCHGEPSLYNSLSIAMQTLKHMPGHTSREVLIIFSSLTTCDPS

181 NIYDLIKTLKAAKIRVSVIGLSAEVRVCTVLARETGGTYHVILDESHYKELLTHHVSPPP
    |||||||||||||||||||||||||||||||
124 NIYDLIKTLKAAKIRVSVIGLSAEVRVCTVL.............................
```

3. GTF2H3 (NM_001516)
1. Product amplified with primers GACAGCCATGGTTTCAGACG (S1; SEQ ID NO: 26) and CAGAAACTTTGCTGGCAGGAT (AS1; SEQ ID NO: 27)
267 aa: 41aa shorter N-term, MVLGNSHLFMNRSNKLAVIASHIQESRFLYPGKNGRLGDFFGDPGNPPEFNPSGSKDGKYELLTSANEVI
VEEIKDLMTKSDIKGQHTETLLAGSLAKALCYIHRMNKEVKDNQEMKSRILVIKAAEDSALQYMNFMNVI
FAAQKQNILIDACVLDSDSGLLQQACDITGGLYLKVPQMPSLLQYLLWVFLPDQDQRSQLILPPPVHVDY
RAACFCHRNLIEIGYVCSVCLSIFCNFSPICTTCETAFKISLPPVLKAKKKKLKVSA* (SEQ ID NO: 28)

Alignment with Q13889 (308 aa: SEQ ID NO: 28 and 29):

```
 20 ASHIQESRFLYPGKNGRLGDFFGDPGNPPEFNPSGSKDGKYELLTSANEVIVEEIKDLMT
    ||||||||||||||||||||||||||||||||||||||||||||||||||||||||||||
 61 ASHIQESRFLYPGKNGRLGDFFGDPGNPPEFNPSGSKDGKYELLTSANEVIVEEIKDLMT

80 KSDIKGQHTETLLAGSLAKALCYIHRMNKEVKDNQEMKSRILVIKAAEDSALQYMNFMNV
    ||||||||||||||||||||||||||||||||||||||||||||||||||||||||||||
121 KSDIKGQHTETLLAGSLAKALCYIHRMNKEVKDNQEMKSRILVIKAAEDSALQYMNFMNV

140 IFAAQKQNILIDACVLDSDSGLLQQACDITGGLYLKVPQMPSLLQYLLWVFLPDQDQRSQ
    ||||||||||||||||||||||||||||||||||||||||||||||||||||||||||||
181 IFAAQKQNILIDACVLDSDSGLLQQACDITGGLYLKVPQMPSLLQYLLWVFLPDQDQRSQ

200 LILPPPVHVDYRAACFCHRNLIEIGYVCSVCLSIFCNFSPICTTCETAFKISLPPVLKAK
    ||||||||||||||||||||||||||||||||||||||||||||||||||||||||||||
241 LILPPPVHVDYRAACFCHRNLIEIGYVCSVCLSIFCNFSPICTTCETAFKISLPPVLKAK

260 KKKLKVSA
    ||||||||
301 KKKLKVSA
```

2 Products amplified with primers GACAGCCATGGTTTCAGACG (S1; SEQ ID NO: 30) and CGTGGTGAAAACATGGTGAAAC (AS3; SEQ ID NO: 31)
a) 43 aa: shorter protein, new product (Δ3-13, different last exon)
Alignment with Q13889 (308 aa; SEQ ID NO: 29):

```
  1 MVSDEDELNLLVIVVDANPIWWGKQALKESQFTLSKCIDAVMILGNSHLFMNRSNKLAVI
    |||||||||||||||||||||||||||||
  1 MVSDEDELNLLVIVVDANPIQQGKQALKESQPPK

61 ASHIQESRFLYPGKNGRLGDFFGDPGNPPEFNPSGSKDGKYELLTSANEVIVEEIKDLMT

35 ............................................................

121 KSDIKGQHTETLLAGSLAKALCYIHRMNKEVKDNQEMKSRILVIKAAEDSALQYMNFMNV

35 ............................................................

181 IFAAQKQNILIDACVLDSDSGLLQQACDITGGLYLKVPQMPSLLQYLLWVFLPDQDQRSQ

35 ............................................................

241 LILPPPVHVDYRAACFCHRNLIEIGYVCSVCLSIFCNFSPICTTCETAFKISLPPVLKAK

35 ............................................................

301 KKKLKVSA

35 ........
```

TABLE 1-continued

Oligonucleotide primers used to isolate and characterize isoforms of transcriptional co-regulators in human melanoma cells.

b) 120 aa; shorter protein, different sequency after 108 aa, new protein (Δ(4)-13, different last exon)

MVSDEDELNLLVIVVDANPTWWGKQALKESQFTLSKCIDAVMVLGNSHLFMNRSNKLAVIASHIQESRFL
YPGKNGRLGDFFGDPGNPPEFNPSGSKDGKYELLTSASQVAGITTLLNP\* (SEQ ID NO: 33)

Alignment with Q13889 (308 aa; SEQ ID NO: 29):

```
  1 MVSDEDELNLLVIVVDANPIWWGKQALKESQFTLSKCIDAVMVLGNSHLFMNRSNKLAVI
    ||||||||||||||||||| ||||||||||||||||||||||||||||||||||||||
  1 MVSDEDELNLLVIVVDANPTWWGKQALKESQFTLSKCIDAVMVLGNSHLFMNRSNKLAVI

61 ASHIQESRFLYPGKNGRLGDFFGDPGNPPEFNPSGSKDGKYELLTSANEVIVEEIKDLMT
    |||||||||||||||||||||||||||||||||||||||||||||||..:|
 61 ASHIQESRFLYPGKNGRLGDFFGDPGNPPEFNPSGSKDGKYELLTSASQVAGITTLLNP.

121 KSDIKGQHTETLLAGSLAKALCYIHRMNKEVKDNQEMKSRILVIKAAEDSALQYMNFMNV
120 ............................................................

181 IFAAQKQNILIDACVLDSDSGLLQQACDITGGLYLKVPQMPSLLQYLLWVFLPDQDQRSQ
120 ............................................................

241 LILPPPVHVDYRAACFCHRNLIEIGYVCSVCLSIFCNFSPICTTCETAFKISLPPVLKAK
120 ............................................................

301 KKKLKVSA
120 ........
``` c) 110 aa: shorter protein, different C-term beginning with 74aa,

MVSDEDELNLLVIVVDANPIWWGKQALKESQFTLSKCIDAVMVLGNSHLFMNRSNKLAVIASHIQESRFL
YPGFTPFSCLSLPSSWDYYSTEPMRQKFETILPNVVKTW\* (SEQ ID NO: 34)

Alignment with Q13889 (308 aa; SEQ ID NO: 29):

```
  1 MVSDEDELNLLVIVVDANPIWWGKQALKESQFTLSKCIDAVMVLGNSHLFMNRSNKLAVI
    ||||||||||||||||||||||||||||||||||||||||||||||||||||||||||||
  1 MVSDEDELNLLVIVVDANPIWWGKQALKESQFTLSKCIDAVMVLGNSHLFMNRSNKLAVI

61 ASHIQESRFLYPGFTPFSCLSLPSSWDYYSTEPMRQKFETILPNVVKTW...........
    |||||||||||||       .   |  |
 61 ASHIQESRFLYPGKNGRLGDFFGDPGNPPEFNPSGSKDGKYELLTSANEVIVEEIKDLMT

110 ............................................................

121 KSDIKGQHTETLLAGSLAKALCYIHRMNKEVKDNQEMKSRILVIKAAEDSALQYMNFMNV
110 ............................................................

181 IFAAQKQNILIDACVLDSDSGLLQQACDITGGLYLKVPQMPSLLQYLLWVFLPDQDQRSQ
110 ............................................................

241 LILPPPVHVDYRAACFCHRNLIEIGYVCSVCLSIFCNFSPICTTCETAFKISLPPVLKAK
110 ............................................................

301 KKKLKVSA
110 ........
``` d) 297 aa: different C-terminus (16 aa), (shorter exon 13, extra exon after exon 13)

...MVLGNSHLFMNRSNKLAVIASHIQESRFLYPGKNGRLGDFFGDPGNPPEFNPSGSKDGKYELLTSANEV
IVEEIKDLMTKSDIKGQHTETLLAGSLAKALCYIHRMNKEVKDNQEMKSRILVIKAAEDSALQYMNFMNV
IFAAQKQNILIDACVLDSDSGLLQQACDITGGLYLKVPQMPSLLQYLLWVFLPDQDQRSQLILPPPVHVD
YRAACFCHRNLIEIGYVCSVCLSIFCNFSPICTTCETAFKISQPPK\* (SEQ ID NO: 35)

Alignment with Q13889 (308 aa; SEQ ID NO: 29):

```
  1 MVSDEDELNLLVIVVDANPIWWGKQALKESPFTLSAKCIDAVMVLGNSHLFMNRSNKLAVI
                                         ||||||||||||||||||||
  1 ........................................MVLGNSHLFMNRSNKLAVI
```

TABLE 1-continued

Oligonucleotide primers used to isolate and characterize isoforms of
transcriptional co-regulators in human melanoma cells.

```
 61  ASHIQESRFLYPGKNGRLGDFFGDPGNPPEFNPSGSKDGKYELLTSANEVIVEEIKDLMT
     ||||||||||||||||||||||||||||||||||||||||||||||||||||||||||||
 20  ASHIQESRFLYPGKNGRLGDFFGDPGNPPEFNPSGSKDGKYELLTSANEVIVEEIKDLMT

121  KSDIKGQHTETLLAGSLAKALCYIHRMNKEVKDNQEMKSRILVIKAAEDSALQYMNFMNV
     ||||||||||||||||||||||||||||||||||||||||||||||||||||||||||||
 80  KSDIKGQHTETLLAGSLAKALCYIHRMNKEVKDNQEMKSRILVIKAAEDSALQYMNFMNV

181  IFAAQKQNILIDACVLDSDSGLLQQACDITGGLYLKVPQMPSLLQYLLWVFLPDQDQRSQ
     ||||||||||||||||||||||||||||||||||||||||||||||||||||||||||||
140  IFAAQKQNILIDACVLDSDSGLLQQACDITGGLYLKVPQMPSLLQYLLWVFLPDQDQRSQ

241  LILPPPVHVDYRAACFCHRNLIEIGYVCSVCLSIFCNFSPICTTCETAFKISLPPVLKAK
     |||||||||||||||||||||||||||||||||||||||||||||||||||||| ||
200  LILPPPVHVDYRAACFCHRNLIEIGYVCSVCLSIFCNFSPICTTCETAFKISQPPK....

301  KKKLKVSA

256  ........
```

4. GTF2H (PC016302)
I. Product amplified with GAGACTTTGGOTCCGATTAAG (S1; SEQ ID NO: 36)
and GAAGTGCTCCAAGGAACAGC (AS1; SEQ ID NO: 37)
81 aa: shorter protein, MESTPSRGLNRVHLQCRNLQEFLGGLSPGVLDRLYGHPATCLAVFRELPSLAKNWVMRMLFLEQPLPQAA
VALWVKKEFSK* (SEQ ID NO: 38)

Alignment with Q92759 (462 aa; SEQ ID NO: 39):

```
  1  MESTPSRGLNRVHLQCRNLQEFLGGLSPGVLDRLYGHPATCLAVFRELPSLAKNWVMRML
     ||||||||||||||||||||||||||||||||||||||||||||||||||||||||||||
  1  MESTPSRGLNRVHLQCRNLQEFLGGLSPGVLDRLYGHPATCLAVFRELPSLAKNWVMRML

61  FLEQPLPQAAVALWVKKEFSKAQEESTGLLSGLRIWHTQLLPGGLQGLILNPIFRQNLRI
     ||||||||||||||||||||
 61  FLEQPLPQAAVALWVKKEFSK.......................................

121  ALLGGGKAWSODTSQLGPDKHARDVPSLDKYASERWEVVLETMVGSPSAAVSQDLAQLLS

82  ............................................................

181  QAGLMKSTEPGEPPCITSAGFQFLLLDTPAQLWYFMLQYLQTAQSRGMDLVEILSFLFQL

82  ............................................................

241  SFSTLGKDYSVEGMSDSLLNFLQHLREFGLVFQRKRKSRRYYPTRLAINLSSGVSGAGGT

82  ............................................................

301  VHQPGFIVVETNYRLYAYTESELQIALIALFSEMLYRFPNMVVAQVTRESVQQAIASGIT

82  ............................................................

361  AQQIIHFLRTRAHPVMLKQRPVLPPTITDQIRLWELERDRLRFTEGVLYNQFLSQVDFEL

82  ............................................................

421  LLAHARELGVLVFENSAKRLMVVTPAGHSDVKRFWKRQKHSS

82  .........................................
```

2. Product amplified with GAGACTTTGGCTCCGATTAAG (S1; SEQ ID NO: 40)
and TGAGCGAGCATCCGCATCA (AS1; SEQ ID NO: 41)
442 aa : internal 20 aa missing (61-82 aa; SEQ ID NO: 42), MESTPSRGLNRVHLQCRNLQEFLGGLSPGVLDRLYGHPATCLAVFRELPSLAKNWVMRMLAQEESTGLLS
GLRIWHTQLLPGGLQGLILNPIFRQNLRIALLGGGKAWSDDTSQLGPDKHARDVPSLDKYAEERWEVVLH
FMVGSPSAAVSQDLAQLLSQAGLMKSTEPGEPPCITSAGFQFLLLDTPAQLWYFMLQYLQTAQSRGMDLV
EILSFLFQLSFSTLGKDYSVEGMSDSLLNFLQHLREFGLVFQRKRKSRRYYPTRLAINLSSGVSGAGGTV
HQPGFIVVETNYRLYAYTESELQIALIALFSEMLYRFPNMVVAQVTRESVQQAIASGITAQQIIHFLRTR
AHPVMLKQTPVLPPTITDQIRLWELERDRLRFTEGVLYNQFLSQVDFELLLAHARELGVLVFENSAKRLM
VVTPAGHSDVKRFWKRQKHSS*

TABLE 1-continued

Oligonucleotide primers used to isolate and characterize isoforms of transcriptional co-regulators in human melanoma cells.

Alignment with Q92759 (462 aa; SEQ ID NO: 43):

```
  1 MESTPSRGLNRVHLQCRNLQEFLGGLSPGVLDRLYGHPATCLAVFRELPSLAKNWVMRML
    ||||||||||||||||||||||||||||||||||||||||||||||||||||||||||||
  1 MESTPSRGLNRVHLQCRNLQEFLGGLSPGVLDRLYGHPATCLAVFRELPSLAKNWVMRML

61 FLEQPLPQAAVALWVKKEFSKAQEESTGLLSGLRIWHTQLLPGGLQGLILNPIFRQNLRI
                        ||||||||||||||||||||||||||||||||||||||||
 61 ....................AQEESTGLLSGLRIWHTQLLPGGLQGLILNPIFRQNLRI

121 ALLGGGKAWSDDTSQLGPDKHARDVPSLDKYAEERWEVVLHFMVGSPSAAVSQDLAQLLS
    ||||||||||||||||||||||||||||||||||||||||||||||||||||||||||||
100 ALLGGGKAWSDDTSQLGPDKHARDVPSLDKYAEERWEVVLHFMVGSPSAAVSQDLAQLLS

181 QAGLMKSTEPGEPPCITSAGFQFLLLDTPAQLWYFMLQYLQTAQSRGMDLVEILSFLFQL
    ||||||||||||||||||||||||||||||||||||||||||||||||||||||||||||
160 QAGLMKSTEPGEPPCITSAGFQFLLLDTPAQLWYFMLQYLQTAQSRGMDLVEILSFLFQL

241 SFSTLGKDYSVEGMSDSLLNFLQHLREFGLVFQRKRKSRRYYPTRLAINLSSGVSGAGGT
    ||||||||||||||||||||||||||||||||||||||||||||||||||||||||||||
220 SFSTLGKDYSVEGMSDSLLNFLQHLREFGLVFQRKRKSRRYYPTRLAINLSSGVSGAGGT

301 VHQPGFIVVETNYRLYAYTESELQIALIALFSEMLYRFPNMVVAQVTRESVQQAIASGIT
    ||||||||||||||||||||||||||||||||||||||||||||||||||||||||||||
280 VHQPGFIVVETNYRLYAYTESELQIALIALFSEMLYRFPNMVVAQVTRESVQQAIASGIT

361 AQQIIHFLRTRAHPVMLKQTPVLPPTITDQIRLWELERDRLRFTEGVLYNQFLSQVDFEL
    ||||||||||||||||||||||||||||||||||||||||||||||||||||||||||||
340 AQQIIHFLRTRAHPVMLKQTPVLPPTITDQIRLWELERDRLRFTEGVLYNQFLSQVDFEL

421 LLAHARELGVLVFENSAKRLMVVTPAGHSDVKRWRQKHSS
    ||||||||||||||||||||||||||||||||||||||||
400 LLAHARELGVLVFENSAKRLMVVTPAGHSDVKRWRQKHSS
```

5. ERCC2 (NM_000400)
Product amplified with TGGGGTCATCGGCTCAACGTG (S2; SEQ ID NO: 44) and
TCTTGAGCAGTAGATGAGTTTGG (AS2; SEQ ID NO: 45)
736 aa: 24 aa shorter N-terminus (SEQ ID NO: 46), MRELKRTLDAKGHGVLEMPSGTGKTVSLLALIMAYQRAYPLEVTKLIYCSRTVPEIEKVIEELRKLLNFY
EKQEGEKLPFLGLALSSRKNLCIHPEVTPLRFGKDVDGKCHSLTASYVRAQYQHDTSLPHCRFYEEFDAH
GREVPLPAGIYNLDDLKALGRRQGWCPYFLARYSTLHANVVVYSYHYLLDPKIADLVSKELARKAVVVFD
EAHNIDNVCIDSMSVNLTRRTLDRCQGNLETLQKTVLKIKETDEQRLRDEYRRLVEGLREASAARETDAH
LANPV...

Alignment with P18074 (760 aa; SEQ ID NO: 47):

```
  1 MKLNVDGLLVYFPYDYIYPEQFSYMRELKRTLDAKGHGVLEMPSGTGKTVSLLALIMAYQ
                            ||||||||||||||||||||||||||||||||||||
  1 ........................MRELKRTLDAKGHGVLEMPSGTGKTVSLLALIMAYQ

61 RAYPLEVTKLIYCSRTVPEIEKVIEELRKLLNFYEKQEGEKLPFLGLALSSRKNLCIHPE
    ||||||||||||||||||||||||||||||||||||||||||||||||||||||||||||
 53 RAYPLEVTKLIYCSRTVPEIEKVIEELRKLLNFYEKQEGEKLPFLGLALSSRKNLCIHPE

121 VTPLRFGKDVDGKCHSLTASYVRAQYQHDTSLPHCRFYEEFDAHGREVPLPAGIYNLDDL
    ||||||||||||||||||||||||||||||||||||||||||||||||||||||||||||
113 VTPLRFGKDVDGKCHSLTASYVRAQYQHDTSLPHCRFYEEFDAHGREVPLPAGIYNLDDL

181 KALGRRQGWCPYFLARYSILHANVVVYSYHYLLDPKIADLVSKELARKAVVVFDEAHNID
    ||||||||||||||||||||||||||||||||||||||||||||||||||||||||||||
173 KALGRRQGWCPYFLARYSILHANVVVYSYHYLLDPKIADLVSKELARKAVVVFDEAHNID

241 NVCIDSMSVNLTRRTLDRCQGNLETLQKTVLRIKETDEQRLRDEYRRLVEGLREASAARE
    ||||||||||||||||||||||||||||||||||||||||||||||||||||||||||||
233 NVCIDSMSVNLTRRTLDRCQGNLETLQKTVLRIKETDEQRLRDEYRRLVEGLREASAARE
```

TABLE 1-continued

Oligonucleotide primers used to isolate and characterize isoforms of transcriptional co-regulators in human melanoma cells.

6. MNAT1 (NM_002431)
Product amplifed with GGTCAACATATTTCACTGGCAG (S2; SEQ ID NO: 48) and
TCCATCAGATGAGGCTTATCGT (AS3; SEQ ID NO: 49)
278 aa: 31 aa shorter C-terminus, different sequence after 271 aa;
(shorter exon 8), (SEQ ID NO: 50),

...MQLEKPKPVKPVTFSTGIKMGQHISLAPIHKLEEALYEYQPLQIETYGPHVPELEMLGRLGGFDTISLI\*

Alignment with P51948 (309 aa; SEQ ID NO: 51):

```
121   KMEIYQKENKDVIQKNLKLTREQEELEEALEVERQENEQRRLFIQKEEQLQQILKRKNK

1   ...........................................................

181   QAFLDELESSDLPVALLLAQHKDRSTQLEMQLEKPKPVKPVTFSTGIKMGQHISLAPIHK
                                 ||||||||||||||||||||||||||||||
  1   ..............................MQLEKPKPVKPVTFSTGIKMGQHISLAPIHK

241   LEEALYEYQPLQIETYGPHVPELEMLGRLGYLNHVRAASPQDLAGGYTSSLACHRALQDA
      ||||||||||||||||||||||||||||| . :
 32   LEEALYEYQPLQIETYGPHVPELEMLGRLGGFDTISLI.......................

301   FSGLFWQPS

70   .........
```

7. Cdk7 (NM_001799)
Product amplified with primers CAAGGCCAGAGATAAGAACACC (S; SEQ ID NO: 52) and GTAGGCTTTGATGTGTGATGGT (AS1; SEQ ID NO: 53)
323 aa: internal 23 aa missing (77-100 aa), new product (Δ5), SEQ ID NO: 54

MALDVKSRAKRYEKLDFLGEGQFATVYKARDKNTNQIVAIKKIKLGHRSEAKDGINRTALREIKLLQELS
HPNIIGVIIKDNSLVLTPSHIKAY...

Alignment with P50613 (346 aa; SEQ ID NO: 55):

```
  1   MALDVKSRAKRYEKLDFLGEGQFATVYKARDKNTNQIVAIKKIKLGHRSEAKDGINRTAL
      ||||||||||||||||||||||||||||||||||||||||||||||||||||||||||||
  1   MALDVKSRAKRYEKLDFLGEGQFATVYKARDKNTNQIVAIKKIKLGHRSEAKDGINRTAL

61   REIKLLQELSHPNIIGLLDAFGHKSNISLVFDFMETDLEVIIKDNSLVLTPSHIKAYMLM
      ||||||||||||||||||                   ||||||||||||||||||||||
 61   REIKLLQELSHPNIIG....................VIIKDNSLVLTPSHIKAY...
```

8. CCNH (NM_001239)
Product amplified with primers CTTGGACAGGAGAAGGCAC (S1; SEQ ID NO: 56) and CAGTATAGTCACACCAGAATG (AS2; SEQ ID NO: 57)
329 aa: longer protein, different C-terminus after 312 aa, (intron retention between exons 8 and 9, longer exon 9), (SEQ ID NO: 58), ...MPRSVVGTACMYFKRFYLNNSVMEYHPRIIMLTCAFLACKVDEFNVSSPQFVGNLRESPLGQEKALEQI
LEYELLLIQQLNFHLIVHNPYRPFEGFLIDLKTRYPILENPEILRKTADDFLNRIALTDAYLLYTPSQIA
LTAILSSASRAGITMESYLSESLMLKENRTCLSQLLDIMKSMRNLVKKYEPPRSEEVAVLKQKLERCHSA
ELAILNVITKKRKGYEDDDYVSKKSKHEEVCFTPKMNSKLFLLYILV\*

Alignment with P51946 (323 aa; DEQ ID NO: 59):

```
  1   MYHNSSQKRHWTFSSEEQLARLRADANRKFRCKAVANGKVLPNDPVFLEPHEEMTLCKYY

1   ...........................................................

61   EKRLLEFCSVFKPAMPRSVVGTACMYFKRFYLNNSVMEYHPRIIMLTCAFLACKVDEFNV
                    ||||||||||||||||||||||||||||||||||||||||||||||
  1   ..............MPRSVVGTACMYFKRFYLNNSVMEYHPRIIMLTCAFLACKVDEFNV

121   SSPQFVGNLRESPLGQEKALEQILEYELLLIQQLNFHLIVHNPYRPFEGFLIDLKTRYPI
      ||||||||||||||||||||||||||||||||||||||||||||||||||||||||||||
 47   SSPQFVGNLRESPLGQEKALEQILEYELLLIQQLNFHLIVHNPYRPFEGFLIDLKTRYPI

181   LENPEILRKTADDFLNRIALTDAYLLYTPSQIALTAILSSASRAGITMESYLSESLMLKE
      ||||||||||||||||||||||||||||||||||||||||||||||||||||||||||||
107   LENPEILRKTADDFLNRIALTDAYLLYTPSQIALTAILSSASRAGITMESYLSESLMLKE
```

TABLE 1-continued

Oligonucleotide primers used to isolate and characterize isoforms of transcriptional co-regulators in human melanoma cells.

```
241  NRTCLSQLLDIMKSMRNLVKKYEPPRSEEVAVLKQKLERCHSAELALNVITKKRKGYEDD
     ||||||||||||||||||||||||||||||||||||||||||||||||||||||||||||
167  NRTCLSQLLDIMKSMRNLVKKYEPPRSEEVAVLKQKLERCHSAELALNVITKKRKGYEDD

301  GYVSKKSKHEEEEWTDDDLVESL......
     ||||||||||| .|       .
227  GYVSKKSKHEEVCFTPKMNSKLFLLYILV
```

9. GTF2F1 (NM_002096)
Produt amplified with primers GCTCGGAGGAAGTTCAAGG (S3; SEQ ID NO: 60) and GTCCTGGTCCTGATCCTTG (AS1; SEQ ID NO: 61)
490 aa: internal 27 aa missing (83-110aa), shorter exon 4, (SEQ ID NO: 62), MAALGPSSQNVTEYVVRVPKNTTKKYNIMAFNAADKVNFATWNQARLERDLSNKKIYQEEEMPESGAGSE
FNRKLREEARRKFKGIKKGGVTENTSYYIFTQCPDGAFEAFPVHNWYNFTPLARHRTLTAEEAEEEWERR
NKVLNHFSIMQQRLKDQKQKEDEEEKEKRGRRKASELRIHDLEDDLEMSSDASDASGE...

Alignment with P35269 (517 aa; SEQ ID NO: 63):

```
  1  MAALGPSSQNVTEYVVRVPKNTTKKYNIMAFNAADKVNFATWNQARLERDLSNKKIYQ
     ||||||||||||||||||||||||||||||||||||||||||||||||||||||||||
  1  MAALGPSSQNVTEYVVRVPKNTTKKYNIMAFNAADKVNFATWNQARLERDLSNKKIYQ

59  EEEMPESGAGSEFNRKLREEARRKKYGIVLKEFRPEDQPWLLRVNGKSGRKFKGIKKGGV
     ||||||||||||||||||||||                    ||||||||||||
 61  EEEMPESGAGSEFNRKLREEAR....................RKFKGIKKGGV

119  TENTSYYIFTQCPDGAFEAFPVHNWYNFTPLARHRTLTAEEAEEEWERRNKVLNHFSIMQ
     ||||||||||||||||||||||||||||||||||||||||||||||||||||||||||||
 94  TENTSYYIFTQCPDGAFEAFPVHNWYNFTPLARHRTLTAEEAEEEWERRNKVLNHFSIMQ

179  QRRLKDQDQDEDEEEKEKRGRRKASELRIHDLEDDLEMSSDASDASGEEGGRVPKAKKKA
     |||||||||||||||||||||||||||||||||||||||||||||||||
154  QRRLKDQDQDEDEEEKEKRGRRKASELRIHDLEDDLEMSSDASDASGE............
```

2. Products amplified with primers AGGCCTGGGCGTCTGTTTG (S5; SEQ ID NO: 64) and GCACGGCATCCTCAGTCAC (AS3; SEQ ID NO: 65)
a) 437 aa: shorter/different C-terminus after 364 aa; new product (intron retentions between exons 10 and 11, 11 and 12), SEQ ID NO: 66)

MAALGPSSQNVTEYVVRVPKNTTKKYNIMAFNAADKVNFATWNQARLERDLSNKKIYQEEEMPESGAGSE
FNRKLREEARRKKYGIVLKEFRPEDQPWLLRVNGKSGRKFKGIKKGGVTENTSYYEFTQCPDGAFEAFPV
HNWYNFTPLARHRTLTAEEAEEEWERRNKVLNHFSIMQQRRLKDQDQDEDEEEKEKRGRRKASELRIHDL
EDDLEMSSDASDASGEEGGRVPKAKKKAPLAKGGRKKKKKKGSDDEAFEDSDDGDFEGQEVDYMSDGSSS
SQEEPESKAKAPQQEEGPKGVDEQSDSSEESEEEKPPEEDKEEEEEKKAPTPQEKKRRKDSSEESDSSEE
SDIDSEASSALFMA**VRPSPVAGEAWASVCRLTHLPTLTSAEEEDATQERAEAVGRELKGQQPPRHAQRRG
WQHLLHPAGGCQQTRAR***

Alignment with P35269 (517 aa; SEQ ID NO: 67):

```
  1  MAALGPSSQNVTEYVVRVPKNTTKKYNIMAFNAADKVNFATWNQARLERDLSNKKIYQEE
     ||||||||||||||||||||||||||||||||||||||||||||||||||||||||||||
  1  MAALGPSSQNVTEYVVRVPKNTTKKYNIMAFNAADKVNFATWNQARLERDLSNKKIYQEE

61  EMPESGAGSEFNRKLREEARRKKYGIVLKEFRPEDQPWLLRVNGKSGRKFKGIKKGGVTE
     ||||||||||||||||||||||||||||||||||||||||||||||||||||||||||||
 61  EMPESGAGSEFNRKLREEARRKKYGIVLKEFRPEDQPWLLRVNGKSGRKFKGIKKGGVTE

121  NTSYYIFTQCPDGAFEAFPVHNWYNFTPLARHRTLTAEEAEEEWERRNKVLNHFSIMQQR
     ||||||||||||||||||||||||||||||||||||||||||||||||||||||||||||
121  NTSYYIFTQCPDGAFEAFPVHNWYNFTPLARHRTLTAEEAEEEWERRNKVLNHFSIMQQR

181  RLKDQDQDEDEEEKEKRGRRKASELRIHDLEDDLEMSSDASDASGEEGGRVPKAKKKAPL
     ||||||||||||||||||||||||||||||||||||||||||||||||||||||||||||
181  RLKDQDQDEDEEEKEKRGRRKASELRIHDLEDDLEMSSDASDASGEEGGRVPKAKKKAPL

241  AKGGRKKKKKKGSDDEAFEDSDDGDFEGQEVDYMSDGSSSSQEEPESKAKAPQQEEGPKG
     ||||||||||||||||||||||||||||||||||||||||||||||||||||||||||||
241  AKGGRKKKKKKGSDDEAFEDSDDGDFEGQEVDYMSDGSSSSQEEPESKAKAPQQEEGPKG

301  VDEQSDSSEESEEEKPPEEDKEEEEEKKAPTPQEKKRRKDSSEESDSSEESDIDSEASSA
     ||||||||||||||||||||||||||||||||||||||||||||||||||||||||||||
301  VDEQSDSSEESEEEKPPEEDKEEEEEKKAPTPQEKKRRKDSSEESDSSEESDIDSEASSA
```

TABLE 1-continued

Oligonucleotide primers used to isolate and characterize isoforms of transcriptional co-regulators in human melanoma cells.

```
361   LFMAKKKTPPKRERKPSGGSSRGNSRPGTPSAEGGSTSSTLRAAASKLEQGKRVSEMPAA
      ||||  : .|    |   |         .    |    .                |
361   LFMAVRPSPVAGEAWASVCRLTHLPTLTSAEEEDATQERAEAVGRELKGQQPPRHAQRRG

421   KRLRLDTGPQSLSGKSTPQPPSGKTTPNSGDVQVTEDAVRRYLTRKPMTTKDLLKKFQTK
       . |                :.
421   WQHLLHPAGGCQQTRAR...........................................
``` b) 481 aa: shorter C-terminus, different sequence after 360 aa: new product (intron retention between exons 10 and 11), (SEQ ID NO: 68), MAALGPSSQNVTEYVVRVPKNTTKKYNIMAFNAADKVNFATWNQARLERDLSNKKIYQEEEMPESGAGSE
FNRKLREEARRKKYGIVLKEFRPEDQPWLLRVNGKSGRKFKGIKKGGVTENTSYYIFTQCPDGAFEAFPV
HNWYNFTPLARHRTLTAEEAEEEWERRNKVLNHFSIMQQRRLKDQDQDEDEEEKEKRGRRKASELRIHDL
EDDLEMSSDASDASGEEGGRVPKAKKKAPLAKGGRKKKKKKGSDDEAFEDSDDGDFEGQEVDYMSDGSSS
SQEEPESKAKAPQQEEGPKGVDEQSDSSEESEEEKPPEEDKEEEEEKKAPTPQEKKRRKDSSEESDSSEE
SDIDSEASSA**FFMAVRPSPVAGEAWASVCRLTHLPTLTSAEEEDATQERAEAVGRELKGQQPPRHAQRRG
WQHLLHPAGGCQQTRAREAGERDACSQAVAAGHGTPEPVWEVDTPATIRQDNTQQRRAGD***

Alignment with P35269 (517 aa) (SEQ ID NO: 69):

```
301   VDEQSDSSEESEEEKPPEEDKEEEEEKKAPTPQEKKRRKDSSEESDSSEESDIDSEASSA
      ||||||||||||||||||||||||||||||||||||||||||||||||||||||||||||
301   VDEQSDSSEESEEEKPPEEDKEEEEEKKAPTPQEKKRRKDSSEESDSSEESDIDSEASSA

361   LFMAKKKTPPKRERKPSGGSSRGNSRPGTPSAEGGSTSSTLRAAASKLEQGKRVSEMPAA
      ||| : .|   |    |         .    |    .                |
361   FFMAVRPSPVAGEAWASVCRLTHLPTLTSAEEEDATQERAEAVGRELKGQQPPRHAQRRG

421   KRLRLDTGPQSLSGKSTPQPPSGKTTPNSGDVQVTEDAVRRYLTRKPMTTKDLLKKFQTK
       . |                :.
421   WQHLLHPAGGCQQTRAREAGERDACSQAVAAGHGTPEPVWEVDTPATIRQDNTQQRRAG

481   KTGLSSEQTVNVLAQILKRLNPERKMINDKMHFSLKE
481   D...................................
```

3. Product amplified with primers TACCAAGAGGAGGAGAAGGAG (S7; SEQ ID NO: 70) and TCCTCTGAGCTGTCCGACTC (AS4; SEQ ID NO: 71)
385 aa: internal 132 aa missing (59-191 aa), (Δ(4)-(6)), (SEQ ID NO: 72)

...MAALGPSSQNVTEYVVRVPKNTTKKYNIMAFNAADKVNFATWNQARLERDLSNKKIYQEEEKEKRGRRK
ASELRIHDLEDDLEMSSDASDASGEEGGRVPKAKKKAPLAKGGRKKKKKKGSDDEAFEDSDDGDFEGQEV
DYMSDGSSSSQEEPESKAKAPQQEEGPKGVDEQSDSSEE...

Alignment with P35269 (517 aa), (SEQ ID NO: 73):

```
  1   ..MAALGPSSQNVTEYVVRVPKNTTKKYNIMAFNAADKVNFATWNQARLERDLSNKKIYQ
        ||||||||||||||||||||||||||||||||||||||||||||||||||||||||||
  1     MAALGPSSQNVTEYVVRVPKNTTKKYNIMAFNAADKVNFATWNQARLERDLSNKKIYQ

59   EEEMPESGAGSEFNRKLREEARRKKYGIVLKEFRPEDQPWLLRVNGKSGRKFKGIKKGGV

61   ............................................................

119   TENTSYYIFTQCPDGAFEAFPVHNWYNFTPLARHRTLTAEEAEEEWERRNKVLNHFSIMQ

61   ............................................................

179   QRRLKDQDQDEDEEEKEKRGRRKASELRIHDLEDDLEMSSDASDASGEEGGRVPKAKKKA
                        ||||||||||||||||||||||||||||||||||||||||||
 61   ............EEEKEKRGRRKASELRIHDLEDDLEMSSDASDASGEEGGRVPKAKKKA

239   PLAKGGRKKKKKKGSDDEAFEDSDDGDFEGQEVDYMSDGSSSSQEEPESKAKAPQQEEGP
      ||||||||||||||||||||||||||||||||||||||||||||||||||||||||||||
109   PLAKGGRKKKKKKGSDDEAFEDSDDGDFEGQEVDYMSDGSSSSQEEPESKAKAPQQEEGP

299   KGVDEQSDSSEESEEEKPPEEDKEEEEEKKAPTPQEKKRRKDSSEESDSSEESDIDSEAS
      |||||||||||||||
169   KGVDEQSDSSEESEE.............................................
```

TABLE 1-continued

Oligonucleotide primers used to isolate and characterize isoforms of transcriptional co-regulators in human melanoma cells.

4. Product amplified with primers CAGAGAACACGTCCTACTAC (S2; SEQ ID NO: 74 and CAGAGAACACGTCCTACTAC (AS2; SEQ ID NO: 75)
360 aa: shorter protein, different C-terminus after 318 aa; new product (Δ(9)-(13)); (SEQ ID NO: 76)

```
...MQQRRLKDQDQDEDEEEKEKRGRRKASELRIHDLEDDLEMSSDASDASGEEGGRVPKAKKKAPLAKGGR
KKKKKKGSDDEAFEDSDDGDFEGQEVDYMSDGSSSSQEEPESKAKAPQQEEGPKGVDEQSDSSEESEEEK
PPEKPPPGSASLTLTKGLCCPLGNFYSSPFHFPKSLFSCDLSTT*
```

Alignment with P35269 (517 aa) (SEQ ID NO: 77):

```
121  NTSYYIFTQCPDGAFEAFPVHNWYNFTPLARHRTLTAEEAEEEWERRNKVLNHFSIMQQR
                                                                 ||||
  1  ............................................................MQQR

181  RLKDQDQDEDEEEKEKRGRRKASELRIHDLEDDLEMSSDASDASGEEGGRVPKAKKKAPL
     ||||||||||||||||||||||||||||||||||||||||||||||||||||||||||||
  5  RLKDQDQDEDEEEKEKRGRRKASELRIHDLEDDLEMSSDASDASGEEGGRVPKAKKKAPL

214  AKGGRKKKKKKGSDDEAFEDSDDGDFEGQEVDYMSDGSSSSQEEPESKAKAPQQEEGPKG
     ||||||||||||||||||||||||||||||||||||||||||||||||||||||||||||
 65  AKGGRKKKKKKGSDDEAFEDSDDGDFEGQEVDYMSDGSSSSQEEPESKAKAPQQEEGPKG

301  VDEQSDSSEESEEEKPPEEDKEEEEEKKAPTPQEKKRRKDSSEESDSSEESDIDSEASSA
     |||||||||||||||||.              |       .             ...
125  VDEQSDSSEESEEEKPPEKPPPGSASLTLTKGLCCPLGNFYSSPFHFPKSLFSCDLETT.
```

TBP ASSOCIATED FACTORS
10. TAF1 (NM_004606)
1. Products amplified with primers AGACACGGACAGCGACGAA (S2, SEQ ID NO: 78) and ACCACCTGAAGCTTGCCTC (AS2; SEQ ID NO: 79)
a) 1417 aa: internal 455 aa missing (105-560 aa), new product (Δ(3)-(11)); (SEQ ID NO: 80)

```
...MEGESVLDDECKKHLAGLGALGLGSLITELTANEELTGTDGALVNDEGWVRSTEVKDPWNLSNDEYYYP
KQQGLRGTFGGNIIQHSIPAVELRQPFFPTHMGPIKLRQFHRPPLKKYSFGALSQPGPHSVQPLLKHIKK
KAEMREQERQASGG...
```

Alignment with P21675-1 (1872 aa) (SEQ ID NO: 81 and 82):

```
  1  MGPGCDLLLRTAATITAAAIMSDTDSDEDSAGGGPFSLAGFLFGNINGAGQLEGESVLDD
                                                       ||||||||||
  1  ..................................................LEGESVLDD

61  ECKKHLAGLGALGLGSLITELTANEELTGTDGALVNDEGWVRSTEDAVDYSDINEVAEDE
     ||||||||||||||||||||||||||||||||||||||||||||
 10  ECKKHLAGLGALGLGSLITELTANEELTGTDGALVNDEGWVRST................

121  SRRYQQTMGSLQPLCHSDYDEDDYDADCEDIDCKLMPPPPPPGPMKKDKDQDSITGEKV

54  ............................................................

181  DFSSSSDSESEMGPQEATQAESEDGKLTLPLAGIMQHDATKLLPSVTELFPEFRPGKVLR

54  ............................................................

241  FLRLFGPGKNVPSVWRSARRKRKKKHRELIQEEQIQEVECSVESEVSQKSLWNYDYAPPP

54  ............................................................

301  PPEQCLSDDEITMMAPVESKFSQSTGDIDKVTDTKPRVAEWRYGPARLWYDMLGVPEDGS

54  ............................................................

361  GFDYGFKLRKTEHEPVIKSRMIEEFRKLEENNGTDLLADENFLMVTQLHWEDDIIWDGED

54  ............................................................

421  VKHKGTKPQRASLAGWLPSSMTRNAMAYNVQQGFAATLDDDKPWYSIFPIDNEDLVYGRW

54  ............................................................

481  EDNIIWDAQAMPRLLEPPVLTLDPNDENLILEIPDEKEEATSNSPSKESKKESSLKKSRI

54  ............................................................
```

TABLE 1-continued

Oligonucleotide primers used to isolate and characterize isoforms of transcriptional co-regulators in human melanoma cells.

```
541  LLGKTGVIKEEPQQNMSQPEVKDPWNLSNDEYYYPKQQGLRGTFGGNIIQHSIPAVELRQ
                     ||||||||||||||||||||||||||||||||||||||||
 54  ....................EVKDPWNLSNDEYYYPKQQGLRGTFGGNIIQHSIPAVELRQ

601  PFFPTHMGPIKLRQFHRPPLKKYSFGALSQPGPHSVQPLLKHIKKKAKMREQERQASGGG
     ||||||||||||||||||||||||||||||||||||||||||||.|||||||||||||
 95  PFFPTHMGPIKLRQFHRPPLKKYSFGALSQPGPHSVQPLLKHIKKKAEMREQERQASGGG
``` b) 1375 aa: internal 497 aa missing (113-610 aa, new product (Δ(3)-(12)); (SEQ ID NO: 83)

...MEGESVLDDECKKHLAGLGALGLGSLITELTANEELTGTDGALVNDEGWVRSTEDAVDYSDIKLRQFHR
PPLKKYSFGALSQPGPHSVQPLLKHIKKKAKMREQERQASGG...

Alignment with P21675-1 (1872 aa); SEQ ID NO: 81 and 84:

```
  1  MGPGCDLLLRTAATITAAAIMSDTDSDEDSAGGGPFSLAGFLFGNINGAGQLEGESVLDD
                                                     :||||||||
  1  ...................................................MEGESVLDD

61  ECKKHLAGLGALGLGSLITELTANEELTGTDGALVNDEGWVRSTEDAVDYSDINEVAEDE
     |||||||||||||||||||||||||||||||||||||||||||||||||||
 10  ECKKHLAGLGALGLGSLITELTANEELTGTDGALVNDEGWVRSTEDAVDYSD........

121  SRRYQQTMGSLQPLCHSDYDEDDYDADCEDIDCKLMPPPPPPPGPMKKDKDQDSITGEKV

62  ............................................................

181  DFSSSSDSESEMGPQEATQAESEDGKLTLPLAGIMQHDATKLLPSVTELFPEFRPGKVLR

62  ............................................................

241  FLRLFGPGKVPSVWRSARRKRKKKHRELIQEEQIQEVECSVESEVSQKSLWNYDYAPPP

62  ............................................................

301  FPEQCLSDDEITMMAPVESKFSQSTGDIDKVTDTKPRVAEWRYGPARLWYDMLGVPEDGS

62  ............................................................

361  GFDYGFKLRKTEHEPVIKSRMIEEFRKLEENNGTDLLADENFLMVTQLHWEDDIIWDGED

62  ............................................................

421  VKHKGTKPQRASLAGWLPSSMTRNAMAYNVQQGFAATLDDDKPWYSIFPIDNEDLVYGRW

62  ............................................................

481  EDNIIWDAQAMPRLLEPPVLTLDPNDENLILEIPDEDEEATSNSPSKESKKESSLKKSRI

62  ............................................................

541  LLGKTGVIKEEPQQNMSQPEVKDPWNLSNDEYYYPKQQGLRGTFGGNIIQHSIPAVELRQ

62  ............................................................

601  PFFPTHMGPIKLRQFHRPPLKKYSFGALSQPGPHSVQPLLKHIKKKAKMREQERQASGGG
                ||||||||||||||||||||||||||||||||||||||||||||||||
 62  .........IKLRQFHRPPLKKYSFGALSQPGPHSVQPLLKHIKKKAKMREQERQASGG.
``` c) 1341 aa: internal 531 aa missing (81-612 aa); new product (Δ(2)-(12)); (SEQ ID NO: 84)

...MEGESVLDDECKKHLAGLGALGLGSLITELRQFHRPPLKKYSFGALSQPGPHSVQPLLKHIKKKAKMRE
QERQASGG...

Alignment with P21675-1 (1872 aa); SEQ ID NO: 81):

```
  1  MGPGCDLLLRTAATITAAAIMSDTDSDEDSAGGGPFSLAGFLFGNINGAGQLEGESVLDD
                                                     :||||||||
  1  ...................................................MEGESVLDD

61  ECKKHLAGLGALGLGSLITELTANEELTGTDGALVNDEGWVRSTEDAVDYSDINEVAEDE
     ||||||||||||||||||
 10  ECKKHLAGLGALGLGSLITE........................................
```

TABLE 1-continued

Oligonucleotide primers used to isolate and characterize isoforms of transcriptional co-regulators in human melanoma cells.

```
121  SRRYQQTMGSLQPLCHSDYDEDDYDADCEDIDCKLMPPPPPPGPMKKDKQDSITGEKV

30  .........................................................

181  DFSSSSDSESEMGPQEATQAESEDGKLTLPLAGIMQHDATKLLPSVTELFPEFRPGKVLR

30  .........................................................

241  FLRLFGPGKNVPSVWRSARRKRKKKHRELIQEEQIQEVESCVESEVSQKSLWNYDYAPPP

30  .........................................................

301  PPEQCLSDDEITMMAPVESKFSQSTGDIDKVTDTKPRVAEWRYGPARLWYDMLGVPEDGS

30  .........................................................

361  GFDYGFKLRKTEHEPVIKSRMIEEFRKLEENNGTDLLADENFLMVTQLHWEDDIIWDGED

30  .........................................................

421  VKHKGTKPQRASLAGWLPSSMTRNAMAYNVQQGFAATLDDDKPWYSIFPIDNEDLVYGRW

30  .........................................................

481  EDNIIWDAQAMPRLLEPPVLTLDPNDENLILEIPDEKEEATSNSPSKESKKESSLKKSRI

30  .........................................................

541  LLGKTGVIKEEPQQNMSQPEVKDPWNLSNDEYYYPKQQGLRGTFGGNIIQHSIPAVELRQ

30  .........................................................

601  PFFPTHMGPIKLRQFHRPPLKKYSFGALSQPGPHSVQPLLKHIKKKAKMREQERQASGGG
                ||||||||||||||||||||||||||||||||||||||||||||||
 30  ..........LRQFHRPPLKKYSFGALSQPGPHSVQPLLKHIKKKAKMREQERQASGG.
```

2. Product amplifeid with primers GAGCTTTCTGGATGATGTAAAC (S1; SEQ ID NO: 85) and CTCCTCATCATCATACCCGGC (AS4; SEQ ID NO: 86):
1906 aa: stra internal domain (1688-1722) aa), (extra exon between exons 35 and 36); SEQ ID NO: 87), ...MDDVNLILANSVKYNGPESQYTKTAQEIVNVCYQTLTEYDEHLTQLEKDICTAKEAALEEAELELDM
TPGPYTPQPPDLYDTNTSLSMSRDASVFQDESNMSVLDIPSATPEKQVTQ**MRQGRRLGEEDSDVDIEGY
DDEEEDGKPKTPAP**EGEDGDGDLADEEEGTVQQPQASVLYEDLLMSEGEDDEEDAGSDEEGDNPFS...

Alignment with P21675-1 (1872 aa); SEQ ID NO: 88):

```
1561  KYQSRESFLDDVNLILANSVKYNGPESQYTKTAQEIVNVCYQTLTEYDEHLTQLEKDICT
             :|||||||||||||||||||||||||||||||||||||||||||||||||||
   1  .......MDDVNLILANSVKYNGPESQYTKTAQEIVNVCYQTLTEYDEHLTQLEKDICT

1621  AKEAALEEAELESLDPMTPGPYTPQPPDLYDTNTSLSMSRDASVFQDESNMSVLDIPSAT
      ||||||||||||||||||||||||||||||||||||||||||||||||||||||||||
  53  AKEAALEEAELESLDPMTPGPYTPQPPDLYDTNTSLSMSRDASVFQDESNMSVLDIPSAT

1681  PEKQVTQ.............................EGEDGDGDLADEEEGTVQQ
      |||||||                             |||||||||||||||||||
 113  PEKQVTQMRQGRGRLGEEDSDVDIEGYDDEEEDGKPKTPAPEGEDGDGDLADEEEGTVQQ

1707  PQASVLYEDLLMSEGEDDEEDAGSDEEGDNPFSAIQLSESGSDSDVGSGGIRPKQPRMLQ
      |||||||||||||||||||||||||||||||||
 173  PQASVLYEDLLMSEGEDDEEDAGSDEEGDNPFS............................
```

3. Products amplifed with primers GAGCTTTCTGGATGATGTAAAC (S3; SEQ ID NO: 89) and CTCCTCATCATCATACCCTTC (AS3; SEQ ID NO: 90):
a) 1466 aa: shorter protein (extra exon after exon 28); (SEQ ID NO: 91)

MGPGCDLLLRTAATITAAAIMSDTDSDEDSAGGGPFSLAGFLFGNINGAGQLEGESVLDDECKKHLAGLG
ALGLGSLITELTANEELTGTDGALVNDEGWVRSTEDAVDYSDINEVAEDESRRYQQTMGSLQPLCHSDYD
EDDYDADCEDIDCLKMPPPPPPGPMKKDKQDSITGEKVDFSSSSDSESEMGPQEATQAESEDGKLTLP
LAGIMQHDATKLLSPVTELFPEFRPGKVLRFLRLFGPGKNVPSVWRSARRKRKKKHRELIQEEQIQEVEC
SVESEVSQKSLWNYDYAPPPPPEQCLSDDEITMMAPVESKFSWSTGDIDKVTDTKPRVAEWRYGPARLWY
DMLGVPEDGSGFDYGFKLRKTEHEPVIKSRMIEEFRKLEENNGTDLLADENFLMVTQLHWEDDIIWDGED
VKHKGTKPQRASLAGWLPSSMTRNAMAYNVQQGFATTLDDDKPWYSIFPIDNEDLVYGRWEDNIIWDAQA
MPRLLEPPVLTLDPNDENLILEIPDEKEEATSNSPSKESKKESSLKKSRILLGKTGVIKEEPQQNMSQPE

TABLE 1-continued

Oligonucleotide primers used to isolate and characterize isoforms of transcriptional co-regulators in human melanoma cells.

```
VKDPWNLSNDEYYYPKQQGLRGTFGGNIIQHSIPAVELRQPFFPTHMGPIKLRQFHRPPLKKYSFGALSQ
PGPHSVQPLLKHIKKKAKMREQERQASGGGEMFFMRTPQDLTGKDGDLILAEYSEENGPLMMQVGMATKI
KNYYKRKPGKDPGAPDCKYGETVYCHTSPFLGSLHPGQLLQAFENNLFRAPIYLHKMPETDFLIIRTRQG
YYIRELVDIFVVGQQCPLFEVPGPNSKRANTHIRDFLWVFIYRLFWKSKDRPRRIRMEDIKKAFPSHSES
SIRKRLKLCADFKRTGMDSNWWVLKSDFRLPTEEEIRAMVSPEQCCAYYSMTAAEQRLKDAGYGEKSFFA
PEEENEEDFQMKIDDEVRTAPWNTTRAFIAAMKGKCLLEVTGVADPTGCGEGFSYVKIPNKPTQQKDDKE
PQPVKKTVTGTDADLRRLSLKNAKQLLRKFGVPEEEIKKLSRWEVIDVVRTMSTEQARSGEGPMSKFARG
SRFSVAEHQERYKEECQRIFDLQNKVLSSTEVLSTDTDSSSAEDSDFEEMGKNIENMLQNKKTSSQLSRE
REEQERKELQRMLLAAGSAASGNNHRDDDTASVTSLNSSATGRCLKIYRTFRDEEGKEYVRCETVRKPAV
IDAYVRIRTTKDEEFIRKFALFDEQHREEMRKERRRIQEQLRRLKRNQEKEKLKGPPEKKPKKMKERPDL
KLKCGACGAIGHMRTNKFCPLYYQTNAPPSNPVAMTEEQEEELEKTVIHNDNEHLIKVEGTKIVLGKQLI
ESADEVRRKSLVLKFPKQQLPPKKKRRVGTTVHCDYLNRPHKSIHRRRTDPMVTLSSILESIINDMRDLP
NTYPFHTPVNAKVVKDYYKIITRPMDLQTLRENVRKRLYPSREEFREHLELIVKNSATYNAGSFSI*
```

Alignment with P21675-1 (1872 aa); (SEQ ID NO: 92):

```
  1 MGPGCDLLLRTAATITAAAIMSDTDSDEDSAGGGPFSLAGFLFGNINGAGQLEGESVLDD
    ||||||||||||||||||||||||||||||||||||||||||||||||||||||||||||
  1 MGPGCDLLLRTAATITAAAIMSDTDSDEDSAGGGPFSLAGFLFGNINGAGQLEGESVLDD

61 ECKKHLAGLGALGLGSLITELTANEELTGTDGALVNDEGWVRSTEDAVDYSDINEVAEDE
    ||||||||||||||||||||||||||||||||||||||||||||||||||||||||||||
 61 ECKKHLAGLGALGLGSLITELTANEELTGTDGALVNDEGWVRSTEDAVDYSDINEVAEDE

121 SRRYQQTMGSLQPLCHSDYDEDDYDADCEDIDCKLMPPPPPPPGPMKKDKDQDSITGEKV
    ||||||||||||||||||||||||||||||||||||||||||||||||||||||||
121 SRRYQQTMGSLQPLCHSDYDEDDYDADCEDIDCKLMPPPPPPPGPMKKDKDQDSITGEKV

181 DFSSSSDSEDEMGPQEATQAESEDGKLTLPLAGIMQHDATKLLPSVTELFPEFRPGKVLR
    ||||||||||||||||||||||||||||||||||||||||||||||||||||||||||||
181 DFSSSSDSEDEMGPQEATQAESEDGKLTLPLAGIMQHDATKLLPSVTELFPEFRPGKVLR

241 FLRLFGPGKNVPSVQRSARRKRKKKHRELIQEEQIQEVECSCESECSQKSLWNYDTAPPP
    ||||||||||||||||||||||||||||||||||||||||||||||||||||||||||||
241 FLRLFGPGKNVPSVQRSARRKRKKKHRELIQEEQIQEVECSCESECSQKSLWNYDTAPPP

301  PPEQCLSDDEITMMAPVESKFSQSTGDIDKVTDTKPRVAEWRYGPARLWYDMLGVPEDGS
     |||||||||||||||||||||||||||||||||||||||||||||||||||||||||||
301  PPEQCLSDDEITMMAPVESKFSQSTGDIDKVTDTKPRVAEWRYGPARLWYDMLGVPEDGS

361 GFDYGFKLRKTEHEPVIKSRMIEEFRKLEENNGTDLLADENFLMVTQLHWEDDITWDGED
    ||||||||||||||||||||||||||||||||||||||||||||||||||||||||||||
361 GFDYGFKLRKTEHEPVIKSRMIEEFRKLEENNGTDLLADENFLMVTQLHWEDDITWDGED

421 VKHKGTKPQRASLADWLPSSMTRNAMAYNVQQGFAATLDDDKPWYSIFPIDNEDLVYGRW
    ||||||||||||||||||||||||||||||||||||||||||||||||||||||||||||
421 VKHKGTKPQRASLADWLPSSMTRNAMAYNVQQGFAATLDDDKPWYSIFPIDNEDLVYGRW

481 EDNIIWDAQAMPRLLEPPVLTLDPNDENLILEIPDEKEEATSNSPSKESKKESSLKKSRI
    ||||||||||||||||||||||||||||||||||||||||||||||||||||||||||||
481 EDNIIWDAQAMPRLLEPPVLTLDPNDENLILEIPDEKEEATSNSPSKESKKESSLKKSRI

541 LLGKTGVIKEEPQQNMSQPEVKDPWNLSNDEYYYPKQQGLRGTFGGNIIQHSIPAVELRQ
    ||||||||||||||||||||||||||||||||||||||||||||||||||||||||||||
541 LLGKTGVIKEEPQQNMSQPEVKDPWNLSNDEYYYPKQQGLRGTFGGNIIQHSIPAVELRQ

601 PFFPTHMGPIKLRQFHRPPLKKYSFGALSQPGPHSVQPLLKHIKKKAKMREQERQASGGG
    ||||||||||||||||||||||||||||||||||||||||||||||||||||||||||||
601 PFFPTHMGPIKLRQFHRPPLKKYSFGALSQPGPHSVQPLLKHIKKKAKMREQERQASGGG

661 EMFFMRTPQDLTGKDGDLILAEYSEENGPLMMQVGMATKIKNYYKRKPGKDPGAPDCKYG
    ||||||||||||||||||||||||||||||||||||||||||||||||||||||||||||
661 EMFFMRTPQDLTGKDGDLILAEYSEENGPLMMQVGMATKIKNYYKRKPGKDPGAPDCKYG

721 ETVYCHTSPFLGSLHPGQLLQAFENNLFRAPIYLHKMPETDFLIIRTRQGYYIRELVDIF
    ||||||||||||||||||||||||||||||||||||||||||||||||||||||||||||
721 ETVYCHTSPFLGSLHPGQLLQAFENNLFRAPIYLHKMPETDFLIIRTRQGYYIRELVDIF

781 VVGQQCPLFEVPGNPNSKRANTHIRDFLQVFIYRLFWKSKDRPRRIMEDIKKAFPSHSES
    ||||||||||||||||||||||||||||||||||||||||||||||||||||||||||||
781 VVGQQCPLFEVPGNPNSKRANTHIRDFLQVFIYRLFWKSKDRPRRIMEDIKKAFPSHSES
```

TABLE 1-continued

Oligonucleotide primers used to isolate and characterize isoforms of transcriptional co-regulators in human melanoma cells.

```
 841  SIRKRLKLCADFKRTGMDSNWWVLKSDFRLPTEEEIRAMVSPEQCCAYYSMIAAEQRLKD
      ||||||||||||||||||||||||||||||||||||||||||||||||||||||||||||
 841  SIRKRLKLCADFKRTGMDSNWWVLKSDFRLPTEEEIRAMVSPEQCCAYYSMIAAEQRLKD

901  AGYGEKSFFAPEEENEEDFQMKIDDEVRTAPWNTTRAFIAAMKGKCLLEVTGVADPTGCG
      ||||||||||||||||||||||||||||||||||||||||||||||||||||||||||||
 901  AGYGEKSFFAPEEENEEDFQMKIDDEVRTAPWNTTRAFIAAMKGKCLLEVTGVADPTGCG

961  EGFSYVKIPNKPTQQKDDKEPQPVKKTVTGTDADLRRLSLKNAKQLLRKFGVPEEEIKKL
      ||||||||||||||||||||||||||||||||||||||||||||||||||||||||||||
 961  EGFSYVKIPNKPTQQKDDKEPQPVKKTVTGTDADLRRLSLKNAKQLLRKFGVPEEEIKKL

1021  SRWEVIDVVRTMSTEQARSGEGPMSKFARGSRFSVAEHQERYKEECQRIFDLQNKVLSST
      ||||||||||||||||||||||||||||||||||||||||||||||||||||||||||||
1021  SRWEVIDVVRTMSTEQARSGEGPMSKFARGSRFSVAEHQERYKEECQRIFDLQNKVLSST

1081  EVLSTDTDSSSAEDSDFEEMGKNIENMLQNKKTSSQLSREREEQERKELQRMLLAAGSAA
      ||||||||||||||||||||||||||||||||||||||||||||||||||||||||||||
1081  EVLSTDTDSSSAEDSDFEEMGKNIENMLQNKKTSSQLSREREEQERKELQRMLLAAGSAA

1141  SGNNHRDDDTASVTSLNSSATGRCLKIYRTFRDEEGKEYVRCETVRKPAVIDAYVRIRTT
      ||||||||||||||||||||||||||||||||||||||||||||||||||||||||||||
1141  SGNNHRDDDTASVTSLNSSATGRCLKIYRTFRDEEGKEYVRCETVRKPAVIDAYVRIRTT

1201  KDEEFIRKFALFDEQHREEMRKERRRIQEQLRRLKRNQEKEKLKGPPEKKPKKMKERPDL
      ||||||||||||||||||||||||||||||||||||||||||||||||||||||||||||
1201  KDEEFIRKFALFDEQHREEMRKERRRIQEQLRRLKRNQEKEKLKGPPEKKPKKMKERPDL

1261  KLKCGACGAIGHMRTNKFCPLYYQTNAPPSNPVAMTEEQEEELEKTVIHNDNEELIKVEG
      ||||||||||||||||||||||||||||||||||||||||||||||||||||||||||||
1261  KLKCGACGAIGHMRTNKFCPLYYQTNAPPSNPVAMTEEQEEELEKTVIHNDNEELIKVEG

1321  TKIVLGKQLIESADEVRRKSLVLKFPKQQLPPKKKKRVGTTVHCDYLNRPHKSIHRRRTD
      ||||||||||||||||||||||||||||||||||||||||||||||||||||||||||||
1321  TKIVLGKQLIESADEVRRKSLVLKFPKQQLPPKKKKRVGTTVHCDYLNRPHKSIHRRRTD

1381  PMVTLSSILESIINDMRDLPNTYPFHTPVNAKVVKDYYKIITRPMDLQTLRENVRKRLYP
      ||||||||||||||||||||||||||||||||||||||||||||||||||||||||||||
1381  PMVTLSSILESIINDMRDLPNTYPFHTPVNAKVVKDYYKIITRPMDLQTLRENVRKRLYP

1441  SREEFREHLELIVKNSATYNGPKHSLTQISQSMLDLCDEKLKEKEDKLARLEKAINPLLD
      |||||||||||||||||||||||     |:
1441  SREEFREHLELIVKNSATYNAGSFSI...................................

1501  DDDQVAFSFILDNIVTQKMMAVPDSWPFHHPVNKKFVPDYYKVIVNPMDLETIRKNISKH

1467  ............................................................

1561  KYQSRESFLDDVNLILANSVKYNGPESQYTKTAQEIVNVCYQTLTEYDEHLTQLEKDICT

1467  ............................................................

1621  AKEAALEEAELESLDPMTPGPYTPQPPDLYDTNTSLSMSRDASVFQDESNMSVLDIPSAT

1467  ............................................................

16S1  PEKQVTQEGEDGDGDLADEEEGTVQQPQASVLYEELLMSEGEDDEEDAGSDEEGDNPFSA

1467  ............................................................

1741  IQLSESGSDSDVGSGGIRPKQPRMLQENTRMDMEHEESMMSYEGDGGEASHGLEDSNISY

1467  ............................................................

1801  GSYEEPDPKSNTQDTSFSSIGGYEVSEEEEDEEEEQRSGPSVLSQVHLSEDEEDSEDFH

1467  ............................................................

1861  SIAGDSDLDSDE

1467  ............
```

TABLE 1-continued

Oligonucleotide primers used to isolate and characterize isoforms of transcriptional co-regulators in human melanoma cells.

b) 1488 aa: shorter protein, different sequence after 1450 aa (extra exon after exon 28, 44 bp shorter exon 28); (SEQ ID NO: 93)

```
MGPGCDLLLRTAATITAAAIMSDTDSDEDSAGGGPFSLAGFLFGNINGAGQLEGESVLDDECKKHLAGLG
ALGLGSLITELTANEELTGTDGALVWDEGWVRSTEDAVDYSDINEVAEDESRRYQQTMGSLQPLCHSDYD
EDDYDADCEDIDCKLMPPPPPPGPMKKDKDQDSITGEKVDFSSSSDSESEMGPQEATQAESEDGKLTLP
LAGIMQHDATKLLPSVTELFPEFRPGKVLRFLRLFGPGKNVPSVWRSARKKRKKKHRELIQEEQIQEVEC
SVESEVSQKSLWNYDYAPPPPPEQCLSDDEITMMAPVESKFSQSTGDIDKVTDTKPRVAEWRYGPARLWY
DMLGVPEDGSGFDYGFKLRKTEHEPVIKSRMIEEFRKLEENNGTDLLADENFLMVTQLHWEDDIIWDGED
VKHKGTKPQRASLAGWLPSSMTRNAMAYNVQQGFAATLDDDKPWYSIFPIDNEDLVYGRWEDNIIWDAQA
MPRLLEPPVLTLDPNDENLILHIPDEKEEATSNSPSKESKKESSLKKSRILLGKTGVIKEEPQQNMSQPE
VKDPWNLSNDEYYYPKQQGLRGTFGGNIIQHSIPAVELRQPFFPTHMGPIKLRQFHRPPLKKYSFGALSQ
PGPHSVQPLLKHIKKKAKMREQERQASGGGEMFFMRTPQDLTGKDGDLIIAEYSEENGPLMMQVGMATKI
KNYYKRKPGKDPGAPDCKYGETVYCHTSPFLGSLHPGQLLQAFENNLFRAPIYLHKMPETDFLIIRTRQG
YYIRELVDIFVVGQQCPLFEVPGPNSKRANTHIRDFLQVFIYRLFWKSKDRPRRIRMEDIKKAFPSHSES
SIRKRLKLCADFKRTGMDSNWWVLKSDFRLPTEEEIRAMVSPEQCCAYYSMIAAEQRLKDAGYGEKSFFA
PEEENEEDFQMKIDDEVRTAPWNTTRAFIAAMKGKCLLEVTGVADPTGCGEGFSYVKIPNKPTQQKDDKE
PQPVKKTVTGTDADLRRLSLKNAKQLLRKFGVPEEEIKKLSRWEVIDVVRTMSTEQARSGEGPMSKFARG
SRFSVAEHQERYKEECQRIFDLQNKVLSSTEVLSTDTDSSSAEDSDFEEMGKNIENMLQNKKTSSQLSRE
REEQERKELQRMLLAAGSAASGNNHRDDDTASVTSLNSSATGRCLKIYRTERDEECKEYVRCETVRKPAV
IDAYVRIRTTKDEEFIRKFALFDEQHREEMRKERRRIQEQLRRLKRNQEKEKLKGPPEKKPKKMKERPDL
KLKCGACGAIGHMRTNKFCPLYYQTNAPPSNPVAMTEEQEEELEKTVIHNDNEELIKVEGTKIVLCKQLI
ESADEVRRKSLVLKFPKQQLPPKKKRRVGTTVHCDYLNRPHKSIHRRRTDPWVTLSSILESIINDMRDLP
NTYPFHTPVNAKVVKDYYKIITRPMDLQTLRENVRKRLYPSREEFREHL**DDRWEPCLKKKKKEEETWLSE
YAFHKPTRGCSLPTQSQF***
```

Alignment with P21675-1 (1872 aa); (SEQ ID NO: 92 and 93):

```
  1 MGPGCDLLLRTAATITAAAIMSDTDSDEDSAGGGPFSLADFLFGNINGAGQLEGESVLDD
    ||||||||||||||||||||||||||||||||||||||||||||||||||||||||||||
  1 MGPGCDLLLRTAATITAAAIMSDTDSDEDSAGGGPFSLADFLFGNINGAGQLEGESVLDD

61 ECKKHLAGLGALGLGSLITELTANEELTGTDGALVNDEGWVRSTEDAVDYSDINEVAEDE
    ||||||||||||||||||||||||||||||||||||||||||||||||||||||||||||
 61 ECKKHLAGLGALGLGSLITELTANEELTGTDGALVNDEGWVRSTEDAVDYSDINEVAEDE

121 SRRYQQTMGSLQPLCHSDYDEDDYDADCEDIDCKLMPPPPPPGPMKKDKDQDSITGEKV
    |||||||||||||||||||||||||||||||||||||||||||||||||||||||||||
121 SRRYQQTMGSLQPLCHSDYDEDDYDADCEDIDCKLMPPPPPPGPMKKDKDQDSITGEKV

181 DFSSSSDSESEMGPQEATQAESEDGKLTLPLAGIMQHDATKLLPSVTELFPEFRPGKVLR
    ||||||||||||||||||||||||||||||||||||||||||||||||||||||||||||
181 DFSSSSDSESEMGPQEATQAESEDGKLTLPLAGIMQHDATKLLPSVTELFPEFRPGKVLR

241 FLRLFGPGKNVPSVWRSARRKRKKKHRELIQEEQIQEVECSVESEVSQKSLWNYDYAPPP
    ||||||||||||||||||||||||||||||||||||||||||||| ||||||||| ||||
241 FLRLFGPGKNVPSVWRSARRKRKKKHRELIQEEQIQEVECSVEVEVSQKSLWNYDTAPPP

301 PPEQCLSDDEITMMAPVESKFSQSTGDIDKVTDTKPRVAEWRYGPARLWYDMLGVPEDGS
    ||||||||||||||||||||||||||||||||||||||||||||||||||||||||||||
301 PPEQCLSDDEITMMAPVESKFSQSTGDIDKVTDTKPRVAEWRYGPARLWYDMLGVPEDGS

361 GFDYDFKLRKTEHEPVIKSRMIEEFRKLEENNGTDLLADENFLMVTQLHWEDDIIWDGED
    ||||||||||||||||||||||||||||||||||||||||||||||||||||||||||||
361 GFDYDFKLRKTEHEPVIKSRMIEEFRKLEENNGTDLLADENFLMVTQLHWEDDIIWDGED

421 VKHKGTKPQRASLAGWLPSSMTRNAMAYNVQQGFAATLDDDKPWYSIFPIDNEDLVYGRW
    ||||||||||||||||||||||||||||||||||||||||||||||||||||||||||||
421 VKHKGTKPQRASLAGWLPSSMTRNAMAYNVQQGFAATLDDDKPWYSIFPIDNEDLVYGRW

481 EDNIIWDAQAMPRLLEPPVLTLDPNDENLILEIPDEKEEATSNSPSKESKKESSLKKSRI
    ||||||||||||||||||||||||||||||||||||||||||||||||||||||||||||
481 EDNIIWDAQAMPRLLEPPVLTLDPNDENLILEIPDEKEEATSNSPSKESKKESSLKKSRI

541 LLGKTGVIKEEPQQNMSQPEVKDPWNLSNDEYYYPKQQGLRGTFGGNIIQHSIPAVELRQ
    ||||||||||||||||||||||||||||||||||||||||||||||||||||||||||||
541 LLGKTGVIKEEPQQNMSQPEVKDPWNLSNDEYYYPKQQGLRGTFGGNIIQHSIPAVELRQ

601 PFFPTHMGPIKLRQFHRPPLKKYSFGALSQPGPHSVQPLLKHIKKKAKMREQERQASGGG
    ||||||||||||||||||||||||||||||||||||||||||||||||||||||||||||
601 PFFPTHMGPIKLRQFHRPPLKKYSFGALSQPGPHSVQPLLKHIKKKAKMREQERQASGGG

661 EMFFMRTPQDLTGKFGDLILAEYSEENGPLMMQVGMATKIKNYYKRKPGKDPGAPDCKYG
    ||||||||||||||||||||||||||||||||||||||||||||||||||||||||||||
661 EMFFMRTPQDLTGKFGDLILAEYSEENGPLMMQVGMATKIKNYYKRKPGKDPGAPDCKYG
```

TABLE 1-continued

Oligonucleotide primers used to isolate and characterize isoforms of transcriptional co-regulators in human melanoma cells.

```
 721  ETVYCHTSPFLGSLHPGQLLQAFENNLFRAPIYLHKMPETDFLIIRTRQGYYIRELVDIF
      ||||||||||||||||||||||||||||||||||||||||||||||||||||||||||||
 721  ETVYCHTSPFLGSLHPGQLLQAFENNLFRAPIYLHKMPETDFLIIRTRQGYYIRELVDIF

781  VVGQQCPLFEVPGPNSKRANTHIRDFLQVFIYRLFWKSKDRPRRIRMEDIKKAFPSHSES
      ||||||||||||||||||||||||||||||||||||||||||||||||||||||||||||
 781  VVGQQCPLFEVPGPNSKRANTHIRDFLQVFIYRLFWKSKDRPRRIRMEDIKKAFPSHSES

841  SIRKRLKLCADFKRTGMDSNWWVLKSDFRLPTEEEIRAMVSPEQCCAYYSMIAAEQRLKD
      ||||||||||||||||||||||||||||||||||||||||||||||||||||||||||||
 841  SIRKRLKLCADFKRTGMDSNWWVLKSDFRLPTEEEIRAMVSPEQCCAYYSMIAAEQRLKD

901  AGYGEKSFFAPEEENEEDFQMKIDDEVRTAPWNTTRAFIAAMKGKCLLEVTGVADPTGCG
      ||||||||||||||||||||||||||||||||||||||||||||||||||||||||||||
 901  AGYGEKSFFAPEEENEEDFQMKIDDEVRTAPWNTTRAFIAAMKGKCLLEVTGVADPTGCG

961  EGFSYVKIPNKPTQQKDDKEPQPVKKTCTGTDADLRRLSLKNAKQLLRKFGVPEEEIKKL
      ||||||||||||||||||||||||||||||||||||||||||||||||||||||||||||
 961  EGFSYVKIPNKPTQQKDDKEPQPVKKTCTGTDADLRRLSLKNAKQLLRKFGVPEEEIKKL

1021  SRWEVIDVVRTMSTEQARSGEGPMSKFARGSRFSVAEHQERYKEECQRIFDLQNKVLSST
      ||||||||||||||||||||||||||||||||||||||||||||||||||||||||||||
1021  SRWEVIDVVRTMSTEQARSGEGPMSKFARGSRFSVAEHQERYKEECQRIFDLQNKVLSST

1081  EVLSTDTDSSSAEDSDFEEMGKNIENMLQNKKTSSQLSREREEQERKELQRMLLAAGSAA
      ||||||||||||||||||||||||||||||||||||||||||||||||||||||||||||
1081  EVLSTDTDSSSAEDSDFEEMGKNIENMLQNKKTSSQLSREREEQERKELQRMLLAAGSAA

1141  SGNNHRDDDTASVTSLNSSATGRCLKIYRTFRDEEGKEYVRCETVRKPAVIDAYVRIRTT
      ||||||||||||||||||||||||||||||||||||||||||||||||||||||||||||
1141  SGNNHRDDDTASVTSLNSSATGRCLKIYRTFRDEEGKEYVRCETVRKPAVIDAYVRIRTT

1201  KDEEFIRKFALFDEQHREEMRKERRRIQEQLRRLKRNQEKEKLKGPPEKKPKKMKERPDL
      ||||||||||||||||||||||||||||||||||||||||||||||||||||||||||||
1201  KDEEFIRKFALFDEQHREEMRKERRRIQEQLRRLKRNQEKEKLKGPPEKKPKKMKERPDL

1261  KLKCGACGAIGHMRTNKFCPLYYQTNAPPSNPVAMTEEQEEELEKTVIHNDNEELIKVEG
      ||||||||||||||||||||||||||||||||||||||||||||||||||||||||||||
1261  KLKCGACGAIGHMRTNKFCPLYYQTNAPPSNPVAMTEEQEEELEKTVIHNDNEELIKVEG

1321  TKIVLGKQLIESADEVRRKSLVLKFPKQQLPPKKKRRVGTTVHCDYLNRPHKSIHRRRTD
      ||||||||||||||||||||||||||||||||||||||||||||||||||||||||||||
1321  TKIVLGKQLIESADEVRRKSLVLKFPKQQLPPKKKRRVGTTVHCDYLNRPHKSIHRRRTD

1381  PMVTLSSILESIINDMRDLPNTYPFHTPVNAKVVKDYYKIITRPMDLQTLRENVRKRLYP
      ||||||||||||||||||||||||||||||||||||||||||||||||||||||||||||
1381  PMVTLSSILESIINDMRDLPNTYPFHTPVNAKVVKDYYKIITRPMDLQTLRENVRKRLYP

1441  SREEFREHLELIVKNSATYNGPKHSLTQISQSMLDLCDEKLKEKEDKLARLEKAINPLLD
      ||||||||||:   :          .         .           :  .
1441  SREEFREHLDDRWRPCLKKKKKEEETWLSEYAFHKPTRGCSLPTQSQF............

1501  DDDQVAFSFILDNIVTQKMMAVPDSWPFHHPVNKKFVPDYYKVIVNPMDLETIRKNISKH

1489  ............................................................

1561  KYQSRESFLDDVNLILANSVKYNGPESQYTKTAQEIVNVCYQTLTEYDEHLTQLEKDICT

1489  ............................................................

1621  AKEAALEEAELESLDPMTPGPYTPQPPDLYDTNTSLSMSRDASVFQDESNMSVLDIPSAT

1489  ............................................................

1681  PEKQVTQEGEDGDGDLADEEEGTVQQPQASVLYEDLLMSEGEDDEEDAGSDEEGDNPFSA

1489  ............................................................

1741  IQLSESGEDSVDGSGGIRPKQPRMLQENTRMDMENEESMMSYEGDGGEASHGLEDSNISY

1489  ............................................................
```

TABLE 1-continued

Oligonucleotide primers used to isolate and characterize isoforms of transcriptional co-regulators in human melanoma cells.

```
1801  GSYEEPDPKSNTQDTSFSSIGGYEVSEEEEDEEEEQRSGPSVLSQVHLSEDEEDSEDFH

1489  ..........................................................

1861  SIAGDSDLDSDE

1489  ............
``` c) 1485 aa: shorter protein, different sequence after 1461 aa (extra exon after 28); (SEQ ID NO: 94),
...MVTLSSILESIINDMRDLPNTYPFHTPVNAKWKDYYKIITRPMDLQTLRENVRKRLYPSREE+
JIVKNSATYNGKNQMFRDCKGHCSDPYSLLALNSD*
Alignment with P21675-1 (1872 aa); (SEQ ID NO: 95):

```
 321  TKIVLGKQLIESADEVRRKSLVLKFPKQQLPPKKKRRVGITVHCDYLNRPHKSIHRRRTD

1  ............................................................

1381  PMVTLSSILESIINDMRDLPNTYPFHTPVNAKVVKDYYKIITRPMDLQTLRENVRKRLYP
      |||||||||||||||||||||||||||||||||||||||||||||||||||||||||||
   1  .MVTLSSILESIINDMRDLPNTYPFHTPVNAKVVKDYYKIITRPMDLQTLRENVRKRLYP

1441  SREEFREHLELIVKNSATYNGPKHSLTQISQSMLDLCDEKLKEKEDKLARLEKAINPLLD
      |||||||||||||||||||||||||||||||           |                :
  60  SREEFREHLELIVKNSATYNGKNQMFRDCKGHCSDPYCLLALNSD...............

1501  DDDQVAFSFILDNIVTQKMMAVPDSWPFHHPVNKKFVPDYYKVIVNPMDLETIRKNISKH

105  ............................................................

1561  KYQSRESFLDDVNLILANSVKYNGPESQYTKTAQEIVNVCYQTLTEYDEHLTQLEKDICT

105  ............................................................

1621  AKEAALEEAELESLDPMTPGPYTPQPPDLYDTNTSLSMSRDASVFQDESNMSVLDIPSAT

105  ............................................................

1681  PEKQVTQEGEDGDGDLADEEEGTVQQPQASVLYEDLLMSEGEDDEEDAGSDEEGDNPFSA

105  ............................................................

1741  IQLSESGSDSDVGSGGIRPKQPRMLQENTRMDMENEESMMSYEGDGGEASHGLEDSNISY

105  ............................................................

1801  GSYEEPDPKSNTQDTSFSSIGGYEVSEEEEDEEEEQRSGPSVLSQVHLSEDEEDSEDFH

105  ............................................................

1861  SIAGDSDLDSDE

105  ............
``` d) 1460 aa, shorter protein (shorter exon 28, extra exon after exon 28); (SEQ ID NO: 96)

MGPGCDLLLRTAATITAAAIMSDTDSDEDSAGGGPFSLAGFLFGNINGAGQLEGESVLDDECKKHLAGLG
ALGLGSLITELTANEELTGTDGALVNDEGWVRSTEDAVDYSDINEVAEDESRRYQQTMGSLQPLCHSDYD
EDDYDADCEDIDCKLMPPPPPPGPMKKDKDQDSITGEDVDFSSSSDSESEMGPQEATQAESEDGKLTLP
LAGIMQHDATKLLPSVTELFPEFRPGKVLRFLRLFGPGKNVPSVWRSARRKRKKKHRELIQEEQIQEVEC
SVESESEVSQKSLWNYDYAPPPPPEQCLSDDEITMMAPVESKFSQSTGDIDKVTDTKPRVAEWRYGPARLWY
DMLGVPEDGSGFDYGFKLRKTEHEPVIKSRMIEEFRKLEEKNGTDLLADENFLMVTQLHWEDDIIWDGED
VKHKGTKPQRASLAGWLPSSMTRNAMAYNVQQGFAATLDDDKPWYSIFPIDNEDLVYGRWEDNIIWDAQA
MPRLLEPPVLTLDPNDENLTLEIPDEKEEATSNSPSKESKKESSLKKSRILLGKTGVIKEEPQQNMSQPE
VKDPWNLSNDEYYYPKQQGLRGTFGGNIIQHSIPAVELRQPFFPTHMGPIKLRQFHRPPLKKYSFGALSQ
PGPHSVQPLLKHIKKKAKMREQERQASGGGEMFFMRTPQDLTGKDGDLILAEYSEENGPLMMQVGMATKI
KNYYKRKPGKDPGAPDCKYGETVYCHTSPFLGSLHPGQLLQAFENNLFRAPIYLHKMPETDFLIIRTRQG
YYIRELVDIFVVGQQCPLFEVPGPNSKRANTHIRDFLQVFIYRLFWKSKDRPRRIRMEDIKKAFPSHSES
SIRKRLKLCADFKRTGMDSNWWVLKSDFRLPTEEEIRAWVSPEQCCAYYSMIAAEQRLKDAGYGEKSFFA
PEEENEEDFQMKIDDEVRTAPWNTTRAFIAAMKGKCLLEVTGVADPTGCGEGFSYVKIPNKPTQQKDDKE
PQPVKKTVTGTDADLRRLSLKNAKQLLRKFGVPEEEIKKLSRWEVIDVVRTMSTEQARSGEGPMSKFARG
SRFSVAEHQERYKEECQRIFDLQNKVLSSTEVLSTDTDSSSAEDSDFEEMGKNIENMLQNKKTSSQLSRE
REEQERKELQRMLLAAGSAASGNNHRDDDTASVTSLNSSATGRCLKIYRTFRDEEGKEYVRCETVRKPAV
IDAYVRITTKDEEFIRKFALFDEQHREEMRKERRRIQEQLRRLKRNQEKEKLKGPPEKKPKKMKERPDL
KLKCGACGAIGHMRTNKFCPLYYQTNAPPSNPVAMTEEQEEELEKTVIHDNEELIKVEGTKIVLGKQLI
ESADEVRRKSLVLKFPKQQLPPKKKRRVGTTVHCDYLNRPHKSIHRRRTDPMVTLSSILESIINDMRDLP
NTYPFHTPAWMTDGDPVSKRKKKKKKRGFQSMLSTSPLGVALCPHRANSEWRGLPPRSLL*

TABLE 1-continued

Oligonucleotide primers used to isolate and characterize isoforms of transcriptional co-regulators in human melanoma cells.

e) 1485 aa, shorter protein, (longer exon 28, extra exon after exon 28); (SEQ ID NO: 97)

MGPGCDLLLRTAATITAAAIMSDTDSDEDSAGGGPFSLAGFLFGNINGAGQLEGESVLDDECKKHLAGLG
ALGLGSLITELTANEELTGTDGALVNDEGWVRSTEDAVDYSDINEVAEDESRRYQQTMGSLQPLCHSDYD
EDDYDADCEDIDCKLMPPPPPPPGPMKKDKDQDSITGEKVDFSSSSDSESEMGPQEATQAESEDGKLTLP
LAGIMQHDATKLLPSVTELFPEFRPGKVLRFLRLFGPGKNVPSVWRSARRKRKKKHRELIQEEQIQEVEC
SVESEVSQKSLWNYDYAPPPPPEQCLSDDEITMMAPVESKFSQSTGDIDKVTDTKPRVAEWRYGPARLWY
DMLGVPEDGSGFDYGFKLRKTEHEPVIKSRMIEEFRKLEENNGTDLLADENFLMVTQLHWEDDIIWDGED
VKHKGTKPQRASLAGWLPSSMTRNAMAYNVQQGFAATLDDDKPWYSIFPIDNEDLVYGRWEDNIIWDAQA
MPRLLEPPVLTLDPNDENLILEIPDEKEEATSNSPSKESKKESSLKKSRILLGKTGVIKEEPQQNMSQPE
VKDPWNLSNDEYYYPKQQGLRGTFGGNIIQHSIPAVELRQPFFPTHMGPIKLRQFHRPPLKKYSFGALSQ
PGPHSVQPLLKHIKKKAKMREQERQASGGGEMFFMRTPQDLTGKDGDLILAEYSEENGPLMMQVGMATKI
KNYYKRKPGKDPGAPDCKYGETVYCHTSPFLGSLHPGQLLQAFENNLFRAPIYLHKMPETDFLIIRTRQG
YYIRELVDIFVVGQQCPLFEVPGPNSKRANTHIRDFLQVFIYRLFWKSKDRPRRIRMEDIKKAFPSHSES
SIRKRLKLCADFKRTGMDSNWWVLKSDFRLPTEEEIRAMVSPEQCCAYYSMIAAEQRLKDAGYGEKSFFA
PEEENEEDFQMKIDDEVRTAPWNTTRAFIAAMKGKCLLEVTGVADPTGCGEGFSYVKIPNKPTQQKDDKE
PQPVKKTVTGTDADLRRLSLKNAKQLLRKVGVPEEEIKKLSREWVIDVVRTMSTEQARSGEGPMSKFARG
SRFSVAEHQERYKEECQRIFDLQNKVLSSTEVLSTDTDSSSAEDSDFEEMGKNIENMLQNKKTSSQLSRE
REEQERKELQRMLLAAGSAASGNNHRDDDTASVTSLNSSATGRCLKIYRTFRDEEGKEYVRCETVRKPAV
IDAYVRIRTTKDEEFIRKFALFDEQHREEMRKERRRIQEQLRRLKRNQEKEKLKGPPEKKPKKMKERPDL
KLKCGACGAIGHMRTNKFCPLYYQTNAPPSNPVAMTEEQEEELEKTVIHNDNEELIKVEGTKIVLGKQLI
ESADEVRRKSLVLKFPKQQLPPKKKRRVGTTVHCDYLNRPHKSIHRRRTDPMVTLSSILESIINDMRDLP
NTYPFHTPVNAKVVKDYYKIITRPMDLQTLRENVRKRLYPSREEFREHLELIVKNSATYNGKNQMFRDCK
GHCSDPYSLLALNSD*

11. TAF2 (NM_003184)
Product amplified with primers CCACTAGAACCTGGTCAAATAC (S1
98) and GACTGAGAGTGGAGCGCTTG (AS1; SEQ ID NO: 99)
1251 aa: extra 52 aa inside the protein, extra exon between exons 23
and 24, (SEQ ID NO: 100)

...LSRPSCLPLPELGLVLNLKEKKAVLNPTIIPESVAGNQEAANNPSSHPQLVGFQNP**EDDHLAKEASCHI
SAHQQQVKRKSDTPLQSPLEPQQILEKNEDSSKVKLKIRF**SSSQDEEEIDMDTVHDSQAFISHHLNMLER
PSTPGLSKYRPASSRSALIPQHSAGCDSTPTTKPQWSLELARKGTGKEQAPLEMSMHPAASAPLSVFTKE
STASKHSDHHHHHHHEHKKKKKKHKKKHKHKHKHDSKEKDKEPFTFSSPASGRSIRSPSLSD*

Alignment with 060668 (1199 aa); (SEQ ID NO: 101):; SEQ ID NO:
  961   TSHDWRLRCGAVDLYFTLFGLSRPSCLPLPELGLVLNLKEKKAVLNPTIIPESVAGNQEA
        ||||||||||||||||||||||||||||||||||||||||||||||||||||||||||||
  961   TSHDWRLRCGAVDLYFTLFGLSRPSCLPLPELGLVLNLKEKKAVLNPTIIPESVAGNQEA 1021   ANNPSSHPQLVGFQNP............................................
        ||||||||||||||||
 1021   ANNPSSHPQLVGFQNPEDDHLAKEASCNISAHQQGVKRKSDTPLGSPLEPGQILEKNEDS 1037   ........FSSSQDEEEIDMDTVHDSQAFISHHLNMLERPSTPGLSKYRPADDRSALIPQ
                ||||||||||||||||||||||||||||||||||||||||||||||||||||
 1081   SKVKLKIRFSSSQDEEEIDMDTVHDSQAFISHHLNMLERPSTPGLSKYRPADDRSALIPQ 1089   HSAGCDSTPTTKPQWSLELARKGTGKEQAPLEMSMHPAASAPLSVFTKESTASKHSDHHH
        ||||||||||||||||||||||||||||||||||||||||||||||||||||||||||||
 1141   HSAGCDSTPTTKPQWSLELARKGTGKEQAPLEMSMHPAASAPLSVFTKESTASKHSDHHH 1149   HHHHEHKKKKKKHKHKHKHKHKHDSKEKDKEPFTFSSPASGRSIRSPSLSD
        |||||||||||||||||||||||||||||||||||||||||||||||||||
 1201   HHHHEHKKKKKKHKHKHKHKHKHDSKEKDKEPFTFSSPASGRSIRSPSLSD 12. TAF4 (Y11354)
Product amplified with primers ATCTGCTGGACGAGGTCTTCT (SI; SEQ ID NO: 102) and TATGGTAGTTGGGGTCACCTG (AS1; SEQ ID NO: 103):
653 aa: internal 432 aa missing (22-454 aa), deletion in exon 1, 65-1355; (SEQ ID NO: 104)

MAAGSDLLDEVFFNSEVDEKVGMVLVRSENGQLLMIPQQALAQMQAQAHAQPQTTMAPRPATPTSAPPVQ
ISTVQAPGTPIIARQVTPTTIIKQVSQAQTTVQPSATLQRSPGVQPQLVLGGAAGTASLGTATAVQTGTP
QRTVPGATTTSSAATETMENVKKCKNFLSTLIKLASSGKQSTETAANVKELVQNLLDGKIEAEDFTSRLY
RELNSSPQPYLVPFLKRSLPALRQLTPDSAAFIQQSQQQPPPPTSQATTALTAWLSSSVQRTAGKTAAT
VTSALQPPVLSLTQPTQVGVGKQGQPTPLVIQQPPKPGALIRPPQVTLTQTPMVALRQPHNRIMLTTPQQ
IQLNPLQPVPWKPAVLPGTKALSAVSAQAAAAQKNKLKEPGGSPSFRDDDDINDVASMAGVNLSEESARI
LATNSELVGTLTRSCKDETFLLQAPLQRRILEIGKKHGITELHPDWSVYSHATQQRLQNLVEKISETAQ
QKNFSYKDDDRYEQASDVRAQLKFFEQLDQIEKQRKDEQEREILMRAAKSRSRQEDPEQLRLKQKAKEMQ
QQELAQMRQRDANLTALAAIGPRKKRKVDCPGPGSGAEGSGPGSVVPGSSGVGTPROFTRQRITRVNLRD
LIFCLENERETSHSLLLYKAFLK*

TABLE 1-continued

Oligonucleotide primers used to isolate and characterize isoforms of transcriptional co-regulators in human melanoma cells.

Alignment with 000268 (1085 aa); (SEQ ID NO: 105):

```
   1 MAAGSDLLDEVFFNSEVDEKVVSDLVGSLESQLAASAAHHHHLAPRTPEVRAAAAGALGN
     ||||||||||||||||||||
   1 MAAGSDLLDEVFFNSEVDEKV.......................................
  61 HVVSGSPAGAAGAGPAAPAEGAPGAAPEPPPAGRARPGGGGPQRPGPPSPRRPLVPAGPA

22 ............................................................
 121 PPAAKLRPPPEGSAGSCAPVPAAAAVAAGPEPAPAGPAKPAGPAALAARAGPGPGPGPGP

22 ............................................................
 181 GPGPGPGKPAGPGAAQTLNGSAALLNSHHAAAPAVSLVNNGPAALLPLPKPAAPGTVIQT

22 ............................................................
 241 PPFVGAAAPPAPAAPSPPAAPAPAAPAAAPPPPPPAPATLARPPGHPAGPPTAAPAVPPP

22 ............................................................
 301 AAAQNGGSAGAAPAPAPAAGGPAGVSGQPGPGAAAAAPAPGVKAESPKRVVQAAPPAAQT

22 ............................................................
 361 LAASGPASTAASMVIGPTMQGALPSPAAVPPPAPGTPTGLPKGAAGAVTQSLSRTPTATT

22 ............................................................
 481 HAQPQTTMAPRPATPTSAPPVQISTVQAPGTPIIARQVTPTTIIKQVSQAQTTCQPSATL
     |||||||||||||||||||||||||||||||||||||||||||||||||||||||||||
  49 HAQPQTTMAPRPATPTSAPPVQISTVQAPGTPIIARQVTPTTIIKQVSQAQTTCQPSATL

541 QRSPGVQPQLVLGGAAQTASLGTATAVQTGTPQRTVPGATTTSSAATETMENVKKVKNFL
     |||||||||||||||||||||||||||||||||||||||||||||||||||||||||||
 109 QRSPGVQPQLVLGGAAQTASLGTATAVQTGTPQRTVPGATTTSSAATETMENVKKVKNFL

601 STLIKLASSGKQSTETAANVKELVQNLLDGKIEAEDFTSRLYRELNSSPQPYLVPFLKRS
     |||||||||||||||||||||||||||||||||||||||||||||||||||||||||||
 169 STLIKLASSGKQSTETAANVKELVQNLLDGKIEAEDFTSRLYRELNSSPQPYLVPFLKRS

661 LPALRQLTPDSAAFIQQSQQQPPPPTSQATTALTAVVLSSSVQRTAGKTAATCTSALQPP
     |||||||||||||||||||||||||||||||||||||||||||||||||||||||||||
 229 LPALRQLTPDSAAFIQQSQQQPPPPTSQATTALTAVVLSSSVQRTAGKTAATCTSALQPP

721 VLSLTQPTQVGVGKQGQPTPLVIQQPPKPGALIRPPQVTLTQTPMVALRQPHNRIMLTTP
     |||||||||||||||||||||||||||||||||||||||||||||||||||||||||||
 289 VLSLTQPTQVGVGKQGQPTPLVIQQPPKPGALIRPPQVTLTQTPMVALRQPHNRIMLTTP

781 QQIQLNPLQPVPVVKPAVLPGTKALSAVSAQAAAAQKNKLKEPGGGSFRDDDDINDVASM
     |||||||||||||||||||||||||||||||||||||||||||||||||||||||||||
 349 QQIQLNPLQPVPVVKPAVLPGTKALSAVSAQAAAAQKNKLKEPGGGSFRDDDDINDVASM

841 AGVNLSEESARILATNSELVGTLTRSCKDETFLLQAPLQRRILEIGKKHGITELHPDVVS
     |||||||||||||||||||||||||||||||||||||||||||||||||||||||||||
 409 AGVNLSEESARILATNSELVGTLTRSCKDETFLLQAPLQRRILEIGKKHGITELHPDVVS

901 YVSHATQQRLQNLVEKISETAQQKNFSYKDDDRYEQASDVRAQLKFFEQLDQIEKQRKDE
     |||||||||||||||||||||||||||||||||||||||||||||||||||||||||||
 469 YVSHATQQRLQNLVEKISETAQQKNFSYKDDDRYEQASDVRAQLKFFEQLDQIEKQRKDE

961 QEREILMRAAKSRSRQEDPEQLRLKQKAKEMQQQELAQMRQRDANLTALAAIGPRKKRKV
     |||||||||||||||||||||||||||||||||||||||||||||||||||||||||||
 529 QEREILMRAAKSRSRQEDPEQLRLKQKAKEMQQQELAQMRQRDANLTALAAIGPRKKRKV

1021 DCPGPGSGAEGSGPGSVVPGSSGVGTPRQFTRQRITRVNLRDLIFCLENERETSHSLLLY
     |||||||||||||||||||||||||||||||||||||||||||||||||||||||||||
 589 DCPGPGSGAEGSGPGSVVPGSSGVGTPRQFTRQRITRVNLRDLIFCLENERETSHSLLLY

1081 KAFLK
     |||||
 649 KAFLK
```

TABLE 1-continued

Oligonucleotide primers used to isolate and characterize isoforms of transcriptional co-regulators in human melanoma cells.

13. TAF5L (NM_014409)
Product amplified with primers CAGTCATGAAACGAGTGCGTA (S1; SEQ ID NO: 106) and GAATCTCTCATCTACAGACAAC (AS4; SEQ ID NO: 107):
85 aa, shorter protein (similar to BE646579 but only one extra exon after exon 3) (SEQ ID NO: 103)
MKRVRTEQIQMAVSCYLKRRQWDSDGPLKQGLRLSQTAEEMAANLTVQSESGCANIVSAAPCQAEPQQY
EVQFGRLRNFLTGCL*
Alignment with O75S29 (S89 aa); (SEQ ID NO: 109):

```
  1 MKRVRTEQIQMAVSCYLKRRQYVDSDGPLKQGLRLSQTAEEMAANLTVQSESGCANIVSA
    ||||||||||||||||||||||||||||||||||||||||||||||||||||||||||||
  1 MKRVRTEQIQMAVSCYLKRRQYVDSDGPLKQGLRLSQTAEEMAANLTVQSESGCANIVSA

61 APCQAEPQQYEVQFGRLRNFLTDSDSQHSHEVMPLLYPLFVYLHLNLVQNSPKSTVESFY
    ||||||||||||||||||||||||||||
 61 APCQAEPQQYEVQFGRLRNFLTGCL...................................
```

14. TAF6L (NM 006473)
Product amplified with primers CCTATTTCGTAATCCGCACCT (S2; SEQ ID NO: 110) and ACTGACTCAGAGCGGCAAGTA (AS2; SEQ ID NO: 111)
different C-terminus after 460 aa (new product, deletion in exon 11);
(SEQ ID NO: 112)
...MCLGPYVRCLVGSVLYCVLEPLAASINPLNDHWTLRDGAALLLSHIFWTHGDLVSGLYQHILLSLQKIL
ADPVRFLCCHYGAVVGLHALGWKAVERVLYPHLSTYWTNLQAVLDDYSVSNAQVKADGHKVYGAILVAVE
RLLKMKAQAAEPNRGGPGGRGCRRLDDLPWDSLLFQESSSGGGAEPSFGSGLPLPPGGAGPEDPSLSVTL
ADIYRELYAFFGDSLATRFGTGLALRAETAHDRPYQPPRPPVGALGLLAVLAALSQ...
Alignment with Q9Y6J9 (622 aa); (SEQ ID NO: 113):

```
181 QDLQTNSKIGALLPYFVYVVSGVKSVSHDLEQLHRLLQVARSLFRNPHLCLGPYVRCLVG
                                               :|||||||||||
  1 ..............................................MCLGPYVRCLVG

241 SVLYCVLEPLAASINPLNDHWTLRDGAALLLSHIFWTHGDLVSGLYQHILLSLQKILADP
    ||||||||||||||||||||||||||||||||||||||||||||||||||||||||||||
 13 SVLYCVLEPLAASINPLNDHWTLRDGAALLLSHIFWTHGDLVSGLYQHILLSLQKILADP

301 VRPLCCHYGACCGLHALGWKAVERVLYPHLSTYWTNLQAVLDDYSVSNAQVKADGHKVYG
    ||||||||||||||||||||||||||||||||||||||||||||||||||||||||||||
 73 VRPLCCHYGACCGLHALGWKAVERVLYPHLSTYWTNLQAVLDDYSVSNAQVKADGHKVYG

361 AILVAVERLLKMKAQAAEPNRGGPGGRGCRRLDDLPWDSLLFQESSSGGGAEPSFGSGLP
    ||||||||||||||||||||||||||||||||||||||||||||||||||||||||||||
133 AILVAVERLLKMKAQAAEPNRGGPGGRGCRRLDDLPWDSLLFQESSSGGGAEPSFGSGLP

421 LPPGGAGPEDPSLSVTLADIYRELYAFFGDSLATRFGTGQPAPTAPRPPGDKKEPAAAPD
    |||||||||||||||||||||||||||||||||||||||||                 .|
193 LPPGGAGPEDPSLSVTLADIYRELYAFFGDSLATRFGTGLALRAETAHDRPYQPPRPPVG

481 SVRKMPQLTASAIVSPHGDESPRGSGGGGPASASGPAASESRPLPRVHRARGAPRQQGPG
    ..  :    | |  .
253 ALGLLAVLAALSQ...............................................
```

15. TAF7L (NM_024885)
Products amplified with primers AGACATGAGTGAAAGCCAGGA (SI; SEQ ID NO: 114) and CATAAGGCAACTGAAGGGACA (AS1; SEQ ID NO: 115):
302 aa: 74 internal aa missing (232-304 aa), ΔA10, alternative 1st exon, (SEQ ID NO: 116),
MSESQDEVPDEVENQFILRLPLEHACTVRNLARSQSVKMKDKLKIDLLPDGRHAVVEVEDVPLAAKLVDL
PCVIESLRTLDKKTFYKTADISQMLVCTADGDIHLSPEEPAASTDPNIVRKKERGREEKCVWKHGITPPL
KNVRKKRFRKTQKKVPDVKEMEKSSFTEYIESPDVENEVKRLLRSDAEAVSTRWEVIAEDGTKEIESQGS
IPGFLISSGMSSHKQGHTSSVMEIQKQIEKKEKKLHKIQNKAQRQKDLIMKVENLTLKNHFQSVLEQLEL
QEKQNEKLISLQEQLQRFLKK*
Alignment with Q5H9L6 (462 aa); (SEQ ID NO: 117):

```
  1 MSESQDECPDEVENQFILRLPLEHACTVRNLARSQSVKMKDKLKIDLLPDGRHAVVEVED
    ||||||||||||||||||||||||||||||||||||||||||||||||||||||||||||
  1 MSESQDECPDEVENQFILRLPLEHACTVRNLARSQSVKMKDKLKIDLLPDGRHAVVEVED

61 VPLAAKLVDLPCVIESLRTLDKKTFYKTADISQMLVCTADGDIHLSPEEPAASTDPNIVR
    ||||||||||||||||||||||||||||||||||||||||||||||||||||||||||||
 61 VPLAAKLVDLPCVIESLRTLDKKTFYKTADISQMLVCTADGDIHLSPEEPAASTDPNIVR

121 KKERGREEKCVWKHGITPPLKNVRKKRFRKTQKKVPDVKEMEKSSFTEYIESPDVENEVK
    ||||||||||||||||||||||||||||||||||||||||||||||||||||||||||||
121 KKERGREEKCVWKHGITPPLKNVRKKRFRKTQKKVPDVKEMEKSSFTEYIESPDVENEVK

181 RLLRSDAEAVSTRWEVIAEDGTKEIESQGSIPGFLISSGMSSHKQGHTSSEYDMLREMFS
    |||||||||||||||||||||||||||||||||||||||||||||||||||
181 RLLRSDAEAVSTRWEVIAEDGTKEIESQGSIPGFLISSGMSSHKQGHTSS..........

241 DSRSNNDDDEDEDDEDEDEDEDEDEDEDKEEEEEDCSEEYLERQLQAEFIESGQYRANEG
231 ............................................................

301 TSSIVMEIQKQIEKKEKKLHKIQNKAQRQKDLIMKVENLTLKNHFQSVLEQLELQEKQKN
       ||||||||||||||||||||||||||||||||||||||||||||||||||||||||
231 ....VMEIQKQIEKKEKKLHKIQNKAQRQKDLIMKVENLTLKNHFQSVLEQLELQEKQKN

361 EKLISLQEQLQRFLKK
    ||||||||||||||||
287 EKLISLQEQLQRFLKK
```

TABLE 1-continued

Oligonucleotide primers used to isolate and characterize isoforms of transcriptional co-regulators in human melanoma cells.

16. TAF8 (AF465841)
Product amplified with primers CACTACGCCAGAACAAGATGG (S1; SEQ ID NO: 118) and GTTTGCTTCCGTGTGTGTCTT (AS1; SEQ ID NO: 119):
214 aa: shorter/different C-terminus (after 164 aa); exons 6-8 spliced out; (SEQ ID NO: 120)

MADAAATAGAGGSGTRSGSKQSTNPADNYHLARRRTLQVVVSSLLTEAGFESAEKASVETLTEMLQSYIS
EIGRSAKSYCEHTARTQPTLSDIVVTLVEMGFNVDTLPAYAKRSQRMVITAPPVTNQPVTPKALTAGQNR
PHPPHIPSHEPEFPDPHTYIKTP**EDSGAEKENTSVLQQNPSLSGSRNGEENIIDNPYLRPVKKPKIRRKK
PDTF**\*

Alignment with Q727C8 (338 aa); (SEQ ID NO: 121):

```
  1 MADAAATAGAGGSGTRSGSKQSTNPADNYHLARRRTLQVVVSSLLTEAGKESAEKASVET
    |||||||||||||||||||||||||||||||||||||||||||||||||||||||||||
  1 MADAAATAGAGGSGTRSGSKQSTNPADNYHLARRRTLQVVVSSLLTEAGKESAEKASVET

61 LTEMLQSYISEIGRSAKSYCEHTARTQPTLSDIVVTLVEMGFNVDTLPAYAKRSQRMVIT
    |||||||||||||||||||||||||||||||||||||||||||||||||||||||||||
 61 LTEMLQSYISEIGRSAKSYCEHTARTQPTLSDIVVTLVEMGFNVDTLPAYAKRSQRMVIT

121 APPVTNQPVTPKALTAGQNRPHPPHIPSHFPEFPDPHTYIKYPTYPREVSDYQVLREKAA
    |||||||||||||||||||||||||||||||||||||||||||||||   :  . :.
121 APPVTNQPVTPKALTAGQNRPHPPHIPSHFPEFPDPHTYIKYPEDSGAEKENTSVLQQNP

181 SQRRDVERALTRFMAKTGETQSLFKDDVSTFPLIAARPFTIPYLTALLPSELEMQQMEET
         |                 |
181 SLSGSRNGEENIIDNPYLRPVKKPKIRRKKPDTF...........................

241 DSSEQDEQTDTENLALHISMIESRSVTQAGVQWQDLGSLQPPPPGFKRFSSLSLLSSWKY

215 .............................................................

301 RRILEPRRRTPLSCSRTPPCRVAGMGRRTSSITLICGR

215 .....................................
```

17. TAF15 (NM_139215)
Product amplified with primers TTGATGACCCTCCTTCAGCTA (S2; SEQ ID NO: 122)) and GCAAAACTCTGGCAATTTCAC (AS2; SEQ ID NO: 123):
457 aa: different C-terminus after 393 aa (Δ15); (SEQ ID NO: 124);

MSDSGSYGQSGGEQQSYSTYGNPGSQGYGQASQSYSGYGQTTDSSYGQNYSGYSSYGQSQSGYSQSYGGY
ENQKQSSYSQQPYNNQGQQQNMESSGSQGGRAPSYDQPDYGQQDSYDQQSGYDQHQGSYDEQSNYDQQHD
SYSQNQQSYHSQRENYSHHTQDDRRDVSRYGEDNRGYGGSQGGGRGRGGYDKDGRGPMTGSSGGDRGGFK
NFGGHRDYGPRTDADSESDNSDNNTIFVQGLGEGVSTDQVGEFFKQIGIIKTNKKTGKPMINLYTDKDTG
KPKGEATVSFDDPPSAKAAIDWFDGKEFHGNIIKVSEATRRPEFMRGGGSGGGRRGRGGYRGRGGFQGRG
GDPKSGDWVCPNPSCGNMNFARRNSCNQCNEPRPEDSRPSGGETTTEMISATDHTDDCFECSFVSDMIHS
EIARVLPAAFLVASSWVVKLSDIWIFIWVGGLGQFFF*

Alignment with Q92804-1 (592 aa); (SEQ ID NO: 125):

```
  1 MSDSGSYGQSGGEQQSYSTYGNPGSQGYGQASQSYSGYGQTTDSSYGQNYSGYSSYGQSQ
    |||||||||||||||||||||||||||||||||||||||||||||||||||||||||||
  1 MSDSGSYGQSGGEQQSYSTYGNPGSQGYGQASQSYSGYGQTTDSSYGQNYSGYSSYGQSQ

61 SGYSQSYGGYENQKQSSYSQQPYNNQGQQQNMESSGSQGGRAPSYDQPDYGQQDSYDQQS
    |||||||||||||||||||||||||||||||||||||||||||||||||||||||||||
 61 SGYSQSYGGYENQKQSSYSQQPYNNQGQQQNMESSGSQGGRAPSYDQPDYGQQDSYDQQS

121 GYDQHQGSYDEQSNYDQQHDSYSQNQQSYHSQRENYSHHTQDDRRDVSRYGEDNRGYGGS
    |||||||||||||||||||||||||||||||||||||||||||||||||||||||||||
121 GYDQHQGSYDEQSNYDQQHDSYSQNQQSYHSQRENYSHHTQDDRRDVSRYGEDNRGYGGS

181 QGGGRGRGGYDKDGRGPMTGSSGGDRGGFKNFGGHRDYGPRTDADSESDNSDNNTIFVQG
    |||||||||||||||||||||||||||||||||||||||||||||||||||||||||||
181 QGGGRGRGGYDKDGRGPMTGSSGGDRGGFKNFGGHRDYGPRTDADSESDNSDNNTIFVQG

241 LGEGVSTDQVGEFFKQIGIIKTNKKTGKPMINLYTDKDTGKPKGEATVSFDDPPSAKAAI
    |||||||||||||||||||||||||||||||||||||||||||||||||||||||||||
241 LGEGVSTDQVGEFFKQIGIIKTNKKTGKPMINLYTDKDTGKPKGEATVSFDDPPSAKAAI

301 DWFDGKEFHGNIIKVSFATRRPEFMRGGGSGGGRRGRGGYRGRGGFQGRGGDPKSGDWVC
    |||||||||||||||||||||||||||||||||||||||||||||||||||||||||||
301 DWFDGKEFHGNIIKVSFATRRPEFMRGGGSGGGRRGRGGYRGRGGFQGRGGDPKSGDWVC
```

TABLE 1-continued

Oligonucleotide primers used to isolate and characterize isoforms of transcriptional co-regulators in human melanoma cells.

```
361  PNPSCGNMNFARRNSCNQCNEPRPEDSRPSGGDFRGRGYGGERGYRGRGGRGGDRGGYGG
     ||||||||||||||||||||||||||||||||:
361  PNPSCGNMNFARRNSCNQCNEPRPEDSRPSGGETTTEMISATDHTDDCFECSFVSDMIHS

421  DRSGGGYGGDRSSGGGYSGDRSGGGYGGDRSGGGYGGDRGGGYGGDRGGGYGGDRGGGYG
     : .             .              :       |  :
421  EIARVLPAAFLVASSWVVKLSDIWIFIWVGGLGQFFF........................

481  GDRGGYGGDRGGGYGGDRGGYGGDRGGYGGDRGGYGGDRGGYGGDRSRGGYGGDRGGGSG

458  ............................................................

541  YGGDRSGGYGGDRSGGGYGGDRGGGYGGDRGGYGGKMGGRNDYRNDQRNRPY

458  ....................................................
```

MEDIATOR COMPLEX COMPONENTS
18. Med4 (MN_014166)
Product amplified with primers GAAAATGGCTGCGTCTTCG (SI; SEQ ID NO: 126) and CTCATCTCTAAATCAGTTGGG (AS; SEQ ID NO: 127)
224 aa: 46 aa shorter N-terminus, shorter 1st exon; (SEQ ID NO: 128);

MLAISRNQKLLQAGEENQVLELLIHRDGEFQELMKLALNQGKIHHEMQVLEKEVEKRDSDIQQLQKQLKE
AEQILATAVYQAKEKLKSIEKARKGAISSEEIIKYAHRISASNAVCAPLTWVPGDPRRPYPTDLEM...

Alignment with Q9NPJ6 (270 aa); (SEQ ID NO: 129):

```
  1  MAASSSGEKEKERLGGGLGVAGGNSTRERLLSALEDLEVLSRELIEMLAISRNQKLLQAG
                                                 |||||||||||||||
  1  ...........................................MLAISRNQKLLQAG

61  EENQVLELLIHRDGEFQELMKLALNQGKIHHEMQVLEKEVEKRDSDIQQLQKQLKEAEQI
     ||||||||||||||||||||||||||||||||||||||||||||||||||||||||||||
 15  EENQVLELLIHRDGEFQELMKLALNQGKIHHEMQVLEKEVEKRDSDIQQLQKQLKEAEQI

121  LATAVYQAKEKLKSIEKARKGAISSEEIIKYAHRISASNAVCAPLTWVPGDPRDPYPTDL
     ||||||||||||||||||||||||||||||||||||||||||||||||||||||||||||
 75  LATAVYQAKEKLKSIEKARKGAISSEEIIKYAHRISASNAVCAPLTWVPGDPRDPYPTDL

181  EMRSGLLGQMNNPSTNGVNGHLPGDALAAGRLPDVLAPQYPWQSNDMSMNMLPPNHSSDF
     ||
135  EM..........................................................

241  LLEPPGHNKENEDDVEIMSTDSSSSSSESD

137  .............................
```

Product amplified with primers CAAATGGCTCAGGCAGGTC (S1; SEQ ID NO: 130) and TGTAGACAATCATGAAGCCACG (AS1; SEQ ID NO: 131):
165 aa: shorter, four different aa-s in C-terminus, shorter 7th exon, two additional 3' exons from gene EL0VL1 - elongation of very long chain fatty acids; SEQ ID NO: 132;

MRQTEGRVPVFSHEVVPDHLRTKPDPEVEEQEKQLTTDAARIGADAAQKQIQSLNKMCSNLLEKISKEER
ESESGGLRPNKQTFNPTDTNALVAAVAFGKGLSNWRPSGSSGPGQAGQPGAGTILAGTSGLQQVQMAGAP
SQQQPMLSGVQMAQAGQPGKCQVE*

Alignment with Q96G25 (268 aa); (SEQ ID NO: 133)

```
  1  MRQTEGRVPVFSHEVVPDHLRTKPHPEVEEQEKQLTTDAARIGADAAQKQIQSLNKMCSN
     ||||||||||||||||||||||| |||||||||||||||||||||||||||||||||||
  1  MRQTEGRVPVFSHEVVPDHLRTKPHPEVEEQEKQLTTDAARIGADAAQKQIQSLNKMCSN

61  LLEKISKEERESESGGLPRNKQTFNPTDTNALVAAVAFGKGLSNWRPSGSSGPGQAGQPG
     ||||||||||||||||||||||||||||||||||||||||||||||||||||||||||||
 61  LLEKISKEERESESGGLPRNKQTFNPTDTNALVAAVAFGKGLSNWRPSGSSGPGQAGQPG

121  AGTILAGTSGLQQVQMAGAPSQQQPMLSGVQMAQAGQPGKMPSGIKTNIKSASMHPYQR
     |||||||||||||||||||||||||||||||||||||||
121  AGTILAGTSGLQQVQMAGAPSQQQPMLSGVQMAQAGQPGKCQVE...............
```

TABLE 1-continued

Oligonucleotide primers used to isolate and characterize isoforms of transcriptional co-regulators in human melanoma cells.

20. Med14 (NM_004229)
1. Product amplified with primers TCAGGATGCTCGAAGAAGGTC (SI; SEQ ID NO: 134) and CAGACACTTGAGGAGATCCTG (AS1; SEQ ID NO: 135):
1410 aa: internal 44 aa missing (1045-1089 aa), A24, (SEQ ID NO: 136)

...MNMFVDSNQDARRRSVNEDDNPPSPIGGDMMDSLISQLQPPPQQQPFPKQPGTSGAYPLTSPPTSYHST
VNQSPSMMHTQSPGTLDPSSPYTMVSPSGRAGNWPGSPQVSGP...

Alignment with 060244 (1454 aa); (SEQ ID NO: 137):

```
 781  LEFARSLPDIPAHLNIFSEVRVYNYRKLILCYGTTKGSSISIQWNSIHQKFHISLGTVGP

1  ............................................................

841  NSGCSNCHNTILHQLQEMFNKTPNVVQLLQVLFDTQAPLNAINKLPTVPMLGLTQRTNTA

1  ............................................................

901  YQCFSILPQSSTHIRLAFRNMYCIDIYCRSRGVVAIRDGAYSLFDNSKLVEGFYPAPGLK

1  ..MNMFVDSNQDARRRSVNEDDNPPSPIGGDMMDSLISQLQPPPQQQPFPKQPGTSGAYP
      :|||||||||||||||||||||||||||||||||||||||||||||||||||||||||||
 961  TFLNMFVDSNQDARRRSVNEDDNPPSPIGGDMMDSLISQLQPPPQQQPFPKQPGTSGAYP

59  LTSPPTSYHSTVNQSPSMMHTQSP....................................
      |||||||||||||||||||||||
1021  LTSPPTSYHSTVNQSPSMMHTQSPGNLHAASSPSGALRAPSPASFVPTPPPSSHGISIGP

83  ........GTLDPSSPYTMVSPSGRAGNWPGSPQVSGP.......................
              |||||||||||||||||||||||||||||
1081  GASFASPHGTLDPSSPYTMVSPSGRAGNWPGSPQVSGPSPAARMPGMSPANPSLHSPVPD

113  ............................................................

1141  ASHSPRAGTSSQTMPTNMPPPRKLPQRSWAASIPTILTHSALNILLLPSPTPGLVPGLAG

113  ............................................................

1201  SYLCSPLERFLGSVIMRRHLQRIIQQETLQLINSNEPGVIMF
```

2. Product amplified with primers GCTCTGCCGATCGACTTCC (S2; SEQ ID NO: 138) and AGGCGATCAGCAGTGTCCAC (AS2; SEQ ID NO: 139):
1382 aa: missing 73 aa at N-terminus( same as CN282118 (alternative 1st exon); (SEQ ID NO: 140);

MPRKSDVERKIEIVQFASRTRQLFVRLLALVKWANNAGKVEKCAMISSFLDQQAILFVDTADRLASLARD
ALVHARLPSFAIPYAIDVLTTGSYPRLPTCIRDKIIPPDPITKIEKQATLHQLNQILRHRLVTTDLPPQL
ANLTVANGRVKFRVEGEFEATLTVMGDDPDVPWRLLKLEILVEDKETGDGRALVHSMQISFIHQLVQSRL
FADEKPI...
Alignment with 060244 (1454 aa); (SEQ ID NO: 141):

```
   1  ............................................................

1  MAPVQLENHQLVPPGGGGGSGGPPSAPAPPPPGAAVAAAAAAAASPGYRLSTLIEFLLH

1  ............MPRKSDVERKIEIVQFASRTRQLFVRLLALVKWANNAGKVEKCAMISS
              :|||||||||||||||||||||||||||||||||||||||||||||||
  61  RAYSELMVLTDLLPRKSDVERKIEIVQFASRTRQLFVRLLALVKWANNAGKVEKCAMISS

49  FLDQQAILFVDTADRLASLARDALVHARLPSFAIPYAIDVLTTGSYPRLPTCIRDKIIPP
      ||||||||||||||||||||||||||||||||||||||||||||||||||||||||||||
 121  FLDQQAILFVDTADRLASLARDALVHARLPSFAIPYAIDVLTTGSYPRLPTCIRDKIIPP

109  DPITKIEKQATLHQLNQILRHRLVTTDLPPQLANLTVANGRVKFRVEGEFEATLTVMGDD
      ||||||||||||||||||||||||||||||||||||||||||||||||||||||||||||
 181  DPITKIEKQATLHQLNQILRHRLVTTDLPPQLANLTVANGRVKFRVEGEFEATLTVMGDD

169  PDVPWRLLKLEILVEDKETGDGRALVHSMQISFIHQLVQSRLFADEKPL...........
      |||||||||||||||||||||||||||||||||||||||||||||||||
 241  PDVPWRLLKLEILVEDKETGDGRALVHSMQISFIHQLVQSRLFADEKPLQDMYNCLHSFC

301  LSLQLEVLHSQTLMLIRERWGDLVQVERYHAGKCLSLSVWNQQVLGRKTGTASVHKVTIK

21  ............................................................
```

TABLE 1-continued

Oligonucleotide primers used to isolate and characterize isoforms of
transcriptional co-regulators in human melanoma cells.

```
361  IDENDVSKPLQIFHDPPLPASDSKLVERAMKIDHLSIEKLLIDSVHARAHQKLQELKAIL

21  ............................................................
```

21. Med1B (NM_001003891)
Product amplified with primers TGGATGTAAGATGAGATTGGG (S2; SEQ ID NO
142) and AATGAGCCTGGCCACGAGA (AS2); (SEQ ID NO: 143):
762 aa: 26 aa shorter N-terminus, alternative 1st exon; (SEQ ID NO:
144);

MRKAGVAHSKSSKDMESHVFLKAKTRDEYLSLVARLITHFRDIHNKKSQASVSDPMNALQSLTGGPAAGA
AGIGMP PRGPGQS LGGMGS L ...

Alignment with Q96RN5 (788 aa); (SEQ ID NO: 145):

```
  1  MDVSGQETDWRSTAFRQKLVSQIEDAMRKAGVAHSKSSKDMESHVFLKAKTRDEYLSLVA
                                 ||||||||||||||||||||||||||||||||
  1  .............................MRKAGVAHSKSSKDMESHVFLKAKTRDEYLSLVA

61  RLIIHFRDIHNKKSQASVSDPMNALQSLTGGPAAGAAGIGMPPRGPGQSLGGMGSLGAMG
     ||||||||||||||||||||||||||||||||||||||||||||||||||||||||
 35  RLIIHFRDIHNKKSQASVSDPMNALQSLTGGPAAGAAGIGMPPRGPGQSLGGMGSL....

121  QPMSLSGQPPPGTSGMAPHSMAVVSTATPQTQPQPQQVALQQQQQQQQFQQQQQAALQQQ
```

22. Med19 (NM_153450)
Product amplified with primers CACGAATCTGATCACACACTAC (S; SEQ ID NO:
146) and CTGGGTGGTCTGGACTATG (AS1; SEQ ID NO: 147):
244 aa: 50 aa longer C-terminus; {SEQ ID NO: 148)

MENFTALFGAQADPPPPPTALGFGPGKPPPPPPPAGGGPGTAPPPTAATAPPGADKSGAGCGPFYLMRE
LPGSTELTGSTNLITHYNLEQAKNKFCGKKVKEKLSNFLPDLPGMIDLPGSHDNSSLRSLIEKPPILSSS
FNPITGTMLAGFRLHTGPLPEQCRLMHIQPPKKKNKHKHKQSRTQDPVPP**ETPSDSDHKKKKKKKEEDPE
RKRKKKEKKKKKNRHSPDHPGMGSSQASSSSSLR***

Alignment with Q8IV02 (194 aa); {SEQ ID NO: 149 and 150):

```
121  SHDNSSLRSLIEKPPILSSSFNPITGTMLAGFRLHTGPLPEQCRLMHIQPPKKKNKHKHK
     ||||||||||||||||||||||||||||||||||||||||||||||||||||||||||
 54  SHDNSSLRSLIEKPPILSSSFNPITGTMLAGFRLHTGPLPEQCRLMHIQPPKKKNKHKHK

181  QSRTQDPVPPGKPS..............................................
     |||||||||| ||
114  QSRTQDPVPPETPSDSDHKKKKKKKEEDPERKRKKKEKKKKKNRHSPDHPGMGSSQASSSSSLR
```

23. TRAP100 (NNL014815)
Product amplified with primers CGTTACTAGAGCAGGCCATG (S2; SEQ ID NO:
151) and TACCCTCGGGAGACTCAATGA (AS4; SEQ ID NO: 152):
1008 aa: longer protein (extra 19 aa inside the protein after 188 aa);
SEQ ID NO: 153)

...MIGPSPNPLILSYLKYAISSQMVSYSSVLTAISKFDDFSRDLCVQALLDIMDMFCDRLSCHGKAEECIG
LCRALLSALHWLLRCTAASAERLREGLEAGTPAAGEKQLAMCLQRLEKTLSSTKNRALLHIAKLEEAS**LH
TSQGLGQGGTRANQPTA**SWTAIEHSLLKLGEILANLSNPQLRSQAEQCGTLIRSIPTMLSVHAEQMHKTG
FPTVHAVILLEGTMNLTGETQSLVEQLTMVKRMQHIPTPLFVLEIWKACFVGLIESPEG...

Alignment with O75448 (989 aa); (SEQ ID NO: 154):

```
  1  MKVVNLKQAILQAWKERWSDYQWAINMKKFFPKGATWDILNLADALLEQAMIGPSPNPLI
                                                     ||||||||||
  1  .................................................MIGPSPNPLI

61  LSYLKYAISSQMVSYSSVLTAISKFDDFSRDLCVQALLDIMDMFCDRLSCHGKAEECIGL
     ||||||||||||||||||||||||||||||||||||||||||||||||||||||||||
 11  LSYLKYAISSQMVSYSSVLTAISKFDDFSRDLCVQALLDIMDMFCDRLSCHGKAEECIGL

121  CRALLSALHWLLRCTAASAERLREGLEAGTPAAGEKQLAMCLQRLEKTLSSTKNRALLHI
     ||||||||||||||||||||||||||||||||||||||||||||||||||||||||||
 71  CRALLSALHWLLRCTAASAERLREGLEAGTPAAGEKQLAMCLQRLEKTLSSTKNRALLHI

181  AKLEEAS..................SWTAIEHSLLKLGEILANLSNPQLRSQAEQCGTL
     |||||||                  ||||||||||||||||||||||||||||||||||
131  AKLEEASLHTSQGLGQGGTRANQPTASWTAIEHSLLKLGEILANLSNPQLRSQAEQCGTL
```

TABLE 1-continued

Oligonucleotide primers used to isolate and characterize isoforms of transcriptional co-regulators in human melanoma cells.

```
222 IRSIPTMLSVHAEQMHKTGFPTVHAVILLEGTMNLTGETQSLVEQLTMVKRMQHIPTPLF
    |||||||||||||||||||||||||||||||||||||||||||||||||||||||||||
191 IRSIPTMLSVHAEQMHKTGFPTVHAVILLEGTMNLTGETQSLVEQLTMVKRMQHIPTPLF

282 VLEIWKACFVGLIESPEGTEELKWTAFTFLKIPQVLVKLKKYSHGDKDFTEDVNCAFEFL
    |||||||||||||||||||
251 VLEIWKACFVGLIESPEG...........................................
```

CHROMATIN REMODELING COMPLEX (SWI/SNF)
24. SMARCA1 (NM_003069)
Product amplified with primers AGATGACTCGCTTGCTGGATA (S3; SEQ ID NO: 155) and AGGTTAATTCCGAGACCTCCA (AS2; SEQ ID NO: 156):
955 aa: internal 12 aa missing (467-477 aa), A13; (SEQ ID NO: 157)

MDPEYEEKMKADRAKRFEFLLKQTELFAHFIQPSAQKSPTSPLNMKLGRPRIKKDEKQSLISAGDYRHRR
TEQEEDEELLSESRKTSNVCIRFEVSPSYVKGGPLRDYQIRGLNWLISLYENGVNGILADEMGLGKTLQT
IALLGYLKHYRNIPGPHMVLVPKSTLH1WMMEFKRWVPSLRVICFVGDKDARAAFIRDEMMPGEWDVCVT
SYEMVIKEKSVFKKFHWRYLVIDEAHRIKNEKSKLSEIVREFKSTNRLLLTGTPLQNNLHELWALLNFLL
PDVFNSADDFDSWFDTKNCLGDQKLVERLHAVLKPFLLRRIKTDVEKSLPPKKEIKIYLGLSKMQREWYT
KILMKDIDVLNSSGKMDKMRLLNILMQLRKCCNHPYLFDGAEPGPPYTTDEHIVSNSGKMWLDKLLAKL
KEQGSRVLIFSQMTRLLDILEDYCMWRGYEYCRLDGQTPHEEREEAIEAFNAPNSSKFIFMLSTRAGGLG
INLASADVVILYDSDWNPQVDLQAMDRAHRIGQKKPVRVFRLITDNTVEERIVERAEIKLRLDSIVIQQG
RLIDQQSNKLAKEEMLQMIRHGATHVFASKESELTDEDITTILERGEKKTAEMNERLQKMGESSLRNFRM
DIEQSLYKEEGEDYREKQKLGMVEWIFPPKRERKANYAVDAYFREALRVSEPKIPKAPRPPKQPNVQDFQ
FFPPRLFELLEKEILYYRKTIGYKVPRNPDIPNPALAQREEQKKIDGAEPLTPEETEEKEKLLTQGFTNW
TKRDFNQFIKANEKYGRDDIDNIAREVEGKSPEEVMEYSAVFWERCNELQDIEKIMAQIERGEARIQRRI
SIKKALDAKIARYKAPFHQLRIQYGTSKGKNYTEEEDRFLICMLHKMGFDRENVYEELRQCVRNAPQFRF
DWFIKSRTAMEFQRRCNTLISLIEKENMEIEERERAKKKK...

Alignment with P28370 (967 aa); SEQ ID NO: 158 and 159):

```
361 NSSGKMDKMRLLNILMQLRKCCNHPYLFDGAEPGPPYTTDEHIVSNSGKMVVLDKLLAKL
    |||||||||||||||||||||||||||||||||||||||||||||||||||||||||||
361 NSSGKMDKMRLLNILMQLRKCCNHPYLFDGAEPGPPYTTDEHIVSNSGKMVVLDKLLAKL

421 KEQGSRVLIFSQMTRLLDILEDYCMWRFYEYCRLDGQTPHEEREDKFLEVEFLGQREAIE
    |||||||||||||||||||||||||||||||||||||||||||||            ||||
421 KEQGSRVLIFSQMTRLLDILEDYCMWRFYEYCRLDGQTPHEERE............EAIE

481 AFNAPNSSKFIFMLSTRAGGLGINLADADVVILYDSDWNPQVDLQAMDRAHRIGQKKPVR
    |||||||||||||||||||||||||||||||||||||||||||||||||||||||||||
469 AFNAPNSSKFIFMLSTRAGGLGINLADADVVILYDSDWNPQVDLQAMDRAHRIGQKKPVR
```

25. SMARCA4 (NM_003 072)
Products amplified with primers ATCATGGCCTACAAGATGCTG (S2; SEQ ID NO: 160) and ATCCGCTCGTTCTCTTTCTTC (AS2; SEQ ID NO: 161):
a) 1438 aa: internal 209 aa missing (198-407 aa); new product (Δ(4)-(7)); (SEQ ID NO: 162)

...MAYKMLARGQPLPDHLLNFQRQLRQEVWCMRRDTALETALNAKAYKRSKRQSLREARITEKLEKQQKI
EQERKRRQKHQEYLNSILQHAKDFKEYHRSVTGKIQKLTKAVATYHANTEREQKKENER...

Alignment with P5153 (1647 aa); (SEQ ID NO: 163):

```
121 PLGGSEHASSPVPASGPSSGPQMSSGPGGAPLDGADPQALGQQNRGPTPFNQNQLHQLRA

1 ............................................................

181 QIMAYKMLARGQPLPDHLQMAVQGKRPMPGMQQQMPTLPPPSVSATGPGPGPGPGPGPGP
    ||||||||||||||||
  1 ..MAYKMLARGQPLPDH............................................

241 GPAPPNYSRPHGMGGPNMPPPGPSGVPPGMPGQPPGGPPKPWPEGPMANAAAPTSTPQKL

16 ............................................................

301 IPPQPTGRPSPAPPAVPPAASPVMPPQTQSPGQPAQPAPMVPLHQKQSRITPIQKPRGLD

16 ............................................................

361 PVEILQEREYRLQARIAHRIQELENLPGSLAGDLRTKATIELKALRLLNFQRQLRQEVVV
                                                  ||||||||||||||
 16 ..................................................LLNFQRQLRQEVVV
```

TABLE 1-continued

Oligonucleotide primers used to isolate and characterize isoforms of transcriptional co-regulators in human melanoma cells.

```
421 CMRRDTALETALNAKAYKRSKRQSLREARIREKLEKQQKIEQERKRRQKHQEYLNSILQH
    ||||||||||||||||||||||||||||||||||||||||||||||||||||||||||||
 30 CMRRDTALETALNAKAYKRSKRQSLREARIREKLEKQQKIEQERKRRQKHQEYLNSILQH

481 AKDFKEYHRSVTGKIQKLTKAVATYHANTEREQKKENERIEKERMRRLMAEDEEGYRKLI
    ||||||||||||||||||||||||||||||||||||||||
 90 AKDFKEYHRSVTGKIQKLTKAVATYHANTEREQKKENER.....................
``` b) 1388 aa: internal 259 aa missing (203-462 aa), new product (Δ(4)-(8)); (SEQ ID NO: 164)

...MAYKMLARGQPLPDHLQMAVQERKRRQKHQEYLNSILQHAKDFKEYHRSVTGKIQKLTKAVATYHANTEREQKKENER...

Alignment with P5153 (1647 aa); (SEQ ID NO: 165):

```
181 QIMAYKMLARGQPLPDHLQMAVQGKRPMPGMQQQMPTLPPPSVSATGPGPGPGPGPGPGP
       ||||||||||||||||||||
  1 ..MAYKMLARGQPLPDHLQMAV......................................

241 GPAPPNYSRPHGMGGPNMPPPGPSGVPPGMPGQPPGGPPKPWPEGPMANAAAPTSTPQKL

21 ............................................................

301 IPPQPTGRPSPAPPAVPPAASPVMPPQTQSPGQPAQPAPMVPLHQKQSRITPIQKPRGLD

21 ............................................................

361 PVEILQEREYRLQARIAHRIQELENLPGSLAGDLRTKATIELKALRLLNFQRQLRQEVVV

21 ............................................................

421 CMRRDTALETALNAKAYKRSKRQSLREARIREKLEKQQKIEQERKRRQKHQEYLNSILQH
                                       ||||||||||||||||||||||||
 21 ...................................QERKRRQKHQEYLNSILQH

481 AKDFKEYHRSVTGKIQKLTKAVATYHANTEREQKKENERIEKERMRRLMAEDEEGYRKLI
    ||||||||||||||||||||||||||||||||||||||
 40 AKDFKEYHRSVTGKIQKLTKAVATYHANTEREQKKENER.....................
```

26. SMARCC2 (NM_003075)
Products amplified with primers GCTCGGCAAGAACTACAAGAA - (SI; SEQ ID NO: 166) and CGGACACTTTGTTCCAGTCAT (AS2; SEQ ID NO: 167);
a) 749 aa: internal 465 aa missing (67-532 aa), new product (Δ(2)-(17)); (SEQ ID NO: 168);

...MLGKNYKKYIQAEPPTNKSLSSLVVQLLQFQEEVFGKHVLADTPSGLVPLQPKTPQQTSASQQMLNFPDKGKEKPTDMQNFGLRTDMYTKKNVPSKSKAAASATREWTEQETLLLLEALEMYKDDWNKVS...

Aligned with Q8TAQ2 (1214 aa); (SEQ ID NO: 169):

```
  1 MAVRKKDGGPNVKYYEAADTVTQFDNVRLWLGKNYKKYIQAEPPTNKSLSSLVVQLLQFQ
                                 |||||||||||||||||||||||||||||||
  1 ..........................MLGKNYKKYIQAEPPTNKSLSSLVVQLLQFQ

61 EEVFGKHVGNNAPLTKLPIKCFLDFKAGGSLCHILAAAYKFKSDQWRRYDFQNPSRMDRN
    ||||||
 31 EEVFGK......................................................

121 VEMFMTIEKSLVQNNCLSRPNIFLCPEIEPKLLGKLKDIIKRHQGTVTEDKNNASHVVYP

38 ............................................................

181 VPGNLEEEEWVRPVMKRDKQVLLHWGYYPDSYDTWIPASEIEASVEDAPTPEKPRKVHAK

38 ............................................................

241 WILDTDTFNEWMNEEDYEVNDDKNPVSRRKKISANTLTDEVNSPDSDRRDKKGGNYKKRK

38 ............................................................

301 RSPSPSPTPEAKKKNAKKGPSTPYTKSKRGHREEEQEDLTKDMDEPSPVPHVEEVTLPKT

38 ............................................................
```

TABLE 1-continued

Oligonucleotide primers used to isolate and characterize isoforms of transcriptional co-regulators in human melanoma cells.

```
361  VNTKKDSESAPVKGGTMTDLDEQEDESMETTGKDEDENSTGNKGEQTKNPDLHEDNVTEQ

38  ............................................................

421  THHIIIPSYAAWFDYNSVHAIERRALPEFFNGKNKSKTPEIYLAYRNFMIDTYRLNPQEY

38  ............................................................

481  LTSTACRRNLAGDVCAIMRVHHFLEQWGLINYQVDAESRPTPMGPPPTSHFHVLADTPSG
                                                      |||||||||
 38  ....................................................HVLADTPSG

541  LVPLQPKTPQQTSASQQMLNFPDKGKEKPTDMQNFGLRTDMYTKKNVPSKSKAAASATRE
     ||||||||||||||||||||||||||||||||||||||||||||||||||||||||||||
 47  LVPLQPKTPQQTSASQQMLNFPDKGKEKPTDMQNFGLRTDMYTKKNVPSKSKAAASATRE

601  WTEQETLLLLAELEMYKDDWNKVSEHVGSRTQDECILHFLRLPIEDPYLEDSEASLGPLA
     |||||||||||||||||||||||
107  WTEQETLLLLAELEMYKDDWNKVS.....................................
``` b) 847 aa: internal 367 aa missing (97-464 aa), new product (Δ(3)-(16)); (SEQ ID NO: 170);

...SSLWQLLQFQEEVFGKHVSNAPLTKLPIKCFLDFKAGGSLCHILAAAYRNFMIDTYRLNPQEYLTSTA
CRRNLAGDVCAIMRVHAFLEQWGLINYQVDAESRPTPMGPPPTSHFHVLADTPSGLVPLQPKTPQQTSAS
QQMLNFPDKGKEKPTDMQNFGLRTDMYTKKNVPSKSKAAASATREWTEQETLLLLEALEMYKDDWNKVS...

Aligned with Q8TAQ2 (1214 aa); (SEQ ID NO: 169 and 170):

```
  1  MAVRKKDGGPNVKYYEAADTVTQFDNVRLWLGKNYKKYIQAEPPTNKSLSSLVVQLLQFQ
                                                   ||||||||||||
  1  ...............................................SSLVVQLLQFQ

61  EEVFGKHVSNAPLTKLPIKCFLDFKAGGSLCHILAAAYKFKSDQGWRRYFDQNPSRMDRN
     |||||||||||||||||||||||||||||||||||||
 12  EEVFGKHVSNAPLTKLPIKCFLDFKAGGSLCHILAA.........................

121  VEMFMTIEKSLVQNNCLSRPNIFLCPEIEPKLLGKLKDIIKRHQGTVTEDKNNASHVVYP

48  ............................................................

181  VPGNLEEEEWVRPVMKRDKQVLLHWGYYPDSYDTWIPASEIEASVEDAPTPEKPRKVHAK

48  ............................................................

241  WILDTDTFNEWMNEEDYEVNDDKNPVSRRKKISAKTLTDEVNSPDSDRRDKKGGNYKKRK

48  ............................................................

301  RSPSPSPTPEAKKKNAKKGPSTPYTKSKRGHREEEQEDLTKDMDEPSPVPNVEEVTLPKT

48  ............................................................

361  VNTKKDSESAPVKGGTMTDLDEQEDESMETTGKDEDENSTGNKGEQTKNPDLHEDNVTEQ

48  ............................................................

421  THHIIIPSYAAWFDYNSVHAIERRALPEFFNGKNKSKTPEIYLAYRNFMIDTYRLNPQEY
                                             |||||||||||||||||||
 48  .....................................AYRNFMIDTYRLNPQEY

481  LTSTACRRNLAGDCCAIMRVHAFLEQWGLINYQVDAESRPTPMGPPPTSHFHVLADTPSG
     ||||||||||||||||||||||||||||||||||||||||||||||||||||||||||||
 65  LTSTACRRNLAGDCCAIMRVHAFLEQWGLINYQVDAESRPTPMGPPPTSHFHVLADTPSG

541  LVPLQPKTPQQTSASQQMLNFPDKGKEKPTDMQNFGLRTDMYTKKNVPSKSKAAASATRE
     ||||||||||||||||||||||||||||||||||||||||||||||||||||||||||||
125  LVPLQPKTPQQTSASQQMLNFPDKGKEKPTDMQNFGLRTDMYTKKNVPSKSKAAASATRE

601  WTEQETLLLLEALEMYKDDWNKVSEHVGSRTQDECILHFLRLPIEDPYLEDSEASLGPLA
     |||||||||||||||||||||||
185  WTEQETLLLLEALEMYKDDWNKVS.....................................
```

TABLE 1-continued

Oligonucleotide primers used to isolate and characterize isoforms of transcriptional co-regulators in human melanoma cells.

c) 734 aa: internal 480 aa missing (83-563 aa), new product (Δ(3)-(19)); (SEQ ID NO: 171);

...MSSLWQLLQFQEEVFGKHVSNAPLTKLPIKCFLDKGKEKPTDMQNFGLRTDMYTKPCNVPSKSKAAASA
TREWTEQETLLLLEALEMYKDDWNKVS...

Aligned with Q8TAQ2 (1214 aa); (SEQ ID NO: 169 and 171):

```
  1  MAVRKKDGGPNVKYYEAADTVTQFDNVRLWLGKNYKKYIQAEPPTNKSLSSLVVQLLQFQ
                                                 :||||||||||
  1  ..........................................MSSLVVQLLQFQ

61  EEVFGKHVSNAPLTKLPIKCFLDFKAGGSLCHILAAAYKFKSDQGWRRYDFQNPSRMDRN
     ||||||||||||||||||
 13  EEVFGKHVSNAPLTKLPIKCFL.......................................

121  VEMFMTIEKSLVQNNCLSRPNIFLCPEIEPKLLGKLKDIIKRHOGTVTEDKNNASHVVYP

35  ............................................................

181  VPGNLEEEEWVRPVMKRDKQVLLHWGYYPDSYDTWIPASEIEASVEDAPTPEKPRKVHAK

35  ............................................................

241  WILDTDTFNEWMNEEDYEVNDDKNPVSRRKKISAKTLTDEVNSPDSDRRDKKGGNYKKRK

35  ............................................................

301  RSPSPSPTPEAKKKNAKKGPSTPYTKSKRGHREEEQEDLTKDMDEPSPVPNVEEVTLPKT

35  ............................................................

361  VNTKKDSESAPVKGGTMTDLDEQEDESMETTGKDEDENSTGNKGEQTKNPDLHEDNVTEQ

35  ............................................................

421  THHIIIPSYAAWFDYNSVHAIERRALPEFFNGKNKSKTPEIYLAYRNFMIDTYRLNPQEY

35  ............................................................

481  LTSTACRRNLAGDVCAIMRVHAFLEQWGLINYQVDAESRPTPMGPPPTSHFHVLADTPSG

35  ............................................................

541  LVPLQPKTPQQTSASQQMLNFPDKGKEKPTDMQNFGLRTDMYTKKNVPSKSKAAASATRE
                      |||||||||||||||||||||||||||||||||||||||||
 35  ....................DKGKEKPTDMQNFGLRTDMYTKKNVPSKSKAAASATRE

601  WTEQETLLLLEALEMYKDDWNKVSEHVGSRTQDECILHFLRLPIEDPYLEDSEASLGPLA
     |||||||||||||||||||||||
 73  WTEQETLLLLEALEMYKDDWNKVS.....................................
```

27. SMARCE1 (NM_003079)
Product amplified with primers GCGGTGTCTCAGATTCATTC (S2; SEQ ID NO: 172) and TTGCCGGATGCTGTAATAGTTG (AS4; SEQ ID NO: 173)
77 aa: shorter protein, different C-term after 52 aa, long exon 4; ID NO: 174);

MSKRPSYAPPPTPAPATQMPSTPGFVGYNPYSHLAYNNYRLGGNPGTNSRVTGESTITASGKQLELTRN
AFRIRSF*

Alignment with Q969G3 (411 aa); (SEQ ID NO: 175):

```
  1  MSKRPSYAPPPTPAPATQMPSTPGFVGYNPYSHLAYNNYRLGGNPGTNSRVTASSGITIP
     |||||||||||||||||||||||||||||||||||||||||||||||||||||
  1  MSKRPSYAPPPTPAPATQMPSTPGFVGYNPYSHLAYNNYRLGGNPGTNSRVTGESTITA

61  KPPKPPDKPLMPYMRYSRKVWDQVKASNPDLKLWEIGKIIGGMWRDLTDEEKQEYLNEYE
     .                                    .|
 61  SGKQLELTRNAFRIRSF............................................

121  AEKIEYNESMKAYHNSPAYLAYINAKSRAEAALEEESRQRQSRMEKGEPYMSIQPAEDPD
```

Peptides

We generated small libraries of CPP-NLS-interfering peptides that potentially interact with melanoma expressed TFCs containing isoforms of co-regulator proteins BAF57 and TRAP100. Initial screening of these libraries identified the two following peptides that were further analyzed.

(1)
(SEQ ID NO: 6)
BAF57 P12-PKKRKV<u>RRRRRRR</u>NDRLSDGDSKYSQTSHKLVQLL (2)
(SEQ ID NO: 5)
TRAP100 P05-PKKRKVRRRRRRRPQMQQNVFQYPGAGMVPQGEANF

First portion - NLS, underlined - CPP; last portion - mimicking domains

NLS - nucleus localizing signal; CPP - cell penetrating peptide

RESULTS

Isoforms of Transcriptional Co-Regulators

We have conducted an extensive in silico analysis of components of transcriptional co-regulators and designed PCR primers to identify novel isoforms with altered function (activity). Identified isoforms are presented in Table 1.

Based on the known assembly and composition of TFCs and function of individual components of TFCs, we predicted changes in TFCs that contain isoforms of MED24. Since these isoforms and corresponding TFCs are expressed specifically in melanoma cells, these TFCs represent a suitable target for drug development. We therefore designed peptides that interact with a melanoma specific TFC and in this way disrupt its function, leading to cell death (apoptosis) and/or cessation of cell proliferation.

Example 2

Effect of Interfering Peptides on Proliferation and Apoptosis of Melanoma Cells Modeling of TFCs that contain isoforms of BAF57 and TRAP100 identified specific interactions that enabled us to synthesize small peptide libraries. Screening of these libraries using melanoma cell line SK-MEL-28 resulted in two peptides, denoted by us as BAF57 P12 and TRAP100 P05 that were found to stimulate apoptosis and inhibit growth of melanoma cells in vitro.

Amino acid sequences of SMARCE1/BAF57 and TRAP100 isoforms. Unique, isoform specific sequences are underlined.

SMARCE1/BAF57
(SEQ ID NO: 10)
MSKRPSYAPPPTPAPATQMPSTPGFVGYNPYSHLAYNNYRLGGNPGTNSR

VTASSGITIPKPPKPPDKPLMPYMRYSRKVWDQVKASNPDLKLWEIGKII

GGMWRDLTDEEKQEYLNEYEAEKIEYNESMKAYHNSPAYLAYINAKSRAE

AALEEESRQRQSRMEKGEPYMSIQPAEDPDDYDDGFSMKHTATARFQRNH

RLISEILSESVVPDVRSVVTTARMQVLKRQVQSLMVHQRKLEAELLQIEE

RHQEKKRKFLESTDSFNNELKRLCGLKVEVDMEKIAAEIAQAEEQARKRQ

EEREKEAAEQAERSQSSIVPEEEQAANKGEEKKDDENIPMETEETHLEET

TESQQNGEEGTSTPEDKESGQEGVDSMAEEGTSDSNTGSESNSATVEEPT

DPIPEDEKKE

SMARCE1/BAF57 isoform 1
(SEQ ID NO: 11)
MSKRPSYAPPPTPAPATQMPSTPGFVGYNPYSHLAYNNYRLGGNPGTNSR VT<u>TLFIGDFLGPCSSVSTVLPASPLEIESRKLERE1LLEVGFLIVARKET VQKWKHILQKHSPA</u>SSGITIPKPPKPPDKPLMPYMRYSRKVWDQVKASNP

DLKLWEIGKIIGGMWRDLTDEEKQEYLNEYEAEKIEYNESMKAYHNSPAY

LAYINAKSRAEAALEEESRQRQSRMEKGEPYMSIQPAEDPDDYDDGFSMK

HTATARFQRNHRLISEILSESVVPDVESVVTTARMQVLKRQVQSLMVHQR

KLEAELLQIEERHQEKKRKFLESTDSFNNELKRLCGLKVEVDMEKIAAEI

AQAEEQARKRQEEREKEAAEQAERSQSSIVPEEEQAANKGEEKKDDENIP

METEETHLEETTESQQNGEEGTSTPEDKESGQEGVDSMAEEGTSDNSTGS

ESNSATVEEPPTDPIPEDEKKE

TRAP100
(SEQ ID NO: 12)
MKVVNLKQAILQAWKERWSYYQWAINMKKFPPKGATWDILNLADALLEQA

MIGPSPNPLILSYLKYAISSQMVSYSSVLTAISKPDDFSRDLCVQALLDI

MDMFCDRLSCHGKAEECIGLCRALLSALHWLLRCTAASAERLREGLEAGT

PAAGEKQLAMCLQRLEKTLSSTKNRALLHTAKLEEASSWTAIEHSLLKLG

EILTNLSNPQLRSQAEQCGTLIRSIPTMLSVHAEQMHKTGFPTVHAVILL

EGTMNLTGETQSLVEQLTMVKRMQHIPTPLFVLEIWKACFVGLIESPEGT

EELKWTAFTFLKIPQVLVKLKKYSHGDKDFTEDVNCAFEFLLKLTPLLDK

ADQRCNCDCTNFLLQECGKQGLLSEASVNNLMAKRKADREHAPQQKSGEN

ANIQPNIQLILRAEPTVTNILKTMDADHSKSPEGLLGVLGHMLSGKSLDL

LLAAAAATGKLKSFARKFINLNEFTTYGSEESTKPASVRALLFDISFLML

CHVAQTYGSEVILSESRTGAEVPFFETWMQTCMPEEGKILNPDHPCFRPD

STKVESLVALLNNSSEMKLVQMKWHEACLSISAAILEILNAWENGVLAFE

SIQKITDNIKGKVCSLAVCAVAWLVAHVRMLGLDEREKSLQMIRQLAGPL

FSENTLQFYNERVVIMNSILERMCADVLQQTATQIKFPSTGVDTMPYWNL

LPPKRPIKEVLTDIFAKVLEKGWVDSRSIHIFDTLLHMGGVYWFCNNLIK

ELLKETRKEHTLRAVELLYSIFCLDMQQVTLVLLGHILPGLLTDSSKWHS

LMDPPGTALAKLAVWCALSSYSSHKGQASTRQKKRHREDIEDYISLFPLD

DVQPSKLMRLLSSNEDDANILSSPTDRSMSSSLSASQLHTVNMRDPLNRV

LANLFLLISSILGSRTAGPHTQFVQWFMEECVDCLEQGGRGSVLQFMPFT

TVSELVKVSAMSSPKVVLAITDLSLPLGRQVAAKAIAAL

TRAP100 isoform 1
(SEQ ID NO: 13)
MKVVNLKQAILQAWKERWSYYQWAINMKKFPPKGATWDILNLADALLEQA

MIGPSPNPLILSYLKYAISSQMVSYSSVLTAISKPDDFSRDLCVQALLDI

MDMFCDRLSCHGKAEECIGLCRALLSALHWLLRCTAASAERLREGLEAGT

PAAGEKQLAMCLQRLEKTLSSTKNRALLHIAKLEEA<u>CPHQALLVGSKTST

-continued

```
SQTRKKLEDKTSTVSIIVFVSMLLIAWKQMTLVFECKLKCSSWTAIEHSL

LKLGEILTNLSNPQLRSQAEQCGTLIRSIPTMLSVHAEQMHKTGFPTVHA

VILLEGTMNLTGETQSLVEQLTMVKRMQHIPTPLFVLEIWKACFVGLIES

PEGTEELKWTAFTFLKIPQVLVKLKKYSHGDKDFTEDVNCAFEFLLKLTP

LLDKADQRCNCDCTNFLLQECGKQGLLSEASVNNLMAKRKADREHAPQQK

SGENANIQPNIQLILRAEPTVTNILKTMDADHSKSPEGLLGVLGHMLSGK

SLDLLLAAAAATGKLKSFARKFINLNEFTTYGSEESTKPASVRALLFDIS

FLMLCHVAQTYGSEVILSESRTGAEVPFFETWMQTCMPEEGKILNPDHPC

FRPDSTKVESLVALLNNSSEMKLVQMKWHEACLSISAAILEILNAWENGV

LAFESIQKITDNIKGKVCSLAVCAVAWLVAHVRMLGLDEREKSLQMIRQL

AGPLFSENTLQFYNERVVIMNSILERMCADVLQQTATQIKFPSTGVDTMP

YWNLLPPKRPIKEVLTDIFAKVLEKGWVDSRSIHIFDTLLHMGGVYWFCN

NLIKELLKETRKEHTLRAVELLYSIFCLDMQQVTLVLLGHILPGLLTDSS

KWHSLMDPPGTALAKLAVWCALSSYSSHKGQASTRQKKRHREDIEDYISL

FPLDDVQPSKLMRLLSSNEDDANILSSPTDRSMSSSLSASQLHTVNMRDP

LNRVLANLFLLISSILGSRTAGPHTQFVQWFMEECVDCLEQGGRGSVLQF

MPFTTVSELVKVSAMSSPKVVLAITDLSLPLGRQVAAKAIAAL
```

Effects of peptide drug candidates BAF57 P12 and TRAP100 P05 on cell proliferation and apoptosis were analyzed using human melanoma cell lines SK-MEL-28 and WM 266-4. Therapeutic peptides were added at a concentration of 10 µM directly to culture media. Internalization and translocation of the therapeutic peptide(s) into the cell nucleus was studied using fluorescein labeled peptides. Peptides showed prominent nuclear localization following 8 hours of incubation with cells. This pattern remained unchanged for 7 days in cells that do not become apoptotic. As controls we used scrambled peptides. Results of these experiments (Table 2) clearly show that peptides BAF57P12 and TRAP100P05 suppress significantly proliferation and induce apoptosis. Simultaneous incubation of melanoma cells with both peptides caused complete inhibition of proliferation and induction of apoptosis in almost all treated cells.

The results of testing and validation of our peptide drug candidates demonstrated that our therapeutic peptides are viable drug candidates for treatment of melanoma in situ as well as metastatic melanoma.

Example 3

Treatment of Human Melanoma Xenografts using CSTC-Targeting Peptides

This example demonstrates the effect of therapeutic peptides on development of human melanomas in 4-week-old BALB/cOlaHsd-nu mice (Harlan, UK). Seven days after injection of melanoma cells, mice were randomly divided into 2 groups, 10 animals each. Control animals received intravenous (tail vein) injections of 50 microliters of phosphate buffer solution (PBS) every other day for 3 weeks. Test animals received intravenous (tail vein) injections of peptides BAF57 P12 and TRAP100 P05 (together) at a concentration of 0.5 mM each in 50 microliters of PBS every other day for 3 weeks. Last 2 injections were done using peptides labeled with fluorescein.

Therapeutic Peptides

BAF57 P12-PKKRKVRRRRRRRNDRLSDGDSKYSQTSHKLVQLL
(SEQ ID NO: 6)

TRAP100 P05-PKKRKVRRRRRRRPQMQQNVFQYPGAGMVPQGEANF
(SEQ ID NO: 5)

Light face type - NLS, bold face type - CPP and normal type - mimicking domains

One day following the last injection, animals were sacrificed and subcutaneous tumors were removed, weighed and measured. Tumor tissue samples were obtained and subjected to molecular analysis.

RESULTS

It was found that in SCID mice bearing cutaneous human melanomas intravenous (systemic) treatment with our peptide drug candidates reduced the weight and size of melanoma tumors by 57±18% (33-85%) compared to matched control animals receiving intravenous injections of PBS (Table 3).

TABLE 2

Effect of peptides BAF57P12 and TRAP100P05 on proliferation and apoptosis of human melanoma SK-MEL-28 and WM 266-4 cells.

| Cell line | Peptide | Concentration | Cell Count Start | 7 days | Apoptosis 7 days/% |
|---|---|---|---|---|---|
| SK-MEL-28 | no | | 10 | 57 | 0 |
| | scrambled BAF | | 10 | 54 | 0 |
| | BAF57 P12 | 10 µM | 10 | 16 | 65 |
| | Scrambled TRAP | 10 µM | 10 | 58 | 0 |
| | TRAP100 P05 | 10 µM | 10 | 12 | 78 |
| | scrambled BAF + TRAP | 10 µM | 10 | 46 | 4 |
| | BAF57 P12 + TRAP100 P05 | 10 µM | 10 | 9 | 95 |
| WM 266-4 | no | 10 µM | 10 | 39 | 0 |
| | scrambled BAF | 10 µM | 10 | 37 | 0 |
| | BAF57 P12 | 10 µM | 10 | 17 | 59 |
| | Scrambled TRAP | 10 µM | 10 | 34 | 1 |
| | TRAP100 P05 | 10 µM | 10 | 15 | 78 |
| | scrambled BAF + TRAP | 10 µM | 10 | 32 | 8 |
| | BAF57 P12 + TRAP100 P05 | 10 µM | 10 | 8 | 98 |

TABLE 3

Effect of BAF57 P12 and TRAP100 P05 on tumor growth in vivo.

| Control tumors | | Peptide treated tumors | | |
| --- | --- | --- | --- | --- |
| Animal | Tumor weight (g) | Animal | Tumor weight (g) | Reduction (%) |
| C1 | 0.6 | T1 | 0.2 | 33 |
| C2 | 0.5 | T2 | 0.1 | 85 |
| C3 | 0.9 | T3 | 0.4 | 56 |
| C4 | 0.6 | T4 | 0.3 | 50 |
| C5 | 0.4 | T5 | 0.1 | 75 |
| C6 | 0.7 | T6 | 0.3 | 57 |
| C7 | 0.9 | T7 | 0.6 | 34 |
| C8 | died | T8 | 0.4 | — |
| C9 | 0.9 | T9 | 0.5 | 46 |
| C10 | 0.4 | T10 | 0.1 | 75 |
| Mean ± SD | 6.8 ± 2.0 g | | 3.0 ± 1.8 g | 57 ± 18% |

Treatment of immune-compromised mice with cutaneous human melanomas with our two peptide drug candidates BAF57 P12 and TRAP100 P05 demonstrated that said therapeutic peptides are viable drug candidates for treatment of melanoma in situ as well as metastatic melanoma.

Example 4

Expression of BAF57 and MED24 Isoforms in Different Cancer Types

This example demonstrates that the cancer-specific isoforms of BAF57 and MED24 described herein are not limited to melanoma, but are also expressed in other types of cancer, including, colorectal, breast and brain cancers. In this study, surgically removed tumor samples from 21 melanoma, 25 colorectal cancer, 27 breast cancer and 11 glioblastoma patients were used to isolate RNA and analyze expression of BAF57 and MED24 isoforms using RT-PCR technique. Results of the analysis are presented in Table 4.

RNA was isolated from surgically removed tumor samples using RNA isolation KIT (Qiagen). RT-PCR was used to identify isoforms of co-regulators. First strand cDNAs were synthesized with reverse transcriptase (SuperscriptII, Life Technologies Inc.) using 5-10 µg of mRNA. PCR reactions were performed in the volume of 25 µl containing one tenth of RT reaction as a template and GC-Rich PCR System or the Expand™ Long Distance PCR System kit (Roche) was used in accordance with manufacturers instructions.

TABLE 4

Expression of isoforms of BAF57 and MED24 in tumor samples.

| Cancer type | # of samples | # of samples with BAF57 isoform | # of samples with MED24 isoform |
| --- | --- | --- | --- |
| Melanoma | 21 | 12 | 16 |
| Colorectal | 25 | 3 | 15 |
| Breast | 27 | 1 | 1 |
| glioblastoma | 11 | 8 | 9 |

REFERENCES

King R, et al. 1999. Am J Pathot. 1999 September; 155(3): 731-8
Opdecamp K, et al. 1997. Development.; 124(12):2377-86.
Salti G I, et al. 2000. Cancer Res.; 60(18):5012-6.
Chang K L, Folpe A L. 2001. Adv Anat Pathol., 8(5):273-5.
Miettinen M, et al. 2001. Am J Surg Pathol. 2001, (2):205-11.
He T C, et al. 1998. Science.; 281(5382):1509-12.
Tetsu O, McCormick F. 1999. Nature. 1999; 398(6726):422-6.
Shtutman M, et al. 1999. Proc Natl Acad Sci USA. 1999; 96(10):5522-7.
Goldberg S F et at. 2003. Cancer Res.; 63(2):432-40.
Roeder R G. 1996. Trends Biochem Sci.; 21(9):327-35.
Malik S, Roeder R G. 2005. Trends Biochem Sci.; 30(5):256-63.
Kalinichenko V V, et al. 2004. Genes Dev.; 18(7):830-50.
Gail R, et al. 2005. J Biol Chem.; 280(8):7107-17.
Rothbard J B, et al. 2000. Nat Med.; 6(11):1253-7.
Chang J, et al. 2003. Cancer. 2003 Feb. 1; 97(3):545-53.
Perou C M, et al. 2000. Nature. 2000; 406(6797):747-52.
Hedenfalk I, et al. 2001. N Engl J Med.; 344(8):539-48.
West M., et al. 2001. Proc. Natl. Acad. Sci., USA., 98,:11462-11467.
Zajchowski D A, et al. 2001. Cancer Res.; 61(13):5168-78.
van't Veer L J, et al. 2002. Nature., 415(6871):530-6.
van de Vijver M J, et al. 2002. N Engl J Med.; 347(25):1999-2009.
Wang Z, et al. 2003. Cancer Res.; 63(3):655-7.
Porter D C, Keyomarsi K. 2000. Nucleic Acids Res. 2000 Dec. 1; 28(23):E101.
Leroy H, et al. 2005. Leukemia. 2005 March; 19(3):329-34.
Keyomarsi K, et al. 2002. N Engl J Med. 2002 Nov. 14; 347(20):1566-75. Erratum in: N Engl J Med 2003 Jan. 9; 348(2);186.
Qin C, et at. 2001. Clin Cancer Res.; 7(4):818-23.
Xia and Barr. 2005. Eur J Cancer. 2005 November; 41(16) 62513-27.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated molecule that specifically binds to the isoform-specific portion of SEQ ID NO: 11 or SEQ ID NO: 13, wherein the molecule is a peptide having fewer than 100 amino acids or an antibody.

2. The molecule of claim 1, which is a peptide.

3. The peptide of claim 2 that comprises the amino acid sequence of SEQ ID NO: 1 or a conservatively modified variant thereof having the amino acid sequence of SEQ ID NO: 7.

4. The peptide of claim 2 that comprises the amino acid sequence of SEQ ID NO: 2 or a conservatively modified variant thereof having the amino acid sequence of SEQ ID NO: 8.

5. The molecule of claim 2, further comprising a cell penetrating peptide (CPP).

6. The molecule of claim 5, wherein the CPP has the amino acid sequence RRRRRRR (SEQ ID NO: 3).

7. The molecule of claim 2, further comprising a nuclear localizing signal (NLS).

8. The molecule of claim 7, wherein the NLS has the amino acid sequence PKKRKV (SEQ ID NO: 4).

9. The molecule of claim 2, wherein the peptide has the amino acid sequence

```
PKKRKVRRRRRRRPQMQQNVFQYPGAGMVPQGEANF
(TRAP100 P05; SEQ ID NO: 5)
or

PKKRKVRRRRRRRNDRLSDGDSKYSQTSHKLVQLL
(BAF57 P12; SEQ ID NO: 6).
```

10. The molecule of claim 2, which disrupts the biological activity of a transcription factor complex (TFC).

11. The molecule of claim 10, which induces apoptosis, inhibits proliferation of cancer cells and/or inhibits tumor growth.

12. A composition comprising the molecule of claim 9, and a pharmaceutically acceptable carrier.

13. A recombinant or synthetic peptide having the amino acid sequence PKKRKVRRRRRRRPQMQQNVFQYP-GAGMVPQGEANF (TRAP100 P05; SEQ ID NO: 5).

14. A recombinant or synthetic peptide having the amino acid sequence PKKRKVRRRRRRRNDRLSDGDSKYSQT-SHKLVQLL (BAF57 P12; SEQ ID NO: 6).

15. The molecule of claim 1, which is an antibody.

16. A method of disrupting the biological activity of a TFC comprising contacting a cancer cell with the molecule of claim 10.

17. A method of inducing apoptosis in a cancer cell comprising contacting the cancer cell with the molecule of claim 11, wherein the cancer cell is a melanoma, glioblastoma, colorectal or breast cancer cell.

18. A method of inhibiting proliferation of cancer cells, comprising contacting the cancer cells with the molecule of claim 11, wherein the cancer cells are melanoma, glioblastoma, colorectal or breast cancer cells.

19. A method of inhibiting tumor growth comprising contacting the tumor with the molecule of claim 11, wherein the tumor is a melanoma, glioblastoma, colorectal or breast tumor.

20. The method of claim 16, wherein the contacting comprises delivering the molecule to the nucleus of the cancer cells.

21. A method for detecting cancer in a tissue specimen, comprising contacting a tissue specimen with the molecule of claim 1, wherein the molecule has been labeled with a detectable marker to form a detectable molecule and detecting binding of the detectable molecule, wherein binding of the detectable molecule is indicative of cancer.

22. The method of claim 21, wherein the cancer is melanoma.

* * * * *